United States Patent
Chen et al.

(10) Patent No.: US 11,643,440 B2
(45) Date of Patent: May 9, 2023

(54) PEPTIDE PAC1 ANTAGONISTS

(71) Applicant: AMGEN INC., Thousand Oaks, CA (US)

(72) Inventors: Irwin Chen, Los Angeles, CA (US); Su Chong, Oxnard, CA (US); Essa Hu Harrington, Camarillo, CA (US); Fang-Tsao Hong, Thousand Oaks, CA (US); Jason C. Long, Newbury Park, CA (US); Leslie P. Miranda, Thousand Oaks, CA (US)

(73) Assignee: AMGEN INC., Thousand Oaks, CA (US)

( * ) Notice: Subject to any disclaimer, the term of this patent is extended or adjusted under 35 U.S.C. 154(b) by 0 days.

(21) Appl. No.: 16/619,874

(22) PCT Filed: Jun. 1, 2018

(86) PCT No.: PCT/US2018/035597
§ 371 (c)(1),
(2) Date: Dec. 5, 2019

(87) PCT Pub. No.: WO2018/222991
PCT Pub. Date: Dec. 6, 2018

(65) Prior Publication Data
US 2021/0395313 A1    Dec. 23, 2021

Related U.S. Application Data

(60) Provisional application No. 62/514,440, filed on Jun. 2, 2017.

(51) Int. Cl.
*C07K 14/00* (2006.01)
*A61P 25/06* (2006.01)
*A61K 38/00* (2006.01)

(52) U.S. Cl.
CPC ............ *C07K 14/001* (2013.01); *A61P 25/06* (2018.01); *A61K 38/00* (2013.01)

(58) Field of Classification Search
None
See application file for complete search history.

(56) References Cited

U.S. PATENT DOCUMENTS

| | | | |
|---|---|---|---|
| 5,397,772 A | 3/1995 | Ribeiro et al. | |
| 5,480,864 A | 1/1996 | Tajima et al. | |
| 5,763,271 A | 6/1998 | Ribeiro et al. | |
| 6,017,533 A | 1/2000 | Moro et al. | |
| 6,462,016 B1 * | 10/2002 | Wakita ............ | C07K 14/43577 514/870 |
| 2002/0182729 A1 | 12/2002 | DiCicco-Bloom et al. | |
| 2004/0038888 A1 | 2/2004 | Mercer et al. | |
| 2007/0149439 A1 * | 6/2007 | DiCicco-Bloom ......................... | A61K 38/2278 514/17.7 |

FOREIGN PATENT DOCUMENTS

| | | |
|---|---|---|
| CN | 101125881 A | 2/2008 |
| WO | 1997/040388 A1 | 10/1997 |
| WO | 2004/039958 A2 | 5/2004 |
| WO | 2009/033489 A2 | 3/2009 |
| WO | 2009/137577 A2 | 11/2009 |
| WO | 2010/078469 A2 | 7/2010 |
| WO | 2011/133948 A2 | 10/2011 |

OTHER PUBLICATIONS

Amin et al., "Investigation of the pathophysiological mechanisms of migraine attacks induced by pituitary adenylate cyclase-activating polypeptide-38," *Brain* 137:779-794 (2014).
Rahmann et al., "Vasoactive intestinal peptide causes marked cephalic vasodilation, but does not induce migraine," *Cephalalgia* 28(3):226-236 (2008).
Rainero et al., "Genes and primary headaches: discovering new potential therapeutic targets," *The Journal of Headache and Pain* 14: 1-8 (2013).
Vollesen et al., "PACAP38: Emerging Drug Target in Migraine and Cluster Headache," *Headache* 57:56-63 (2017).

* cited by examiner

*Primary Examiner* — Sudhakar Katakam
*Assistant Examiner* — Zachary J Miknis
(74) *Attorney, Agent, or Firm* — Olga Mekhovich

(57) ABSTRACT

Novel peptides that bind to human PAC1 are provided. These peptides that are antagonists of PAC1 are useful in a number of PAC1 related disorders, including the treatment and/or prevention of headache disorders, including migraine, such as acute migraine.

4 Claims, No Drawings
Specification includes a Sequence Listing.

SEQUENCE LISTING

```
<160> NUMBER OF SEQ ID NOS: 451

<210> SEQ ID NO 1
<211> LENGTH: 43
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(31)
<220> FEATURE:
<221> NAME/KEY: MOD_RES
<222> LOCATION: (43)..(43)
<223> OTHER INFORMATION: C-terminal amidation

<400> SEQUENCE: 1

Cys Asp Ala Thr Cys Gln Phe Arg Lys Ala Ile Asp Asp Cys Ala Lys
1               5                   10                  15

Ala Ser Trp His Ser Asn Val Pro Gly Ser Val Phe Lys Ser Cys Met
```

```
                    20                  25                  30

Lys Gln Lys Lys Lys Glu Trp Lys Ala Gly His
        35                  40

<210> SEQ ID NO 2
<211> LENGTH: 43
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(31)
<220> FEATURE:
<221> NAME/KEY: MOD_RES
<222> LOCATION: (43)..(43)
<223> OTHER INFORMATION: C-terminal amidation

<400> SEQUENCE: 2

Cys Asp Ala Thr Cys Gln Phe Arg Lys Ala Ile Asp Asp Cys Ala Arg
1               5                   10                  15

Gln Ala His His Ser Asn Val Pro Gly Ser Val Phe Lys Ala Cys Met
                20                  25                  30

Lys Gln Lys Lys Lys Glu Trp Lys Ala Gly His
        35                  40

<210> SEQ ID NO 3
<211> LENGTH: 39
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(27)

<400> SEQUENCE: 3

Cys Asp Ala Thr Cys Gln Phe Arg Lys Ala Ile Asp Asp Cys Val Arg
1               5                   10                  15

Gln Ala His His Ser Ser Val Phe Lys Ala Cys Met Lys Gln Lys Lys
                20                  25                  30

Lys Glu Trp Lys Ala Gly Tyr
        35

<210> SEQ ID NO 4

<400> SEQUENCE: 4

000

<210> SEQ ID NO 5
<211> LENGTH: 35
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(27)
```

```
<220> FEATURE:
<221> NAME/KEY: MOD_RES
<222> LOCATION: (35)..(35)
<223> OTHER INFORMATION: C-terminal amidation

<400> SEQUENCE: 5

Cys Asp Ala Thr Cys Gln Tyr Arg Lys Gly Leu Val Ala Cys Ala Arg
1               5                   10                  15

Gln Ala Tyr His Ser Ser Val Phe Lys Ala Cys Met Lys Gln Lys Lys
            20                  25                  30

Lys Glu Trp
        35

<210> SEQ ID NO 6
<211> LENGTH: 38
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(27)
<220> FEATURE:
<221> NAME/KEY: MOD_RES
<222> LOCATION: (28)..(28)
<223> OTHER INFORMATION: Xaa = selenomethionine amino acid
<220> FEATURE:
<221> NAME/KEY: MOD_RES
<222> LOCATION: (38)..(38)
<223> OTHER INFORMATION: C-terminal amidation

<400> SEQUENCE: 6

Cys Asp Ala Thr Cys Gln Phe Arg Lys Ala Ile Asp Asp Cys Ala Arg
1               5                   10                  15

Gln Ala Tyr His Ser Ser Val Phe Lys Ala Cys Xaa Lys Gln Lys Lys
            20                  25                  30

Lys Glu Trp Lys Ala Gly
        35

<210> SEQ ID NO 7
<211> LENGTH: 43
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(31)
<220> FEATURE:
<221> NAME/KEY: MOD_RES
<222> LOCATION: (32)..(32)
<223> OTHER INFORMATION: Xaa = selenomethionine amino acid

<400> SEQUENCE: 7

Cys Asp Ala Thr Cys Gln Phe Arg Lys Ala Ile Asp Asp Cys Ala Arg
1               5                   10                  15

Gln Ala His His Ser Asn Val Pro Gly Ser Val Phe Lys Ala Cys Xaa
            20                  25                  30

Lys Gln Lys Lys Lys Glu Trp Lys Ala Gly His
        35                  40
```

-continued

<210> SEQ ID NO 8
<211> LENGTH: 43
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(31)

<400> SEQUENCE: 8

Cys Asp Ala Thr Cys Gln Phe Arg Lys Ala Ile Asp Asp Cys Ala Arg
1               5                   10                  15

Gln Ala His His Ala Asn Val Pro Gly Ser Val Phe Lys Ala Cys Met
            20                  25                  30

Lys Gln Lys Lys Lys Glu Trp Lys Ala Gly His
        35                  40

<210> SEQ ID NO 9
<211> LENGTH: 43
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(31)

<400> SEQUENCE: 9

Cys Asp Ala Thr Cys Gln Phe Arg Lys Ala Ile Asp Asp Cys Ala Arg
1               5                   10                  15

Gln Ala His His Ser Asn Val Pro Gly Ser Val Phe Lys Ala Cys Ile
            20                  25                  30

Lys Gln Lys Lys Lys Glu Trp Lys Ala Gly His
        35                  40

<210> SEQ ID NO 10
<211> LENGTH: 43
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(31)

<400> SEQUENCE: 10

Cys Asp Ala Thr Cys Gln Phe Arg Lys Ala Ile Asp Asp Cys Ala Arg
1               5                   10                  15

Gln Ala His His Ser Asn Val Pro Gly Ser Val Phe Lys Ala Cys Met
            20                  25                  30

Lys Gln Lys Lys Lys Glu Tyr Lys Ala Gly His
        35                  40

<210> SEQ ID NO 11
<211> LENGTH: 43
<212> TYPE: PRT
<213> ORGANISM: Artificial Sequence

```
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(31)

<400> SEQUENCE: 11

Cys Glu Ala Thr Cys Gln Phe Arg Lys Ala Ile Asp Asp Cys Ala Arg
1               5                   10                  15

Gln Ala His His Ser Asn Val Pro Gly Ser Val Phe Lys Ala Cys Met
            20                  25                  30

Lys Gln Lys Lys Lys Glu Trp Lys Ala Gly His
        35                  40

<210> SEQ ID NO 12
<211> LENGTH: 42
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(31)
<220> FEATURE:
<221> NAME/KEY: MOD_RES
<222> LOCATION: (42)..(42)
<223> OTHER INFORMATION: C-terminal amidation

<400> SEQUENCE: 12

Cys Asp Ala Thr Cys Gln Phe Arg Lys Ala Ile Asp Glu Cys Ala Lys
1               5                   10                  15

Gln Ala His His Ser Asn Val Pro Gly Ser Val Phe Lys Ala Cys Met
            20                  25                  30

Lys Gln Lys Lys Lys Glu Phe Lys Ala Gly
        35                  40

<210> SEQ ID NO 13
<211> LENGTH: 42
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(31)
<220> FEATURE:
<221> NAME/KEY: MOD_RES
<222> LOCATION: (42)..(42)
<223> OTHER INFORMATION: C-terminal amidation

<400> SEQUENCE: 13

Cys Asp Ala Thr Cys Gln Phe Arg Lys Ala Ile Asp Asp Cys Ala Lys
1               5                   10                  15

Gln Ala His His Ala Asn Val Pro Gly Ser Val Phe Lys Ala Cys Met
            20                  25                  30

Lys Gln Lys Lys Lys Glu Phe Lys Ala Gly
        35                  40
```

<210> SEQ ID NO 14
<211> LENGTH: 42
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(31)
<220> FEATURE:
<221> NAME/KEY: MOD_RES
<222> LOCATION: (42)..(42)
<223> OTHER INFORMATION: C-terminal amidation

<400> SEQUENCE: 14

Cys Asp Ala Thr Cys Gln Phe Arg Lys Ala Ile Asp Asp Cys Ala Lys
1               5                   10                  15

Gln Ala His His Ser Asn Val Pro Gly Ser Val Phe Lys Ala Cys Ile
            20                  25                  30

Lys Gln Lys Lys Lys Glu Phe Lys Ala Gly
        35                  40

<210> SEQ ID NO 15
<211> LENGTH: 40
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (2)..(6)
<220> FEATURE:
<221> NAME/KEY: DISULFID
<222> LOCATION: (15)..(28)

<400> SEQUENCE: 15

Gly Cys Asp Ala Thr Cys Gln Phe Arg Lys Ala Ile Asp Asp Cys Val
1               5                   10                  15

Arg Gln Ala His His Ser Ser Val Phe Lys Ala Cys Met Lys Gln Lys
            20                  25                  30

Lys Lys Glu Trp Lys Ala Gly His
        35                  40

<210> SEQ ID NO 16
<211> LENGTH: 38
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(27)
<220> FEATURE:
<221> NAME/KEY: MOD_RES
<222> LOCATION: (38)..(38)
<223> OTHER INFORMATION: C-terminal amidation

<400> SEQUENCE: 16

Cys Asp Ala Thr Cys Gln Phe Arg Lys Ala Ile Asp Asp Cys Asp Arg
1               5                   10                  15

Gln Ala His His Ser Ser Val Phe Lys Ala Cys Met Lys Gln Lys Lys
            20                  25                  30

```
Lys Glu Trp Lys Ala Gly
        35

<210> SEQ ID NO 17
<211> LENGTH: 42
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(31)
<220> FEATURE:
<221> NAME/KEY: MOD_RES
<222> LOCATION: (42)..(42)
<223> OTHER INFORMATION: C-terminal amidation

<400> SEQUENCE: 17

Cys Asp Ala Thr Cys Gln Phe Arg Lys Ala Ile Asp Asp Cys Ala Arg
1               5                   10                  15

Gln Ala His His Ser Asn Val Pro Gly Ser Val Phe Lys Ala Cys Met
            20                  25                  30

Lys Gln Lys Lys Lys Glu Phe Lys Ala Gly
        35                  40

<210> SEQ ID NO 18
<211> LENGTH: 42
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(31)
<220> FEATURE:
<221> NAME/KEY: MOD_RES
<222> LOCATION: (42)..(42)
<223> OTHER INFORMATION: C-terminal amidation

<400> SEQUENCE: 18

Cys Asp Ala Thr Cys Gln Phe Arg Lys Ala Ile Asp Asp Cys Ala Lys
1               5                   10                  15

Gln Ala His His Ser Asn Val Pro Gly Ser Val Phe Lys Leu Cys Met
            20                  25                  30

Lys Gln Lys Lys Lys Glu Phe Lys Ala Gly
        35                  40

<210> SEQ ID NO 19
<211> LENGTH: 39
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(27)

<400> SEQUENCE: 19

Cys Asp Ala Thr Cys Gln Phe Arg Lys Ala Ile Asp Asp Cys Val Lys
1               5                   10                  15
```

```
Gln Ala His His Ser Ser Val Phe Lys Ala Cys Met Lys Gln Lys Lys
            20                  25                  30

Lys Glu Phe Lys Ala Gly His
        35

<210> SEQ ID NO 20
<211> LENGTH: 37
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(26)
<220> FEATURE:
<221> NAME/KEY: MOD_RES
<222> LOCATION: (37)..(37)
<223> OTHER INFORMATION: C-terminal amidation

<400> SEQUENCE: 20

Cys Asp Ala Thr Cys Gln Phe Arg Lys Ala Ile Asp Asp Cys Ala Arg
1               5                   10                  15

Gln Ala Tyr His Ser Ser Phe Lys Ala Cys Met Lys Gln Lys Lys Lys
            20                  25                  30

Glu Trp Lys Ala Gly
        35

<210> SEQ ID NO 21
<211> LENGTH: 38
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(27)
<220> FEATURE:
<221> NAME/KEY: MOD_RES
<222> LOCATION: (21)..(21)
<223> OTHER INFORMATION: C-terminal amidation

<400> SEQUENCE: 21

Cys Asp Ala Thr Cys Gln Phe Arg Lys Ala Ile Asp Asp Cys Asp Arg
1               5                   10                  15

Gln Ala Tyr His Ser Ser Val Phe Lys Ala Cys Met Lys Gln Lys Lys
            20                  25                  30

Lys Glu Trp Lys Ala Gly
        35

<210> SEQ ID NO 22
<211> LENGTH: 43
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(31)
```

-continued

```
<400> SEQUENCE: 22

Cys Asp Ala Thr Cys Gln Phe Arg Lys Ala Ile Asp Asp Cys Ala Arg
1               5                   10                  15

Gln Ala His His Ser Gln Val Pro Gly Ser Val Phe Lys Ala Cys Met
            20                  25                  30

Lys Gln Lys Lys Lys Glu Trp Lys Ala Gly His
        35                  40

<210> SEQ ID NO 23
<211> LENGTH: 43
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(31)

<400> SEQUENCE: 23

Cys Asp Ala Thr Cys Gln Phe Arg Lys Ala Ile Asp Asp Cys Ala Arg
1               5                   10                  15

Gln Ala His His Ser Asn Val Pro Gly Ser Val Phe Lys Leu Cys Met
            20                  25                  30

Lys Gln Lys Lys Lys Glu Trp Lys Ala Gly His
        35                  40

<210> SEQ ID NO 24
<211> LENGTH: 43
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(31)

<400> SEQUENCE: 24

Cys Asp Ala Thr Cys Gln Phe Arg Lys Ala Ile Asp Asp Cys Ala Arg
1               5                   10                  15

Gln Ala His His Ser Asn Val Pro Gly Ser Val Phe Lys Ser Cys Met
            20                  25                  30

Lys Gln Lys Lys Lys Glu Trp Lys Ala Gly His
        35                  40

<210> SEQ ID NO 25
<211> LENGTH: 43
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(31)

<400> SEQUENCE: 25

Cys Asp Ala Thr Cys Gln Phe Arg Lys Ala Ile Asp Glu Cys Ala Arg
1               5                   10                  15
```

Gln Ala His His Ser Asn Val Pro Gly Ser Val Phe Lys Ala Cys Met
            20                  25                  30

Lys Gln Lys Lys Lys Glu Trp Lys Ala Gly His
            35                  40

<210> SEQ ID NO 26
<211> LENGTH: 39
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(27)

<400> SEQUENCE: 26

Cys Asp Ala Thr Cys Gln Phe Arg Lys Ala Ile Asp Asp Cys Ala Lys
1               5                   10                  15

Gln Ala His His Ser Ser Val Phe Lys Ala Cys Met Lys Gln Lys Lys
            20                  25                  30

Lys Glu Trp Lys Ala Gly His
            35

<210> SEQ ID NO 27
<211> LENGTH: 39
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(27)

<400> SEQUENCE: 27

Cys Asp Ala Thr Cys Gln Phe Arg Lys Ala Ile Asp Asp Cys Ala Arg
1               5                   10                  15

Gln Ala Tyr His Ser Ser Val Phe Lys Ala Cys Met Lys Gln Lys Lys
            20                  25                  30

Lys Glu Trp Lys Ala Gly His
            35

<210> SEQ ID NO 28
<211> LENGTH: 39
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(27)

<400> SEQUENCE: 28

Cys Asp Ala Thr Cys Gln Phe Arg Lys Ala Ile Asp Asp Cys Ala Arg
1               5                   10                  15

Gln Ala His His Ser Ser Val Phe Lys Ala Cys Met Lys Gln Lys Lys
            20                  25                  30

Lys Glu Trp Lys Ala Gly His
        35

<210> SEQ ID NO 29
<211> LENGTH: 39
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(27)

<400> SEQUENCE: 29

Cys Asp Ala Thr Cys Gln Phe Arg Lys Ala Ile Asp Asp Cys Ala Lys
1               5                   10                  15

Gln Ala His His Ser Ser Val Phe Lys Ala Cys Met Lys Gln Lys Lys
            20                  25                  30

Lys Glu Phe Lys Ala Gly Tyr
        35

<210> SEQ ID NO 30
<211> LENGTH: 39
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(27)

<400> SEQUENCE: 30

Cys Asp Ala Thr Cys Gln Phe Arg Lys Ala Ile Asp Asp Cys Ala Lys
1               5                   10                  15

Gln Ala Tyr His Ser Ser Val Phe Lys Ala Cys Met Lys Gln Lys Lys
            20                  25                  30

Lys Glu Phe Lys Ala Gly Tyr
        35

<210> SEQ ID NO 31
<211> LENGTH: 42
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(31)
<220> FEATURE:
<221> NAME/KEY: MOD_RES
<222> LOCATION: (42)..(42)
<223> OTHER INFORMATION: C-terminal amidation

<400> SEQUENCE: 31

Cys Asp Ala Thr Cys Gln Phe Arg Lys Ala Ile Asp Asp Cys Ala Lys
1               5                   10                  15

Gln Ala His His Ser Asn Val Pro Gly Ser Val Phe Lys Ser Cys Met
            20                  25                  30

Lys Gln Lys Lys Lys Glu Phe Lys Ala Gly
        35                  40

<210> SEQ ID NO 32
<211> LENGTH: 42
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(31)
<220> FEATURE:
<221> NAME/KEY: MOD_RES
<222> LOCATION: (18)..(18)
<223> OTHER INFORMATION: Xaa = propargylglycine
<220> FEATURE:
<221> NAME/KEY: MOD_RES
<222> LOCATION: (42)..(42)
<223> OTHER INFORMATION: C-terminal amidation

<400> SEQUENCE: 32

Cys Asp Ala Thr Cys Gln Phe Arg Lys Ala Ile Asp Asp Cys Gln Lys
1               5                   10                  15

Gln Xaa His His Ser Asn Val Pro Gly Ser Val Phe Lys Ala Cys Met
                20                  25                  30

Lys Gln Lys Lys Lys Glu Phe Lys Ala Gly
        35                  40

<210> SEQ ID NO 33
<211> LENGTH: 42
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(31)
<220> FEATURE:
<221> NAME/KEY: MOD_RES
<222> LOCATION: (16)..(16)
<223> OTHER INFORMATION: Xaa = propargylglycine
<220> FEATURE:
<221> NAME/KEY: MOD_RES
<222> LOCATION: (42)..(42)
<223> OTHER INFORMATION: C-terminal amidation

<400> SEQUENCE: 33

Cys Asp Ala Thr Cys Gln Phe Arg Lys Ala Ile Asp Asp Cys Gln Xaa
1               5                   10                  15

Gln Ala His His Ser Asn Val Pro Gly Ser Val Phe Lys Ala Cys Met
                20                  25                  30

Lys Gln Lys Lys Lys Glu Phe Lys Ala Gly
        35                  40

<210> SEQ ID NO 34
<211> LENGTH: 42
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)

```
<220> FEATURE:
<221> NAME/KEY: DISULFID
<222> LOCATION: (14)..(31)
<220> FEATURE:
<221> NAME/KEY: MOD_RES
<222> LOCATION: (26)..(26)
<223> OTHER INFORMATION: Xaa = propargylglycine
<220> FEATURE:
<221> NAME/KEY: MOD_RES
<222> LOCATION: (42)..(42)
<223> OTHER INFORMATION: C-terminal amidation

<400> SEQUENCE: 34

Cys Asp Ala Thr Cys Gln Phe Arg Lys Ala Ile Asp Asp Cys Gln Lys
1               5                   10                  15

Gln Ala His His Ser Asn Val Pro Xaa Ser Val Phe Lys Ala Cys Met
            20                  25                  30

Lys Gln Lys Lys Lys Glu Phe Lys Ala Gly
        35                  40

<210> SEQ ID NO 35
<211> LENGTH: 39
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(27)

<400> SEQUENCE: 35

Cys Asp Ala Thr Cys Gln Phe Arg Lys Ala Ile Asp Asp Cys Ala Arg
1               5                   10                  15

Gln Ala Tyr His Ser Ser Val Phe Lys Ala Cys Met Lys Gln Lys Lys
            20                  25                  30

Lys Glu Phe Lys Ala Gly His
        35

<210> SEQ ID NO 36
<211> LENGTH: 39
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(27)

<400> SEQUENCE: 36

Cys Asp Ala Thr Cys Gln Phe Arg Lys Ala Ile Asp Asp Cys Ala Arg
1               5                   10                  15

Gln Ala His His Ser Ser Val Phe Lys Ala Cys Met Lys Gln Lys Lys
            20                  25                  30

Lys Glu Phe Lys Ala Gly His
        35

<210> SEQ ID NO 37
<211> LENGTH: 38
<212> TYPE: PRT
<213> ORGANISM: Artificial Sequence
<220> FEATURE:
```

```
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(26)

<400> SEQUENCE: 37

Cys Asp Ala Thr Cys Gln Phe Arg Lys Ala Ile Asp Asp Cys Ala Lys
1               5                   10                  15

Gln Ala His Ser Ser Val Phe Lys Ala Cys Met Lys Gln Lys Lys
            20                  25                  30

Glu Phe Lys Ala Gly Tyr
        35

<210> SEQ ID NO 38

<400> SEQUENCE: 38

000

<210> SEQ ID NO 39
<211> LENGTH: 43
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(31)

<400> SEQUENCE: 39

Cys Asp Ala Thr Cys Gln Phe Arg Lys Ala Ile Asp Asp Cys Ala Arg
1               5                   10                  15

Gln Ala His His Ser Asn Val Pro Gly Ser Val Phe Lys Ala Cys Phe
            20                  25                  30

Lys Gln Lys Lys Lys Glu Trp Lys Ala Gly His
        35                  40

<210> SEQ ID NO 40
<211> LENGTH: 43
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(31)

<400> SEQUENCE: 40

Cys Asp Ala Thr Cys Gln Phe Arg Lys Ala Ile Asp Asp Cys Ala Arg
1               5                   10                  15

Gln Ala His His Ser Asn Val Pro Gly Ser Val Phe Lys Ala Cys Ser
            20                  25                  30

Lys Gln Lys Lys Lys Glu Trp Lys Ala Gly His
        35                  40

<210> SEQ ID NO 41
<211> LENGTH: 43
```

```
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(31)

<400> SEQUENCE: 41

Cys Asp Ala Thr Cys Gln Phe Arg Lys Ala Ile Asp Asp Cys Ala Arg
1               5                   10                  15

Gln Ala His His Ser Asn Val Pro Gly Ser Val Phe Lys Ala Cys Leu
            20                  25                  30

Lys Gln Lys Lys Lys Glu Trp Lys Ala Gly His
        35                  40

<210> SEQ ID NO 42
<211> LENGTH: 41
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(30)
<220> FEATURE:
<221> NAME/KEY: MOD_RES
<222> LOCATION: (41)..(41)
<223> OTHER INFORMATION: C-terminal amidation

<400> SEQUENCE: 42

Cys Asp Ala Thr Cys Gln Phe Arg Lys Ala Ile Asp Asp Cys Tyr Tyr
1               5                   10                  15

Arg Ser His Ser Asn Val Pro Gly Ser Val Phe Lys Ala Cys Met Lys
            20                  25                  30

Gln Lys Lys Lys Glu Phe Lys Ala Gly
        35                  40

<210> SEQ ID NO 43
<211> LENGTH: 42
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(31)
<220> FEATURE:
<221> NAME/KEY: MOD_RES
<222> LOCATION: (42)..(42)
<223> OTHER INFORMATION: C-terminal amidation

<400> SEQUENCE: 43

Cys Asp Ala Thr Cys Gln Phe Arg Lys Ala Ile Asp Asp Cys Tyr Tyr
1               5                   10                  15

Arg Ser Lys His Ser Asn Val Pro Gly Ser Val Phe Lys Ala Cys Met
            20                  25                  30

Lys Gln Lys Lys Lys Glu Phe Lys Ala Gly
        35                  40
```

<210> SEQ ID NO 44
<211> LENGTH: 42
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(31)
<220> FEATURE:
<221> NAME/KEY: MOD_RES
<222> LOCATION: (42)..(42)
<223> OTHER INFORMATION: C-terminal amidation

<400> SEQUENCE: 44

Cys Asp Ala Thr Cys Gln Phe Arg Lys Ala Ile Asp Cys Tyr Tyr
1               5                   10                  15

Arg Ser Arg His Ser Asn Val Pro Gly Ser Val Phe Lys Ala Cys Met
            20                  25                  30

Lys Gln Lys Lys Lys Glu Phe Lys Ala Gly
        35                  40

<210> SEQ ID NO 45
<211> LENGTH: 42
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(31)
<220> FEATURE:
<221> NAME/KEY: MOD_RES
<222> LOCATION: (42)..(42)
<223> OTHER INFORMATION: C-terminal amidation

<400> SEQUENCE: 45

Cys Asp Ala Thr Cys Gln Phe Arg Lys Ala Ile Asp Cys Tyr Tyr
1               5                   10                  15

Arg Ser His His Ser Asn Val Pro Gly Ser Val Phe Lys Ala Cys Met
            20                  25                  30

Lys Gln Lys Lys Lys Glu Phe Lys Ala Gly
        35                  40

<210> SEQ ID NO 46
<211> LENGTH: 42
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(31)
<220> FEATURE:
<221> NAME/KEY: MOD_RES
<222> LOCATION: (42)..(42)
<223> OTHER INFORMATION: C-terminal amidation

<400> SEQUENCE: 46

Cys Asp Ala Thr Cys Gln Tyr Arg Lys Gly Leu Val Ala Cys Leu Tyr
1               5                   10                  15

Lys Lys Val Ala Met Gln Lys Arg Tyr Ser Val Phe Lys Ala Cys Met
            20                  25                  30

Lys Gln Lys Lys Lys Glu Phe Lys Ala Gly
        35                  40

<210> SEQ ID NO 47
<211> LENGTH: 43
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(31)

<400> SEQUENCE: 47

Cys Asp Ala Thr Cys Gln Phe Arg Lys Ala Ile Asp Cys Tyr Lys
1               5                   10                  15

Gln Ala His His Ser Asn Val Pro Gly Ser Val Phe Lys Ala Cys Met
            20                  25                  30

Lys Gln Lys Lys Lys Glu Phe Lys Ala Gly His
        35                  40

<210> SEQ ID NO 48
<211> LENGTH: 43
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(31)

<400> SEQUENCE: 48

Cys Asp Ala Thr Cys Gln Phe Arg Lys Ala Ile Asp Cys Val Lys
1               5                   10                  15

Gln Ala His His Ser Asn Val Pro Gly Ser Val Phe Lys Ala Cys Met
            20                  25                  30

Lys Gln Lys Lys Lys Glu Phe Lys Ala Gly Tyr
        35                  40

<210> SEQ ID NO 49

<400> SEQUENCE: 49

000

<210> SEQ ID NO 50

<400> SEQUENCE: 50

000

<210> SEQ ID NO 51
<211> LENGTH: 45
<212> TYPE: PRT
<213> ORGANISM: Artificial Sequence
<220> FEATURE:

<223> OTHER INFORMATION: Synthetic Polypeptide
<220> FEATURE:
<221> NAME/KEY: MOD_RES
<222> LOCATION: (1)..(1)
<223> OTHER INFORMATION: Xaa = propargylglycine
<220> FEATURE:
<221> NAME/KEY: DISULFID
<222> LOCATION: (2)..(6)
<220> FEATURE:
<221> NAME/KEY: DISULFID
<222> LOCATION: (15)..(33)
<220> FEATURE:
<221> NAME/KEY: MOD_RES
<222> LOCATION: (26)..(26)
<223> OTHER INFORMATION: Xaa = propargylglycine

<400> SEQUENCE: 51

Xaa Cys Asp Ala Thr Cys Gln Phe Arg Lys Ala Ile Asp Asp Cys Gln
1               5                   10                  15

Lys Gln Ala His His Ser Asn Val Pro Xaa Asn Ser Val Phe Lys Glu
            20                  25                  30

Cys Met Lys Gln Lys Lys Lys Glu Phe Lys Ala Gly Lys
        35                  40                  45

<210> SEQ ID NO 52
<211> LENGTH: 45
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MOD_RES
<222> LOCATION: (1)..(1)
<223> OTHER INFORMATION: Xaa = propargylglycine
<220> FEATURE:
<221> NAME/KEY: DISULFID
<222> LOCATION: (2)..(6)
<220> FEATURE:
<221> NAME/KEY: DISULFID
<222> LOCATION: (15)..(33)

<400> SEQUENCE: 52

Xaa Cys Asp Ala Thr Cys Gln Phe Arg Lys Ala Ile Asp Asp Cys Gln
1               5                   10                  15

Lys Gln Ala His His Ser Asn Val Pro Gly Asn Ser Val Phe Lys Glu
            20                  25                  30

Cys Met Lys Gln Lys Lys Lys Glu Phe Lys Ala Gly Lys
        35                  40                  45

<210> SEQ ID NO 53
<211> LENGTH: 44
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(32)
<220> FEATURE:
<221> NAME/KEY: MOD_RES
<222> LOCATION: (25)..(25)
<223> OTHER INFORMATION: Xaa = propargylglycine

<400> SEQUENCE: 53

Cys Asp Ala Thr Cys Gln Phe Arg Lys Ala Ile Asp Asp Cys Gln Lys
1               5                   10                  15

```
Gln Ala His His Ser Asn Val Pro Xaa Asn Ser Val Phe Lys Glu Cys
            20                  25                  30

Met Lys Gln Lys Lys Glu Phe Lys Ala Gly Lys
            35                  40
```

<210> SEQ ID NO 54
<211> LENGTH: 42
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(31)
<220> FEATURE:
<221> NAME/KEY: MOD_RES
<222> LOCATION: (42)..(42)
<223> OTHER INFORMATION: C-terminal amidation

<400> SEQUENCE: 54

```
Cys Asp Ala Thr Cys Gln Phe Arg Lys Ala Ile Asp Asp Cys Tyr Trp
1               5                   10                  15

Gln Ala Ile His Ala Asn Val Pro Gly Ser Val Trp Lys Ala Cys Met
            20                  25                  30

Lys Phe Arg Phe Asn Val Trp Lys Ala Gly
            35                  40
```

<210> SEQ ID NO 55
<211> LENGTH: 42
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(31)
<220> FEATURE:
<221> NAME/KEY: MOD_RES
<222> LOCATION: (42)..(42)
<223> OTHER INFORMATION: C-terminal amidation

<400> SEQUENCE: 55

```
Cys Asp Ala Thr Cys Gln Phe Arg Lys Ala Ile Asp Asp Cys Phe Tyr
1               5                   10                  15

Gln Ala Trp His Ser Asn Val Pro Gly Ser Val Trp Lys Ala Cys Met
            20                  25                  30

Lys Phe Arg Phe Asn Val Trp Lys Ala Gly
            35                  40
```

<210> SEQ ID NO 56
<211> LENGTH: 43
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(31)

<400> SEQUENCE: 56

```
Cys Asp Ala Thr Cys Gln Phe Arg Lys Ala Ile Asp Asp Cys Ala Lys
1               5                   10                  15

Gln Ala His His Ser Asn Val Pro Gly Ser Val Phe Lys Ala Cys Met
            20                  25                  30

Lys Gln Lys Lys Lys Glu Phe Lys Ala Gly Tyr
        35                  40
```

<210> SEQ ID NO 57
<211> LENGTH: 43
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(31)

<400> SEQUENCE: 57

```
Cys Asp Ala Thr Cys Gln Phe Arg Lys Ala Ile Asp Asp Cys Ala Lys
1               5                   10                  15

Gln Ala His His Ser Asn Val Pro Gly Ser Val Phe Lys Ala Cys Met
            20                  25                  30

Lys Gln Lys Lys Lys Glu Phe Lys Ala Gly His
        35                  40
```

<210> SEQ ID NO 58
<211> LENGTH: 44
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (2)..(6)
<220> FEATURE:
<221> NAME/KEY: DISULFID
<222> LOCATION: (15)..(32)

<400> SEQUENCE: 58

```
Gly Cys Asp Ala Thr Cys Gln Phe Arg Lys Ala Ile Asp Asp Cys Ala
1               5                   10                  15

Lys Gln Ala His His Ser Asn Val Pro Gly Ser Val Phe Lys Ala Cys
            20                  25                  30

Met Lys Gln Lys Lys Lys Glu Phe Lys Ala Gly Tyr
        35                  40
```

<210> SEQ ID NO 59
<211> LENGTH: 44
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (2)..(6)
<220> FEATURE:
<221> NAME/KEY: DISULFID
<222> LOCATION: (15)..(32)

<400> SEQUENCE: 59

```
Gly Cys Asp Ala Thr Cys Gln Phe Arg Lys Ala Ile Asp Asp Cys Ala
1               5                   10                  15
```

Lys Gln Ala His His Ser Asn Val Pro Gly Ser Val Phe Lys Ala Cys
            20                  25                  30

Met Lys Gln Lys Lys Lys Glu Phe Lys Ala Gly His
            35                  40

<210> SEQ ID NO 60
<211> LENGTH: 42
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(31)
<220> FEATURE:
<221> NAME/KEY: MOD_RES
<222> LOCATION: (42)..(42)
<223> OTHER INFORMATION: C-terminal amidation

<400> SEQUENCE: 60

Cys Asp Ala Thr Cys Gln Phe Arg Lys Ala Ile Asp Asp Cys Tyr Tyr
1               5                   10                  15

Arg Ser Trp His Ala Asn Val Pro Gly Ser Val Phe Lys Ala Cys Met
            20                  25                  30

Lys Gln Lys Lys Lys Glu Trp Lys Ala Gly
            35                  40

<210> SEQ ID NO 61
<211> LENGTH: 38
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(27)
<220> FEATURE:
<221> NAME/KEY: MOD_RES
<222> LOCATION: (38)..(38)
<223> OTHER INFORMATION: C-terminal amidation

<400> SEQUENCE: 61

Cys Asp Ala Thr Cys Gln Phe Arg Lys Ala Ile Asp Asp Cys Tyr Tyr
1               5                   10                  15

Arg Ser Trp His Ser Ser Val Phe Lys Ala Cys Met Lys Gln Lys Lys
            20                  25                  30

Lys Glu Trp Lys Ala Gly
            35

<210> SEQ ID NO 62
<211> LENGTH: 43
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(31)

<400> SEQUENCE: 62

Cys Asp Ala Thr Cys Gln Phe Arg Lys Ala Ile Asp Asp Cys Tyr Tyr
1               5                   10                  15

Arg Ser Trp His Ala Asn Val Pro Gly Ser Val Phe Lys Ala Cys Met
                20                  25                  30

Lys Gln Lys Lys Lys Glu Trp Lys Ala Gly Asn
            35                  40

<210> SEQ ID NO 63
<211> LENGTH: 37
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(26)
<220> FEATURE:
<221> NAME/KEY: MOD_RES
<222> LOCATION: (37)..(37)
<223> OTHER INFORMATION: C-terminal amidation

<400> SEQUENCE: 63

Cys Asp Ala Thr Cys Gln Phe Arg Lys Ala Ile Asp Asp Cys Tyr Tyr
1               5                   10                  15

Arg Ser Trp His Ser Ser Phe Lys Ala Cys Met Lys Gln Lys Lys Lys
                20                  25                  30

Glu Phe Lys Ala Gly
            35

<210> SEQ ID NO 64
<211> LENGTH: 42
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(31)

<400> SEQUENCE: 64

Cys Asp Ala Thr Cys Gln Phe Arg Lys Ala Ile Asp Asp Cys Tyr Tyr
1               5                   10                  15

Arg Ser Trp His Ser Asn Val Pro Gly Ser Val Phe Lys Ala Cys Met
                20                  25                  30

Lys Gln Lys Lys Lys Glu Phe Lys Ala Gly
            35                  40

<210> SEQ ID NO 65
<211> LENGTH: 38
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(27)
<220> FEATURE:
<221> NAME/KEY: MOD_RES

```
<222> LOCATION: (38)..(38)
<223> OTHER INFORMATION: C-terminal amidation

<400> SEQUENCE: 65

Cys Asp Ala Thr Cys Gln Phe Arg Lys Ala Ile Asp Asp Cys Ala Arg
1               5                   10                  15

Gln Ala Tyr His Ser Ser Val Phe Lys Ala Cys Met Lys Gln Lys Lys
            20                  25                  30

Lys Glu Trp Lys Ala Gly
        35

<210> SEQ ID NO 66
<211> LENGTH: 43
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(31)

<400> SEQUENCE: 66

Cys Asp Ala Thr Cys Gln Phe Arg Lys Ala Ile Asp Asp Cys Tyr Tyr
1               5                   10                  15

Arg Ser Trp His Ala Asn Val Pro Gly Ser Val Phe Lys Ala Cys Met
            20                  25                  30

Lys Gln Lys Lys Lys Glu Trp Lys Ala Gly Tyr
        35                  40

<210> SEQ ID NO 67
<211> LENGTH: 42
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(31)
<220> FEATURE:
<221> NAME/KEY: MOD_RES
<222> LOCATION: (42)..(42)
<223> OTHER INFORMATION: C-terminal amidation

<400> SEQUENCE: 67

Cys Asp Ala Thr Cys Gln Phe Arg Lys Ala Ile Asp Asp Cys Tyr Tyr
1               5                   10                  15

Arg Ser Trp His Ser Asn Val Pro Gly Ser Val Phe Lys Ala Cys Met
            20                  25                  30

Lys Phe Arg Phe Asn Val Trp Lys Ala Gly
        35                  40

<210> SEQ ID NO 68
<211> LENGTH: 42
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
```

<221> NAME/KEY: DISULFID
<222> LOCATION: (14)..(31)

<400> SEQUENCE: 68

Cys Asp Ala Thr Cys Gln Phe Arg Lys Ala Ile Asp Asp Cys Gln Lys
1               5                   10                  15

Gln Ala His His Ser Asn Val Pro Gly Ser Val Phe Lys Ala Cys Met
            20                  25                  30

Lys Gln Lys Lys Lys Glu Phe Lys Ala Arg
        35                  40

<210> SEQ ID NO 69
<211> LENGTH: 42
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(31)
<220> FEATURE:
<221> NAME/KEY: MOD_RES
<222> LOCATION: (42)..(42)
<223> OTHER INFORMATION: C-terminal amidation

<400> SEQUENCE: 69

Cys Asp Ala Thr Cys Gln Phe Arg Lys Ala Ile Asp Asp Cys Tyr Tyr
1               5                   10                  15

Arg Ser Trp His Ser Asn Val Pro Gly Ser Val Phe Lys Ala Cys Met
            20                  25                  30

Lys Gln Arg Lys Lys Arg Trp Leu Ala Gly
        35                  40

<210> SEQ ID NO 70
<211> LENGTH: 42
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(31)
<220> FEATURE:
<221> NAME/KEY: MOD_RES
<222> LOCATION: (42)..(42)
<223> OTHER INFORMATION: C-terminal amidation

<400> SEQUENCE: 70

Cys Asp Ala Thr Cys Phe Phe Arg Lys Val Ile Asp Asp Cys Tyr Tyr
1               5                   10                  15

Arg Ser Trp His Ser Asn Val Pro Gly Ser Val Phe Lys Ala Cys Met
            20                  25                  30

Lys Gln Leu Lys Lys Arg Trp Gln Ala Gly
        35                  40

<210> SEQ ID NO 71
<211> LENGTH: 42
<212> TYPE: PRT
<213> ORGANISM: Artificial Sequence
<220> FEATURE:
<223> OTHER INFORMATION: Synthetic Polypeptide

```
<220> FEATURE:
<221> NAME/KEY: DISULFID
<222> LOCATION: (1)..(5)
<220> FEATURE:
<221> NAME/KEY: DISULFID
<222> LOCATION: (14)..(31)
<220> FEATURE:
<221> NAME/KEY: MOD_RES
<222> LOCATION: (42)..(42)
<223> OTHER INFORMATION: C-terminal amidation

<400> SEQUENCE: 71

Cys Asp Ala Thr Cys His Phe Arg Lys Ala Ile Asp Asp Cys Tyr Tyr
1               5                   10                  15

Arg Ser Trp His Ser Asn Val Pro Gly Ser Val Phe Lys Ala Cys Met
            20                  25                  30

Lys Gln His Lys Lys Arg Trp Arg Ala Gly
        35                  40

<210> SEQ ID NO 72
<211> LENGTH: 39
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(27)

<400> SEQUENCE: 72

Cys Asp Ala Thr Cys Gln Phe Arg Lys Ala Ile Asp Asp Cys Tyr Tyr
1               5                   10                  15

Arg Ser Trp His Ser Ser Val Phe Lys Ala Cys Met Lys Gln Lys Lys
            20                  25                  30

Lys Glu Trp Lys Ala Gly His
        35

<210> SEQ ID NO 73
<211> LENGTH: 42
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(31)
<220> FEATURE:
<221> NAME/KEY: MOD_RES
<222> LOCATION: (42)..(42)
<223> OTHER INFORMATION: C-terminal amidation

<400> SEQUENCE: 73

Cys Asp Ala Thr Cys Gln Phe Arg Lys Ala Ile Asp Asp Cys Trp Ile
1               5                   10                  15

Val Ala Trp His Ser Asn Val Pro Gly Ser Val Phe Lys Ala Cys Met
            20                  25                  30

Lys Gln Lys Lys Lys Glu Phe Lys Ala Gly
        35                  40

<210> SEQ ID NO 74
<211> LENGTH: 42
```

```
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(31)
<220> FEATURE:
<221> NAME/KEY: MOD_RES
<222> LOCATION: (42)..(42)
<223> OTHER INFORMATION: C-terminal amidation

<400> SEQUENCE: 74

Cys Asp Ala Thr Cys Gln Phe Arg Lys Ala Ile Asp Asp Cys Phe Thr
1               5                   10                  15

Trp Ala Trp His Ser Asn Val Pro Gly Ser Val Phe Lys Ala Cys Met
            20                  25                  30

Lys Gln Lys Lys Lys Glu Phe Lys Ala Gly
        35                  40

<210> SEQ ID NO 75
<211> LENGTH: 39
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(27)

<400> SEQUENCE: 75

Cys Asp Ala Thr Cys Gln Phe Arg Lys Ala Ile Asp Asp Cys Val Arg
1               5                   10                  15

Gln Ala His His Ser Ser Val Phe Lys Ala Cys Met Lys Gln Lys Lys
            20                  25                  30

Lys Glu Trp Lys Ala Gly His
        35

<210> SEQ ID NO 76
<211> LENGTH: 42
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(31)
<220> FEATURE:
<221> NAME/KEY: MOD_RES
<222> LOCATION: (42)..(42)
<223> OTHER INFORMATION: C-terminal amidation

<400> SEQUENCE: 76

Cys Asp Ala Thr Cys Gln Phe Arg Lys Ala Ile Asp Asp Cys His Leu
1               5                   10                  15

Leu Ala Trp His Ser Asn Val Pro Gly Ser Val Phe Lys Ala Cys Met
            20                  25                  30

Lys Gln Lys Lys Lys Glu Phe Lys Ala Gly
        35                  40
```

```
<210> SEQ ID NO 77
<211> LENGTH: 42
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(31)
<220> FEATURE:
<221> NAME/KEY: MOD_RES
<222> LOCATION: (42)..(42)
<223> OTHER INFORMATION: C-terminal amidation

<400> SEQUENCE: 77

Cys Asp Ala Thr Cys Gln Phe Arg Lys Ala Ile Asp Cys Tyr Tyr
1               5                   10                  15

Arg Ser Trp His Ser Asn Val Pro Gly Ser Val Phe Lys Ala Cys Met
                20                  25                  30

Lys Gln Lys Lys Lys Glu Trp Lys Ala Gly
        35                  40

<210> SEQ ID NO 78
<211> LENGTH: 42
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(31)
<220> FEATURE:
<221> NAME/KEY: MOD_RES
<222> LOCATION: (42)..(42)
<223> OTHER INFORMATION: C-terminal amidation

<400> SEQUENCE: 78

Cys Asp Ala Thr Cys Gln Phe Arg Lys Ala Ile Asp Cys Tyr Tyr
1               5                   10                  15

Tyr Ala Met His Ser Asn Val Pro Gly Ser Val Trp Lys Ala Cys Leu
                20                  25                  30

Lys Gln Lys Lys Lys Glu Phe Lys Ala Gly
        35                  40

<210> SEQ ID NO 79
<211> LENGTH: 42
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(31)
<220> FEATURE:
<221> NAME/KEY: MOD_RES
<222> LOCATION: (42)..(42)
<223> OTHER INFORMATION: C-terminal amidation

<400> SEQUENCE: 79
```

Cys Asp Ala Thr Cys Gln Phe Arg Lys Ala Ile Asp Asp Cys Val Arg
1               5                   10                  15

Gln Ala His His Ser Asn Val Pro Gly Ser Val Phe Lys Ala Cys Met
            20                  25                  30

Lys Gln Lys Lys Lys Glu Trp Lys Ala Gly
        35                  40

<210> SEQ ID NO 80
<211> LENGTH: 42
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(31)
<220> FEATURE:
<221> NAME/KEY: MOD_RES
<222> LOCATION: (42)..(42)
<223> OTHER INFORMATION: C-terminal amidation

<400> SEQUENCE: 80

Cys Asp Ala Thr Cys Gln Phe Arg Lys Ala Ile Asp Asp Cys Trp Lys
1               5                   10                  15

Gln Ala His His Ser Asn Val Pro Gly Ser Val Phe Lys Ala Cys Met
            20                  25                  30

Lys Gln Lys Lys Lys Glu Phe Lys Ala Gly
        35                  40

<210> SEQ ID NO 81
<211> LENGTH: 42
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(31)

<400> SEQUENCE: 81

Cys Asp Ala Thr Cys Gln Phe Arg Lys Ala Ile Asp Asp Cys Asp Arg
1               5                   10                  15

Gln Ala His His Ser Asn Val Pro Gly Ser Val Phe Lys Ala Cys Met
            20                  25                  30

Lys Gln Lys Lys Lys Glu Trp Lys Ala Gly
        35                  40

<210> SEQ ID NO 82
<211> LENGTH: 42
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(31)

<400> SEQUENCE: 82

Cys Asp Ala Thr Cys Gln Phe Arg Lys Ala Ile Asp Asp Cys Val Arg
1               5                   10                  15

Gln Ala His His Ser Asn Val Pro Gly Ser Val Phe Lys Ala Cys Met
            20                  25                  30

Lys Gln Lys Lys Lys Glu Trp Lys Ala Gly
        35                  40

<210> SEQ ID NO 83
<211> LENGTH: 42
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(31)
<220> FEATURE:
<221> NAME/KEY: MOD_RES
<222> LOCATION: (42)..(42)
<223> OTHER INFORMATION: C-terminal amidation

<400> SEQUENCE: 83

Cys Asp Ala Thr Cys Gln Phe Arg Lys Ala Ile Asp Asp Cys Val Tyr
1               5                   10                  15

Ser Ala Trp His Ser Asn Val Pro Gly Ser Val Phe Lys Ala Cys Met
            20                  25                  30

Lys Gln Lys Lys Lys Glu Phe Lys Ala Gly
        35                  40

<210> SEQ ID NO 84
<211> LENGTH: 43
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(31)

<400> SEQUENCE: 84

Cys Asp Ala Thr Cys Gln Phe Arg Lys Ala Ile Asp Asp Cys Val Arg
1               5                   10                  15

Gln Ala Tyr His Ser Asn Val Pro Gly Ser Val Phe Lys Ala Cys Met
            20                  25                  30

Lys Gln Lys Lys Lys Glu Trp Lys Ala Gly His
        35                  40

<210> SEQ ID NO 85
<211> LENGTH: 42
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(31)
<220> FEATURE:
<221> NAME/KEY: MOD_RES
<222> LOCATION: (42)..(42)

<223> OTHER INFORMATION: C-terminal amidation

<400> SEQUENCE: 85

Cys Asp Ala Thr Cys Gln Phe Arg Lys Ala Ile Asp Cys Leu Leu
1               5                   10                  15
Arg Ala Trp His Ser Asn Val Pro Gly Ser Val Phe Lys Ala Cys Met
            20                  25                  30
Lys Gln Lys Lys Lys Glu Phe Lys Ala Gly
        35                  40

<210> SEQ ID NO 86
<211> LENGTH: 43
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(31)

<400> SEQUENCE: 86

Cys Asp Ala Thr Cys Gln Phe Arg Lys Ala Ile Asp Cys Val Arg
1               5                   10                  15
Gln Ala His His Ser Asn Val Pro Gly Ser Val Phe Lys Ala Cys Met
            20                  25                  30
Lys Gln Lys Lys Lys Glu Trp Lys Ala Gly Tyr
        35                  40

<210> SEQ ID NO 87
<211> LENGTH: 42
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(31)

<400> SEQUENCE: 87

Cys Asp Ala Thr Cys Gln Phe Arg Lys Ala Ile Asp Cys Val Arg
1               5                   10                  15
Gln Ala His His Ser Asn Val Pro Gly Ser Val Phe Lys Ala Cys Met
            20                  25                  30
Lys Gln Lys Lys Lys Glu Trp Lys Ala Asn
        35                  40

<210> SEQ ID NO 88
<211> LENGTH: 44
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (2)..(6)
<220> FEATURE:
<221> NAME/KEY: DISULFID
<222> LOCATION: (15)..(32)

<400> SEQUENCE: 88

Gly Cys Asp Ala Thr Cys Gln Phe Arg Lys Ala Ile Asp Asp Cys Val
1               5                   10                  15

Arg Gln Ala His His Ser Asn Val Pro Gly Ser Val Phe Lys Ala Cys
            20                  25                  30

Met Lys Gln Lys Lys Lys Glu Trp Lys Ala Gly His
            35                  40

<210> SEQ ID NO 89
<211> LENGTH: 42
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(31)
<220> FEATURE:
<221> NAME/KEY: MOD_RES
<222> LOCATION: (42)..(42)
<223> OTHER INFORMATION: C-terminal amidation

<400> SEQUENCE: 89

Cys Asp Ala Thr Cys Gln Phe Arg Lys Ala Ile Asp Asp Cys Gln Lys
1               5                   10                  15

Gln Ala His His Ser Asn Val Pro Gly Ser Val Phe Lys Ala Cys Met
            20                  25                  30

Lys Phe Arg Arg Thr Leu Trp Lys Ala Gly
            35                  40

<210> SEQ ID NO 90
<211> LENGTH: 42
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(31)
<220> FEATURE:
<221> NAME/KEY: MOD_RES
<222> LOCATION: (42)..(42)
<223> OTHER INFORMATION: C-terminal amidation

<400> SEQUENCE: 90

Cys Asp Ala Thr Cys Gln Phe Arg Lys Ala Ile Asp Asp Cys Ala Trp
1               5                   10                  15

Phe Ala Met His Ser Asn Val Pro Gly Ser Val Phe Lys Ala Cys Met
            20                  25                  30

Lys Gln Lys Lys Lys Glu Phe Lys Ala Gly
            35                  40

<210> SEQ ID NO 91
<211> LENGTH: 42
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID

```
<222> LOCATION: (14)..(31)
<220> FEATURE:
<221> NAME/KEY: MOD_RES
<222> LOCATION: (42)..(42)
<223> OTHER INFORMATION: C-terminal amidation

<400> SEQUENCE: 91

Cys Asp Ala Thr Cys Gln Phe Arg Lys Ala Ile Asp Asp Cys Ala Trp
1               5                   10                  15

Phe Ala Leu His Ser Asn Val Pro Gly Ser Val Phe Lys Ala Cys Met
            20                  25                  30

Lys Gln Lys Lys Lys Glu Phe Lys Ala Gly
        35                  40

<210> SEQ ID NO 92
<211> LENGTH: 42
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(31)
<220> FEATURE:
<221> NAME/KEY: MOD_RES
<222> LOCATION: (42)..(42)
<223> OTHER INFORMATION: C-terminal amidation

<400> SEQUENCE: 92

Cys Asp Ala Thr Cys Gln Phe Arg Lys Ala Ile Asp Asp Cys Trp Met
1               5                   10                  15

Leu Ser Trp His Ala Asn Val Pro Gly Ser Val Phe Lys Ala Cys Met
            20                  25                  30

Lys Gln Lys Lys Lys Glu Phe Lys Ala Gly
        35                  40

<210> SEQ ID NO 93
<211> LENGTH: 42
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(31)
<220> FEATURE:
<221> NAME/KEY: MOD_RES
<222> LOCATION: (42)..(42)
<223> OTHER INFORMATION: C-terminal amidation

<400> SEQUENCE: 93

Cys Asp Ala Thr Cys Gln Phe Arg Lys Ala Ile Asp Asp Cys Gln Lys
1               5                   10                  15

Gln Ala His His Ser Asn Val Pro Gly Ser Val Phe Lys Ala Cys Val
            20                  25                  30

Leu Gln Lys Lys Lys Glu Phe Lys Ala Gly
        35                  40

<210> SEQ ID NO 94
<211> LENGTH: 43
<212> TYPE: PRT
```

```
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(31)

<400> SEQUENCE: 94

Cys Asp Ala Thr Cys Gln Phe Arg Lys Ala Ile Asp Asp Cys Val Lys
1               5                   10                  15

Gln Ala His His Ser Asn Val Pro Gly Ser Val Phe Lys Ala Cys Met
            20                  25                  30

Lys Gln Lys Lys Lys Glu Phe Lys Ala Gly His
        35                  40

<210> SEQ ID NO 95
<211> LENGTH: 42
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(31)

<400> SEQUENCE: 95

Cys Asp Ala Thr Cys Gln Phe Arg Lys Ala Ile Asp Asp Cys Gln Lys
1               5                   10                  15

Gln Ala His His Ser Asn Val Pro Gly Ser Val Phe Lys Ala Cys Met
            20                  25                  30

Lys Gln Lys Lys Lys Glu Phe Lys Ala Trp
        35                  40

<210> SEQ ID NO 96
<211> LENGTH: 42
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(31)

<400> SEQUENCE: 96

Cys Asp Ala Thr Cys Gln Phe Arg Lys Ala Ile Asp Asp Cys Gln Lys
1               5                   10                  15

Gln Ala His His Ser Asn Val Pro Gly Ser Val Phe Lys Ala Cys Met
            20                  25                  30

Lys Gln Lys Lys Lys Glu Phe Lys Ala Gln
        35                  40

<210> SEQ ID NO 97
<211> LENGTH: 42
<212> TYPE: PRT
<213> ORGANISM: Artificial Sequence
<220> FEATURE:
<223> OTHER INFORMATION: Synthetic Polypeptide
<220> FEATURE:
```

```
<221> NAME/KEY: DISULFID
<222> LOCATION: (1)..(5)
<220> FEATURE:
<221> NAME/KEY: DISULFID
<222> LOCATION: (14)..(31)
<220> FEATURE:
<221> NAME/KEY: MOD_RES
<222> LOCATION: (30)..(30)
<223> OTHER INFORMATION: Xaa = 2-aminoisobutyric acid
<220> FEATURE:
<221> NAME/KEY: MOD_RES
<222> LOCATION: (42)..(42)
<223> OTHER INFORMATION: C-terminal amidation

<400> SEQUENCE: 97

Cys Asp Ala Thr Cys Gln Phe Arg Lys Ala Ile Asp Asp Cys Gln Lys
1               5                   10                  15

Gln Glu His His Ser Asn Val Pro Gly Ser Lys Phe Lys Xaa Cys Met
            20                  25                  30

Lys Gln Lys Lys Lys Glu Phe Lys Ala Gly
        35                  40

<210> SEQ ID NO 98
<211> LENGTH: 42
<212> TYPE: PRT
<213> ORGANISM: Artificial Sequence
<220> FEATURE:
<223> OTHER INFORMATION: Syntehtic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(31)
<220> FEATURE:
<221> NAME/KEY: MOD_RES
<222> LOCATION: (30)..(30)
<223> OTHER INFORMATION: Xaa = 2-aminoisobutyric acid
<220> FEATURE:
<221> NAME/KEY: MOD_RES
<222> LOCATION: (42)..(42)
<223> OTHER INFORMATION: C-terminal amidation

<400> SEQUENCE: 98

Cys Asp Ala Thr Cys Gln Phe Arg Lys Ala Ile Asp Asp Cys Gln Lys
1               5                   10                  15

Gln Ala His His Ser Asn Val Pro Gly Ser Val Phe Lys Xaa Cys Met
            20                  25                  30

Lys Gln Lys Lys Lys Glu Phe Lys Ala Ala
        35                  40

<210> SEQ ID NO 99
<211> LENGTH: 42
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(31)

<400> SEQUENCE: 99

Cys Asp Ala Thr Cys Gln Phe Arg Lys Ala Ile Asp Asp Cys Val Arg
1               5                   10                  15

Gln Ala His His Ser Asn Val Pro Gly Ser Val Phe Lys Ala Cys Met
            20                  25                  30
```

```
Lys Gln Lys Lys Lys Glu Trp Lys Ala His
        35                  40
```

<210> SEQ ID NO 100
<211> LENGTH: 42
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(31)
<220> FEATURE:
<221> NAME/KEY: MOD_RES
<222> LOCATION: (42)..(42)
<223> OTHER INFORMATION: C-terminal amidation

<400> SEQUENCE: 100

```
Cys Asp Ala Thr Cys Gln Phe Arg Lys Ala Ile Asp Asp Cys Gln Lys
1               5                   10                  15

Gln Ala His His Ser Asn Val Pro Gly Ser Val Phe Lys Ala Cys Leu
            20                  25                  30

Leu Gln Lys Lys Lys Glu Phe Lys Ala Gly
        35                  40
```

<210> SEQ ID NO 101
<211> LENGTH: 42
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(31)
<220> FEATURE:
<221> NAME/KEY: MOD_RES
<222> LOCATION: (42)..(42)
<223> OTHER INFORMATION: C-terminal amidation

<400> SEQUENCE: 101

```
Cys Asp Ala Thr Cys Gln Phe Arg Lys Ala Ile Asp Asp Cys Gln Lys
1               5                   10                  15

Gln Ala His His Ser Asn Val Pro Gly Ser Val Phe Lys Ala Cys Leu
            20                  25                  30

Val Gln Lys Lys Lys Glu Phe Lys Ala Gly
        35                  40
```

<210> SEQ ID NO 102
<211> LENGTH: 42
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(31)
<220> FEATURE:
<221> NAME/KEY: MOD_RES
<222> LOCATION: (42)..(42)
<223> OTHER INFORMATION: C-terminal amidation

<400> SEQUENCE: 102

Cys Asp Ala Thr Cys Gln Phe Arg Lys Ala Ile Asp Asp Cys Gln Lys
1               5                   10                  15

Gln Ala His His Ser Asn Val Pro Gly Ser Val Phe Lys Ala Cys Met
            20                  25                  30

Val Gln Lys Lys Lys Glu Phe Lys Ala Gly
        35                  40

<210> SEQ ID NO 103
<211> LENGTH: 42
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(31)
<220> FEATURE:
<221> NAME/KEY: MOD_RES
<222> LOCATION: (42)..(42)
<223> OTHER INFORMATION: C-terminal amidation

<400> SEQUENCE: 103

Cys Asp Ala Thr Cys Gln Phe Arg Lys Ala Ile Asp Asp Cys Gln Lys
1               5                   10                  15

Gln Ala His His Ser Asn Val Pro Gly Ser Val Phe Lys Ala Cys Met
            20                  25                  30

Leu Gln Lys Lys Lys Glu Phe Lys Ala Gly
        35                  40

<210> SEQ ID NO 104
<211> LENGTH: 42
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(31)
<220> FEATURE:
<221> NAME/KEY: MOD_RES
<222> LOCATION: (42)..(42)
<223> OTHER INFORMATION: C-terminal amidation

<400> SEQUENCE: 104

Cys Asp Ala Thr Cys Gln Phe Arg Lys Ala Ile Asp Asp Cys Tyr Tyr
1               5                   10                  15

Arg Ala Trp His Ser Asn Val Pro Gly Ser Val Phe Lys Ala Cys Met
            20                  25                  30

Lys Gln Lys Lys Lys Glu Phe Lys Ala Gly
        35                  40

<210> SEQ ID NO 105
<211> LENGTH: 43
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(31)

<400> SEQUENCE: 105

Cys Asp Ala Thr Cys Gln Phe Arg Lys Ala Ile Asp Asp Cys Ala Arg
1               5                   10                  15

Gln Ala His His Ser Asn Val Pro Gly Ser Val Trp Lys Ala Cys Met
            20                  25                  30

Lys Gln Lys Lys Lys Glu Trp Lys Ala Gly His
        35                  40

<210> SEQ ID NO 106
<211> LENGTH: 43
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(31)

<400> SEQUENCE: 106

Cys Asp Ala Thr Cys Gln Phe Arg Lys Ala Ile Asp Asp Cys Val Arg
1               5                   10                  15

Gln Ala His His Ser Asn Val Pro Gly Ser Val Trp Lys Ala Cys Met
            20                  25                  30

Lys Gln Lys Lys Lys Glu Trp Lys Ala Gly His
        35                  40

<210> SEQ ID NO 107
<211> LENGTH: 43
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(31)

<400> SEQUENCE: 107

Cys Asp Ala Thr Cys Gln Phe Arg Lys Ala Ile Asp Asp Cys Phe Thr
1               5                   10                  15

Trp Ser Trp His Ser Asn Val Pro Gly Ser Val Phe Lys Ala Cys Met
            20                  25                  30

Lys Gln Lys Lys Lys Glu Phe Lys Ala Gly His
        35                  40

<210> SEQ ID NO 108
<211> LENGTH: 43
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(31)

<400> SEQUENCE: 108

Cys Asp Ala Thr Cys Gln Phe Arg Lys Ala Ile Asp Asp Cys Tyr Trp
1               5                   10                  15

Gln Ala Ile His Ala Asn Val Pro Gly Ser Val Trp Lys Ala Cys Met
            20                  25                  30

Lys Gln Lys Lys Lys Glu Phe Lys Ala Gly His
        35                  40

<210> SEQ ID NO 109
<211> LENGTH: 43
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(31)

<400> SEQUENCE: 109

Cys Asp Ala Thr Cys Gln Phe Arg Lys Ala Ile Asp Asp Cys Phe Tyr
1               5                   10                  15

Gln Ala Trp His Ser Asn Val Pro Gly Ser Val Trp Lys Ala Cys Met
            20                  25                  30

Lys Gln Lys Lys Lys Glu Phe Lys Ala Gly His
        35                  40

<210> SEQ ID NO 110
<211> LENGTH: 43
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(31)

<400> SEQUENCE: 110

Cys Asp Ala Thr Cys Gln Phe Arg Lys Ala Ile Asp Asp Cys Val Trp
1               5                   10                  15

Phe Ala Trp His Ser Asn Val Pro Gly Ser Val Phe Lys Ala Cys Met
            20                  25                  30

Lys Gln Lys Lys Lys Glu Phe Lys Ala Gly His
        35                  40

<210> SEQ ID NO 111
<211> LENGTH: 43
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(31)

<400> SEQUENCE: 111

Cys Asp Ala Thr Cys Gln Phe Arg Lys Ala Ile Asp Asp Cys Trp Met

```
                1               5                   10                  15
Leu Ser Trp His Ala Asn Val Pro Gly Ser Val Phe Lys Ala Cys Met
                20                  25                  30

Lys Gln Lys Lys Lys Glu Phe Lys Ala Gly His
        35                  40
```

<210> SEQ ID NO 112
<211> LENGTH: 43
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(31)

<400> SEQUENCE: 112

```
Cys Asp Ala Thr Cys Gln Phe Arg Lys Ala Ile Asp Asp Cys Tyr Tyr
1               5                   10                  15

Arg Ser Trp His Ser Asn Val Pro Gly Ser Val Phe Lys Ala Cys Met
                20                  25                  30

Lys Gln Lys Lys Lys Glu Phe Lys Ala Gly His
        35                  40
```

<210> SEQ ID NO 113
<211> LENGTH: 42
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(31)
<220> FEATURE:
<221> NAME/KEY: MOD_RES
<222> LOCATION: (42)..(42)
<223> OTHER INFORMATION: C-terminal amidation

<400> SEQUENCE: 113

```
Cys Asp Ala Thr Cys Gln Phe Arg Lys Ala Ile Asp Asp Cys Gln Lys
1               5                   10                  15

Gln Ala His His Ser Asn Val Pro Gly Ser Val Phe Lys Ala Cys Met
                20                  25                  30

Lys Arg Arg Arg Leu Leu Trp Lys Ala Gly
        35                  40
```

<210> SEQ ID NO 114
<211> LENGTH: 42
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(31)
<220> FEATURE:
<221> NAME/KEY: MOD_RES
<222> LOCATION: (42)..(42)
<223> OTHER INFORMATION: C-terminal amidation

<400> SEQUENCE: 114

Cys Asp Ala Thr Cys Gln Phe Arg Lys Ala Ile Asp Asp Cys Gln Lys
1               5                   10                  15

Gln Ala His His Ser Asn Val Pro Gly Ser Val Phe Lys Ala Cys Met
            20                  25                  30

Lys Glu Arg Arg Arg Trp Lys Ala Gly
        35                  40

<210> SEQ ID NO 115
<211> LENGTH: 42
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(31)
<220> FEATURE:
<221> NAME/KEY: MOD_RES
<222> LOCATION: (42)..(42)
<223> OTHER INFORMATION: C-terminal amidation

<400> SEQUENCE: 115

Cys Asp Ala Thr Cys Gln Phe Arg Lys Ala Ile Asp Asp Cys Ser Trp
1               5                   10                  15

Phe Ala Ile His Ser Asn Val Pro Gly Ser Val Phe Lys Ala Cys Met
            20                  25                  30

Lys Gln Lys Lys Lys Glu Phe Lys Ala Gly
        35                  40

<210> SEQ ID NO 116
<211> LENGTH: 42
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(31)
<220> FEATURE:
<221> NAME/KEY: MOD_RES
<222> LOCATION: (42)..(42)

<400> SEQUENCE: 116

Cys Asp Ala Thr Cys Gln Phe Arg Lys Ala Ile Asp Asp Cys Met Trp
1               5                   10                  15

Tyr Ala Tyr His Ser Asn Val Pro Gly Ser Val Phe Lys Ala Cys Met
            20                  25                  30

Lys Gln Lys Lys Lys Glu Phe Lys Ala Gly
        35                  40

<210> SEQ ID NO 117
<211> LENGTH: 42
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)

```
<220> FEATURE:
<221> NAME/KEY: DISULFID
<222> LOCATION: (14)..(31)
<220> FEATURE:
<221> NAME/KEY: MOD_RES
<222> LOCATION: (42)..(42)
<223> OTHER INFORMATION: C-terminal amidation

<400> SEQUENCE: 117

Cys Asp Ala Thr Cys Gln Phe Arg Lys Ala Ile Asp Asp Cys Leu Trp
1               5                   10                  15

Trp Ser Gln His Ser Asn Val Pro Gly Ser Val Phe Lys Ala Cys Met
                20                  25                  30

Lys Gln Lys Lys Lys Glu Phe Lys Ala Gly
            35                  40

<210> SEQ ID NO 118
<211> LENGTH: 42
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(31)
<220> FEATURE:
<221> NAME/KEY: MOD_RES
<222> LOCATION: (42)..(42)
<223> OTHER INFORMATION: C-terminal amidation

<400> SEQUENCE: 118

Cys Asp Ala Thr Cys Gln Phe Arg Lys Ala Ile Asp Asp Cys Val Trp
1               5                   10                  15

Lys Ala Phe His Ala Asn Val Pro Gly Ser Val Phe Lys Ala Cys Met
                20                  25                  30

Lys Gln Lys Lys Lys Glu Phe Lys Ala Gly
            35                  40

<210> SEQ ID NO 119
<211> LENGTH: 42
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(31)
<220> FEATURE:
<221> NAME/KEY: MOD_RES
<222> LOCATION: (42)..(42)
<223> OTHER INFORMATION: C-terminal amidation

<400> SEQUENCE: 119

Cys Asp Ala Thr Cys Gln Phe Arg Lys Ala Ile Asp Asp Cys Phe Trp
1               5                   10                  15

Leu Ala Ser His Ser Asn Val Pro Gly Ser Val Trp Lys Ala Cys Met
                20                  25                  30

Lys Gln Lys Lys Lys Glu Phe Lys Ala Gly
            35                  40

<210> SEQ ID NO 120
```

```
<211> LENGTH: 42
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(31)
<220> FEATURE:
<221> NAME/KEY: MOD_RES
<222> LOCATION: (42)..(42)
<223> OTHER INFORMATION: C-terminal amidation

<400> SEQUENCE: 120

Cys Asp Ala Thr Cys Gln Phe Arg Lys Ala Ile Asp Asp Cys Leu Trp
1               5                   10                  15

Tyr Ala Arg His Ser Asn Val Pro Gly Ser Val Phe Lys Ala Cys Met
            20                  25                  30

Lys Gln Lys Lys Lys Glu Phe Lys Ala Gly
        35                  40

<210> SEQ ID NO 121
<211> LENGTH: 42
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(31)
<220> FEATURE:
<221> NAME/KEY: MOD_RES
<222> LOCATION: (42)..(42)
<223> OTHER INFORMATION: C-terminal amidation

<400> SEQUENCE: 121

Cys Asp Ala Thr Cys Gln Phe Arg Lys Ala Ile Asp Asp Cys Met Trp
1               5                   10                  15

Tyr Ser Arg His Ser Asn Val Pro Gly Ser Val Phe Lys Ala Cys Met
            20                  25                  30

Lys Gln Lys Lys Lys Glu Phe Lys Ala Gly
        35                  40

<210> SEQ ID NO 122
<211> LENGTH: 42
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(31)
<220> FEATURE:
<221> NAME/KEY: MOD_RES
<222> LOCATION: (42)..(42)
<223> OTHER INFORMATION: C-terminal amidation

<400> SEQUENCE: 122

Cys Asp Ala Thr Cys Gln Phe Arg Lys Ala Ile Asp Asp Cys Met Trp
1               5                   10                  15
```

Phe Ala Trp His Ser Asn Val Pro Gly Ser Val Phe Lys Ala Cys Met
                20                  25                  30

Lys Gln Lys Lys Lys Glu Phe Lys Ala Gly
        35                  40

<210> SEQ ID NO 123
<211> LENGTH: 42
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(31)
<220> FEATURE:
<221> NAME/KEY: MOD_RES
<222> LOCATION: (42)..(42)
<223> OTHER INFORMATION: C-terminal amidation

<400> SEQUENCE: 123

Cys Asp Ala Thr Cys Gln Phe Arg Lys Ala Ile Asp Asp Cys Ile Phe
1               5                   10                  15

Trp Ala Ala His Ser Asn Val Pro Gly Ser Val Phe Lys Ala Cys Met
                20                  25                  30

Lys Gln Lys Lys Lys Glu Phe Lys Ala Gly
        35                  40

<210> SEQ ID NO 124
<211> LENGTH: 42
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(31)
<220> FEATURE:
<221> NAME/KEY: MOD_RES
<222> LOCATION: (42)..(42)
<223> OTHER INFORMATION: C-terminal amidation

<400> SEQUENCE: 124

Cys Asp Ala Thr Cys His Phe Arg Lys Ala Ile Asp Asp Cys Gln Lys
1               5                   10                  15

Gln Ala His Ser Asn Val Pro Gly Ser Val Phe Lys Ala Cys Met
                20                  25                  30

Lys Gln His Lys Lys Arg Trp Arg Ala Gly
        35                  40

<210> SEQ ID NO 125
<211> LENGTH: 42
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(31)
<220> FEATURE:
<221> NAME/KEY: MOD_RES
<222> LOCATION: (42)..(42)
<223> OTHER INFORMATION: C-terminal amidation

<400> SEQUENCE: 125

Cys Asp Ala Thr Cys Phe Phe Arg Lys Val Ile Asp Asp Cys Gln Lys
1               5                   10                  15

Gln Ala His His Ser Asn Val Pro Gly Ser Val Phe Lys Ala Cys Met
            20                  25                  30

Lys Gln Leu Lys Lys Arg Trp Gln Ala Gly
        35                  40

<210> SEQ ID NO 126
<211> LENGTH: 42
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(31)
<220> FEATURE:
<221> NAME/KEY: MOD_RES
<222> LOCATION: (42)..(42)
<223> OTHER INFORMATION: C-terminal amidation

<400> SEQUENCE: 126

Cys Asp Ala Thr Cys Gln Phe Arg Lys Ala Ile Asp Asp Cys Gln Lys
1               5                   10                  15

Gln Ala His His Ser Asn Val Pro Gly Ser Val Phe Lys Ala Cys Met
            20                  25                  30

Lys Gln Arg Lys Lys Arg Trp Leu Ala Gly
        35                  40

<210> SEQ ID NO 127
<211> LENGTH: 42
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(31)
<220> FEATURE:
<221> NAME/KEY: MOD_RES
<222> LOCATION: (42)..(42)
<223> OTHER INFORMATION: C-terminal amidation

<400> SEQUENCE: 127

Cys Asp Ala Thr Cys Gln Phe Arg Lys Ala Ile Asp Asp Cys Gln Lys
1               5                   10                  15

Gln Ala His His Ser Asn Val Pro Gly Ser Val Phe Lys Ala Cys Met
            20                  25                  30

Lys Phe Arg Phe Asn Val Trp Lys Ala Gly
        35                  40

<210> SEQ ID NO 128
<211> LENGTH: 42
<212> TYPE: PRT
<213> ORGANISM: Artificial Sequence
<220> FEATURE:
<223> OTHER INFORMATION: Synthetic Polypeptide

```
<220> FEATURE:
<221> NAME/KEY: DISULFID
<222> LOCATION: (1)..(5)
<220> FEATURE:
<221> NAME/KEY: DISULFID
<222> LOCATION: (14)..(31)
<220> FEATURE:
<221> NAME/KEY: MOD_RES
<222> LOCATION: (42)..(42)
<223> OTHER INFORMATION: C-terminal amidation

<400> SEQUENCE: 128

Cys Asp Ala Thr Cys Gln Phe Arg Lys Ala Ile Asp Asp Cys Gln Lys
1               5                   10                  15

Gln Ala His His Ser Asn Val Pro Gly Ser Val Phe Lys Ala Cys Met
            20                  25                  30

Lys Phe Arg Arg Phe Leu Trp Lys Ala Gly
        35                  40

<210> SEQ ID NO 129
<211> LENGTH: 42
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(31)
<220> FEATURE:
<221> NAME/KEY: MOD_RES
<222> LOCATION: (42)..(42)
<223> OTHER INFORMATION: C-terminal amidation

<400> SEQUENCE: 129

Cys Asp Ala Thr Cys Gln Phe Arg Lys Ala Ile Asp Asp Cys Trp Ile
1               5                   10                  15

Val Ala Trp His Ala Asn Val Pro Gly Ser Val Phe Lys Ala Cys Met
            20                  25                  30

Lys Gln Lys Lys Lys Glu Phe Lys Ala Gly
        35                  40

<210> SEQ ID NO 130
<211> LENGTH: 42
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(31)
<220> FEATURE:
<221> NAME/KEY: MOD_RES
<222> LOCATION: (42)..(42)
<223> OTHER INFORMATION: C-terminal amidation

<400> SEQUENCE: 130

Cys Asp Ala Thr Cys Gln Phe Arg Lys Ala Ile Asp Asp Cys Trp Val
1               5                   10                  15

Ile Ala Trp His Ser Asn Val Pro Gly Ser Val Phe Lys Ala Cys Met
            20                  25                  30

Lys Gln Lys Lys Lys Glu Phe Lys Ala Gly
        35                  40
```

<210> SEQ ID NO 131
<211> LENGTH: 42
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(31)
<220> FEATURE:
<221> NAME/KEY: MOD_RES
<222> LOCATION: (42)..(42)
<223> OTHER INFORMATION: C-terminal amidation

<400> SEQUENCE: 131

Cys Asp Ala Thr Cys Gln Phe Arg Lys Ala Ile Asp Cys Met Leu
1               5                   10                  15

Phe Ser Trp His Ser Asn Val Pro Gly Ser Val Phe Lys Ala Cys Met
                20                  25                  30

Lys Gln Lys Lys Lys Glu Phe Lys Ala Gly
            35                  40

<210> SEQ ID NO 132
<211> LENGTH: 42
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(31)
<220> FEATURE:
<221> NAME/KEY: MOD_RES
<222> LOCATION: (42)..(42)
<223> OTHER INFORMATION: C-terminal amidation

<400> SEQUENCE: 132

Cys Asp Ala Thr Cys Gln Phe Arg Lys Ala Ile Asp Cys Met Leu
1               5                   10                  15

Leu Ser Trp His Ser Asn Val Pro Gly Ser Val Phe Lys Ala Cys Met
                20                  25                  30

Lys Gln Lys Lys Lys Glu Phe Lys Ala Gly
            35                  40

<210> SEQ ID NO 133
<211> LENGTH: 42
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(31)
<220> FEATURE:
<221> NAME/KEY: MOD_RES
<222> LOCATION: (42)..(42)
<223> OTHER INFORMATION: C-terminal amidation

<400> SEQUENCE: 133

Cys Asp Ala Thr Cys Gln Phe Arg Lys Ala Ile Asp Asp Cys Val Trp
1               5                   10                  15

Tyr Ser Met His Ser Asn Val Pro Gly Ser Val Phe Lys Ala Cys Met
            20                  25                  30

Lys Gln Lys Lys Lys Glu Phe Lys Ala Gly
        35                  40

<210> SEQ ID NO 134
<211> LENGTH: 42
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(31)
<220> FEATURE:
<221> NAME/KEY: MOD_RES
<222> LOCATION: (42)..(42)
<223> OTHER INFORMATION: C-terminal amidation

<400> SEQUENCE: 134

Cys Asp Ala Thr Cys Gln Phe Arg Lys Ala Ile Asp Asp Cys Trp Val
1               5                   10                  15

Gln Ala Trp His Ser Asn Val Pro Gly Ser Val Phe Lys Ala Cys Met
            20                  25                  30

Lys Gln Lys Lys Lys Glu Phe Lys Ala Gly
        35                  40

<210> SEQ ID NO 135
<211> LENGTH: 42
<212> TYPE: PRT
<213> ORGANISM: Artificial Sequence
<220> FEATURE:
<223> OTHER INFORMATION: Synthetic Polyppeptide
<220> FEATURE:
<221> NAME/KEY: DISULFID
<222> LOCATION: (1)..(5)
<220> FEATURE:
<221> NAME/KEY: DISULFID
<222> LOCATION: (14)..(31)
<220> FEATURE:
<221> NAME/KEY: MOD_RES
<222> LOCATION: (42)..(42)
<223> OTHER INFORMATION: C-terminal amidation

<400> SEQUENCE: 135

Cys Asp Ala Thr Cys Gln Phe Arg Lys Ala Ile Asp Asp Cys Phe Thr
1               5                   10                  15

Trp Ser Trp His Ser Asn Val Pro Gly Ser Val Phe Lys Ala Cys Met
            20                  25                  30

Lys Gln Lys Lys Lys Glu Phe Lys Ala Gly
        35                  40

<210> SEQ ID NO 136
<211> LENGTH: 42
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID

```
<222> LOCATION: (14)..(31)
<220> FEATURE:
<221> NAME/KEY: MOD_RES
<222> LOCATION: (42)..(42)
<223> OTHER INFORMATION: C-terminal amidation

<400> SEQUENCE: 136

Cys Asp Ala Thr Cys Gln Phe Arg Lys Ala Ile Asp Asp Cys Val Phe
1               5                   10                  15
Trp Ala Ala His Ser Asn Val Pro Gly Ser Val Phe Lys Ala Cys Met
            20                  25                  30
Lys Gln Lys Lys Lys Glu Phe Lys Ala Gly
        35                  40

<210> SEQ ID NO 137
<211> LENGTH: 42
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(31)
<220> FEATURE:
<221> NAME/KEY: MOD_RES
<222> LOCATION: (42)..(42)
<223> OTHER INFORMATION: C-terminal amidation

<400> SEQUENCE: 137

Cys Asp Ala Thr Cys Gln Phe Arg Lys Ala Ile Asp Asp Cys Val Tyr
1               5                   10                  15
Ser Ala Trp His Ala Asn Val Pro Gly Ser Val Phe Lys Ala Cys Met
            20                  25                  30
Lys Gln Lys Lys Lys Glu Phe Lys Ala Gly
        35                  40

<210> SEQ ID NO 138
<211> LENGTH: 42
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(31)
<220> FEATURE:
<221> NAME/KEY: MOD_RES
<222> LOCATION: (42)..(42)
<223> OTHER INFORMATION: C-terminal amidation

<400> SEQUENCE: 138

Cys Asp Ala Thr Cys Gln Phe Arg Lys Ala Ile Asp Asp Cys Tyr Trp
1               5                   10                  15
Gln Ala Ile His Ala Asn Val Pro Gly Ser Val Trp Lys Ala Cys Met
            20                  25                  30
Lys Gln Lys Lys Lys Glu Phe Lys Ala Gly
        35                  40

<210> SEQ ID NO 139
<211> LENGTH: 42
<212> TYPE: PRT
```

```
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(31)
<220> FEATURE:
<221> NAME/KEY: MOD_RES
<222> LOCATION: (42)..(42)
<223> OTHER INFORMATION: C-terminal amidation

<400> SEQUENCE: 139

Cys Asp Ala Thr Cys Gln Phe Arg Lys Ala Ile Asp Asp Cys Phe Tyr
1               5                   10                  15

Gln Ala Trp His Ser Asn Val Pro Gly Ser Val Trp Lys Ala Cys Met
            20                  25                  30

Lys Gln Lys Lys Lys Glu Phe Lys Ala Gly
        35                  40

<210> SEQ ID NO 140
<211> LENGTH: 42
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(31)
<220> FEATURE:
<221> NAME/KEY: MOD_RES
<222> LOCATION: (42)..(42)
<223> OTHER INFORMATION: C-terminal amidation

<400> SEQUENCE: 140

Cys Asp Ala Thr Cys Gln Phe Arg Lys Ala Ile Asp Asp Cys His Leu
1               5                   10                  15

Leu Ala Trp His Ala Asn Val Pro Gly Ser Val Phe Lys Ala Cys Met
            20                  25                  30

Lys Gln Lys Lys Lys Glu Phe Lys Ala Gly
        35                  40

<210> SEQ ID NO 141
<211> LENGTH: 42
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(31)
<220> FEATURE:
<221> NAME/KEY: MOD_RES
<222> LOCATION: (42)..(42)
<223> OTHER INFORMATION: C-terminal amidation

<400> SEQUENCE: 141

Cys Asp Ala Thr Cys Gln Phe Arg Lys Ala Ile Asp Asp Cys His Trp
1               5                   10                  15

Tyr Ser Leu His Ser Asn Val Pro Gly Ser Val Phe Lys Ala Cys Met
            20                  25                  30
```

```
Lys Gln Lys Lys Lys Glu Phe Lys Ala Gly
        35                  40
```

<210> SEQ ID NO 142
<211> LENGTH: 42
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(31)
<220> FEATURE:
<221> NAME/KEY: MOD_RES
<222> LOCATION: (42)..(42)
<223> OTHER INFORMATION: C-terminal amidation

<400> SEQUENCE: 142

```
Cys Asp Ala Thr Cys Gln Phe Arg Lys Ala Ile Asp Asp Cys Gln Lys
1               5                   10                  15

Gln Ala His His Ser Asn Val Pro Gly Ser Val Phe Lys Ala Cys Val
            20                  25                  30

Lys Gln Lys Lys Lys Glu Phe Lys Ala Gly
        35                  40
```

<210> SEQ ID NO 143
<211> LENGTH: 42
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(31)
<220> FEATURE:
<221> NAME/KEY: MOD_RES
<222> LOCATION: (42)..(42)
<223> OTHER INFORMATION: C-terminal amidation

<400> SEQUENCE: 143

```
Cys Asp Ala Thr Cys Gln Phe Arg Lys Ala Ile Asp Asp Cys Gln Lys
1               5                   10                  15

Gln Ala His His Ser Asn Val Pro Gly Ser Val Phe Lys Ala Cys Leu
            20                  25                  30

Lys Gln Lys Lys Lys Glu Phe Lys Ala Gly
        35                  40
```

<210> SEQ ID NO 144
<211> LENGTH: 42
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(31)
<220> FEATURE:
<221> NAME/KEY: MOD_RES
<222> LOCATION: (42)..(42)
<223> OTHER INFORMATION: C-terminal amidation

<400> SEQUENCE: 144

Cys Asp Ala Thr Cys Gln Phe Arg Lys Ala Ile Asp Asp Cys Asp Arg
1               5                   10                  15

Gln Ala Tyr His Ser Asn Val Pro Gly Ser Val Phe Lys Ala Cys Met
            20                  25                  30

Lys Gln Lys Lys Lys Glu Trp Lys Ala Gly
        35                  40

<210> SEQ ID NO 145
<211> LENGTH: 43
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(31)

<400> SEQUENCE: 145

Cys Asp Ala Thr Cys Gln Phe Arg Lys Ala Ile Asp Asp Cys Gln Lys
1               5                   10                  15

Gln Ala His His Ser Asn Val Pro Gly Ser Val Phe Lys Ala Cys Met
            20                  25                  30

Lys Gln Lys Lys Lys Glu Phe Lys Ala Gly Trp
        35                  40

<210> SEQ ID NO 146
<211> LENGTH: 42
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(31)
<220> FEATURE:
<221> NAME/KEY: MOD_RES
<222> LOCATION: (42)..(42)
<223> OTHER INFORMATION: C-terminal amidation

<400> SEQUENCE: 146

Cys Asp Ala Thr Cys Gln Phe Arg Lys Ala Ile Asp Asp Cys Gln Lys
1               5                   10                  15

Gln Ala His His Ser Asn Val Pro Gly Ser Val Phe Lys Thr Cys Met
            20                  25                  30

Lys Gln Lys Lys Lys Glu Phe Lys Ala Gly
        35                  40

<210> SEQ ID NO 147
<211> LENGTH: 42
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(31)

```
<220> FEATURE:
<221> NAME/KEY: MOD_RES
<222> LOCATION: (42)..(42)
<223> OTHER INFORMATION: C-terminal amidation

<400> SEQUENCE: 147

Cys Asp Ala Thr Cys Gln Phe Arg Lys Ala Ile Asp Asp Cys Tyr Trp
1               5                   10                  15

Ile Ala Met His Ser Asn Val Pro Gly Ser Val Trp Lys Ala Cys Met
            20                  25                  30

Lys Gln Lys Lys Lys Glu Phe Lys Ala Gly
            35                  40

<210> SEQ ID NO 148
<211> LENGTH: 42
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(31)
<220> FEATURE:
<221> NAME/KEY: MOD_RES
<222> LOCATION: (42)..(42)
<223> OTHER INFORMATION: C-terminal amidation

<400> SEQUENCE: 148

Cys Asp Ala Thr Cys Gln Phe Arg Lys Ala Ile Asp Asp Cys Val Trp
1               5                   10                  15

Phe Ala Trp His Ser Asn Val Pro Gly Ser Val Phe Lys Ala Cys Met
            20                  25                  30

Lys Gln Lys Lys Lys Glu Phe Lys Ala Gly
            35                  40

<210> SEQ ID NO 149
<211> LENGTH: 42
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(31)
<220> FEATURE:
<221> NAME/KEY: MOD_RES
<222> LOCATION: (42)..(42)
<223> OTHER INFORMATION: C-terminal amidation

<400> SEQUENCE: 149

Cys Asp Ala Thr Cys Gln Phe Arg Lys Ala Ile Asp Asp Cys Tyr Tyr
1               5                   10                  15

Arg Ser Trp His Ser Asn Val Pro Gly Ser Val Phe Lys Ala Cys Met
            20                  25                  30

Lys Gln Lys Lys Lys Glu Phe Lys Ala Gly
            35                  40

<210> SEQ ID NO 150
<211> LENGTH: 42
<212> TYPE: PRT
<213> ORGANISM: Artificial Sequence
```

```
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(31)
<220> FEATURE:
<221> NAME/KEY: MOD_RES
<222> LOCATION: (42)..(42)
<223> OTHER INFORMATION: C-terminal amidation

<400> SEQUENCE: 150

Cys Asp Ala Thr Cys Gln Phe Arg Lys Ala Ile Asp Asp Cys Tyr Tyr
1               5                   10                  15

Tyr Ala Met His Ser Asn Val Pro Gly Ser Val Trp Lys Ala Cys Met
            20                  25                  30

Lys Gln Lys Lys Lys Glu Phe Lys Ala Gly
            35                  40

<210> SEQ ID NO 151
<211> LENGTH: 43
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(31)

<400> SEQUENCE: 151

Cys Asp Ala Thr Cys Gln Phe Arg Lys Ala Ile Asp Asp Cys Ala Arg
1               5                   10                  15

Gln Ala His His Ser Asn Val Pro Gly Ser Val Phe Lys Ala Cys Met
            20                  25                  30

Lys Gln Lys Lys Lys Glu Trp Lys Ala Gly His
            35                  40

<210> SEQ ID NO 152
<211> LENGTH: 43
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(31)

<400> SEQUENCE: 152

Cys Asp Ala Thr Cys Gln Phe Arg Lys Ala Ile Asp Asp Cys Ala Lys
1               5                   10                  15

Gln Ala His His Ser Asn Val Pro Gly Ser Val Phe Lys Ala Cys Met
            20                  25                  30

Lys Gln Lys Lys Lys Glu Trp Lys Ala Gly His
            35                  40

<210> SEQ ID NO 153
<211> LENGTH: 42
<212> TYPE: PRT
<213> ORGANISM: Artificial Sequence
```

```
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(31)

<400> SEQUENCE: 153

Cys Asp Ala Thr Cys Gln Phe Arg Lys Ala Ile Asp Asp Cys Gln Lys
1               5                   10                  15

Gln Ala His His Ser Asn Val Pro Gly Ser Val Phe Lys Ala Cys Met
            20                  25                  30

Lys Gln Lys Lys Lys Glu Phe Lys Ala His
        35                  40

<210> SEQ ID NO 154
<211> LENGTH: 43
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(31)

<400> SEQUENCE: 154

Cys Asp Ala Thr Cys Gln Phe Arg Lys Ala Ile Asp Asp Cys Asp Arg
1               5                   10                  15

Gln Ala His His Ser Asn Val Pro Gly Ser Val Phe Lys Ala Cys Met
            20                  25                  30

Lys Gln Lys Lys Lys Glu Trp Lys Ala Asn Asn
        35                  40

<210> SEQ ID NO 155
<211> LENGTH: 43
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(31)

<400> SEQUENCE: 155

Cys Asp Ala Thr Cys Gln Phe Arg Lys Ala Ile Asp Asp Cys Asp Arg
1               5                   10                  15

Gln Ala His His Ser Asn Val Pro Gly Ser Val Phe Lys Ala Cys Met
            20                  25                  30

Lys Gln Lys Lys Lys Glu Phe Lys Ala Gly His
        35                  40

<210> SEQ ID NO 156
<211> LENGTH: 43
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
```

```
<222> LOCATION: (1)..(5)
<220> FEATURE:
<221> NAME/KEY: DISULFID
<222> LOCATION: (14)..(31)

<400> SEQUENCE: 156

Cys Asp Ala Thr Cys Gln Phe Arg Lys Ala Ile Asp Asp Cys Val Arg
1               5                   10                  15

Gln Ala His His Ser Asn Val Pro Gly Ser Val Phe Lys Ala Cys Met
            20                  25                  30

Lys Gln Lys Lys Lys Glu Trp Lys Ala Gly His
            35                  40

<210> SEQ ID NO 157
<211> LENGTH: 44
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(31)
<220> FEATURE:
<221> NAME/KEY: MOD_RES
<222> LOCATION: (30)..(30)
<223> OTHER INFORMATION: Xaa = 2-aminoisobutyric acid

<400> SEQUENCE: 157

Cys Asp Ala Thr Cys Gln Phe Arg Lys Ala Ile Asp Asp Cys Gln Lys
1               5                   10                  15

Gln Ala His His Ser Asn Val Pro Gly Ser Val Phe Lys Xaa Cys Met
            20                  25                  30

Lys Gln Lys Lys Lys Glu Phe Lys Ala Gly Gly Ser
            35                  40

<210> SEQ ID NO 158
<211> LENGTH: 42
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(31)
<220> FEATURE:
<221> NAME/KEY: MOD_RES
<222> LOCATION: (42)..(42)
<223> OTHER INFORMATION: C-terminal amidation

<400> SEQUENCE: 158

Cys Asp Ala Thr Cys Gln Phe Arg Lys Ala Ile Asp Asp Cys Asp Arg
1               5                   10                  15

Gln Ala His His Ser Asn Val Pro Gly Ser Val Phe Lys Ala Cys Met
            20                  25                  30

Lys Gln Lys Lys Lys Glu Trp Lys Ala Asn
            35                  40

<210> SEQ ID NO 159
<211> LENGTH: 42
<212> TYPE: PRT
<213> ORGANISM: Artificial Sequence
```

```
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(31)

<400> SEQUENCE: 159

Cys Asp Ala Thr Cys Gln Phe Arg Lys Ala Ile Asp Asp Cys Asp Arg
1               5                   10                  15

Gln Ala His His Ser Asn Val Pro Gly Ser Val Phe Lys Ala Cys Met
            20                  25                  30

Lys Gln Lys Lys Lys Glu Trp Lys Ala Asn
        35                  40

<210> SEQ ID NO 160
<211> LENGTH: 48
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(31)

<400> SEQUENCE: 160

Cys Asp Ala Thr Cys Gln Phe Arg Lys Ala Ile Asp Asp Cys Gln Lys
1               5                   10                  15

Gln Ala His His Ser Asn Val Pro Gly Ser Val Phe Lys Ala Cys Met
            20                  25                  30

Lys Gln Lys Lys Lys Glu Phe Lys Ala Gly His His His His His His
        35                  40                  45

<210> SEQ ID NO 161
<211> LENGTH: 43
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(31)
<220> FEATURE:
<221> NAME/KEY: MOD_RES
<222> LOCATION: (30)..(30)
<223> OTHER INFORMATION: Xaa = 2-aminoisobutyric acid

<400> SEQUENCE: 161

Cys Asp Ala Thr Cys Gln Phe Arg Lys Ala Ile Asp Asp Cys Gln Lys
1               5                   10                  15

Gln Ala His His Ser Asn Val Pro Gly Ser Val Phe Lys Xaa Cys Met
            20                  25                  30

Lys Gln Lys Lys Lys Glu Phe Lys Ala Asn Lys
        35                  40

<210> SEQ ID NO 162
<211> LENGTH: 42
<212> TYPE: PRT
<213> ORGANISM: Artificial Sequence
```

```
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(31)
<220> FEATURE:
<221> NAME/KEY: MOD_RES
<222> LOCATION: (30)..(30)
<223> OTHER INFORMATION: Xaa = 2-aminoisobutyric acid

<400> SEQUENCE: 162
```

Cys Asp Ala Thr Cys Gln Phe Arg Lys Ala Ile Asp Asp Cys Gln Lys
1               5                   10                  15

Gln Ala His His Ser Asn Val Pro Gly Ser Val Phe Lys Xaa Cys Met
            20                  25                  30

Lys Gln Lys Lys Lys Glu Trp Lys Ala Asn
        35                  40

```
<210> SEQ ID NO 163
<211> LENGTH: 42
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(31)
<220> FEATURE:
<221> NAME/KEY: MOD_RES
<222> LOCATION: (42)..(42)
<223> OTHER INFORMATION: C-terminal amidation

<400> SEQUENCE: 163
```

Cys Asp Ala Thr Cys Gln Phe Arg Lys Ala Ile Asp Asp Cys Asp Arg
1               5                   10                  15

Gln Ala His His Ser Asn Val Pro Gly Ser Val Phe Lys Ala Cys Met
            20                  25                  30

Lys Gln Lys Lys Lys Glu Trp Lys Ala Gly
        35                  40

```
<210> SEQ ID NO 164
<211> LENGTH: 43
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(31)

<400> SEQUENCE: 164
```

Cys Asp Ala Thr Cys Gln Phe Arg Lys Ala Ile Asp Asp Cys Gln Lys
1               5                   10                  15

Gln Ala His His Ser Asn Val Pro Gly Ser Val Phe Lys Ala Cys Met
            20                  25                  30

Lys Gln Lys Lys Lys Glu Phe Lys Ala Gly Tyr
        35                  40

-continued

```
<210> SEQ ID NO 165
<400> SEQUENCE: 165

000

<210> SEQ ID NO 166
<211> LENGTH: 42
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(31)
<220> FEATURE:
<221> NAME/KEY: MOD_RES
<222> LOCATION: (30)..(30)
<223> OTHER INFORMATION: Xaa = 2-aminoisobutyric acid
<220> FEATURE:
<221> NAME/KEY: MOD_RES
<222> LOCATION: (42)..(42)
<223> OTHER INFORMATION: C-terminal amidation

<400> SEQUENCE: 166

Cys Asp Ala Thr Cys Gln Phe Arg Lys Ala Ile Asp Asp Cys Gln Lys
1               5                   10                  15

Gln Ala His His Ser Asn Val Pro Gly Ser Val Phe Lys Xaa Cys Met
            20                  25                  30

Lys Gln Lys Lys Lys Glu Trp Lys Ala Asn
        35                  40

<210> SEQ ID NO 167
<211> LENGTH: 43
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(31)

<400> SEQUENCE: 167

Cys Asp Ala Thr Cys Gln Phe Arg Lys Ala Ile Asp Asp Cys Asp Arg
1               5                   10                  15

Gln Ala His His Ser Asn Val Pro Gly Ser Val Phe Lys Ala Cys Met
            20                  25                  30

Lys Gln Lys Lys Lys Glu Trp Lys Ala Gly His
        35                  40

<210> SEQ ID NO 168
<211> LENGTH: 42
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(31)
<220> FEATURE:
<221> NAME/KEY: MOD_RES
```

-continued

<222> LOCATION: (42)..(42)
<223> OTHER INFORMATION: C-terminal amidation

<400> SEQUENCE: 168

Cys Asp Ala Thr Cys Gln Phe Arg Lys Ala Ile Asp Asp Cys Asp Arg
1               5                   10                  15

Gln Ala His His Ser Asn Val Pro Gly Ser Val Phe Lys Ala Cys Met
            20                  25                  30

Lys Gln Lys Lys Lys Glu Phe Lys Ala Gly
        35                  40

<210> SEQ ID NO 169
<211> LENGTH: 42
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(31)
<220> FEATURE:
<221> NAME/KEY: MOD_RES
<222> LOCATION: (42)..(42)
<223> OTHER INFORMATION: C-terminal amidation

<400> SEQUENCE: 169

Cys Asp Ala Thr Cys Gln Phe Arg Lys Ala Ile Asp Asp Cys Asp Lys
1               5                   10                  15

Gln Ala His His Ser Asn Val Pro Gly Ser Val Phe Lys Ala Cys Met
            20                  25                  30

Lys Gln Lys Lys Lys Glu Phe Gln Ala Gly
        35                  40

<210> SEQ ID NO 170
<211> LENGTH: 43
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(31)

<400> SEQUENCE: 170

Cys Asp Ala Thr Cys Gln Phe Arg Lys Ala Ile Asp Asp Cys Gln Lys
1               5                   10                  15

Gln Ala His His Ser Asn Val Pro Gly Ser Val Phe Lys Ala Cys Met
            20                  25                  30

Lys Gln Lys Lys Lys Glu Phe Lys Ala Gly Arg
        35                  40

<210> SEQ ID NO 171
<211> LENGTH: 43
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:

<221> NAME/KEY: DISULFID
<222> LOCATION: (14)..(31)

<400> SEQUENCE: 171

Cys Asp Ala Thr Cys Gln Phe Arg Lys Ala Ile Asp Asp Cys Gln Lys
1               5                   10                  15

Gln Ala His His Ser Asn Val Pro Gly Ser Val Phe Lys Ala Cys Met
            20                  25                  30

Lys Gln Lys Lys Lys Glu Phe Lys Ala Gly His
        35                  40

<210> SEQ ID NO 172
<211> LENGTH: 43
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(31)

<400> SEQUENCE: 172

Cys Asp Ala Thr Cys Gln Phe Arg Lys Ala Ile Asp Asp Cys Gln Lys
1               5                   10                  15

Gln Ala His His Ser Asn Val Pro Gly Ser Val Phe Lys Ala Cys Met
            20                  25                  30

Lys Gln Lys Lys Lys Glu Phe Lys Ala Gly Phe
        35                  40

<210> SEQ ID NO 173
<211> LENGTH: 43
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(31)

<400> SEQUENCE: 173

Cys Asp Ala Thr Cys Gln Phe Arg Lys Ala Ile Asp Asp Cys Gln Lys
1               5                   10                  15

Gln Ala His His Ser Asn Val Pro Gly Ser Val Phe Lys Ala Cys Met
            20                  25                  30

Lys Gln Lys Lys Lys Glu Phe Lys Ala Gly Glu
        35                  40

<210> SEQ ID NO 174
<211> LENGTH: 43
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(31)

<400> SEQUENCE: 174

Cys Asp Ala Thr Cys Gln Phe Arg Lys Ala Ile Asp Asp Cys Gln Lys
1               5                   10                  15

Gln Ala His His Ser Asn Val Pro Gly Ser Val Phe Lys Ala Cys Met
            20                  25                  30

Lys Gln Lys Lys Lys Glu Phe Lys Ala Gly Gln
        35                  40

<210> SEQ ID NO 175
<211> LENGTH: 43
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(31)

<400> SEQUENCE: 175

Cys Asp Ala Thr Cys Gln Phe Arg Lys Ala Ile Asp Asp Cys Gln Lys
1               5                   10                  15

Gln Ala His His Ser Asn Val Pro Gly Ser Val Phe Lys Ala Cys Met
            20                  25                  30

Lys Gln Lys Lys Lys Glu Phe Lys Ala Gly Ala
        35                  40

<210> SEQ ID NO 176
<211> LENGTH: 42
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (10)..(35)
<220> FEATURE:
<221> NAME/KEY: MOD_RES
<222> LOCATION: (42)..(42)
<223> OTHER INFORMATION: C-terminal amidation

<400> SEQUENCE: 176

Cys Asp Ala Thr Cys Gln Phe Arg Lys Cys Ile Asp Asp Trp Gln Lys
1               5                   10                  15

Gln Ala His His Ser Asn Val Pro Gly Ser Val Phe Lys Ala Arg Met
            20                  25                  30

Lys Gln Cys Lys Lys Glu Phe Lys Ala Gly
        35                  40

<210> SEQ ID NO 177
<211> LENGTH: 46
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(31)

<400> SEQUENCE: 177

```
Cys Asp Ala Thr Cys Gln Phe Arg Lys Ala Ile Asp Asp Cys Gln Lys
1               5                   10                  15

Gln Ala His His Ser Asn Val Pro Gly Ser Val Phe Lys Ala Cys Met
                20                  25                  30

Lys Gln Lys Lys Lys Glu Phe Lys Ala Gly Gly Gly Gly Ser
            35                  40                  45

<210> SEQ ID NO 178
<211> LENGTH: 37
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(26)
<220> FEATURE:
<221> NAME/KEY: DISULFID
<222> LOCATION: (25)..(25)
<223> OTHER INFORMATION: Xaa = 2-aminoisobutyric acid
<220> FEATURE:
<221> NAME/KEY: MOD_RES
<222> LOCATION: (37)..(37)
<223> OTHER INFORMATION: C-terminal amidation

<400> SEQUENCE: 178

Cys Asp Ala Thr Cys Gln Phe Arg Lys Ala Ile Asp Asp Cys Asp Lys
1               5                   10                  15

Gln Ala Tyr His Ser Ser Phe Lys Xaa Cys Met Lys Lys Lys Lys Lys
                20                  25                  30

Glu Phe Lys Ala Gly
            35

<210> SEQ ID NO 179
<211> LENGTH: 42
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(31)
<220> FEATURE:
<221> NAME/KEY: MOD_RES
<222> LOCATION: (42)..(42)
<223> OTHER INFORMATION: C-terminal amidation

<400> SEQUENCE: 179

Cys Asp Ala Thr Cys Gln Phe Arg Lys Ala Ile Asp Asp Cys Val Lys
1               5                   10                  15

Gln Ala His His Ser Asn Val Pro Gly Ser Val Phe Lys Ala Cys Met
                20                  25                  30

Lys Gln Lys Lys Lys Glu Phe Lys Ala Gly
            35                  40

<210> SEQ ID NO 180
<211> LENGTH: 42
<212> TYPE: PRT
<213> ORGANISM: Artificial Sequence
<220> FEATURE:
<223> OTHER INFORMATION: Synthetic Polypeptide
```

```
<220> FEATURE:
<221> NAME/KEY: DISULFID
<222> LOCATION: (1)..(5)
<220> FEATURE:
<221> NAME/KEY: DISULFID
<222> LOCATION: (14)..(31)
<220> FEATURE:
<221> NAME/KEY: MOD_RES
<222> LOCATION: (42)..(42)
<223> OTHER INFORMATION: C-terminal amidation

<400> SEQUENCE: 180

Cys Asp Ala Thr Cys Gln Phe Arg Lys Ala Ile Asp Asp Cys Ala Lys
1               5                   10                  15

Gln Ala His His Ser Asn Val Pro Gly Ser Val Phe Lys Ala Cys Met
            20                  25                  30

Lys Gln Lys Lys Lys Glu Phe Lys Ala Gly
        35                  40

<210> SEQ ID NO 181
<211> LENGTH: 43
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (2)..(6)
<220> FEATURE:
<221> NAME/KEY: DISULFID
<222> LOCATION: (15)..(32)
<220> FEATURE:
<221> NAME/KEY: MOD_RES
<222> LOCATION: (43)..(43)
<223> OTHER INFORMATION: C-terminal amidation

<400> SEQUENCE: 181

Gly Cys Asp Ala Thr Cys Gln Phe Arg Lys Ala Ile Asp Asp Cys Gln
1               5                   10                  15

Lys Gln Ala His His Ser Asn Val Pro Gly Ser Val Phe Lys Ala Cys
            20                  25                  30

Met Lys Gln Lys Lys Lys Glu Phe Lys Ala Gly
        35                  40

<210> SEQ ID NO 182
<211> LENGTH: 43
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(31)

<400> SEQUENCE: 182

Cys Asp Ala Thr Cys Gln Phe Arg Lys Ala Ile Asp Asp Cys Gln Lys
1               5                   10                  15

Gln Ala His His Ser Asn Val Pro Gly Ser Val Phe Lys Ala Cys Met
            20                  25                  30

Lys Gln Lys Lys Lys Glu Phe Lys Ala Gly Lys
        35                  40

<210> SEQ ID NO 183
<211> LENGTH: 43
```

```
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (2)..(6)
<220> FEATURE:
<221> NAME/KEY: DISULFID
<222> LOCATION: (15)..(32)
<220> FEATURE:
<221> NAME/KEY: MOD_RES
<222> LOCATION: (43)..(43)
<223> OTHER INFORMATION: C-terminal amidation

<400> SEQUENCE: 183

Ser Cys Asp Ala Thr Cys Gln Phe Arg Lys Ala Ile Asp Asp Cys Gln
1               5                   10                  15

Lys Gln Ala His His Ser Asn Val Pro Gly Ser Val Phe Lys Ala Cys
            20                  25                  30

Met Lys Gln Lys Lys Lys Glu Phe Lys Ala Gly
        35                  40

<210> SEQ ID NO 184
<211> LENGTH: 43
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (2)..(6)
<220> FEATURE:
<221> NAME/KEY: DISULFID
<222> LOCATION: (15)..(32)
<220> FEATURE:
<221> NAME/KEY: MOD_RES
<222> LOCATION: (43)..(43)
<223> OTHER INFORMATION: C-terminal amidation

<400> SEQUENCE: 184

Ala Cys Asp Ala Thr Cys Gln Phe Arg Lys Ala Ile Asp Asp Cys Gln
1               5                   10                  15

Lys Gln Ala His His Ser Asn Val Pro Gly Ser Val Phe Lys Ala Cys
            20                  25                  30

Met Lys Gln Lys Lys Lys Glu Phe Lys Ala Gly
        35                  40

<210> SEQ ID NO 185
<211> LENGTH: 44
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (3)..(7)
<220> FEATURE:
<221> NAME/KEY: DISULFID
<222> LOCATION: (16)..(33)
<220> FEATURE:
<221> NAME/KEY: MOD_RES
<222> LOCATION: (44)..(44)
<223> OTHER INFORMATION: C-terminal amidation

<400> SEQUENCE: 185

Gly Ser Cys Asp Ala Thr Cys Gln Phe Arg Lys Ala Ile Asp Asp Cys
1               5                   10                  15

Gln Lys Gln Ala His His Ser Asn Val Pro Gly Ser Val Phe Lys Ala
```

```
                20                  25                  30
Cys Met Lys Gln Lys Lys Lys Glu Phe Lys Ala Gly
            35                  40

<210> SEQ ID NO 186
<211> LENGTH: 42
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(31)
<220> FEATURE:
<221> NAME/KEY: MOD_RES
<222> LOCATION: (30)..(30)
<223> OTHER INFORMATION: Xaa = 2-aminoisobutyric acid
<220> FEATURE:
<221> NAME/KEY: MOD_RES
<222> LOCATION: (42)..(42)
<223> OTHER INFORMATION: C-terminal amidation

<400> SEQUENCE: 186

Cys Asp Ala Thr Cys Gln Phe Arg Lys Ala Ile Asp Asp Cys Gln Lys
1               5                   10                  15

Gln Ala His His Ser Asn Val Pro Gly Asn Ser Phe Lys Xaa Cys Met
            20                  25                  30

Lys Gln Lys Lys Lys Glu Phe Lys Ala Gly
            35                  40

<210> SEQ ID NO 187
<211> LENGTH: 42
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(31)
<220> FEATURE:
<221> NAME/KEY: MOD_RES
<222> LOCATION: (30)..(30)
<223> OTHER INFORMATION: Xaa = 2-aminoisobutyric acid
<220> FEATURE:
<221> NAME/KEY: MOD_RES
<222> LOCATION: (39)..(39)
<223> OTHER INFORMATION: Xaa = para-iodophenylalanine
<220> FEATURE:
<221> NAME/KEY: MOD_RES
<222> LOCATION: (42)..(42)
<223> OTHER INFORMATION: C-terminal amidation

<400> SEQUENCE: 187

Cys Asp Ala Thr Cys Gln Phe Arg Lys Ala Ile Asp Asp Cys Gln Lys
1               5                   10                  15

Gln Ala His His Ser Asn Val Pro Gly Ser Val Phe Lys Xaa Cys Met
            20                  25                  30

Lys Gln Lys Lys Lys Glu Xaa Lys Ala Gly
            35                  40

<210> SEQ ID NO 188
<211> LENGTH: 42
<212> TYPE: PRT
```

<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(31)
<220> FEATURE:
<221> NAME/KEY: MOD_RES
<222> LOCATION: (24)..(24)
<223> OTHER INFORMATION: Xaa = 3,4-Dehydro-Proline
<220> FEATURE:
<221> NAME/KEY: MOD_RES
<222> LOCATION: (30)..(30)
<223> OTHER INFORMATION: Xaa = 2-aminoisobutyric acid
<220> FEATURE:
<221> NAME/KEY: MOD_RES
<222> LOCATION: (42)..(42)
<223> OTHER INFORMATION: C-terminal amidation

<400> SEQUENCE: 188

Cys Asp Ala Thr Cys Gln Phe Arg Lys Ala Ile Asp Asp Cys Gln Lys
1               5                   10                  15

Gln Ala His His Ser Asn Val Xaa Gly Ser Val Phe Lys Xaa Cys Met
            20                  25                  30

Lys Gln Lys Lys Lys Glu Phe Lys Ala Gly
        35                  40

<210> SEQ ID NO 189
<211> LENGTH: 43
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(32)
<220> FEATURE:
<221> NAME/KEY: MOD_RES
<222> LOCATION: (31)..(31)
<223> OTHER INFORMATION: Xaa = 2-aminoisobutyric acid
<220> FEATURE:
<221> NAME/KEY: MOD_RES
<222> LOCATION: (43)..(43)
<223> OTHER INFORMATION: C-terminal amidation

<400> SEQUENCE: 189

Cys Asp Ala Thr Cys Gln Phe Arg Lys Ala Ile Asp Asp Cys Gln Lys
1               5                   10                  15

Gln Ala His His Ser Asn Val Pro Gly Asn Ser Val Phe Lys Xaa Cys
            20                  25                  30

Met Lys Gln Lys Lys Lys Glu Phe Lys Ala Gly
        35                  40

<210> SEQ ID NO 190
<211> LENGTH: 42
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(31)

<400> SEQUENCE: 190

Cys Asp Ala Thr Cys Gln Phe Arg Lys Ala Ile Asp Asp Cys Gln Lys
1               5                   10                  15

Gln Ala His His Ser Asn Val Pro Gly Ser Val Phe Lys Ala Cys Met
            20                  25                  30

Lys Gln Lys Lys Lys Glu Phe Lys Ala Gly
        35                  40

<210> SEQ ID NO 191
<211> LENGTH: 42
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(31)
<220> FEATURE:
<221> NAME/KEY: MOD_RES
<222> LOCATION: (30)..(30)
<223> OTHER INFORMATION: Xaa = 2-aminoisobutyric acid
<220> FEATURE:
<221> NAME/KEY: MOD_RES
<222> LOCATION: (42)..(42)
<223> OTHER INFORMATION: C-terminal amidation

<400> SEQUENCE: 191

Cys Asp Ala Thr Cys Gln Phe Arg Lys Ala Ile Asp Asp Cys Gln Lys
1               5                   10                  15

Gln Ala His His Ser Asn Glu Pro Gly Ser Val Phe Lys Xaa Cys Met
            20                  25                  30

Lys Gln Lys Lys Lys Glu Phe Lys Ala Gly
        35                  40

<210> SEQ ID NO 192
<211> LENGTH: 42
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(31)
<220> FEATURE:
<221> NAME/KEY: MOD_RES
<222> LOCATION: (30)..(30)
<223> OTHER INFORMATION: Xaa = 2-aminoisobutyric acid
<220> FEATURE:
<221> NAME/KEY: MOD_RES
<222> LOCATION: (42)..(42)
<223> OTHER INFORMATION: C-terminal amidation

<400> SEQUENCE: 192

Cys Asp Ala Thr Cys Gln Phe Arg Lys Ala Ile Asp Asp Cys Gln Lys
1               5                   10                  15

Gln Ala His His Ser Glu Val Pro Gly Ser Val Phe Lys Xaa Cys Met
            20                  25                  30

Lys Gln Lys Lys Lys Glu Phe Lys Ala Gly
        35                  40

```
<210> SEQ ID NO 193
<211> LENGTH: 42
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(31)
<220> FEATURE:
<221> NAME/KEY: MOD_RES
<222> LOCATION: (30)..(30)
<223> OTHER INFORMATION: Xaa = 2-aminoisobutyric acid
<220> FEATURE:
<221> NAME/KEY: MOD_RES
<222> LOCATION: (42)..(42)
<223> OTHER INFORMATION: C-terminal amidation

<400> SEQUENCE: 193

Cys Asp Ala Thr Cys Gln Phe Arg Lys Ala Ile Asp Asp Cys Gln Lys
1               5                   10                  15

Gln Ala His His Ser Asn Val Pro Asn Ser Val Phe Lys Xaa Cys Met
            20                  25                  30

Lys Gln Lys Lys Lys Glu Phe Lys Ala Gly
        35                  40

<210> SEQ ID NO 194
<211> LENGTH: 42
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(31)
<220> FEATURE:
<221> NAME/KEY: MOD_RES
<222> LOCATION: (30)..(30)
<223> OTHER INFORMATION: Xaa = 2-aminoisobutyric acid
<220> FEATURE:
<221> NAME/KEY: MOD_RES
<222> LOCATION: (42)..(42)
<223> OTHER INFORMATION: C-terminal amidation

<400> SEQUENCE: 194

Cys Asp Ala Thr Cys Gln Phe Arg Lys Ala Ile Asp Asp Cys Gln Lys
1               5                   10                  15

Gln Ala His His Ser Asn Val Gly Asn Ser Val Phe Lys Xaa Cys Met
            20                  25                  30

Lys Gln Lys Lys Lys Glu Phe Lys Ala Gly
        35                  40

<210> SEQ ID NO 195

<400> SEQUENCE: 195

000

<210> SEQ ID NO 196

<400> SEQUENCE: 196

000
```

```
<210> SEQ ID NO 197
<211> LENGTH: 47
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(36)
<220> FEATURE:
<221> NAME/KEY: MOD_RES
<222> LOCATION: (35)..(35)
<223> OTHER INFORMATION: Xaa = 2-aminoisobutyric acid
<220> FEATURE:
<221> NAME/KEY: MOD_RES
<222> LOCATION: (47)..(47)
<223> OTHER INFORMATION: C-terminal amidation

<400> SEQUENCE: 197

Cys Asp Ala Thr Cys Gln Phe Arg Lys Ala Ile Asp Asp Cys Gln Lys
1               5                   10                  15

Gln Ala His His Ser Asn Val Pro Gly Leu Gln Thr Ser Val Ser Val
            20                  25                  30

Phe Lys Xaa Cys Met Lys Gln Lys Lys Lys Glu Phe Lys Ala Gly
            35                  40                  45

<210> SEQ ID NO 198
<211> LENGTH: 42
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(31)
<220> FEATURE:
<221> NAME/KEY: MOD_RES
<222> LOCATION: (26)..(26)
<223> OTHER INFORMATION: Xaa = 2-aminoisobutyric acid
<220> FEATURE:
<221> NAME/KEY: MOD_RES
<222> LOCATION: (30)..(30)
<223> OTHER INFORMATION: Xaa = 2-aminoisobutyric acid
<220> FEATURE:
<221> NAME/KEY: MOD_RES
<222> LOCATION: (42)..(42)
<223> OTHER INFORMATION: C-terminal amidation

<400> SEQUENCE: 198

Cys Asp Ala Thr Cys Gln Phe Arg Lys Ala Ile Asp Asp Cys Gln Lys
1               5                   10                  15

Gln Ala His His Ser Asn Val Pro Gly Xaa Val Phe Lys Xaa Cys Met
            20                  25                  30

Lys Gln Lys Lys Lys Glu Phe Lys Ala Gly
            35                  40

<210> SEQ ID NO 199
<211> LENGTH: 48
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
```

```
<222> LOCATION: (2)..(6)
<220> FEATURE:
<221> NAME/KEY: DISULFID
<222> LOCATION: (15)..(32)

<400> SEQUENCE: 199

Met Cys Asp Ala Thr Cys Gln Phe Arg Lys Ala Ile Asp Asp Cys Gln
1               5                   10                  15

Lys Gln Ala His His Ser Asn Val Pro Gly Ser Val Phe Lys Ala Cys
            20                  25                  30

Met Lys Gln Lys Lys Lys Glu Phe Lys Ala Gly His His His His
        35                  40                  45

<210> SEQ ID NO 200
<211> LENGTH: 42
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(31)
<220> FEATURE:
<221> NAME/KEY: MOD_RES
<222> LOCATION: (30)..(30)
<223> OTHER INFORMATION: Xaa = 2-aminoisobutyric acid
<220> FEATURE:
<221> NAME/KEY: MOD_RES
<222> LOCATION: (42)..(42)
<223> OTHER INFORMATION: C-terminal amidation

<400> SEQUENCE: 200

Cys Asp Ala Thr Cys Gln Phe Arg Lys Ala Ile Asp Asp Cys Gln Lys
1               5                   10                  15

Gln Ala His His Ser Asn Val Pro Gly Asp Val Phe Lys Xaa Cys Met
            20                  25                  30

Lys Gln Lys Lys Lys Glu Phe Lys Ala Gly
        35                  40

<210> SEQ ID NO 201
<211> LENGTH: 41
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(30)
<220> FEATURE:
<221> NAME/KEY: MOD_RES
<222> LOCATION: (29)..(29)
<223> OTHER INFORMATION: Xaa = 2-aminoisobutyric acid
<220> FEATURE:
<221> NAME/KEY: MOD_RES
<222> LOCATION: (41)..(41)
<223> OTHER INFORMATION: C-terminal amidation

<400> SEQUENCE: 201

Cys Asp Ala Thr Cys Gln Phe Arg Lys Ala Ile Asp Asp Cys Asp Lys
1               5                   10                  15

Gln Ala Tyr His Ser Asn Val Pro Gly Ser Phe Lys Xaa Cys Met Lys
            20                  25                  30
```

```
Gln Lys Lys Lys Glu Phe Lys Ala Gly
        35                  40
```

<210> SEQ ID NO 202
<211> LENGTH: 42
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(31)

<400> SEQUENCE: 202

```
Cys Asp Ala Thr Cys Gln Phe Arg Lys Ala Ile Asp Asp Cys Gln Lys
1               5                   10                  15

Gln Ala His His Ser Asn Val Pro Gly Ser Val Phe Lys Ala Cys Met
            20                  25                  30

Lys Gln Lys Lys Lys Glu Phe Lys Ala Asn
        35                  40
```

<210> SEQ ID NO 203
<211> LENGTH: 42
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(31)
<220> FEATURE:
<221> NAME/KEY: MOD_RES
<222> LOCATION: (30)..(30)
<223> OTHER INFORMATION: Xaa = 2-aminoisobutyric acid
<220> FEATURE:
<221> NAME/KEY: MOD_RES
<222> LOCATION: (42)..(42)
<223> OTHER INFORMATION: C-terminal amidation

<400> SEQUENCE: 203

```
Cys Asp Ala Thr Cys Gln Phe Arg Lys Ala Ile Glu Asp Cys Gln Lys
1               5                   10                  15

Gln Ala His His Ser Asn Val Pro Gly Ser Val Phe Lys Xaa Cys Met
            20                  25                  30

Lys Gln Lys Lys Lys Glu Phe Lys Ala Gly
        35                  40
```

<210> SEQ ID NO 204
<211> LENGTH: 49
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (2)..(6)
<220> FEATURE:
<221> NAME/KEY: DISULFID
<222> LOCATION: (15)..(32)

<400> SEQUENCE: 204

```
Met Cys Asp Ala Thr Cys Gln Phe Arg Lys Ala Ile Asp Asp Cys Gln
1               5                   10                  15
```

-continued

Lys Gln Ala His His Ser Asn Val Pro Gly Ser Val Phe Lys Ala Cys
            20                  25                  30

Met Lys Gln Lys Lys Glu Phe Lys Ala Gly His His His His
        35                  40                  45

His

<210> SEQ ID NO 205
<211> LENGTH: 42
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(31)
<220> FEATURE:
<221> NAME/KEY: MOD_RES
<222> LOCATION: (42)..(42)
<223> OTHER INFORMATION: C-terminal amidation

<400> SEQUENCE: 205

Cys Asp Ala Thr Cys Gln Phe Arg Lys Ala Ile Asp Asp Cys Gln Lys
1               5                   10                  15

Gln Ala His His Ser Asn Val Pro Gly Ser Val Phe Lys Ala Cys Met
            20                  25                  30

Lys Gln Lys Lys Lys Glu Phe Lys Ala Asn
        35                  40

<210> SEQ ID NO 206
<211> LENGTH: 42
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(31)
<220> FEATURE:
<221> NAME/KEY: MOD_RES
<222> LOCATION: (30)..(30)
<223> OTHER INFORMATION: Xaa = 2-aminoisobutyric acid

<400> SEQUENCE: 206

Cys Asp Ala Thr Cys Gln Phe Arg Lys Ala Ile Asp Asp Cys Gln Lys
1               5                   10                  15

Gln Ala His His Ser Asn Val Pro Gly Ser Val Phe Lys Xaa Cys Met
            20                  25                  30

Lys Gln Lys Lys Lys Glu Phe Lys Ala Asn
        35                  40

<210> SEQ ID NO 207
<211> LENGTH: 42
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID

```
<222> LOCATION: (14)..(31)
<220> FEATURE:
<221> NAME/KEY: MOD_RES
<222> LOCATION: (42)..(42)
<223> OTHER INFORMATION: C-terminal amidation

<400> SEQUENCE: 207

Cys Asp Ala Thr Cys Gln Phe Arg Lys Ala Ile Asp Asp Cys Gln Lys
1               5                   10                  15
Gln Ala His His Ser Asn Val Pro Gly Ser Val Phe Lys Ser Cys Met
            20                  25                  30
Lys Gln Lys Lys Lys Glu Phe Lys Ala Gly
        35                  40

<210> SEQ ID NO 208
<211> LENGTH: 42
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(31)
<220> FEATURE:
<221> NAME/KEY: MOD_RES
<222> LOCATION: (30)..(30)
<223> OTHER INFORMATION: Xaa = 2-aminoisobutyric acid
<220> FEATURE:
<221> NAME/KEY: MOD_RES
<222> LOCATION: (42)..(42)
<223> OTHER INFORMATION: C-terminal amidation

<400> SEQUENCE: 208

Cys Asp Ala Thr Cys Gln Phe Arg Lys Ala Ile Asp Asp Cys Gln Lys
1               5                   10                  15
Gln Ala His His Ser Asn Val Pro Gly Asn Val Phe Lys Xaa Cys Met
            20                  25                  30
Lys Gln Lys Lys Lys Glu Phe Lys Ala Gly
        35                  40

<210> SEQ ID NO 209
<211> LENGTH: 42
<212> TYPE: PRT
<213> ORGANISM: Artificial Sequence
<220> FEATURE:
<223> OTHER INFORMATION: Synthetic Popypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(31)
<220> FEATURE:
<221> NAME/KEY: MOD_RES
<222> LOCATION: (30)..(30)
<223> OTHER INFORMATION: Xaa = 2-aminoisobutyric acid
<220> FEATURE:
<221> NAME/KEY: MOD_RES
<222> LOCATION: (42)..(42)
<223> OTHER INFORMATION: C-terminal amidation

<400> SEQUENCE: 209

Cys Asp Ala Thr Cys Gln Phe Arg Lys Ala Ile Asp Asp Cys Gln Lys
1               5                   10                  15
Gln Ala His His Ser Asn Val Pro Gly Gly Val Phe Lys Xaa Cys Met
            20                  25                  30
```

Lys Gln Lys Lys Lys Glu Phe Lys Ala Gly
        35                  40

<210> SEQ ID NO 210
<211> LENGTH: 42
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(41)
<220> FEATURE:
<221> NAME/KEY: MOD_RES
<222> LOCATION: (30)..(30)
<223> OTHER INFORMATION: Xaa = 2-aminoisobutyric acid
<220> FEATURE:
<221> NAME/KEY: MOD_RES
<222> LOCATION: (42)..(42)
<223> OTHER INFORMATION: C-terminal amidation

<400> SEQUENCE: 210

Cys Asp Ala Thr Cys Gln Phe Arg Lys Ala Ile Asp Asp Cys Gln Lys
1               5                   10                  15

Gln Ala His His Ser Asn Val Pro Gly Gly Val Phe Lys Xaa Cys Met
            20                  25                  30

Lys Gln Lys Lys Lys Glu Phe Lys Ala Gly
        35                  40

<210> SEQ ID NO 211
<211> LENGTH: 42
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(31)
<220> FEATURE:
<221> NAME/KEY: MOD_RES
<222> LOCATION: (42)..(42)
<223> OTHER INFORMATION: C-terminal amidation

<400> SEQUENCE: 211

Cys Asp Ala Thr Cys Gln Phe Arg Lys Ala Ile Asp Asp Cys Gln Lys
1               5                   10                  15

Gln Ala His His Ser Asn Val Pro Gly Ser Val Phe Lys Val Cys Met
            20                  25                  30

Lys Gln Lys Lys Lys Glu Phe Lys Ala Gly
        35                  40

<210> SEQ ID NO 212

<400> SEQUENCE: 212

000

<210> SEQ ID NO 213
<211> LENGTH: 42
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID

```
<222> LOCATION: (14)..(31)
<220> FEATURE:
<221> NAME/KEY: MOD_RES
<222> LOCATION: (30)..(30)
<223> OTHER INFORMATION: Xaa = 2-aminoisobutyric acid
<220> FEATURE:
<221> NAME/KEY: MOD_RES
<222> LOCATION: (42)..(42)
<223> OTHER INFORMATION: C-terminal amidation

<400> SEQUENCE: 213

Ser Asp Pro Thr Ser Gln Phe Arg Lys Ala Ile Asp Asp Cys Gln Lys
1               5                   10                  15

Gln Ala His His Ser Asn Val Pro Gly Ser Val Phe Lys Xaa Cys Met
            20                  25                  30

Lys Gln Lys Lys Lys Glu Phe Lys Ala Gly
        35                  40

<210> SEQ ID NO 214
<211> LENGTH: 41
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(31)
<220> FEATURE:
<221> NAME/KEY: MOD_RES
<222> LOCATION: (41)..(41)
<223> OTHER INFORMATION: C-terminal amidation

<400> SEQUENCE: 214

Cys Asp Ala Thr Cys Gln Phe Arg Lys Ala Ile Asp Asp Cys Gln Lys
1               5                   10                  15

Gln Ala His His Ser Asn Val Pro Gly Ser Val Phe Lys Ala Cys Met
            20                  25                  30

Lys Gln Lys Lys Lys Glu Phe Lys Ala
        35                  40

<210> SEQ ID NO 215
<211> LENGTH: 42
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(31)
<220> FEATURE:
<221> NAME/KEY: MOD_RES
<222> LOCATION: (30)..(30)
<223> OTHER INFORMATION: Xaa = 2-aminoisobutyric acid
<220> FEATURE:
<221> NAME/KEY: MOD_RES
<222> LOCATION: (42)..(42)
<223> OTHER INFORMATION: C-terminal amidation

<400> SEQUENCE: 215

Cys Asp Ala Thr Cys Gln Phe Arg Lys Ala Ile Asp Glu Cys Gln Lys
1               5                   10                  15

Gln Ala His His Ser Asn Val Pro Gly Ser Val Phe Lys Xaa Cys Met
            20                  25                  30
```

```
Lys Gln Lys Lys Lys Glu Phe Lys Ala Gly
        35                  40

<210> SEQ ID NO 216
<211> LENGTH: 41
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(30)
<220> FEATURE:
<221> NAME/KEY: MOD_RES
<222> LOCATION: (29)..(29)
<223> OTHER INFORMATION: Xaa = 2-aminoisobutyric acid
<220> FEATURE:
<221> NAME/KEY: MOD_RES
<222> LOCATION: (41)..(41)
<223> OTHER INFORMATION: C-terminal amidation

<400> SEQUENCE: 216

Cys Asp Ala Thr Cys Gln Phe Arg Lys Ala Ile Asp Asp Cys Gln Lys
1               5                   10                  15

Gln Ala His His Ser Asn Val Pro Gly Ser Phe Lys Xaa Cys Met Lys
            20                  25                  30

Gln Lys Lys Lys Glu Phe Lys Ala Gly
        35                  40

<210> SEQ ID NO 217
<211> LENGTH: 35
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(26)
<220> FEATURE:
<221> NAME/KEY: MOD_RES
<222> LOCATION: (25)..(25)
<223> OTHER INFORMATION: Xaa = 2-aminoisobutyric acid
<220> FEATURE:
<221> NAME/KEY: MOD_RES
<222> LOCATION: (27)..(27)
<223> OTHER INFORMATION: Xaa = norleucine
<220> FEATURE:
<221> NAME/KEY: MOD_RES
<222> LOCATION: (35)..(35)
<223> OTHER INFORMATION: C-terminal amidation

<400> SEQUENCE: 217

Cys Asp Ala Thr Cys Gln Phe Arg Lys Ala Ile Asp Asp Cys Gln Lys
1               5                   10                  15

Gln Ala His His Ser Ser Phe Lys Xaa Cys Xaa Lys Gln Lys Lys Lys
            20                  25                  30

Glu Phe Lys
        35

<210> SEQ ID NO 218
<211> LENGTH: 36
<212> TYPE: PRT
<213> ORGANISM: Artificial Sequence
```

```
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(27)
<220> FEATURE:
<221> NAME/KEY: MOD_RES
<222> LOCATION: (26)..(26)
<223> OTHER INFORMATION: Xaa = 2-aminoisobutyric acid
<220> FEATURE:
<221> NAME/KEY: MOD_RES
<222> LOCATION: (28)..(28)
<223> OTHER INFORMATION: Xaa = norleucine
<220> FEATURE:
<221> NAME/KEY: MOD_RES
<222> LOCATION: (36)..(36)
<223> OTHER INFORMATION: C-terminal amidation

<400> SEQUENCE: 218

Cys Asp Ala Thr Cys Gln Phe Arg Lys Ala Ile Asp Asp Cys Asp Lys
1               5                   10                  15

Gln Ala His His Ser Ser Val Phe Lys Xaa Cys Xaa Lys Gln Lys Lys
            20                  25                  30

Lys Glu Phe Lys
        35

<210> SEQ ID NO 219
<211> LENGTH: 35
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(26)
<220> FEATURE:
<221> NAME/KEY: MOD_RES
<222> LOCATION: (27)..(27)
<223> OTHER INFORMATION: Xaa = norleucine
<220> FEATURE:
<221> NAME/KEY: MOD_RES
<222> LOCATION: (35)..(35)
<223> OTHER INFORMATION: C-terminal amidation

<400> SEQUENCE: 219

Cys Asp Ala Thr Cys Gln Phe Arg Lys Ala Ile Asp Asp Cys Asp Lys
1               5                   10                  15

Gln Ala His His Ser Ser Phe Lys Glu Cys Xaa Lys Gln Lys Lys Lys
            20                  25                  30

Glu Phe Lys
        35

<210> SEQ ID NO 220
<211> LENGTH: 36
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(27)
<220> FEATURE:
```

```
<221> NAME/KEY: MOD_RES
<222> LOCATION: (28)..(28)
<223> OTHER INFORMATION: Xaa = norleucine
<220> FEATURE:
<221> NAME/KEY: MOD_RES
<222> LOCATION: (36)..(36)
<223> OTHER INFORMATION: C-terminal amidation

<400> SEQUENCE: 220

Cys Asp Ala Thr Cys Gln Phe Arg Lys Ala Ile Asp Asp Cys Asp Lys
1               5                   10                  15

Gln Ala His His Ser Asn Ser Phe Lys Glu Cys Xaa Lys Gln Lys Lys
            20                  25                  30

Lys Glu Phe Lys
        35

<210> SEQ ID NO 221
<211> LENGTH: 36
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(27)
<220> FEATURE:
<221> NAME/KEY: MOD_RES
<222> LOCATION: (28)..(28)
<223> OTHER INFORMATION: Xaa = norleucine
<220> FEATURE:
<221> NAME/KEY: MOD_RES
<222> LOCATION: (36)..(36)
<223> OTHER INFORMATION: C-terminal amidation

<400> SEQUENCE: 221

Cys Asp Ala Thr Cys Gln Phe Arg Lys Ala Ile Asp Asp Cys Asp Lys
1               5                   10                  15

Gln Ala His His Ser Ser Val Phe Lys Glu Cys Xaa Lys Gln Lys Lys
            20                  25                  30

Lys Glu Phe Lys
        35

<210> SEQ ID NO 222
<211> LENGTH: 36
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(27)
<220> FEATURE:
<221> NAME/KEY: MOD_RES
<222> LOCATION: (36)..(36)
<223> OTHER INFORMATION: C-terminal amidation

<400> SEQUENCE: 222

Cys Asp Ala Thr Cys Gln Phe Arg Lys Ala Ile Asp Asp Cys Asp Lys
1               5                   10                  15

Gln Ala His His Ser Asn Ser Phe Lys Glu Cys Met Lys Gln Lys Lys
            20                  25                  30

Lys Glu Phe Lys
```

-continued

```
                35

<210> SEQ ID NO 223
<211> LENGTH: 36
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(27)
<220> FEATURE:
<221> NAME/KEY: MOD_RES
<222> LOCATION: (36)..(36)
<223> OTHER INFORMATION: C-terminal amidation

<400> SEQUENCE: 223

Cys Asp Ala Thr Cys Gln Phe Arg Lys Ala Ile Asp Asp Cys Asp Lys
1               5                   10                  15

Gln Ala His His Ser Ser Val Phe Lys Glu Cys Met Lys Gln Lys Lys
            20                  25                  30

Lys Glu Phe Lys
        35

<210> SEQ ID NO 224
<211> LENGTH: 36
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(27)
<220> FEATURE:
<221> NAME/KEY: MOD_RES
<222> LOCATION: (36)..(36)
<223> OTHER INFORMATION: C-terminal amidation

<400> SEQUENCE: 224

Cys Asp Ala Thr Cys Gln Phe Arg Lys Ala Ile Asp Asp Cys Gln Lys
1               5                   10                  15

Gln Ala His His Ser Asn Ser Phe Lys Glu Cys Met Lys Gln Lys Lys
            20                  25                  30

Lys Glu Phe Lys
        35

<210> SEQ ID NO 225
<211> LENGTH: 36
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(27)
<220> FEATURE:
<221> NAME/KEY: MOD_RES
<222> LOCATION: (36)..(36)
<223> OTHER INFORMATION: C-terminal amidation

<400> SEQUENCE: 225
```

Cys Asp Ala Thr Cys Gln Phe Arg Lys Ala Ile Asp Asp Cys Gln Lys
1               5                   10                  15

Gln Ala His His Ser Ser Val Phe Lys Glu Cys Met Lys Gln Lys Lys
            20                  25                  30

Lys Glu Phe Lys
        35

<210> SEQ ID NO 226
<211> LENGTH: 42
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(31)
<220> FEATURE:
<221> NAME/KEY: MOD_RES
<222> LOCATION: (42)..(42)
<223> OTHER INFORMATION: C-terminal amidation

<400> SEQUENCE: 226

Cys Asp Ala Thr Cys Gln Phe Arg Lys Ala Ile Asp Asp Cys Gln Lys
1               5                   10                  15

Gln Ala His His Ser Asn Val Pro Gly Ser Val Phe Lys Leu Cys Met
            20                  25                  30

Lys Gln Lys Lys Lys Glu Phe Lys Ala Gly
        35                  40

<210> SEQ ID NO 227
<211> LENGTH: 42
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(31)
<220> FEATURE:
<221> NAME/KEY: MOD_RES
<222> LOCATION: (30)..(30)
<223> OTHER INFORMATION: Xaa = 2-aminoisobutyric acid
<220> FEATURE:
<221> NAME/KEY: MOD_RES
<222> LOCATION: (42)..(42)
<223> OTHER INFORMATION: C-terminal amidation

<400> SEQUENCE: 227

Cys Asp Ala Thr Cys Gln Phe Arg Lys Ala Ile Asp Asp Cys Gln Lys
1               5                   10                  15

Gln Ala His His Ser Asn Gly Pro Ala Ala Val Phe Lys Xaa Cys Met
            20                  25                  30

Lys Gln Lys Lys Lys Glu Phe Lys Ala Gly
        35                  40

<210> SEQ ID NO 228
<211> LENGTH: 42
<212> TYPE: PRT
<213> ORGANISM: Artificial Sequence
<220> FEATURE:
<223> OTHER INFORMATION: Synthetic Polypeptide

```
<220> FEATURE:
<221> NAME/KEY: DISULFID
<222> LOCATION: (1)..(5)
<220> FEATURE:
<221> NAME/KEY: DISULFID
<222> LOCATION: (14)..(31)
<220> FEATURE:
<221> NAME/KEY: MOD_RES
<222> LOCATION: (30)..(30)
<223> OTHER INFORMATION: Xaa = 2-aminoisobutyric acid
<220> FEATURE:
<221> NAME/KEY: MOD_RES
<222> LOCATION: (42)..(42)
<223> OTHER INFORMATION: C-terminal amidation

<400> SEQUENCE: 228

Cys Asp Ala Thr Cys Gln Phe Arg Lys Ala Ile Asp Asp Cys Gln Lys
1               5                   10                  15

Gln Ala His His Ser Asn Val Pro Gly Ser Val Phe Lys Xaa Cys Met
            20                  25                  30

Lys Gln Lys Lys Lys Glu Phe Lys Ala Asn
        35                  40

<210> SEQ ID NO 229
<211> LENGTH: 42
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(31)
<220> FEATURE:
<221> NAME/KEY: MOD_RES
<222> LOCATION: (30)..(30)
<223> OTHER INFORMATION: Xaa = 2-aminoisobutyric acid
<220> FEATURE:
<221> NAME/KEY: MOD_RES
<222> LOCATION: (42)..(42)
<223> OTHER INFORMATION: C-terminal amidation

<400> SEQUENCE: 229

Cys Asp Ala Thr Cys Gln Phe Arg Lys Ala Ile Asp Asp Cys Asp Arg
1               5                   10                  15

Gln Ala His His Ser Asn Val Pro Gly Ser Val Phe Lys Xaa Cys Met
            20                  25                  30

Lys Gln Lys Lys Lys Glu Phe Lys Ala Gly
        35                  40

<210> SEQ ID NO 230
<211> LENGTH: 42
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(31)
<220> FEATURE:
<221> NAME/KEY: MOD_RES
<222> LOCATION: (30)..(30)
<223> OTHER INFORMATION: Xaa = D-alanine
<220> FEATURE:
<221> NAME/KEY: MOD_RES
<222> LOCATION: (42)..(42)
```

<223> OTHER INFORMATION: C-terminal amidation

<400> SEQUENCE: 230

Cys Asp Ala Thr Cys Gln Phe Arg Lys Ala Ile Asp Asp Cys Gln Lys
1               5                   10                  15

Gln Ala His His Ser Asn Val Pro Gly Ser Val Phe Lys Xaa Cys Met
            20                  25                  30

Lys Gln Lys Lys Lys Glu Phe Lys Ala Gly
        35                  40

<210> SEQ ID NO 231
<211> LENGTH: 42
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(31)
<220> FEATURE:
<221> NAME/KEY: MOD_RES
<222> LOCATION: (30)..(30)
<223> OTHER INFORMATION: Xaa = 2-aminoisobutyric acid
<220> FEATURE:
<221> NAME/KEY: MOD_RES
<222> LOCATION: (42)..(42)
<223> OTHER INFORMATION: C-terminal amidation

<400> SEQUENCE: 231

Cys Asp Ala Thr Cys Gln Phe Arg Lys Ala Ile Asp Asp Cys Gln Lys
1               5                   10                  15

Gln Ala His His Ser Asn Val Pro Gly Ser Val Phe Lys Xaa Cys Met
            20                  25                  30

Lys Gln Lys Lys Lys Glu Trp Lys Ala Gly
        35                  40

<210> SEQ ID NO 232
<211> LENGTH: 15
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MOD_RES
<222> LOCATION: (3)..(3)
<223> OTHER INFORMATION: Xaa = 2-aminoisobutyric acid
<220> FEATURE:
<221> NAME/KEY: MOD_RES
<222> LOCATION: (15)..(15)
<223> OTHER INFORMATION: C-terminal amidation

<400> SEQUENCE: 232

Phe Lys Xaa Cys Met Lys Gln Lys Lys Lys Glu Phe Lys Ala Gly
1               5                   10                  15

<210> SEQ ID NO 233
<211> LENGTH: 42
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID

```
<222> LOCATION: (14)..(31)
<220> FEATURE:
<221> NAME/KEY: MOD_RES
<222> LOCATION: (42)..(42)
<223> OTHER INFORMATION: C-terminal amidation

<400> SEQUENCE: 233

Cys Asp Ala Thr Cys Gln Phe Arg Lys Ala Ile Asp Asp Cys Gln Lys
1               5                   10                  15

Gln Ala His His Ser Asn Val Pro Gly Ser Val Phe Lys Ala Cys Met
            20                  25                  30

Lys Gln Lys Lys Lys Glu Phe Lys Ala Gly
        35                  40

<210> SEQ ID NO 234
<211> LENGTH: 41
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(30)
<220> FEATURE:
<221> NAME/KEY: MOD_RES
<222> LOCATION: (29)..(29)
<223> OTHER INFORMATION: Xaa = 2-aminoisobutyric acid
<220> FEATURE:
<221> NAME/KEY: MOD_RES
<222> LOCATION: (41)..(41)
<223> OTHER INFORMATION: C-terminal amidation

<400> SEQUENCE: 234

Cys Asp Ala Thr Cys Gln Phe Arg Lys Ala Ile Asp Asp Cys Asp Lys
1               5                   10                  15

Gln Ala His His Ser Asn Val Pro Gly Ser Phe Lys Xaa Cys Met Lys
            20                  25                  30

Gln Lys Lys Lys Glu Phe Lys Ala Gly
        35                  40

<210> SEQ ID NO 235
<211> LENGTH: 42
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(31)
<220> FEATURE:
<221> NAME/KEY: MOD_RES
<222> LOCATION: (30)..(30)
<223> OTHER INFORMATION: Xaa = 2-aminoisobutyric acid
<220> FEATURE:
<221> NAME/KEY: MOD_RES
<222> LOCATION: (42)..(42)
<223> OTHER INFORMATION: C-terminal amidation

<400> SEQUENCE: 235

Cys Asp Ala Thr Cys Gln Phe Arg Lys Ala Ile Asp Asp Cys Gln Lys
1               5                   10                  15

Gln Ala Tyr His Ser Asn Val Pro Gly Ser Val Phe Lys Xaa Cys Met
            20                  25                  30
```

Lys Gln Lys Lys Lys Glu Phe Lys Ala Gly
        35                  40

<210> SEQ ID NO 236
<211> LENGTH: 42
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: MOD_RES
<222> LOCATION: (1)..(1)
<223> OTHER INFORMATION: Xaa = N-terminal acetylation
<220> FEATURE:
<221> NAME/KEY: DISULFID
<222> LOCATION: (14)..(31)
<220> FEATURE:
<221> NAME/KEY: MOD_RES
<222> LOCATION: (30)..(30)
<223> OTHER INFORMATION: Xaa = 2-aminoisobutyric acid
<220> FEATURE:
<221> NAME/KEY: MOD_RES
<222> LOCATION: (42)..(42)
<223> OTHER INFORMATION: C-terminal amidation

<400> SEQUENCE: 236

Cys Asp Ala Thr Cys Gln Phe Arg Lys Ala Ile Asp Asp Cys Asp Lys
1               5                   10                  15

Gln Ala His His Ser Asn Val Pro Gly Ser Val Phe Lys Xaa Cys Met
            20                  25                  30

Lys Gln Lys Lys Lys Glu Phe Lys Ala Gly
        35                  40

<210> SEQ ID NO 237
<211> LENGTH: 41
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(30)
<220> FEATURE:
<221> NAME/KEY: MOD_RES
<222> LOCATION: (29)..(29)
<223> OTHER INFORMATION: Xaa = 2-aminoisobutyric acid
<220> FEATURE:
<221> NAME/KEY: MOD_RES
<222> LOCATION: (41)..(41)
<223> OTHER INFORMATION: C-terminal amidation

<400> SEQUENCE: 237

Cys Asp Ala Thr Cys Gln Phe Arg Lys Ala Ile Asp Asp Cys Gln Lys
1               5                   10                  15

Gln Ala His His Ser Asn Val Pro Gly Val Phe Lys Xaa Cys Met Lys
            20                  25                  30

Gln Lys Lys Lys Glu Phe Lys Ala Gly
        35                  40

<210> SEQ ID NO 238
<211> LENGTH: 41
<212> TYPE: PRT
<213> ORGANISM: Artificial Sequence

```
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(30)
<220> FEATURE:
<221> NAME/KEY: MOD_RES
<222> LOCATION: (29)..(29)
<223> OTHER INFORMATION: Xaa = 2-aminoisobutyric acid
<220> FEATURE:
<221> NAME/KEY: MOD_RES
<222> LOCATION: (41)..(41)
<223> OTHER INFORMATION: C-terminal amidation

<400> SEQUENCE: 238

Cys Asp Ala Thr Cys Gln Phe Arg Lys Ala Ile Asp Asp Cys Asp Lys
1               5                   10                  15

Gln Ala His His Ser Asn Val Pro Gly Val Phe Lys Xaa Cys Met Lys
            20                  25                  30

Gln Lys Lys Lys Glu Phe Lys Ala Gly
        35                  40

<210> SEQ ID NO 239
<211> LENGTH: 41
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: MOD_RES
<222> LOCATION: (1)..(1)
<223> OTHER INFORMATION: Xaa = N-terminal acetylation
<220> FEATURE:
<221> NAME/KEY: DISULFID
<222> LOCATION: (14)..(30)
<220> FEATURE:
<221> NAME/KEY: MOD_RES
<222> LOCATION: (29)..(29)
<223> OTHER INFORMATION: Xaa = 2-aminoisobutyric acid
<220> FEATURE:
<221> NAME/KEY: MOD_RES
<222> LOCATION: (41)..(41)
<223> OTHER INFORMATION: C-terminal amidation

<400> SEQUENCE: 239

Cys Asp Ala Thr Cys Gln Phe Arg Lys Ala Ile Asp Asp Cys Asp Lys
1               5                   10                  15

Gln Ala His His Ser Asn Val Pro Gly Ser Phe Lys Xaa Cys Met Lys
            20                  25                  30

Gln Lys Lys Lys Glu Phe Lys Ala Gly
        35                  40

<210> SEQ ID NO 240
<211> LENGTH: 35
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(26)
<220> FEATURE:
```

<221> NAME/KEY: MOD_RES
<222> LOCATION: (25)..(25)
<223> OTHER INFORMATION: Xaa = 2-aminoisobutyric acid
<220> FEATURE:
<221> NAME/KEY: MOD_RES
<222> LOCATION: (35)..(35)
<223> OTHER INFORMATION: C-terminal amidation

<400> SEQUENCE: 240

Cys Asp Ala Thr Cys Gln Phe Arg Lys Ala Ile Asp Asp Cys Asp Lys
1               5                   10                  15

Gln Ala His His Ser Ser Phe Lys Xaa Cys Met Lys Gln Lys Lys Lys
                20                  25                  30

Glu Phe Lys
        35

<210> SEQ ID NO 241
<211> LENGTH: 36
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(27)
<220> FEATURE:
<221> NAME/KEY: MOD_RES
<222> LOCATION: (26)..(26)
<223> OTHER INFORMATION: Xaa = 2-aminoisobutyric acid
<220> FEATURE:
<221> NAME/KEY: MOD_RES
<222> LOCATION: (28)..(28)
<223> OTHER INFORMATION: Xaa = norleucine
<220> FEATURE:
<221> NAME/KEY: MOD_RES
<222> LOCATION: (36)..(36)
<223> OTHER INFORMATION: C-terminal amidation

<400> SEQUENCE: 241

Cys Asp Ala Thr Cys Gln Phe Arg Lys Ala Ile Asp Asp Cys Gln Lys
1               5                   10                  15

Gln Ala His His Ser Asn Ser Phe Lys Xaa Cys Xaa Lys Gln Lys Lys
                20                  25                  30

Lys Glu Phe Lys
            35

<210> SEQ ID NO 242
<211> LENGTH: 36
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(27)
<220> FEATURE:
<221> NAME/KEY: MOD_RES
<222> LOCATION: (26)..(26)
<223> OTHER INFORMATION: Xaa = 2-aminoisobutyric acid
<220> FEATURE:
<221> NAME/KEY: MOD_RES
<222> LOCATION: (28)..(28)
<223> OTHER INFORMATION: Xaa = norleucine
<220> FEATURE:
<221> NAME/KEY: MOD_RES

```
<222> LOCATION: (36)..(36)
<223> OTHER INFORMATION: C-terminal amidation

<400> SEQUENCE: 242

Cys Asp Ala Thr Cys Gln Phe Arg Lys Ala Ile Asp Asp Cys Gln Lys
1               5                   10                  15

Gln Ala His His Ser Ser Val Phe Lys Xaa Cys Xaa Lys Gln Lys Lys
            20                  25                  30

Lys Glu Phe Lys
        35

<210> SEQ ID NO 243
<211> LENGTH: 35
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(26)
<220> FEATURE:
<221> NAME/KEY: MOD_RES
<222> LOCATION: (25)..(25)
<223> OTHER INFORMATION: Xaa = 2-aminoisobutyric acid
<220> FEATURE:
<221> NAME/KEY: MOD_RES
<222> LOCATION: (35)..(35)
<223> OTHER INFORMATION: C-terminal amidation

<400> SEQUENCE: 243

Cys Asp Ala Thr Cys Gln Phe Arg Lys Ala Ile Asp Asp Cys Gln Lys
1               5                   10                  15

Gln Ala His His Ser Ser Phe Lys Xaa Cys Met Lys Gln Lys Lys Lys
            20                  25                  30

Glu Phe Lys
        35

<210> SEQ ID NO 244
<211> LENGTH: 36
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(27)
<220> FEATURE:
<221> NAME/KEY: MOD_RES
<222> LOCATION: (26)..(26)
<223> OTHER INFORMATION: Xaa = 2-aminoisobutyric acid
<220> FEATURE:
<221> NAME/KEY: MOD_RES
<222> LOCATION: (36)..(36)
<223> OTHER INFORMATION: C-terminal amidation

<400> SEQUENCE: 244

Cys Asp Ala Thr Cys Gln Phe Arg Lys Ala Ile Asp Asp Cys Asp Lys
1               5                   10                  15

Gln Ala His His Ser Asn Ser Phe Lys Xaa Cys Met Lys Gln Lys Lys
            20                  25                  30

Lys Glu Phe Lys
        35
```

<210> SEQ ID NO 245
<211> LENGTH: 36
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(27)
<220> FEATURE:
<221> NAME/KEY: MOD_RES
<222> LOCATION: (26)..(26)
<223> OTHER INFORMATION: Xaa = 2-aminoisobutyric acid
<220> FEATURE:
<221> NAME/KEY: MOD_RES
<222> LOCATION: (36)..(36)
<223> OTHER INFORMATION: C-terminal amidation

<400> SEQUENCE: 245

Cys Asp Ala Thr Cys Gln Phe Arg Lys Ala Ile Asp Asp Cys Asp Lys
1               5                   10                  15

Gln Ala His His Ser Ser Val Phe Lys Xaa Cys Met Lys Gln Lys Lys
            20                  25                  30

Lys Glu Phe Lys
        35

<210> SEQ ID NO 246
<211> LENGTH: 37
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(28)
<220> FEATURE:
<221> NAME/KEY: MOD_RES
<222> LOCATION: (27)..(27)
<223> OTHER INFORMATION: Xaa = 2-aminoisobutyric acid
<220> FEATURE:
<221> NAME/KEY: MOD_RES
<222> LOCATION: (29)..(29)
<223> OTHER INFORMATION: Xaa = norleucine
<220> FEATURE:
<221> NAME/KEY: MOD_RES
<222> LOCATION: (37)..(37)
<223> OTHER INFORMATION: C-terminal amidation

<400> SEQUENCE: 246

Cys Asp Ala Thr Cys Gln Phe Arg Lys Ala Ile Asp Asp Cys Gln Lys
1               5                   10                  15

Gln Ala His His Ser Asn Ser Val Phe Lys Xaa Cys Xaa Lys Gln Lys
            20                  25                  30

Lys Lys Glu Phe Lys
        35

<210> SEQ ID NO 247
<211> LENGTH: 36
<212> TYPE: PRT
<213> ORGANISM: Artificial Sequence
<220> FEATURE:
<223> OTHER INFORMATION: Synthetic Polypeptide
<220> FEATURE:

-continued

```
<221> NAME/KEY: DISULFID
<222> LOCATION: (1)..(5)
<220> FEATURE:
<221> NAME/KEY: DISULFID
<222> LOCATION: (14)..(27)
<220> FEATURE:
<221> NAME/KEY: MOD_RES
<222> LOCATION: (26)..(26)
<223> OTHER INFORMATION: Xaa = 2-aminoisobutyric acid
<220> FEATURE:
<221> NAME/KEY: MOD_RES
<222> LOCATION: (36)..(36)
<223> OTHER INFORMATION: C-terminal amidation

<400> SEQUENCE: 247

Cys Asp Ala Thr Cys Gln Phe Arg Lys Ala Ile Asp Asp Cys Gln Lys
1               5                   10                  15

Gln Ala His His Ser Asn Ser Phe Lys Xaa Cys Met Lys Gln Lys Lys
            20                  25                  30

Lys Glu Phe Lys
        35

<210> SEQ ID NO 248
<211> LENGTH: 41
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(30)
<220> FEATURE:
<221> NAME/KEY: MOD_RES
<222> LOCATION: (29)..(29)
<223> OTHER INFORMATION: Xaa = 2-aminoisobutyric acid
<220> FEATURE:
<221> NAME/KEY: MOD_RES
<222> LOCATION: (31)..(31)
<223> OTHER INFORMATION: Xaa = norleucine
<220> FEATURE:
<221> NAME/KEY: MOD_RES
<222> LOCATION: (41)..(41)
<223> OTHER INFORMATION: C-terminal amidation

<400> SEQUENCE: 248

Cys Asp Ala Thr Cys Gln Phe Arg Lys Ala Ile Asp Asp Cys Asp Lys
1               5                   10                  15

Gln Ala His His Ser Asn Val Pro Ser Val Phe Lys Xaa Cys Xaa Lys
            20                  25                  30

Gln Lys Lys Lys Glu Phe Lys Ala Gly
        35                  40

<210> SEQ ID NO 249
<211> LENGTH: 41
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: MOD_RES
<222> LOCATION: (1)..(1)
<223> OTHER INFORMATION: Xaa = N-terminal acetylation
<220> FEATURE:
<221> NAME/KEY: DISULFID
<222> LOCATION: (14)..(31)
```

```
<220> FEATURE:
<221> NAME/KEY: MOD_RES
<222> LOCATION: (30)..(30)
<223> OTHER INFORMATION: Xaa = 2-aminoisobutyric acid
<220> FEATURE:
<221> NAME/KEY: MOD_RES
<222> LOCATION: (41)..(41)
<223> OTHER INFORMATION: C-terminal amidation

<400> SEQUENCE: 249

Cys Asp Ala Thr Cys Gln Phe Arg Lys Ala Ile Asp Asp Cys Gln Lys
1               5                   10                  15

Gln Ala His His Ser Asn Val Pro Gly Ser Val Phe Lys Xaa Cys Met
            20                  25                  30

Lys Gln Lys Lys Lys Glu Phe Lys Ala
        35                  40

<210> SEQ ID NO 250
<211> LENGTH: 41
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(31)
<220> FEATURE:
<221> NAME/KEY: MOD_RES
<222> LOCATION: (30)..(30)
<223> OTHER INFORMATION: Xaa = 2-aminoisobutyric acid
<220> FEATURE:
<221> NAME/KEY: MOD_RES
<222> LOCATION: (41)..(41)
<223> OTHER INFORMATION: C-terminal amidation

<400> SEQUENCE: 250

Cys Asp Ala Thr Cys Gln Phe Arg Lys Ala Ile Asp Asp Cys Gln Lys
1               5                   10                  15

Gln Ala His His Ser Asn Val Pro Gly Ser Val Phe Lys Xaa Cys Met
            20                  25                  30

Lys Gln Lys Lys Lys Glu Phe Lys Ala
        35                  40

<210> SEQ ID NO 251
<211> LENGTH: 41
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(30)
<220> FEATURE:
<221> NAME/KEY: MOD_RES
<222> LOCATION: (29)..(29)
<223> OTHER INFORMATION: Xaa = 2-aminoisobutyric acid
<220> FEATURE:
<221> NAME/KEY: MOD_RES
<222> LOCATION: (31)..(31)
<223> OTHER INFORMATION: Xaa = norleucine
<220> FEATURE:
<221> NAME/KEY: MOD_RES
<222> LOCATION: (41)..(41)
<223> OTHER INFORMATION: C-terminal amidation
```

<400> SEQUENCE: 251

Cys Asp Ala Thr Cys Gln Phe Arg Lys Ala Ile Asp Asp Cys Asp Lys
1               5                   10                  15

Gln Ala Tyr His Ser Asn Val Pro Ser Val Phe Lys Xaa Cys Xaa Lys
            20                  25                  30

Gln Lys Lys Lys Glu Phe Lys Ala Gly
        35                  40

<210> SEQ ID NO 252
<211> LENGTH: 41
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(30)
<220> FEATURE:
<221> NAME/KEY: MOD_RES
<222> LOCATION: (29)..(29)
<223> OTHER INFORMATION: Xaa = 2-aminoisobutyric acid
<220> FEATURE:
<221> NAME/KEY: MOD_RES
<222> LOCATION: (31)..(31)
<223> OTHER INFORMATION: Xaa = norleucine
<220> FEATURE:
<221> NAME/KEY: MOD_RES
<222> LOCATION: (41)..(41)
<223> OTHER INFORMATION: C-terminal amidation

<400> SEQUENCE: 252

Cys Asp Ala Thr Cys Gln Phe Arg Lys Ala Ile Asp Asp Cys Asp Lys
1               5                   10                  15

Gln Ala His His Ser Asn Val Pro Gly Ser Phe Lys Xaa Cys Xaa Lys
            20                  25                  30

Gln Lys Lys Lys Glu Phe Lys Ala Gly
        35                  40

<210> SEQ ID NO 253
<211> LENGTH: 42
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MOD_RES
<222> LOCATION: (1)..(1)
<223> OTHER INFORMATION: Xaa = N-terminal acetylation
<220> FEATURE:
<221> NAME/KEY: DISULFID
<222> LOCATION: (1)..(5)
<220> FEATURE:
<221> NAME/KEY: DISULFID
<222> LOCATION: (14)..(31)
<220> FEATURE:
<221> NAME/KEY: MOD_RES
<222> LOCATION: (30)..(30)
<223> OTHER INFORMATION: Xaa = 2-aminoisobutyric acid
<220> FEATURE:
<221> NAME/KEY: MOD_RES
<222> LOCATION: (42)..(42)
<223> OTHER INFORMATION: C-terminal amidation

<400> SEQUENCE: 253

Cys Asp Ala Thr Cys Gln Phe Arg Lys Ala Ile Asp Asp Cys Gln Lys
1               5                   10                  15

Gln Ala His His Ser Asn Val Pro Gly Ser Val Phe Lys Xaa Cys Met
            20                  25                  30

Lys Gln Lys Lys Lys Glu Phe Lys Ala Gly
            35                  40

<210> SEQ ID NO 254
<211> LENGTH: 42
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(31)
<220> FEATURE:
<221> NAME/KEY: MOD_RES
<222> LOCATION: (30)..(30)
<223> OTHER INFORMATION: Xaa = 2-aminoisobutyric acid
<220> FEATURE:
<221> NAME/KEY: MOD_RES
<222> LOCATION: (42)..(42)
<223> OTHER INFORMATION: C-terminal amidation

<400> SEQUENCE: 254

Cys Asp Ala Thr Cys Gln Phe Arg Lys Ala Ile Asp Asp Cys Asp Lys
1               5                   10                  15

Gln Ala His His Ser Asn Val Pro Gly Ser Val Phe Lys Xaa Cys Met
            20                  25                  30

Lys Gln Lys Lys Lys Glu Phe Lys Ala Gly
            35                  40

<210> SEQ ID NO 255
<211> LENGTH: 42
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(31)
<220> FEATURE:
<221> NAME/KEY: MOD_RES
<222> LOCATION: (30)..(30)
<223> OTHER INFORMATION: Xaa = 2-aminoisobutyric acid
<220> FEATURE:
<221> NAME/KEY: MOD_RES
<222> LOCATION: (32)..(32)
<223> OTHER INFORMATION: Xaa = norleucine
<220> FEATURE:
<221> NAME/KEY: MOD_RES
<222> LOCATION: (42)..(42)
<223> OTHER INFORMATION: C-terminal amidation

<400> SEQUENCE: 255

Cys Asp Ala Thr Cys Gln Phe Arg Lys Ala Ile Asp Asp Cys Asp Lys
1               5                   10                  15

Gln Ala His His Ser Asn Val Pro Gly Ser Val Phe Lys Xaa Cys Xaa
            20                  25                  30

Lys Gln Lys Lys Lys Glu Phe Lys Ala Gly
            35                  40

<210> SEQ ID NO 256
<211> LENGTH: 37

```
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(28)
<220> FEATURE:
<221> NAME/KEY: MOD_RES
<222> LOCATION: (27)..(27)
<223> OTHER INFORMATION: Xaa = 2-aminoisobutyric acid
<220> FEATURE:
<221> NAME/KEY: MOD_RES
<222> LOCATION: (37)..(37)
<223> OTHER INFORMATION: C-terminal amidation

<400> SEQUENCE: 256

Cys Asp Ala Thr Cys Gln Phe Arg Lys Ala Ile Asp Asp Cys Gln Lys
1               5                   10                  15

Gln Ala His His Ser Asn Ser Val Phe Lys Xaa Cys Met Lys Gln Lys
            20                  25                  30

Lys Lys Glu Phe Lys
        35

<210> SEQ ID NO 257
<211> LENGTH: 39
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(30)
<220> FEATURE:
<221> NAME/KEY: MOD_RES
<222> LOCATION: (29)..(29)
<223> OTHER INFORMATION: Xaa = 2-aminoisobutyric acid
<220> FEATURE:
<221> NAME/KEY: MOD_RES
<222> LOCATION: (31)..(31)
<223> OTHER INFORMATION: Xaa = norleucine
<220> FEATURE:
<221> NAME/KEY: MOD_RES
<222> LOCATION: (39)..(39)
<223> OTHER INFORMATION: C-terminal amidation

<400> SEQUENCE: 257

Cys Asp Ala Thr Cys Gln Phe Arg Lys Ala Ile Asp Asp Cys Asp Lys
1               5                   10                  15

Gln Ala His His Ser Asn Val Pro Gly Ser Phe Lys Xaa Cys Xaa Lys
            20                  25                  30

Gln Lys Lys Lys Glu Phe Lys
        35

<210> SEQ ID NO 258
<211> LENGTH: 40
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
```

```
<222> LOCATION: (14)..(31)
<220> FEATURE:
<221> NAME/KEY: MOD_RES
<222> LOCATION: (30)..(30)
<223> OTHER INFORMATION: Xaa = 2-aminoisobutyric acid
<220> FEATURE:
<221> NAME/KEY: MOD_RES
<222> LOCATION: (32)..(32)
<223> OTHER INFORMATION: Xaa = norleucine
<220> FEATURE:
<221> NAME/KEY: MOD_RES
<222> LOCATION: (40)..(40)
<223> OTHER INFORMATION: C-terminal amidation

<400> SEQUENCE: 258

Cys Asp Ala Thr Cys Gln Phe Arg Lys Ala Ile Asp Asp Cys Asp Lys
1               5                   10                  15

Gln Ala His His Ser Asn Val Pro Gly Asn Ser Phe Lys Xaa Cys Xaa
            20                  25                  30

Lys Gln Lys Lys Lys Glu Phe Lys
        35                  40

<210> SEQ ID NO 259
<211> LENGTH: 40
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(31)
<220> FEATURE:
<221> NAME/KEY: MOD_RES
<222> LOCATION: (30)..(30)
<223> OTHER INFORMATION: Xaa = 2-aminoisobutyric acid
<220> FEATURE:
<221> NAME/KEY: MOD_RES
<222> LOCATION: (32)..(32)
<223> OTHER INFORMATION: Xaa = norleucine
<220> FEATURE:
<221> NAME/KEY: MOD_RES
<222> LOCATION: (40)..(40)
<223> OTHER INFORMATION: C-terminal amidation

<400> SEQUENCE: 259

Cys Asp Ala Thr Cys Gln Phe Arg Lys Ala Ile Asp Asp Cys Asp Lys
1               5                   10                  15

Gln Ala His His Ser Asn Val Pro Gly Ser Val Phe Lys Xaa Cys Xaa
            20                  25                  30

Lys Gln Lys Lys Lys Glu Phe Lys
        35                  40

<210> SEQ ID NO 260
<211> LENGTH: 40
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: MOD_RES
<222> LOCATION: (1)..(1)
<223> OTHER INFORMATION: Xaa = N-terminal acetylation
<220> FEATURE:
<221> NAME/KEY: DISULFID
<222> LOCATION: (14)..(31)
```

```
<220> FEATURE:
<221> NAME/KEY: MOD_RES
<222> LOCATION: (30)..(30)
<223> OTHER INFORMATION: Xaa = 2-aminoisobutyric acid
<220> FEATURE:
<221> NAME/KEY: MOD_RES
<222> LOCATION: (32)..(32)
<223> OTHER INFORMATION: Xaa = norleucine
<220> FEATURE:
<221> NAME/KEY: MOD_RES
<222> LOCATION: (40)..(40)
<223> OTHER INFORMATION: C-terminal amidation

<400> SEQUENCE: 260

Cys Asp Ala Thr Cys Gln Phe Arg Lys Ala Ile Asp Asp Cys Gln Lys
1               5                   10                  15

Gln Ala His His Ser Asn Val Pro Gly Ser Val Phe Lys Xaa Cys Xaa
            20                  25                  30

Lys Gln Lys Lys Lys Glu Phe Lys
        35                  40

<210> SEQ ID NO 261
<211> LENGTH: 41
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(32)
<220> FEATURE:
<221> NAME/KEY: MOD_RES
<222> LOCATION: (31)..(31)
<223> OTHER INFORMATION: Xaa = 2-aminoisobutyric acid
<220> FEATURE:
<221> NAME/KEY: MOD_RES
<222> LOCATION: (33)..(33)
<223> OTHER INFORMATION: Xaa = norleucine
<220> FEATURE:
<221> NAME/KEY: MOD_RES
<222> LOCATION: (41)..(41)
<223> OTHER INFORMATION: C-terminal amidation

<400> SEQUENCE: 261

Cys Asp Ala Thr Cys Gln Phe Arg Lys Ala Ile Asp Asp Cys Asp Lys
1               5                   10                  15

Gln Ala His His Ser Asn Val Pro Gly Asn Ser Val Phe Lys Xaa Cys
            20                  25                  30

Xaa Lys Gln Lys Lys Lys Glu Phe Lys
        35                  40

<210> SEQ ID NO 262
<211> LENGTH: 41
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(30)
<220> FEATURE:
<221> NAME/KEY: MOD_RES
<222> LOCATION: (29)..(29)
<223> OTHER INFORMATION: Xaa = 2-aminoisobutyric acid
<220> FEATURE:
```

<221> NAME/KEY: MOD_RES
<222> LOCATION: (41)..(41)
<223> OTHER INFORMATION: C-terminal amidation

<400> SEQUENCE: 262

Cys Asp Ala Thr Cys Gln Phe Arg Lys Ala Ile Asp Asp Cys Gln Lys
1               5                   10                  15

Gln Ala His His Ser Asn Val Gly Ser Val Phe Lys Xaa Cys Met Lys
            20                  25                  30

Gln Lys Lys Lys Glu Phe Lys Ala Gly
        35                  40

<210> SEQ ID NO 263
<211> LENGTH: 42
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(31)
<220> FEATURE:
<221> NAME/KEY: MOD_RES
<222> LOCATION: (30)..(30)
<223> OTHER INFORMATION: Xaa = 2-aminoisobutyric acid
<220> FEATURE:
<221> NAME/KEY: MOD_RES
<222> LOCATION: (32)..(32)
<223> OTHER INFORMATION: Xaa = norleucine
<220> FEATURE:
<221> NAME/KEY: MOD_RES
<222> LOCATION: (42)..(42)
<223> OTHER INFORMATION: C-terminal amidation

<400> SEQUENCE: 263

Cys Asp Ala Thr Cys Gln Phe Arg Lys Ala Ile Asp Asp Cys Gln Lys
1               5                   10                  15

Gln Ala His His Ser Asn Val Pro Gly Ser Val Phe Lys Xaa Cys Xaa
            20                  25                  30

Lys Gln Lys Lys Lys Glu Phe Lys Ala Gly
        35                  40

<210> SEQ ID NO 264
<211> LENGTH: 40
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(31)
<220> FEATURE:
<221> NAME/KEY: MOD_RES
<222> LOCATION: (30)..(30)
<223> OTHER INFORMATION: Xaa = 2-aminoisobutyric acid
<220> FEATURE:
<221> NAME/KEY: MOD_RES
<222> LOCATION: (32)..(32)
<223> OTHER INFORMATION: Xaa = norleucine
<220> FEATURE:
<221> NAME/KEY: MOD_RES
<222> LOCATION: (40)..(40)
<223> OTHER INFORMATION: C-terminal amidation

<400> SEQUENCE: 264

```
Cys Asp Ala Thr Cys Gln Phe Arg Lys Ala Ile Asp Asp Cys Gln Lys
1               5                   10                  15

Gln Ala His His Ser Asn Val Pro Gly Ser Val Phe Lys Xaa Cys Xaa
            20                  25                  30

Lys Gln Lys Lys Lys Glu Phe Lys
        35                  40
```

<210> SEQ ID NO 265
<211> LENGTH: 40
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(4)
<220> FEATURE:
<221> NAME/KEY: DISULFID
<222> LOCATION: (13)..(31)
<220> FEATURE:
<221> NAME/KEY: MOD_RES
<222> LOCATION: (39)..(39)
<223> OTHER INFORMATION: Xaa = alpha-methyl-phenylalanine
<220> FEATURE:
<221> NAME/KEY: MOD_RES
<222> LOCATION: (40)..(40)
<223> OTHER INFORMATION: C-terminal amidation

<400> SEQUENCE: 265

```
Cys Asp Ala Cys Gln Phe Arg Lys Ala Ile Asp Asp Cys Gln Lys Gln
1               5                   10                  15

Ala His His Ser Asn Val Pro Gly Asn Ser Val Phe Lys Glu Cys Met
            20                  25                  30

Lys Gln Lys Lys Lys Glu Xaa Lys
        35                  40
```

<210> SEQ ID NO 266
<211> LENGTH: 41
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(32)
<220> FEATURE:
<221> NAME/KEY: MOD_RES
<222> LOCATION: (33)..(33)
<223> OTHER INFORMATION: Xaa = norleucine
<220> FEATURE:
<221> NAME/KEY: MOD_RES
<222> LOCATION: (41)..(41)
<223> OTHER INFORMATION: C-terminal amidation

<400> SEQUENCE: 266

```
Cys Asp Ala Thr Cys Gln Phe Arg Lys Ala Ile Asp Asp Cys Asp Lys
1               5                   10                  15

Gln Ala His His Ser Asn Val Pro Gly Asn Ser Val Phe Lys Glu Cys
            20                  25                  30

Xaa Lys Gln Lys Lys Lys Glu Phe Lys
        35                  40
```

<210> SEQ ID NO 267
<211> LENGTH: 40

```
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(31)
<220> FEATURE:
<221> NAME/KEY: MOD_RES
<222> LOCATION: (30)..(30)
<223> OTHER INFORMATION: Xaa = 2-aminoisobutyric acid
<220> FEATURE:
<221> NAME/KEY: MOD_RES
<222> LOCATION: (32)..(32)
<223> OTHER INFORMATION: Xaa = norleucine
<220> FEATURE:
<221> NAME/KEY: MOD_RES
<222> LOCATION: (40)..(40)
<223> OTHER INFORMATION: C-terminal amidation

<400> SEQUENCE: 267

Cys Asp Ala Thr Cys Gln Phe Arg Lys Ala Ile Asp Asp Cys Gln Lys
1               5                   10                  15

Gln Ala His His Ser Asn Val Pro Gly Asn Ser Phe Lys Xaa Cys Xaa
            20                  25                  30

Lys Gln Lys Lys Lys Glu Phe Lys
        35                  40

<210> SEQ ID NO 268
<211> LENGTH: 41
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(32)
<220> FEATURE:
<221> NAME/KEY: MOD_RES
<222> LOCATION: (31)..(31)
<223> OTHER INFORMATION: Xaa = 2-aminoisobutyric acid
<220> FEATURE:
<221> NAME/KEY: MOD_RES
<222> LOCATION: (33)..(33)
<223> OTHER INFORMATION: Xaa = norleucine
<220> FEATURE:
<221> NAME/KEY: MOD_RES
<222> LOCATION: (41)..(41)
<223> OTHER INFORMATION: C-terminal amidation

<400> SEQUENCE: 268

Cys Asp Ala Thr Cys Gln Phe Arg Lys Ala Ile Asp Asp Cys Gln Lys
1               5                   10                  15

Gln Ala His His Ser Asn Val Pro Gly Asn Ser Val Phe Lys Xaa Cys
            20                  25                  30

Xaa Lys Gln Lys Lys Lys Glu Phe Lys
            35                  40

<210> SEQ ID NO 269
<211> LENGTH: 40
<212> TYPE: PRT
<213> ORGANISM: Artificial Sequence
<220> FEATURE:
<223> OTHER INFORMATION: Synthetic Polypeptide
<220> FEATURE:
```

<220> FEATURE:
<221> NAME/KEY: DISULFID
<222> LOCATION: (1)..(5)
<220> FEATURE:
<221> NAME/KEY: DISULFID
<222> LOCATION: (14)..(31)
<220> FEATURE:
<221> NAME/KEY: MOD_RES
<222> LOCATION: (32)..(32)
<223> OTHER INFORMATION: Xaa = norleucine
<220> FEATURE:
<221> NAME/KEY: MOD_RES
<222> LOCATION: (40)..(40)
<223> OTHER INFORMATION: C-terminal amidation

<400> SEQUENCE: 269

Cys Asp Ala Thr Cys Gln Phe Arg Lys Ala Ile Asp Asp Cys Gln Lys
1               5                   10                  15

Gln Ala His His Ser Asn Val Pro Gly Ser Val Phe Lys Glu Cys Xaa
            20                  25                  30

Lys Gln Lys Lys Lys Glu Phe Lys
        35                  40

<210> SEQ ID NO 270
<211> LENGTH: 40
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(31)
<220> FEATURE:
<221> NAME/KEY: MOD_RES
<222> LOCATION: (30)..(30)
<223> OTHER INFORMATION: Xaa = 2-aminoisobutyric acid
<220> FEATURE:
<221> NAME/KEY: MOD_RES
<222> LOCATION: (40)..(40)
<223> OTHER INFORMATION: C-terminal amidation

<400> SEQUENCE: 270

Cys Asp Ala Thr Cys Gln Phe Arg Lys Ala Ile Asp Asp Cys Asp Lys
1               5                   10                  15

Gln Ala His His Ser Asn Val Pro Gly Asn Ser Phe Lys Xaa Cys Met
            20                  25                  30

Lys Gln Lys Lys Lys Glu Phe Lys
        35                  40

<210> SEQ ID NO 271
<211> LENGTH: 40
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(31)
<220> FEATURE:
<221> NAME/KEY: MOD_RES
<222> LOCATION: (30)..(30)
<223> OTHER INFORMATION: Xaa = 2-aminoisobutyric acid
<220> FEATURE:
<221> NAME/KEY: MOD_RES
<222> LOCATION: (40)..(40)
<223> OTHER INFORMATION: C-terminal amidation

<400> SEQUENCE: 271

Cys Asp Ala Thr Cys Gln Phe Arg Lys Ala Ile Asp Asp Cys Asp Lys
1               5                   10                  15

Gln Ala His His Ser Asn Val Pro Gly Ser Val Phe Lys Xaa Cys Met
            20                  25                  30

Lys Gln Lys Lys Lys Glu Phe Lys
        35                  40

<210> SEQ ID NO 272
<211> LENGTH: 42
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(32)

<400> SEQUENCE: 272

Cys Asp Ala Thr Cys Gln Phe Arg Lys Ala Ile Asp Asp Cys Gln Lys
1               5                   10                  15

Gln Ala His His Ser Asn Val Pro Gly Asn Ser Val Phe Lys Glu Cys
            20                  25                  30

Met Lys Gln Lys Lys Lys Glu Phe Lys Ala
        35                  40

<210> SEQ ID NO 273
<211> LENGTH: 43
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(32)

<400> SEQUENCE: 273

Cys Asp Ala Thr Cys Gln Phe Arg Lys Ala Ile Asp Asp Cys Gln Lys
1               5                   10                  15

Gln Ala His His Ser Asn Val Pro Gly Asn Ser Val Phe Lys Glu Cys
            20                  25                  30

Met Lys Gln Lys Lys Lys Glu Phe Lys Ala Gly
        35                  40

<210> SEQ ID NO 274
<211> LENGTH: 35
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(26)
<220> FEATURE:
<221> NAME/KEY: MOD_RES
<222> LOCATION: (25)..(25)
<223> OTHER INFORMATION: Xaa = 2-aminoisobutyric acid

```
<220> FEATURE:
<221> NAME/KEY: MOD_RES
<222> LOCATION: (27)..(27)
<223> OTHER INFORMATION: Xaa = norleucine
<220> FEATURE:
<221> NAME/KEY: MOD_RES
<222> LOCATION: (35)..(35)
<223> OTHER INFORMATION: C-terminal amidation

<400> SEQUENCE: 274

Cys Asp Ala Thr Cys Gln Phe Arg Lys Ala Ile Asp Asp Cys Asp Lys
1               5                   10                  15

Gln Ala His His Ser Ser Phe Lys Xaa Cys Xaa Lys Gln Lys Lys
            20                  25                  30

Glu Phe Lys
        35

<210> SEQ ID NO 275
<211> LENGTH: 40
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(31)
<220> FEATURE:
<221> NAME/KEY: MOD_RES
<222> LOCATION: (40)..(40)
<223> OTHER INFORMATION: C-terminal amidation

<400> SEQUENCE: 275

Cys Asp Ala Thr Cys Gln Phe Arg Lys Ala Ile Asp Asp Cys Gln Lys
1               5                   10                  15

Gln Ala His His Ser Asn Val Gly Asn Ser Val Phe Lys Glu Cys Met
            20                  25                  30

Lys Gln Lys Lys Lys Glu Phe Lys
        35                  40

<210> SEQ ID NO 276
<211> LENGTH: 41
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(32)
<220> FEATURE:
<221> NAME/KEY: MOD_RES
<222> LOCATION: (41)..(41)
<223> OTHER INFORMATION: C-terminal amidation

<400> SEQUENCE: 276

Cys Asp Ala Thr Cys Gln Phe Arg Lys Ala Ile Asp Asp Cys Gln Lys
1               5                   10                  15

Gln Ala His His Ser Asn Val Pro Gly Asn Ser Val Phe Lys Glu Cys
            20                  25                  30

Met Lys Gln Lys Lys Gln Glu Phe Lys
        35                  40
```

```
<210> SEQ ID NO 277
<211> LENGTH: 41
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(32)
<220> FEATURE:
<221> NAME/KEY: MOD_RES
<222> LOCATION: (38)..(38)
<223> OTHER INFORMATION: Xaa = ornithine
<220> FEATURE:
<221> NAME/KEY: MOD_RES
<222> LOCATION: (41)..(41)
<223> OTHER INFORMATION: C-terminal amidation

<400> SEQUENCE: 277

Cys Asp Ala Thr Cys Gln Phe Arg Lys Ala Ile Asp Asp Cys Gln Lys
1               5                   10                  15

Gln Ala His His Ser Asn Val Pro Gly Asn Ser Val Phe Lys Glu Cys
            20                  25                  30

Met Lys Gln Lys Lys Xaa Glu Phe Lys
        35                  40

<210> SEQ ID NO 278
<211> LENGTH: 41
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(32)
<220> FEATURE:
<221> NAME/KEY: MOD_RES
<222> LOCATION: (38)..(38)
<223> OTHER INFORMATION: Xaa = D-Lysine
<220> FEATURE:
<221> NAME/KEY: MOD_RES
<222> LOCATION: (41)..(41)
<223> OTHER INFORMATION: C-terminal amidation

<400> SEQUENCE: 278

Cys Asp Ala Thr Cys Gln Phe Arg Lys Ala Ile Asp Asp Cys Gln Lys
1               5                   10                  15

Gln Ala His His Ser Asn Val Pro Gly Asn Ser Val Phe Lys Glu Cys
            20                  25                  30

Met Lys Gln Lys Lys Xaa Glu Phe Lys
        35                  40

<210> SEQ ID NO 279
<211> LENGTH: 41
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(32)
<220> FEATURE:
```

```
<221> NAME/KEY: MOD_RES
<222> LOCATION: (41)..(41)
<223> OTHER INFORMATION: C-terminal amidation

<400> SEQUENCE: 279
```

Cys Asp Ala Thr Cys Gln Phe Arg Lys Ala Ile Asp Asp Cys Gln Lys
1               5                   10                  15

Gln Ala His His Ser Asn Val Pro Gly Asn Ser Val Phe Lys Glu Cys
                20                  25                  30

Met Lys Gln Lys Lys Ala Glu Phe Lys
            35                  40

```
<210> SEQ ID NO 280
<211> LENGTH: 41
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(32)
<220> FEATURE:
<221> NAME/KEY: MOD_RES
<222> LOCATION: (41)..(41)
<223> OTHER INFORMATION: C-terminal amidation

<400> SEQUENCE: 280
```

Cys Asp Ala Thr Cys Gln Phe Arg Lys Ala Ile Asp Asp Cys Gln Lys
1               5                   10                  15

Gln Ala His His Ser Asn Val Pro Gly Asn Ser Val Phe Lys Glu Cys
                20                  25                  30

Met Lys Gln Lys Lys Gly Glu Phe Lys
            35                  40

```
<210> SEQ ID NO 281
<211> LENGTH: 41
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(32)
<220> FEATURE:
<221> NAME/KEY: MOD_RES
<222> LOCATION: (36)..(36)
<223> OTHER INFORMATION: Xaa = D-lysine
<220> FEATURE:
<221> NAME/KEY: MOD_RES
<222> LOCATION: (41)..(41)
<223> OTHER INFORMATION: C-terminal amidation

<400> SEQUENCE: 281
```

Cys Asp Ala Thr Cys Gln Phe Arg Lys Ala Ile Asp Asp Cys Gln Lys
1               5                   10                  15

Gln Ala His His Ser Asn Val Pro Gly Asn Ser Val Phe Lys Glu Cys
                20                  25                  30

Met Lys Gln Xaa Lys Lys Glu Phe Lys
            35                  40

```
<210> SEQ ID NO 282
```

```
<211> LENGTH: 41
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(32)
<220> FEATURE:
<221> NAME/KEY: MOD_RES
<222> LOCATION: (40)..(40)
<223> OTHER INFORMATION: Xaa = homophenylalanine
<220> FEATURE:
<221> NAME/KEY: MOD_RES
<222> LOCATION: (41)..(41)
<223> OTHER INFORMATION: C-terminal amidation

<400> SEQUENCE: 282

Cys Asp Ala Thr Cys Gln Phe Arg Lys Ala Ile Asp Asp Cys Gln Lys
1               5                   10                  15

Gln Ala His His Ser Asn Val Pro Gly Asn Ser Val Phe Lys Glu Cys
            20                  25                  30

Met Lys Gln Lys Lys Lys Glu Xaa Lys
        35                  40

<210> SEQ ID NO 283
<211> LENGTH: 42
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(31)
<220> FEATURE:
<221> NAME/KEY: MOD_RES
<222> LOCATION: (30)..(30)
<223> OTHER INFORMATION: Xaa = 2-aminoisobutyric acid
<220> FEATURE:
<221> NAME/KEY: MOD_RES
<222> LOCATION: (42)..(42)
<223> OTHER INFORMATION: C-terminal amidation

<400> SEQUENCE: 283

Cys Asp Ala Thr Cys Gln Phe Arg Lys Ala Ile Asp Asp Cys Gln Lys
1               5                   10                  15

Gln Ala His His Ser Asn Val Pro Gly Ser Val Phe Lys Xaa Cys Met
            20                  25                  30

Lys Gln Lys Lys Lys Glu Phe Lys Ala Gly
        35                  40

<210> SEQ ID NO 284
<211> LENGTH: 41
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(32)
<220> FEATURE:
<221> NAME/KEY: MOD_RES
```

```
<222> LOCATION: (41)..(41)
<223> OTHER INFORMATION: C-terminal amidation

<400> SEQUENCE: 284

Cys Asp Ala Thr Cys Gln Phe Arg Lys Ala Ile Asp Asp Cys Gln Lys
1               5                   10                  15

Gln Ala His His Ser Asn Val Pro Gly Asn Ser Val Phe Lys Glu Cys
            20                  25                  30

Met Lys Gln Lys Gln Lys Glu Phe Lys
            35                  40

<210> SEQ ID NO 285
<211> LENGTH: 41
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(32)
<220> FEATURE:
<221> NAME/KEY: MOD_RES
<222> LOCATION: (41)..(41)
<223> OTHER INFORMATION: C-terminal amidation

<400> SEQUENCE: 285

Cys Asp Ala Thr Cys Gln Phe Arg Lys Ala Ile Asp Asp Cys Gln Lys
1               5                   10                  15

Gln Ala His His Ser Asn Val Pro Gly Asn Ser Val Phe Lys Glu Cys
            20                  25                  30

Met Lys Gln Gly Lys Lys Glu Phe Lys
            35                  40

<210> SEQ ID NO 286
<211> LENGTH: 41
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(32)
<220> FEATURE:
<221> NAME/KEY: MOD_RES
<222> LOCATION: (17)..(17)
<223> OTHER INFORMATION: Xaa = 2-aminoisobutyric acid
<220> FEATURE:
<221> NAME/KEY: MOD_RES
<222> LOCATION: (41)..(41)
<223> OTHER INFORMATION: C-terminal amidation

<400> SEQUENCE: 286

Cys Asp Ala Thr Cys Gln Phe Arg Lys Ala Ile Asp Asp Cys Gln Lys
1               5                   10                  15

Xaa Ala His His Ser Asn Val Pro Gly Asn Ser Val Phe Lys Glu Cys
            20                  25                  30

Met Lys Gln Lys Lys Lys Glu Phe Lys
            35                  40

<210> SEQ ID NO 287
<211> LENGTH: 41
```

```
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(32)
<220> FEATURE:
<221> NAME/KEY: MOD_RES
<222> LOCATION: (41)..(41)
<223> OTHER INFORMATION: C-terminal amidation

<400> SEQUENCE: 287

Cys Asp Ala Thr Cys Gln Phe Arg Lys Ala Ile Asp Cys Gln Lys
1               5                   10                  15

Gln Ala His His Ser Asn Val Pro Gly Asn Ser Val Phe Lys Glu Cys
            20                  25                  30

Met Lys Gln Lys Lys Lys Ala Phe Lys
        35                  40

<210> SEQ ID NO 288
<211> LENGTH: 41
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(32)
<220> FEATURE:
<221> NAME/KEY: MOD_RES
<222> LOCATION: (41)..(41)
<223> OTHER INFORMATION: C-terminal amidation

<400> SEQUENCE: 288

Cys Asp Ala Thr Cys Gln Phe Arg Lys Ala Ile Asp Cys Gln Arg
1               5                   10                  15

Gln Ala His His Ser Asn Val Pro Gly Asn Ser Val Phe Lys Glu Cys
            20                  25                  30

Met Lys Gln Lys Lys Lys Glu Phe Lys
        35                  40

<210> SEQ ID NO 289
<211> LENGTH: 41
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(32)
<220> FEATURE:
<221> NAME/KEY: MOD_RES
<222> LOCATION: (20)..(20)
<223> OTHER INFORMATION: Xaa = 2-aminoisobutyric acid
<220> FEATURE:
<221> NAME/KEY: MOD_RES
<222> LOCATION: (41)..(41)
<223> OTHER INFORMATION: C-terminal amidation

<400> SEQUENCE: 289
```

-continued

```
Cys Asp Ala Thr Cys Gln Phe Arg Lys Ala Ile Asp Asp Cys Gln Lys
1               5                   10                  15

Gln Ala His Xaa Ser Asn Val Pro Gly Asn Ser Val Phe Lys Glu Cys
            20                  25                  30

Met Lys Gln Lys Lys Lys Glu Phe Lys
        35                  40
```

<210> SEQ ID NO 290
<211> LENGTH: 44
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: MOD_RES
<222> LOCATION: (1)..(1)
<223> OTHER INFORMATION: Xaa = N-terminal acetylation
<220> FEATURE:
<221> NAME/KEY: DISULFID
<222> LOCATION: (14)..(32)

<400> SEQUENCE: 290

```
Cys Asp Ala Thr Cys Gln Phe Arg Lys Ala Ile Asp Asp Cys Gln Lys
1               5                   10                  15

Gln Ala His His Ser Asn Val Pro Gly Asn Ser Val Phe Lys Glu Cys
            20                  25                  30

Met Lys Gln Lys Lys Lys Glu Phe Lys Ala Gly Lys
        35                  40
```

<210> SEQ ID NO 291
<211> LENGTH: 41
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(32)
<220> FEATURE:
<221> NAME/KEY: MOD_RES
<222> LOCATION: (38)..(38)
<223> OTHER INFORMATION: Xaa = N-methyllysine
<220> FEATURE:
<221> NAME/KEY: MOD_RES
<222> LOCATION: (41)..(41)
<223> OTHER INFORMATION: C-terminal amidation

<400> SEQUENCE: 291

```
Cys Asp Ala Thr Cys Gln Phe Arg Lys Ala Ile Asp Asp Cys Gln Lys
1               5                   10                  15

Gln Ala His His Ser Asn Val Pro Gly Asn Ser Val Phe Lys Glu Cys
            20                  25                  30

Met Lys Gln Lys Lys Xaa Glu Phe Lys
        35                  40
```

<210> SEQ ID NO 292
<211> LENGTH: 41
<212> TYPE: PRT
<213> ORGANISM: Artificial Sequence
<220> FEATURE:
<223> OTHER INFORMATION: Synthetic Polypeptide
<220> FEATURE:

```
<221> NAME/KEY: DISULFID
<222> LOCATION: (1)..(5)
<220> FEATURE:
<221> NAME/KEY: DISULFID
<222> LOCATION: (14)..(32)
<220> FEATURE:
<221> NAME/KEY: MOD_RES
<222> LOCATION: (41)..(41)
<223> OTHER INFORMATION: Xaa = C-terminal amidation
<220> FEATURE:
<221> NAME/KEY: MOD_RES
<222> LOCATION: (41)..(41)
<223> OTHER INFORMATION: Xaa = N -methyllysine

<400> SEQUENCE: 292

Cys Asp Ala Thr Cys Gln Phe Arg Lys Ala Ile Asp Asp Cys Gln Lys
1               5                   10                  15

Gln Ala His His Ser Asn Val Pro Gly Asn Ser Val Phe Lys Glu Cys
            20                  25                  30

Met Lys Gln Lys Lys Lys Glu Phe Xaa
            35                  40

<210> SEQ ID NO 293
<211> LENGTH: 40
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(31)
<220> FEATURE:
<221> NAME/KEY: MOD_RES
<222> LOCATION: (40)..(40)
<223> OTHER INFORMATION: C-terminal amidation

<400> SEQUENCE: 293

Cys Asp Ala Thr Cys Gln Phe Arg Lys Ala Ile Asp Asp Cys Gln Lys
1               5                   10                  15

Gln Ala His His Ser Asn Val Pro Gly Ser Val Phe Lys Glu Cys Met
            20                  25                  30

Lys Gln Lys Lys Lys Glu Phe Lys
            35                  40

<210> SEQ ID NO 294
<211> LENGTH: 44
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(32)
<220> FEATURE:
<221> NAME/KEY: MOD_RES
<222> LOCATION: (44)..(44)
<223> OTHER INFORMATION: C-terminal amidation

<400> SEQUENCE: 294

Cys Asp Ala Thr Cys Gln Phe Arg Lys Ala Ile Asp Asp Cys Gln Lys
1               5                   10                  15

Gln Ala His His Ser Asn Val Pro Gly Asn Ser Val Phe Lys Glu Cys
            20                  25                  30
```

```
Met Lys Gln Lys Lys Lys Glu Phe Lys Ala Gly Lys
        35                  40
```

<210> SEQ ID NO 295
<211> LENGTH: 41
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(32)
<220> FEATURE:
<221> NAME/KEY: MOD_RES
<222> LOCATION: (41)..(41)
<223> OTHER INFORMATION: C-terminal amidation

<400> SEQUENCE: 295

```
Cys Asp Ala Thr Cys Gln Phe Arg Lys Ala Ile Asp Asp Cys Asp Lys
1               5                   10                  15

Gln Ala His His Ser Asn Val Pro Gly Asn Ser Val Phe Lys Glu Cys
            20                  25                  30

Met Lys Gln Lys Lys Lys Glu Phe Lys
        35                  40
```

<210> SEQ ID NO 296
<211> LENGTH: 41
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(32)
<220> FEATURE:
<221> NAME/KEY: MOD_RES
<222> LOCATION: (31)..(31)
<223> OTHER INFORMATION: Xaa = 2-aminoisobutyric acid
<220> FEATURE:
<221> NAME/KEY: MOD_RES
<222> LOCATION: (41)..(41)
<223> OTHER INFORMATION: C-terminal amidation

<400> SEQUENCE: 296

```
Cys Asp Ala Thr Cys Gln Phe Arg Lys Ala Ile Asp Asp Cys Gln Lys
1               5                   10                  15

Gln Ala His His Ser Asn Val Pro Gly Asn Ser Val Phe Lys Xaa Cys
            20                  25                  30

Met Lys Gln Lys Lys Lys Glu Phe Lys
        35                  40
```

<210> SEQ ID NO 297
<211> LENGTH: 41
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(32)

<220> FEATURE:
<221> NAME/KEY: MOD_RES
<222> LOCATION: (40)..(40)
<223> OTHER INFORMATION: Xaa = alpha-methyl-phenylalanine
<220> FEATURE:
<221> NAME/KEY: MOD_RES
<222> LOCATION: (41)..(41)
<223> OTHER INFORMATION: C-terminal amidation

<400> SEQUENCE: 297

Cys Asp Ala Thr Cys Gln Phe Arg Lys Ala Ile Asp Asp Cys Gln Lys
1               5                   10                  15

Gln Ala His His Ser Asn Val Pro Gly Asn Ser Val Phe Lys Glu Cys
            20                  25                  30

Met Lys Gln Lys Lys Lys Glu Xaa Lys
        35                  40

<210> SEQ ID NO 298
<211> LENGTH: 41
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(32)
<220> FEATURE:
<221> NAME/KEY: MOD_RES
<222> LOCATION: (33)..(33)
<223> OTHER INFORMATION: Xaa = norleucine
<220> FEATURE:
<221> NAME/KEY: MOD_RES
<222> LOCATION: (41)..(41)
<223> OTHER INFORMATION: C-terminal amidation

<400> SEQUENCE: 298

Cys Asp Ala Thr Cys Gln Phe Arg Lys Ala Ile Asp Asp Cys Gln Lys
1               5                   10                  15

Gln Ala His His Ser Asn Val Pro Gly Asn Ser Val Phe Lys Glu Cys
            20                  25                  30

Xaa Lys Gln Lys Lys Lys Glu Phe Lys
        35                  40

<210> SEQ ID NO 299
<211> LENGTH: 41
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(32)
<220> FEATURE:
<221> NAME/KEY: MOD_RES
<222> LOCATION: (36)..(36)
<223> OTHER INFORMATION: Xaa = ornithine
<220> FEATURE:
<221> NAME/KEY: MOD_RES
<222> LOCATION: (41)..(41)
<223> OTHER INFORMATION: C-terminal amidation

<400> SEQUENCE: 299

Cys Asp Ala Thr Cys Gln Phe Arg Lys Ala Ile Asp Asp Cys Gln Lys
1               5                   10                  15

Gln Ala His His Ser Asn Val Pro Gly Asn Ser Val Phe Lys Glu Cys
            20                  25                  30

Met Lys Gln Xaa Lys Lys Glu Phe Lys
            35                  40

<210> SEQ ID NO 300
<211> LENGTH: 44
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(32)

<400> SEQUENCE: 300

Cys Asp Ala Thr Cys Gln Phe Arg Lys Ala Ile Asp Asp Cys Gln Lys
1               5                   10                  15

Gln Ala His His Ser Asn Val Pro Gly Asn Ser Val Phe Lys Glu Cys
            20                  25                  30

Met Lys Gln Lys Lys Lys Glu Phe Lys Ala Gly His
            35                  40

<210> SEQ ID NO 301
<211> LENGTH: 41
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(32)
<220> FEATURE:
<221> NAME/KEY: MOD_RES
<222> LOCATION: (41)..(41)
<223> OTHER INFORMATION: C-terminal amidation

<400> SEQUENCE: 301

Cys Asp Ala Thr Cys Gln Phe Arg Lys Ala Ile Asp Asp Cys Gln Lys
1               5                   10                  15

Gln Ala His His Ser Asn Val Pro Gly Asn Ser Val Phe Lys Glu Cys
            20                  25                  30

Met Lys Gln Lys Lys Lys Glu Trp Lys
            35                  40

<210> SEQ ID NO 302
<211> LENGTH: 41
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(32)
<220> FEATURE:
<221> NAME/KEY: MOD_RES
<222> LOCATION: (41)..(41)
<223> OTHER INFORMATION: C-terminal amidation

```
<400> SEQUENCE: 302

Cys Asp Ala Thr Cys Gln Phe Arg Lys Ala Ile Asp Asp Cys Gln Lys
1               5                   10                  15

Gln Ala His His Ser Asn Val Pro Gly Asn Ser Val Phe Lys Glu Cys
            20                  25                  30

Met Lys Gln Lys Lys Lys Glu Phe His
            35                  40

<210> SEQ ID NO 303
<211> LENGTH: 41
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(32)
<220> FEATURE:
<221> NAME/KEY: MOD_RES
<222> LOCATION: (41)..(41)
<223> OTHER INFORMATION: C-terminal amidation

<400> SEQUENCE: 303

Cys Asp Ala Thr Cys Gln Phe Arg Lys Ala Ile Asp Asp Cys Gln Lys
1               5                   10                  15

Gln Ala His His Ser Asn Val Pro Gly Asn Ser Val Phe Lys Glu Cys
            20                  25                  30

Met Lys Gln Lys Lys Lys Glu Phe Gln
            35                  40

<210> SEQ ID NO 304
<211> LENGTH: 41
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(32)
<220> FEATURE:
<221> NAME/KEY: MOD_RES
<222> LOCATION: (41)..(41)
<223> OTHER INFORMATION: Xaa = C-terminal amidation
<220> FEATURE:
<221> NAME/KEY: MOD_RES
<222> LOCATION: (41)..(41)
<223> OTHER INFORMATION: Xaa = D-lysine

<400> SEQUENCE: 304

Cys Asp Ala Thr Cys Gln Phe Arg Lys Ala Ile Asp Asp Cys Gln Lys
1               5                   10                  15

Gln Ala His His Ser Asn Val Pro Gly Asn Ser Val Phe Lys Glu Cys
            20                  25                  30

Met Lys Gln Lys Lys Lys Glu Phe Xaa
            35                  40

<210> SEQ ID NO 305

<400> SEQUENCE: 305

000
```

<210> SEQ ID NO 306
<211> LENGTH: 41
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(32)
<220> FEATURE:
<221> NAME/KEY: MOD_RES
<222> LOCATION: (41)..(41)
<223> OTHER INFORMATION: C-terminal amidation

<400> SEQUENCE: 306

Cys Asp Ala Thr Cys Gln Phe Arg Lys Ala Ile Asp Cys Gln Lys
1               5                   10                  15

Gln Ala Tyr His Ser Asn Val Pro Gly Asn Ser Val Phe Lys Glu Cys
            20                  25                  30

Met Lys Gln Lys Lys Lys Glu Phe Lys
        35                  40

<210> SEQ ID NO 307
<211> LENGTH: 41
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(32)
<220> FEATURE:
<221> NAME/KEY: MOD_RES
<222> LOCATION: (41)..(41)
<223> OTHER INFORMATION: C-terminal amidation

<400> SEQUENCE: 307

Cys Asp Ala Thr Cys Gln Phe Arg Lys Ala Ile Asp Cys Gln Lys
1               5                   10                  15

Gln Ala His His Ser Asn Val Pro Gly Asn Ser Val Phe Lys Glu Cys
            20                  25                  30

Met Lys Gln Gln Lys Lys Glu Phe Lys
        35                  40

<210> SEQ ID NO 308
<211> LENGTH: 41
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(32)
<220> FEATURE:
<221> NAME/KEY: MOD_RES
<222> LOCATION: (41)..(41)
<223> OTHER INFORMATION: C-terminal amidation

<400> SEQUENCE: 308

Cys Asp Ala Thr Cys Gln Phe Arg Lys Ala Ile Asp Asp Cys Gln Lys
1               5                   10                  15

Gln Ala His His Ser Asn Val Pro Gly Asn Ser Val Phe Lys Glu Cys
            20                  25                  30

Met Lys Gln Ala Lys Lys Glu Phe Lys
        35                  40

<210> SEQ ID NO 309
<211> LENGTH: 41
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(32)
<220> FEATURE:
<221> NAME/KEY: MOD_RES
<222> LOCATION: (40)..(40)
<223> OTHER INFORMATION: Xaa = D-phenylalanine
<220> FEATURE:
<221> NAME/KEY: MOD_RES
<222> LOCATION: (41)..(41)
<223> OTHER INFORMATION: C-terminal amidation

<400> SEQUENCE: 309

Cys Asp Ala Thr Cys Gln Phe Arg Lys Ala Ile Asp Asp Cys Gln Lys
1               5                   10                  15

Gln Ala His His Ser Asn Val Pro Gly Asn Ser Val Phe Lys Glu Cys
            20                  25                  30

Met Lys Gln Lys Lys Lys Glu Xaa Lys
        35                  40

<210> SEQ ID NO 310
<211> LENGTH: 41
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(32)
<220> FEATURE:
<221> NAME/KEY: MOD_RES
<222> LOCATION: (41)..(41)
<223> OTHER INFORMATION: C-terminal amidation

<400> SEQUENCE: 310

Cys Asp Ala Thr Cys Gln Phe Arg Lys Ala Ile Asp Asp Cys Gln Lys
1               5                   10                  15

Gln Ala His His Ser Asn Val Pro Gly Asn Ser Val Phe Lys Glu Cys
            20                  25                  30

Met Lys Gln Lys Lys Lys Glu Phe Glu
        35                  40

<210> SEQ ID NO 311
<211> LENGTH: 40
<212> TYPE: PRT
<213> ORGANISM: Artificial Sequence
<220> FEATURE:
<223> OTHER INFORMATION: Synthetic Polypeptide
<220> FEATURE:

```
<221> NAME/KEY: DISULFID
<222> LOCATION: (1)..(5)
<220> FEATURE:
<221> NAME/KEY: DISULFID
<222> LOCATION: (14)..(31)
<220> FEATURE:
<221> NAME/KEY: MOD_RES
<222> LOCATION: (40)..(40)
<223> OTHER INFORMATION: C-terminal amidation

<400> SEQUENCE: 311

Cys Asp Ala Thr Cys Gln Phe Arg Lys Ala Ile Asp Asp Cys Gln Lys
1               5                   10                  15

Gln Ala His His Ser Asn Val Pro Asn Ser Val Phe Lys Glu Cys Met
            20                  25                  30

Lys Gln Lys Lys Lys Glu Phe Lys
        35                  40

<210> SEQ ID NO 312
<211> LENGTH: 44
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(32)
<220> FEATURE:
<221> NAME/KEY: MOD_RES
<222> LOCATION: (40)..(40)
<223> OTHER INFORMATION: Xaa = homophenylalanine

<400> SEQUENCE: 312

Cys Asp Ala Thr Cys Gln Phe Arg Lys Ala Ile Asp Asp Cys Gln Lys
1               5                   10                  15

Gln Ala His His Ser Asn Val Pro Gly Asn Ser Val Phe Lys Glu Cys
            20                  25                  30

Met Lys Gln Lys Lys Lys Glu Xaa Lys Ala Gly Lys
        35                  40

<210> SEQ ID NO 313
<211> LENGTH: 41
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(32)

<400> SEQUENCE: 313

Cys Asp Ala Thr Cys Gln Phe Arg Lys Ala Ile Asp Asp Cys Gln Lys
1               5                   10                  15

Gln Ala His His Ser Asn Val Pro Gly Asn Ser Val Phe Lys Glu Cys
            20                  25                  30

Met Lys Gln Lys Lys Lys Glu Phe Lys
        35                  40

<210> SEQ ID NO 314
<211> LENGTH: 44
<212> TYPE: PRT
```

```
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(32)

<400> SEQUENCE: 314

Cys Asp Ala Thr Cys Gln Phe Arg Lys Ala Ile Asp Asp Cys Gln Lys
1               5                   10                  15

Gln Ala His His Ser Asn Val Pro Gly Asn Ser Val Phe Lys Glu Cys
            20                  25                  30

Met Lys Gln Lys Lys Lys Glu Phe Lys Pro Gly Lys
        35                  40

<210> SEQ ID NO 315
<211> LENGTH: 44
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(32)

<400> SEQUENCE: 315

Cys Asp Ala Thr Cys Gln Phe Arg Lys Ala Ile Asp Asp Cys Gln Lys
1               5                   10                  15

Gln Ala His His Ser Asn Val Pro Gly Asn Ser Val Phe Lys Glu Cys
            20                  25                  30

Met Lys Gln Lys Lys Lys Glu Trp Lys Ala Gly Lys
        35                  40

<210> SEQ ID NO 316
<211> LENGTH: 44
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(32)

<400> SEQUENCE: 316

Cys Asp Ala Thr Cys Gln Phe Arg Lys Ala Ile Asp Asp Cys Gln Lys
1               5                   10                  15

Gln Ala His His Ser Asn Val Pro Gly Asn Ser Val Phe Lys Glu Cys
            20                  25                  30

Met Lys Gln Lys Lys Lys Glu Phe Glu Ala Gly Lys
        35                  40

<210> SEQ ID NO 317
<211> LENGTH: 44
<212> TYPE: PRT
<213> ORGANISM: Artificial Sequence
<220> FEATURE:
<223> OTHER INFORMATION: Synthetic Polypeptide
<220> FEATURE:
```

```
<221> NAME/KEY: DISULFID
<222> LOCATION: (1)..(5)
<220> FEATURE:
<221> NAME/KEY: DISULFID
<222> LOCATION: (14)..(32)

<400> SEQUENCE: 317

Cys Asp Ala Thr Cys Gln Phe Arg Lys Ala Ile Asp Asp Cys Gln Lys
1               5                   10                  15

Gln Ala His His Ser Asn Val Pro Gly Asn Ser Val Phe Lys Glu Cys
            20                  25                  30

Met Lys Gln Lys Lys Lys Glu Phe Gln Ala Gly Lys
        35                  40

<210> SEQ ID NO 318
<211> LENGTH: 44
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(32)
<220> FEATURE:
<221> NAME/KEY: MOD_RES
<222> LOCATION: (41)..(41)
<223> OTHER INFORMATION: Xaa = D-lysine

<400> SEQUENCE: 318

Cys Asp Ala Thr Cys Gln Phe Arg Lys Ala Ile Asp Asp Cys Gln Lys
1               5                   10                  15

Gln Ala His His Ser Asn Val Pro Gly Asn Ser Val Phe Lys Glu Cys
            20                  25                  30

Met Lys Gln Lys Lys Lys Glu Phe Xaa Ala Gly Lys
        35                  40

<210> SEQ ID NO 319
<211> LENGTH: 44
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(32)

<400> SEQUENCE: 319

Cys Asp Ala Thr Cys Gln Phe Arg Lys Ala Ile Asp Asp Cys Gln Lys
1               5                   10                  15

Gln Ala His His Ser Asn Val Pro Gly Asn Ser Val Phe Lys Glu Cys
            20                  25                  30

Met Lys Gln Lys Lys Lys Glu Tyr Lys Ala Gly Lys
        35                  40

<210> SEQ ID NO 320
<211> LENGTH: 44
<212> TYPE: PRT
<213> ORGANISM: Artificial Sequence
<220> FEATURE:
<223> OTHER INFORMATION: Synthetic Polypeptide
<220> FEATURE:
```

<221> NAME/KEY: DISULFID
<222> LOCATION: (1)..(5)
<220> FEATURE:
<221> NAME/KEY: DISULFID
<222> LOCATION: (14)..(32)

<400> SEQUENCE: 320

Cys Asp Ala Thr Cys Gln Phe Arg Lys Ala Ile Asp Asp Cys Gln Lys
1               5                   10                  15

Gln Ala His His Ser Asn Val Pro Gly Asn Ser Val Phe Lys Glu Cys
            20                  25                  30

Met Lys Gln His Lys Lys Glu Phe Lys Ala Gly Lys
        35                  40

<210> SEQ ID NO 321
<211> LENGTH: 44
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(32)

<400> SEQUENCE: 321

Cys Asp Ala Thr Cys Gln Phe Arg Lys Ala Ile Asp Asp Cys Gln Lys
1               5                   10                  15

Gln Ala His His Ser Asn Val Pro Gly Asn Ser Val Phe Lys Glu Cys
            20                  25                  30

Met Lys Gln Gln Lys Lys Glu Phe Lys Ala Gly Lys
        35                  40

<210> SEQ ID NO 322
<211> LENGTH: 44
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(32)
<220> FEATURE:
<221> NAME/KEY: MOD_RES
<222> LOCATION: (36)..(36)
<223> OTHER INFORMATION: Xaa = D-lysine

<400> SEQUENCE: 322

Cys Asp Ala Thr Cys Gln Phe Arg Lys Ala Ile Asp Asp Cys Gln Lys
1               5                   10                  15

Gln Ala His His Ser Asn Val Pro Gly Asn Ser Val Phe Lys Glu Cys
            20                  25                  30

Met Lys Gln Xaa Lys Lys Glu Phe Lys Ala Gly Lys
        35                  40

<210> SEQ ID NO 323
<211> LENGTH: 44
<212> TYPE: PRT
<213> ORGANISM: Artificial Sequence
<220> FEATURE:
<223> OTHER INFORMATION: Synthetic Polypeptide
<220> FEATURE:

<221> NAME/KEY: DISULFID
<222> LOCATION: (1)..(5)
<220> FEATURE:
<221> NAME/KEY: DISULFID
<222> LOCATION: (14)..(32)

<400> SEQUENCE: 323

Cys Asp Ala Thr Cys Gln Phe Arg Lys Ala Ile Asp Asp Cys Gln Lys
1               5                   10                  15

Gln Ala His His Ser Asn Val Pro Gly Asn Ser Val Phe Lys Glu Cys
            20                  25                  30

Met Lys Asn Lys Lys Lys Glu Phe Lys Ala Gly Lys
        35                  40

<210> SEQ ID NO 324
<211> LENGTH: 44
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(32)

<400> SEQUENCE: 324

Cys Asp Ala Thr Cys Gln Phe Arg Lys Ala Ile Asp Asp Cys Gln Lys
1               5                   10                  15

Gln Ala His His Ser Asn Val Pro Gly Asn Ser Val Phe Lys Glu Cys
            20                  25                  30

Met Lys Pro Lys Lys Lys Glu Phe Lys Ala Gly Lys
        35                  40

<210> SEQ ID NO 325
<211> LENGTH: 44
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(32)

<400> SEQUENCE: 325

Cys Asp Ala Thr Cys Gln Phe Arg Lys Ala Ile Asp Asp Cys Gln Lys
1               5                   10                  15

Gln Ala His His Ser Asn Val Pro Gly Asn Ser Val Phe Lys Glu Cys
            20                  25                  30

Met Lys Glu Lys Lys Lys Glu Phe Lys Ala Gly Lys
        35                  40

<210> SEQ ID NO 326
<211> LENGTH: 44
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID

<222> LOCATION: (14)..(32)

<400> SEQUENCE: 326

Cys Asp Ala Thr Cys Gln Phe Arg Lys Ala Ile Asp Asp Cys Gln Lys
1               5                   10                  15

Gln Ala His His Ser Asn Val Pro Gly Asn Ser Val Phe Lys Glu Cys
            20                  25                  30

Met Lys Gln Ala Lys Lys Glu Phe Lys Ala Gly Lys
        35                  40

<210> SEQ ID NO 327
<211> LENGTH: 44
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(32)

<400> SEQUENCE: 327

Cys Asp Ala Thr Cys Gln Phe Arg Lys Ala Ile Asp Asp Cys Gln Lys
1               5                   10                  15

Gln Ala His His Ser Asn Val Pro Gly Asn Ser Val Phe Lys Glu Cys
            20                  25                  30

Met Lys Thr Lys Lys Lys Glu Phe Lys Ala Gly Lys
        35                  40

<210> SEQ ID NO 328
<211> LENGTH: 44
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: MOD_RES
<222> LOCATION: (1)..(1)
<223> OTHER INFORMATION: Xaa = N-terminal acetylation
<220> FEATURE:
<221> NAME/KEY: DISULFID
<222> LOCATION: (14)..(32)
<220> FEATURE:
<221> NAME/KEY: MOD_RES
<222> LOCATION: (44)..(44)
<223> OTHER INFORMATION: C-terminal amidation

<400> SEQUENCE: 328

Cys Asp Ala Thr Cys Gln Phe Arg Lys Ala Ile Asp Asp Cys Gln Lys
1               5                   10                  15

Gln Ala His His Ser Asn Val Pro Gly Asn Ser Val Phe Lys Glu Cys
            20                  25                  30

Met Lys Gln Lys Lys Lys Glu Phe Lys Ala Gly Lys
        35                  40

<210> SEQ ID NO 329
<211> LENGTH: 44
<212> TYPE: PRT
<213> ORGANISM: Artificial Sequence
<220> FEATURE:
<223> OTHER INFORMATION: Synthetic Polypeptide
<220> FEATURE:

```
<221> NAME/KEY: DISULFID
<222> LOCATION: (1)..(5)
<220> FEATURE:
<221> NAME/KEY: DISULFID
<222> LOCATION: (14)..(32)

<400> SEQUENCE: 329

Cys Asp Ala Thr Cys Gln Phe Arg Lys Ala Ile Asp Asp Cys Gln Lys
1               5                   10                  15

Gln Ala His His Ser Asn Val Pro Gly Asn Ser Val Phe Glu Lys Cys
            20                  25                  30

Met Lys Gln Lys Lys Lys Glu Phe Lys Ala Gly Lys
        35                  40

<210> SEQ ID NO 330
<211> LENGTH: 44
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(32)

<400> SEQUENCE: 330

Cys Asp Ala Thr Cys Gln Phe Arg Lys Ala Ile Asp Asp Cys Gln Lys
1               5                   10                  15

Gln Ala His His Ser Asn Val Pro Gly Asn Ser Val Trp Lys Glu Cys
            20                  25                  30

Met Lys Gln Lys Lys Lys Glu Phe Lys Ala Gly Lys
        35                  40

<210> SEQ ID NO 331
<211> LENGTH: 44
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(32)

<400> SEQUENCE: 331

Cys Asp Ala Thr Cys Gln Phe Arg Lys Ala Ile Asp Asp Cys Gln Lys
1               5                   10                  15

Gln Ala His His Ser Asn Val Pro Gly Asn Ser Val Tyr Lys Glu Cys
            20                  25                  30

Met Lys Gln Lys Lys Lys Glu Phe Lys Ala Gly Lys
        35                  40

<210> SEQ ID NO 332
<211> LENGTH: 44
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
```

<222> LOCATION: (14)..(32)

<400> SEQUENCE: 332

Cys Asp Ala Thr Cys Gln Phe Arg Lys Ala Ile Asp Asp Cys Gln Lys
1               5                   10                  15

Gln Ala His His Ser Asn Val Pro Gly Gln Ser Val Phe Lys Glu Cys
            20                  25                  30

Met Lys Gln Lys Lys Lys Glu Phe Lys Ala Gly Lys
        35                  40

<210> SEQ ID NO 333
<211> LENGTH: 44
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(32)

<400> SEQUENCE: 333

Cys Asp Ala Thr Cys Gln Phe Arg Lys Ala Ile Asp Asp Cys Gln Lys
1               5                   10                  15

Gln Ala His His Ser His Val Pro Gly Asn Ser Val Phe Lys Glu Cys
            20                  25                  30

Met Lys Gln Lys Lys Lys Glu Phe Lys Ala Gly Lys
        35                  40

<210> SEQ ID NO 334
<211> LENGTH: 44
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(32)
<220> FEATURE:
<221> NAME/KEY: MOD_RES
<222> LOCATION: (24)..(24)
<223> OTHER INFORMATION: Xaa = pipecolic acid

<400> SEQUENCE: 334

Cys Asp Ala Thr Cys Gln Phe Arg Lys Ala Ile Asp Asp Cys Gln Lys
1               5                   10                  15

Gln Ala His His Ser Asn Val Xaa Gly Asn Ser Val Lys Glu Cys
            20                  25                  30

Met Lys Gln Lys Lys Lys Glu Phe Lys Ala Gly Lys
        35                  40

<210> SEQ ID NO 335
<211> LENGTH: 44
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID

```
<222> LOCATION: (14)..(32)

<400> SEQUENCE: 335

Cys Asp Ala Thr Cys Gln Phe Arg Lys Ala Ile Asp Asp Cys Gln Lys
1               5                   10                  15

Gln Ala His His Ser Asn Val Pro Gly Asn Ser Val Phe Lys Glu Cys
            20                  25                  30

Met Lys Gln Lys Lys Lys Glu Glu Lys Ala Gly Lys
        35                  40

<210> SEQ ID NO 336
<211> LENGTH: 44
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(32)

<400> SEQUENCE: 336

Cys Asp Ala Thr Cys Gln Phe Arg Lys Ala Ile Asp Asp Cys Gln Lys
1               5                   10                  15

Gln Ala His His Ser Asn Val Pro Gly Asn Ser Val Phe Lys Glu Cys
            20                  25                  30

Met Lys Gln Lys Lys Glu Glu Phe Lys Ala Gly Lys
        35                  40

<210> SEQ ID NO 337
<211> LENGTH: 44
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: MOD_RES
<222> LOCATION: (13)..(13)
<223> OTHER INFORMATION: Xaa = 2-aminoisobutyric acid
<220> FEATURE:
<221> NAME/KEY: DISULFID
<222> LOCATION: (14)..(32)

<400> SEQUENCE: 337

Cys Asp Ala Thr Cys Gln Phe Arg Lys Ala Ile Asp Xaa Cys Gln Lys
1               5                   10                  15

Gln Ala His His Ser Asn Val Pro Gly Asn Ser Val Phe Lys Glu Cys
            20                  25                  30

Met Lys Gln Lys Lys Glu Glu Phe Lys Ala Gly Lys
        35                  40

<210> SEQ ID NO 338
<211> LENGTH: 44
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: MOD_RES
```

```
<222> LOCATION: (11)..(11)
<223> OTHER INFORMATION: Xaa = 2-aminoisobutyric acid
<220> FEATURE:
<221> NAME/KEY: DISULFID
<222> LOCATION: (14)..(32)

<400> SEQUENCE: 338

Cys Asp Ala Thr Cys Gln Phe Arg Lys Ala Xaa Asp Asp Cys Gln Lys
1               5                   10                  15

Gln Ala His His Ser Asn Val Pro Gly Asn Ser Val Phe Lys Glu Cys
            20                  25                  30

Met Lys Gln Lys Lys Lys Glu Phe Lys Ala Gly Lys
        35                  40

<210> SEQ ID NO 339
<211> LENGTH: 44
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(32)
<220> FEATURE:
<221> NAME/KEY: MOD_RES
<222> LOCATION: (44)..(44)
<223> OTHER INFORMATION: Xaa = D-lysine

<400> SEQUENCE: 339

Cys Asp Ala Thr Cys Gln Phe Arg Lys Ala Ile Asp Asp Cys Gln Lys
1               5                   10                  15

Gln Ala His His Ser Asn Val Pro Gly Asn Ser Val Phe Lys Glu Cys
            20                  25                  30

Met Lys Gln Lys Lys Lys Glu Phe Lys Ala Gly Xaa
        35                  40

<210> SEQ ID NO 340
<211> LENGTH: 44
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(32)

<400> SEQUENCE: 340

Cys Asp Ala Thr Cys Gln Phe Arg Lys Ala Ile Asp Asp Cys Gln Lys
1               5                   10                  15

Gln Ala His His Ser Asn Val Pro Gly Asn Ser Val Phe Lys Glu Cys
            20                  25                  30

Met Lys Gln Glu Lys Lys Glu Phe Lys Ala Gly Lys
        35                  40

<210> SEQ ID NO 341
<211> LENGTH: 44
<212> TYPE: PRT
<213> ORGANISM: Artificial Sequence
<220> FEATURE:
<223> OTHER INFORMATION: Synthetic Polypeptide
<220> FEATURE:
```

```
<221> NAME/KEY: DISULFID
<222> LOCATION: (1)..(5)
<220> FEATURE:
<221> NAME/KEY: DISULFID
<222> LOCATION: (14)..(32)

<400> SEQUENCE: 341

Cys Asp Ala Thr Cys Gln Phe Arg Lys Ala Ile Asp Asp Cys Gln Lys
1               5                   10                  15

Gln Ala His His Ser Asn Val Pro Gly Asn Ser Val Phe Lys Glu Cys
            20                  25                  30

Met Glu Gln Lys Lys Lys Glu Phe Lys Ala Gly Lys
        35                  40

<210> SEQ ID NO 342
<211> LENGTH: 44
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(32)

<400> SEQUENCE: 342

Cys Asp Ala Thr Cys Gln Phe Arg Lys Ala Ile Asp Asp Cys Gln Lys
1               5                   10                  15

Gln Ala His His Ser Asn Val Pro Gly Asn Ser Val Phe Lys Glu Cys
            20                  25                  30

Glu Lys Gln Lys Lys Lys Glu Phe Lys Ala Gly Lys
        35                  40

<210> SEQ ID NO 343
<211> LENGTH: 44
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(32)

<400> SEQUENCE: 343

Cys Asp Ala Thr Cys Gln Phe Arg Lys Ala Ile Asp Asp Cys Gln Lys
1               5                   10                  15

Gln Ala His His Ser Asn Val Pro Gly Asn Ser Val Phe Lys Glu Cys
            20                  25                  30

Met Lys Gln Lys Lys Lys Glu Phe Lys Ala Ala Lys
        35                  40

<210> SEQ ID NO 344
<211> LENGTH: 44
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
```

<222> LOCATION: (14)..(32)

<400> SEQUENCE: 344

Cys Asp Ala Thr Cys Gln Phe Arg Lys Ala Ile Asp Asp Cys Gln Lys
1               5                   10                  15

Gln Ala His His Ser Asn Val Pro Gly Asn Ser Val Phe Lys Glu Cys
            20                  25                  30

Met Lys Gln Lys Lys Lys Glu Phe Ala Ala Gly Lys
        35                  40

<210> SEQ ID NO 345
<211> LENGTH: 44
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(32)
<220> FEATURE:
<221> NAME/KEY: MOD_RES
<222> LOCATION: (35)..(35)
<223> OTHER INFORMATION: Xaa = 2-aminoisobutyric acid

<400> SEQUENCE: 345

Cys Asp Ala Thr Cys Gln Phe Arg Lys Ala Ile Asp Asp Cys Gln Lys
1               5                   10                  15

Gln Ala His His Ser Asn Val Pro Gly Asn Ser Val Phe Lys Glu Cys
            20                  25                  30

Met Lys Xaa Lys Lys Lys Glu Phe Lys Ala Gly Lys
        35                  40

<210> SEQ ID NO 346
<211> LENGTH: 44
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(32)

<400> SEQUENCE: 346

Cys Asp Ala Thr Cys Gln Phe Arg Lys Ala Ile Asp Asp Cys Lys Gln
1               5                   10                  15

Gln Ala His His Ser Asn Val Pro Gly Asn Ser Val Phe Glu Lys Cys
            20                  25                  30

Met Lys Gln Lys Lys Lys Glu Phe Lys Ala Gly Lys
        35                  40

<210> SEQ ID NO 347
<211> LENGTH: 44
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID

<222> LOCATION: (14)..(32)

<400> SEQUENCE: 347

Cys Asp Ala Thr Cys Gln Phe Arg Lys Ala Ile Asp Asp Cys Gln Lys
1               5                   10                  15

Gln Ala His His Ser Gln Val Pro Gly Asn Ser Val Phe Lys Glu Cys
            20                  25                  30

Met Lys Gln Lys Lys Lys Glu Phe Lys Ala Gly Lys
        35                  40

<210> SEQ ID NO 348
<211> LENGTH: 44
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(32)
<220> FEATURE:
<221> NAME/KEY: MOD_RES
<222> LOCATION: (17)..(17)
<223> OTHER INFORMATION: Xaa = citrulline

<400> SEQUENCE: 348

Cys Asp Ala Thr Cys Gln Phe Arg Lys Ala Ile Asp Asp Cys Gln Lys
1               5                   10                  15

Xaa Ala His His Ser Asn Val Pro Gly Asn Ser Val Phe Lys Glu Cys
            20                  25                  30

Met Lys Gln Lys Lys Lys Glu Phe Lys Ala Gly Lys
        35                  40

<210> SEQ ID NO 349
<211> LENGTH: 44
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(32)

<400> SEQUENCE: 349

Cys Asp Ala Thr Cys Gln Phe Arg Lys Ala Ile Asp Asp Cys Gln Lys
1               5                   10                  15

Asp Ala His His Ser Asn Val Pro Gly Asn Ser Val Phe Lys Glu Cys
            20                  25                  30

Met Lys Gln Lys Lys Lys Glu Phe Lys Ala Gly Lys
        35                  40

<210> SEQ ID NO 350
<211> LENGTH: 44
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID

<222> LOCATION: (14)..(32)

<400> SEQUENCE: 350

Cys Asp Ala Thr Cys Gln Phe Arg Lys Ala Ile Asp Asp Cys Gln Gln
1               5                   10                  15

Gln Ala His His Ser Asn Val Pro Gly Asn Ser Val Phe Lys Glu Cys
            20                  25                  30

Met Lys Gln Lys Lys Lys Glu Phe Lys Ala Gly Lys
        35                  40

<210> SEQ ID NO 351
<211> LENGTH: 44
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(32)
<220> FEATURE:
<221> NAME/KEY: MOD_RES
<222> LOCATION: (16)..(16)
<223> OTHER INFORMATION: Xaa = homoglutamic acid

<400> SEQUENCE: 351

Cys Asp Ala Thr Cys Gln Phe Arg Lys Ala Ile Asp Asp Cys Gln Xaa
1               5                   10                  15

Gln Ala His His Ser Asn Val Pro Gly Asn Ser Val Phe Lys Glu Cys
            20                  25                  30

Met Lys Gln Lys Lys Lys Glu Phe Lys Ala Gly Lys
        35                  40

<210> SEQ ID NO 352
<211> LENGTH: 44
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(32)

<400> SEQUENCE: 352

Cys Asp Ala Thr Cys Gln Phe Arg Lys Ala Ile Asp Asp Cys Gln Arg
1               5                   10                  15

Gln Ala His His Ser Asn Val Pro Gly Asn Ser Val Phe Lys Glu Cys
            20                  25                  30

Met Lys Gln Lys Lys Lys Glu Phe Lys Ala Gly Lys
        35                  40

<210> SEQ ID NO 353
<211> LENGTH: 44
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID

```
<222> LOCATION: (14)..(32)
<220> FEATURE:
<221> NAME/KEY: MOD_RES
<222> LOCATION: (15)..(15)
<223> OTHER INFORMATION: Xaa = citrulline

<400> SEQUENCE: 353

Cys Asp Ala Thr Cys Gln Phe Arg Lys Ala Ile Asp Asp Cys Xaa Lys
1               5                   10                  15
Gln Ala His His Ser Asn Val Pro Gly Asn Ser Val Phe Lys Glu Cys
            20                  25                  30
Met Lys Gln Lys Lys Lys Glu Phe Lys Ala Gly Lys
        35                  40

<210> SEQ ID NO 354
<211> LENGTH: 44
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(32)

<400> SEQUENCE: 354

Cys Asp Ala Thr Cys Gln Phe Arg Lys Ala Ile Asp Asp Cys Asp Lys
1               5                   10                  15
Gln Ala His His Ser Asn Val Pro Gly Asn Ser Val Phe Lys Glu Cys
            20                  25                  30
Met Lys Gln Lys Lys Lys Glu Phe Lys Ala Gly Lys
        35                  40

<210> SEQ ID NO 355
<211> LENGTH: 44
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(32)

<400> SEQUENCE: 355

Cys Asp Ala Thr Cys Gln Phe Arg Lys Ala Ile Asp Asp Cys Gln Lys
1               5                   10                  15
Gln Ala His Tyr Ser Asn Val Pro Gly Asn Ser Val Phe Lys Glu Cys
            20                  25                  30
Met Lys Gln Lys Lys Lys Glu Phe Lys Ala Gly Lys
        35                  40

<210> SEQ ID NO 356
<211> LENGTH: 44
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
```

<222> LOCATION: (14)..(32)

<400> SEQUENCE: 356

Cys Asp Ala Thr Cys Gln Phe Arg Lys Ala Ile Asp Asp Cys Gln Lys
1               5                   10                  15

Gln Ala Tyr His Ser Asn Val Pro Gly Asn Ser Val Phe Lys Glu Cys
            20                  25                  30

Met Lys Gln Lys Lys Lys Glu Phe Lys Ala Gly Lys
        35                  40

<210> SEQ ID NO 357
<211> LENGTH: 44
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(32)

<400> SEQUENCE: 357

Cys Asp Ala Thr Cys Gln Phe Arg Lys Ala Ile Asp Asp Cys Gln Lys
1               5                   10                  15

Gln Ala His His Val Asn Val Pro Gly Asn Ser Val Phe Lys Glu Cys
            20                  25                  30

Met Lys Gln Lys Lys Lys Glu Phe Lys Ala Gly Lys
        35                  40

<210> SEQ ID NO 358
<211> LENGTH: 44
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(32)

<400> SEQUENCE: 358

Cys Asp Ala Thr Cys Gln Phe Arg Lys Ala Ile Asp Asp Cys Gln Lys
1               5                   10                  15

Gln Ala His His Ser Asn Thr Pro Gly Asn Ser Val Phe Lys Glu Cys
            20                  25                  30

Met Lys Gln Lys Lys Lys Glu Phe Lys Ala Gly Lys
        35                  40

<210> SEQ ID NO 359
<211> LENGTH: 44
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(32)

<400> SEQUENCE: 359

```
Cys Asp Ala Thr Cys Gln Phe Arg Lys Ala Ile Asp Asp Cys Gln Lys
1               5                  10                  15

Gln Ala His His Ser Asn Val Pro Gly Asn Ser Thr Phe Lys Glu Cys
            20                  25                  30

Met Lys Gln Lys Lys Lys Glu Phe Lys Ala Gly Lys
        35                  40
```

<210> SEQ ID NO 360
<211> LENGTH: 44
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(32)

<400> SEQUENCE: 360

```
Cys Asp Ala Thr Cys Gln Phe Arg Lys Ala Ile Asp Asp Cys Gln Lys
1               5                  10                  15

Gln Leu His His Ser Asn Val Pro Gly Asn Ser Val Phe Lys Glu Cys
            20                  25                  30

Met Lys Gln Lys Lys Lys Glu Phe Lys Ala Gly Lys
        35                  40
```

<210> SEQ ID NO 361
<211> LENGTH: 44
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(32)

<400> SEQUENCE: 361

```
Cys Asp Ala Thr Cys Gln Phe Arg Lys Leu Ile Asp Asp Cys Gln Lys
1               5                  10                  15

Gln Ala His His Ser Asn Val Pro Gly Asn Ser Val Phe Lys Glu Cys
            20                  25                  30

Met Lys Gln Lys Lys Lys Glu Phe Lys Ala Gly Lys
        35                  40
```

<210> SEQ ID NO 362
<211> LENGTH: 43
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(31)

<400> SEQUENCE: 362

```
Cys Asp Ala Thr Cys Gln Phe Arg Lys Ala Ile Asp Asp Cys Gln Lys
1               5                  10                  15

Gln Ala His His Ser Asn Val Pro Gly Asn Ser Val Lys Glu Cys Met
```

```
            20                  25                  30

Lys Gln Lys Lys Lys Glu Phe Lys Ala Gly Lys
        35                  40

<210> SEQ ID NO 363
<211> LENGTH: 43
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(31)

<400> SEQUENCE: 363

Cys Asp Ala Thr Cys Gln Phe Arg Lys Ala Ile Asp Asp Cys Gln Lys
1               5                   10                  15

Gln Ala His His Ser Asn Val Pro Gly Asn Ser Phe Lys Glu Cys Met
            20                  25                  30

Lys Gln Lys Lys Lys Glu Phe Lys Ala Gly Lys
        35                  40

<210> SEQ ID NO 364
<211> LENGTH: 43
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(31)

<400> SEQUENCE: 364

Cys Asp Ala Thr Cys Gln Phe Arg Lys Ala Ile Asp Asp Cys Gln Lys
1               5                   10                  15

Gln Ala His His Ser Asn Val Pro Gly Ser Val Phe Lys Glu Cys Met
            20                  25                  30

Lys Gln Lys Lys Lys Glu Phe Lys Ala Gly Lys
        35                  40

<210> SEQ ID NO 365
<211> LENGTH: 43
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(31)

<400> SEQUENCE: 365

Cys Asp Ala Thr Cys Gln Phe Arg Lys Ala Ile Asp Asp Cys Gln Lys
1               5                   10                  15

Gln Ala His His Ser Asn Val Pro Asn Ser Val Phe Lys Glu Cys Met
            20                  25                  30

Lys Gln Lys Lys Lys Glu Phe Lys Ala Gly Lys
        35                  40
```

<210> SEQ ID NO 366
<211> LENGTH: 44
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(32)
<220> FEATURE:
<221> NAME/KEY: MOD_RES
<222> LOCATION: (24)..(24)
<223> OTHER INFORMATION: Xaa = sarcosine

<400> SEQUENCE: 366

Cys Asp Ala Thr Cys Gln Phe Arg Lys Ala Ile Asp Asp Cys Gln Lys
1               5                   10                  15

Gln Ala His His Ser Asn Val Xaa Gly Asn Ser Val Phe Lys Glu Cys
            20                  25                  30

Met Lys Gln Lys Lys Lys Glu Phe Lys Ala Gly Lys
        35                  40

<210> SEQ ID NO 367
<211> LENGTH: 44
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(32)
<220> FEATURE:
<221> NAME/KEY: MOD_RES
<222> LOCATION: (24)..(24)
<223> OTHER INFORMATION: Xaa = 4-hydroxyproline

<400> SEQUENCE: 367

Cys Asp Ala Thr Cys Gln Phe Arg Lys Ala Ile Asp Asp Cys Gln Lys
1               5                   10                  15

Gln Ala His His Ser Asn Val Xaa Gly Asn Ser Val Phe Lys Glu Cys
            20                  25                  30

Met Lys Gln Lys Lys Lys Glu Phe Lys Ala Gly Lys
        35                  40

<210> SEQ ID NO 368
<211> LENGTH: 44
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(32)

<400> SEQUENCE: 368

Cys Asp Ala Thr Cys Gln Phe Arg Lys Ala Ile Asp Glu Cys Gln Lys
1               5                   10                  15

Gln Ala His His Ser Asn Val Pro Gly Asn Ser Val Phe Lys Glu Cys

```
                    20                  25                  30

Met Lys Gln Lys Lys Lys Glu Phe Lys Ala Gly Lys
        35                  40

<210> SEQ ID NO 369
<211> LENGTH: 44
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(32)

<400> SEQUENCE: 369

Cys Asp Ala Thr Cys Gln Phe Arg Lys Ala Ile Glu Asp Cys Gln Lys
1               5                   10                  15

Gln Ala His His Ser Asn Val Pro Gly Asn Ser Val Phe Lys Glu Cys
            20                  25                  30

Met Lys Gln Lys Lys Lys Glu Phe Lys Ala Gly Lys
        35                  40

<210> SEQ ID NO 370
<211> LENGTH: 44
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: MOD_RES
<222> LOCATION: (6)..(6)
<223> OTHER INFORMATION: Xaa = citrulline
<220> FEATURE:
<221> NAME/KEY: DISULFID
<222> LOCATION: (14)..(32)

<400> SEQUENCE: 370

Cys Asp Ala Thr Cys Xaa Phe Arg Lys Ala Ile Asp Asp Cys Gln Lys
1               5                   10                  15

Gln Ala His His Ser Asn Val Pro Gly Asn Ser Val Phe Lys Glu Cys
            20                  25                  30

Met Lys Gln Lys Lys Lys Glu Phe Lys Ala Gly Lys
        35                  40

<210> SEQ ID NO 371
<211> LENGTH: 44
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(32)

<400> SEQUENCE: 371

Cys Asp Ala Thr Cys Lys Phe Arg Lys Ala Ile Asp Asp Cys Gln Lys
1               5                   10                  15

Gln Ala His His Ser Asn Val Pro Gly Asn Ser Val Phe Lys Glu Cys
```

Met Lys Gln Lys Lys Lys Glu Phe Lys Ala Gly Lys
        35                  40

<210> SEQ ID NO 372
<211> LENGTH: 44
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(32)

<400> SEQUENCE: 372

Cys Asp Ala Thr Cys Glu Phe Arg Lys Ala Ile Asp Asp Cys Gln Lys
1               5                   10                  15

Gln Ala His His Ser Asn Val Pro Gly Asn Ser Val Phe Lys Glu Cys
            20                  25                  30

Met Lys Gln Lys Lys Lys Glu Phe Lys Ala Gly Lys
        35                  40

<210> SEQ ID NO 373
<211> LENGTH: 44
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(32)

<400> SEQUENCE: 373

Cys Asp Ala Thr Cys Asn Phe Arg Lys Ala Ile Asp Asp Cys Gln Lys
1               5                   10                  15

Gln Ala His His Ser Asn Val Pro Gly Asn Ser Val Phe Lys Glu Cys
            20                  25                  30

Met Lys Gln Lys Lys Lys Glu Phe Lys Ala Gly Lys
        35                  40

<210> SEQ ID NO 374
<211> LENGTH: 44
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(32)

<400> SEQUENCE: 374

Cys Asp Ala Thr Cys Gln Tyr Arg Lys Ala Ile Asp Asp Cys Gln Lys
1               5                   10                  15

Gln Ala His His Ser Asn Val Pro Gly Asn Ser Val Phe Lys Glu Cys
            20                  25                  30

Met Lys Gln Lys Lys Lys Glu Phe Lys Ala Gly Lys
        35                  40

<210> SEQ ID NO 375
<211> LENGTH: 44
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(32)

<400> SEQUENCE: 375

Cys Asp Ala Thr Cys Gln Phe Lys Arg Ala Ile Asp Asp Cys Gln Lys
1               5                   10                  15

Gln Ala His His Ser Asn Val Pro Gly Asn Ser Val Phe Lys Glu Cys
            20                  25                  30

Met Lys Gln Lys Lys Lys Glu Phe Lys Ala Gly Lys
        35                  40

<210> SEQ ID NO 376
<211> LENGTH: 44
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(32)

<400> SEQUENCE: 376

Cys Asp Ala Ser Cys Gln Phe Arg Lys Ala Ile Asp Asp Cys Gln Lys
1               5                   10                  15

Gln Ala His His Ser Asn Val Pro Gly Asn Ser Val Phe Lys Glu Cys
            20                  25                  30

Met Lys Gln Lys Lys Lys Glu Phe Lys Ala Gly Lys
        35                  40

<210> SEQ ID NO 377
<211> LENGTH: 44
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(32)

<400> SEQUENCE: 377

Cys Asp Ala Val Cys Gln Phe Arg Lys Ala Ile Asp Asp Cys Gln Lys
1               5                   10                  15

Gln Ala His His Ser Asn Val Pro Gly Asn Ser Val Phe Lys Glu Cys
            20                  25                  30

Met Lys Gln Lys Lys Lys Glu Phe Lys Ala Gly Lys
        35                  40

<210> SEQ ID NO 378
<211> LENGTH: 44

<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: MOD_RES
<222> LOCATION: (3)..(3)
<223> OTHER INFORMATION: Xaa = 2-aminoisobutyric acid
<220> FEATURE:
<221> NAME/KEY: DISULFID
<222> LOCATION: (14)..(32)

<400> SEQUENCE: 378

Cys Asp Xaa Thr Cys Gln Phe Arg Lys Ala Ile Asp Asp Cys Gln Lys
1               5                   10                  15

Gln Ala His His Ser Asn Val Pro Gly Asn Ser Val Phe Lys Glu Cys
            20                  25                  30

Met Lys Gln Lys Lys Lys Glu Phe Lys Ala Gly Lys
        35                  40

<210> SEQ ID NO 379
<211> LENGTH: 44
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(32)

<400> SEQUENCE: 379

Cys Asp Pro Thr Cys Gln Phe Arg Lys Ala Ile Asp Asp Cys Gln Lys
1               5                   10                  15

Gln Ala His His Ser Asn Val Pro Gly Asn Ser Val Phe Lys Glu Cys
            20                  25                  30

Met Lys Gln Lys Lys Lys Glu Phe Lys Ala Gly Lys
        35                  40

<210> SEQ ID NO 380
<211> LENGTH: 44
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(32)

<400> SEQUENCE: 380

Cys Glu Ala Thr Cys Gln Phe Arg Lys Ala Ile Asp Asp Cys Gln Lys
1               5                   10                  15

Gln Ala His His Ser Asn Val Pro Gly Asn Ser Val Phe Lys Glu Cys
            20                  25                  30

Met Lys Gln Lys Lys Lys Glu Phe Lys Ala Gly Lys
        35                  40

<210> SEQ ID NO 381
<211> LENGTH: 44

```
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (14)..(32)

<400> SEQUENCE: 381

Ser Asp Ala Thr Ser Gln Phe Arg Lys Ala Ile Asp Asp Cys Gln Lys
1               5                   10                  15

Gln Ala His His Ser Asn Val Pro Gly Asn Ser Val Phe Lys Glu Cys
            20                  25                  30

Met Lys Gln Lys Lys Lys Glu Phe Lys Ala Gly Lys
            35                  40

<210> SEQ ID NO 382
<211> LENGTH: 44
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(32)
<220> FEATURE:
<221> NAME/KEY: MOD_RES
<222> LOCATION: (34)..(34)
<223> OTHER INFORMATION: Xaa = 2-aminoisobutyric acid

<400> SEQUENCE: 382

Cys Asp Ala Thr Cys Gln Phe Arg Lys Ala Ile Asp Asp Cys Gln Lys
1               5                   10                  15

Gln Ala His His Ser Asn Val Pro Gly Asn Ser Val Phe Lys Glu Cys
            20                  25                  30

Met Xaa Gln Lys Lys Lys Glu Phe Lys Ala Gly Lys
            35                  40

<210> SEQ ID NO 383
<211> LENGTH: 44
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(32)
<220> FEATURE:
<221> NAME/KEY: MOD_RES
<222> LOCATION: (31)..(31)
<223> OTHER INFORMATION: Xaa = 2-aminoisobutyric acid

<400> SEQUENCE: 383

Cys Asp Ala Thr Cys Gln Phe Arg Lys Ala Ile Asp Asp Cys Gln Lys
1               5                   10                  15

Gln Ala His His Ser Asn Val Pro Gly Asn Ser Val Phe Lys Xaa Cys
            20                  25                  30

Met Lys Gln Lys Lys Lys Glu Phe Lys Ala Gly Lys
            35                  40

<210> SEQ ID NO 384
```

```
<211> LENGTH: 44
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(32)
<220> FEATURE:
<221> NAME/KEY: MOD_RES
<222> LOCATION: (30)..(30)
<223> OTHER INFORMATION: Xaa = 2-aminoisobutyric acid

<400> SEQUENCE: 384

Cys Asp Ala Thr Cys Gln Phe Arg Lys Ala Ile Asp Asp Cys Gln Lys
1               5                   10                  15

Gln Ala His His Ser Asn Val Pro Gly Asn Ser Val Phe Xaa Glu Cys
            20                  25                  30

Met Lys Gln Lys Lys Lys Glu Phe Lys Ala Gly Lys
        35                  40

<210> SEQ ID NO 385
<211> LENGTH: 44
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(32)
<220> FEATURE:
<221> NAME/KEY: MOD_RES
<222> LOCATION: (29)..(29)
<223> OTHER INFORMATION: Xaa = 2-aminoisobutyric acid

<400> SEQUENCE: 385

Cys Asp Ala Thr Cys Gln Phe Arg Lys Ala Ile Asp Asp Cys Gln Lys
1               5                   10                  15

Gln Ala His His Ser Asn Val Pro Gly Asn Ser Val Xaa Lys Glu Cys
            20                  25                  30

Met Lys Gln Lys Lys Lys Glu Phe Lys Ala Gly Lys
        35                  40

<210> SEQ ID NO 386
<211> LENGTH: 44
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(32)
<220> FEATURE:
<221> NAME/KEY: MOD_RES
<222> LOCATION: (21)..(21)
<223> OTHER INFORMATION: Xaa = 2-aminoisobutyric acid

<400> SEQUENCE: 386

Cys Asp Ala Thr Cys Gln Phe Arg Lys Ala Ile Asp Asp Cys Gln Lys
1               5                   10                  15
```

Gln Ala His His Xaa Asn Val Pro Gly Asn Ser Val Phe Lys Glu Cys
            20                  25                  30

Met Lys Gln Lys Lys Lys Glu Phe Lys Ala Gly Lys
            35                  40

<210> SEQ ID NO 387
<211> LENGTH: 44
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(32)

<400> SEQUENCE: 387

Cys Asp Ala Thr Cys Gln Phe Arg Lys Ala Ile Asp Asp Cys Gln Lys
1               5                   10                  15

Gln Ala His His Ser Asn Val Pro Gly Asn Ser Val Phe Ala Glu Cys
            20                  25                  30

Met Lys Gln Lys Lys Lys Glu Phe Lys Ala Gly Lys
            35                  40

<210> SEQ ID NO 388
<211> LENGTH: 44
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(32)

<400> SEQUENCE: 388

Cys Asp Ala Thr Cys Gln Phe Arg Lys Ala Ile Asp Asp Cys Gln Lys
1               5                   10                  15

Gln Ala His His Ser Asn Val Pro Gly Asn Ser Val Phe Lys Ala Cys
            20                  25                  30

Met Lys Gln Lys Lys Lys Glu Phe Lys Ala Gly Lys
            35                  40

<210> SEQ ID NO 389
<211> LENGTH: 44
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(32)

<400> SEQUENCE: 389

Cys Asp Ala Thr Cys Gln Phe Arg Lys Ala Ile Asp Asp Cys Gln Lys
1               5                   10                  15

Gln Ala His His Ser Asn Val Pro Gly Asn Ser Val Phe Lys Glu Cys
            20                  25                  30

Met Lys Gln Lys Lys Lys Glu Phe Lys Ala Glu Lys

<210> SEQ ID NO 390
<211> LENGTH: 44
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(32)

<400> SEQUENCE: 390

Cys Asp Ala Thr Cys Gln Phe Arg Lys Ala Ile Asp Asp Cys Gln Lys
1               5                   10                  15

Gln Ala His His Ser Asn Val Pro Gly Asn Ser Val Phe Lys Glu Cys
            20                  25                  30

Met Lys Gln Lys Lys Glu Phe Lys Glu Gly Lys
        35                  40

<210> SEQ ID NO 391
<211> LENGTH: 44
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(32)

<400> SEQUENCE: 391

Cys Asp Ala Thr Cys Gln Phe Arg Lys Ala Ile Asp Asp Cys Gln Lys
1               5                   10                  15

Gln Ala His His Ser Asn Val Pro Gly Asn Ser Val Phe Lys Glu Cys
            20                  25                  30

Met Lys Gln Lys Lys Ala Phe Lys Ala Gly Lys
        35                  40

<210> SEQ ID NO 392
<211> LENGTH: 44
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(32)

<400> SEQUENCE: 392

Cys Asp Ala Thr Cys Gln Phe Arg Lys Ala Ile Asp Asp Cys Gln Lys
1               5                   10                  15

Gln Ala His His Ser Asn Val Pro Gly Asn Ser Val Phe Lys Glu Cys
            20                  25                  30

Met Lys Gln Lys Ala Lys Glu Phe Lys Ala Gly Lys
        35                  40

<210> SEQ ID NO 393

```
<211> LENGTH: 44
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(32)

<400> SEQUENCE: 393
```

Cys Asp Ala Thr Cys Gln Phe Arg Lys Ala Ile Asp Asp Cys Gln Lys
1               5                   10                  15

Gln Ala His His Ser Asn Val Pro Gly Asn Ser Val Phe Lys Glu Cys
            20                  25                  30

Met Lys Ala Lys Lys Lys Glu Phe Lys Ala Gly Lys
        35                  40

```
<210> SEQ ID NO 394
<211> LENGTH: 44
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(32)

<400> SEQUENCE: 394
```

Cys Asp Ala Thr Cys Gln Phe Arg Lys Ala Ile Asp Asp Cys Gln Lys
1               5                   10                  15

Gln Ala His His Ser Asn Val Pro Gly Asn Ser Val Phe Lys Glu Cys
            20                  25                  30

Met Ala Gln Lys Lys Lys Glu Phe Lys Ala Gly Lys
        35                  40

```
<210> SEQ ID NO 395
<211> LENGTH: 44
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(32)

<400> SEQUENCE: 395
```

Cys Asp Ala Thr Cys Gln Phe Arg Lys Ala Ile Asp Asp Cys Gln Lys
1               5                   10                  15

Gln Ala His His Ser Asn Val Pro Gly Asn Ser Val Phe Lys Glu Cys
            20                  25                  30

Ala Lys Gln Lys Lys Lys Glu Phe Lys Ala Gly Lys
        35                  40

```
<210> SEQ ID NO 396
<211> LENGTH: 40
<212> TYPE: PRT
<213> ORGANISM: Artificial Sequence
<220> FEATURE:
```

```
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(28)

<400> SEQUENCE: 396

Cys Asp Ala Thr Cys Gln Phe Arg Lys Ala Ile Asp Asp Cys Gln Lys
1               5                   10                  15

Gln Ala His His Ser Asn Ser Val Phe Lys Glu Cys Met Lys Gln Lys
            20                  25                  30

Lys Lys Glu Phe Lys Ala Gly Lys
        35                  40

<210> SEQ ID NO 397
<211> LENGTH: 41
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(29)

<400> SEQUENCE: 397

Cys Asp Ala Thr Cys Gln Phe Arg Lys Ala Ile Asp Asp Cys Gln Lys
1               5                   10                  15

Gln Ala His His Ser Asn Val Ser Val Phe Lys Glu Cys Met Lys Gln
            20                  25                  30

Lys Lys Lys Glu Phe Lys Ala Gly Lys
        35                  40

<210> SEQ ID NO 398
<211> LENGTH: 43
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(31)

<400> SEQUENCE: 398

Cys Asp Ala Thr Cys Gln Phe Arg Lys Ala Ile Asp Asp Cys Gln Lys
1               5                   10                  15

Gln Ala His His Ser Asn Val Gly Asn Ser Val Phe Lys Glu Cys Met
            20                  25                  30

Lys Gln Lys Lys Lys Glu Phe Lys Ala Gly Lys
        35                  40

<210> SEQ ID NO 399
<211> LENGTH: 44
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
```

<220> FEATURE:
<221> NAME/KEY: DISULFID
<222> LOCATION: (14)..(32)
<220> FEATURE:
<221> NAME/KEY: MOD_RES
<222> LOCATION: (33)..(33)
<223> OTHER INFORMATION: Xaa = norleucine

<400> SEQUENCE: 399

Cys Asp Ala Thr Cys Gln Phe Arg Lys Ala Ile Asp Asp Cys Gln Lys
1               5                   10                  15

Gln Ala His His Ser Asn Val Pro Gly Asn Ser Val Phe Lys Glu Cys
            20                  25                  30

Xaa Lys Gln Lys Lys Lys Glu Phe Lys Ala Gly Lys
        35                  40

<210> SEQ ID NO 400
<211> LENGTH: 44
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(32)
<220> FEATURE:
<221> NAME/KEY: MOD_RES
<222> LOCATION: (43)..(43)
<223> OTHER INFORMATION: Xaa = 2-aminoisobutyric acid

<400> SEQUENCE: 400

Cys Asp Ala Thr Cys Gln Phe Arg Lys Ala Ile Asp Asp Cys Gln Lys
1               5                   10                  15

Gln Ala His His Ser Asn Val Pro Gly Asn Ser Val Phe Lys Glu Cys
            20                  25                  30

Met Lys Gln Lys Lys Lys Glu Phe Lys Ala Xaa Lys
        35                  40

<210> SEQ ID NO 401
<211> LENGTH: 44
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(32)
<220> FEATURE:
<221> NAME/KEY: MOD_RES
<222> LOCATION: (42)..(42)
<223> OTHER INFORMATION: Xaa = 2-aminoisobutyric acid

<400> SEQUENCE: 401

Cys Asp Ala Thr Cys Gln Phe Arg Lys Ala Ile Asp Asp Cys Gln Lys
1               5                   10                  15

Gln Ala His His Ser Asn Val Pro Gly Asn Ser Val Phe Lys Glu Cys
            20                  25                  30

Met Lys Gln Lys Lys Lys Glu Phe Lys Xaa Gly Lys
        35                  40

<210> SEQ ID NO 402

```
<211> LENGTH: 44
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(32)
<220> FEATURE:
<221> NAME/KEY: MOD_RES
<222> LOCATION: (41)..(41)
<223> OTHER INFORMATION: Xaa = 2-aminoisobutyric acid

<400> SEQUENCE: 402

Cys Asp Ala Thr Cys Gln Phe Arg Lys Ala Ile Asp Asp Cys Gln Lys
1               5                   10                  15

Gln Ala His His Ser Asn Val Pro Gly Asn Ser Val Phe Lys Glu Cys
            20                  25                  30

Met Lys Gln Lys Lys Lys Glu Phe Xaa Ala Gly Lys
            35                  40

<210> SEQ ID NO 403
<211> LENGTH: 44
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(32)
<220> FEATURE:
<221> NAME/KEY: MOD_RES
<222> LOCATION: (40)..(40)
<223> OTHER INFORMATION: Xaa = 2-aminoisobutyric acid

<400> SEQUENCE: 403

Cys Asp Ala Thr Cys Gln Phe Arg Lys Ala Ile Asp Asp Cys Gln Lys
1               5                   10                  15

Gln Ala His His Ser Asn Val Pro Gly Asn Ser Val Phe Lys Glu Cys
            20                  25                  30

Met Lys Gln Lys Lys Lys Glu Xaa Lys Ala Gly Lys
            35                  40

<210> SEQ ID NO 404
<211> LENGTH: 44
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(32)
<220> FEATURE:
<221> NAME/KEY: MOD_RES
<222> LOCATION: (39)..(39)
<223> OTHER INFORMATION: Xaa = 2-aminoisobutyric acid

<400> SEQUENCE: 404

Cys Asp Ala Thr Cys Gln Phe Arg Lys Ala Ile Asp Asp Cys Gln Lys
1               5                   10                  15
```

```
Gln Ala His His Ser Asn Val Pro Gly Asn Ser Val Phe Lys Glu Cys
            20                  25                  30

Met Lys Gln Lys Lys Lys Xaa Phe Lys Ala Gly Lys
        35                  40
```

<210> SEQ ID NO 405
<211> LENGTH: 44
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(32)
<220> FEATURE:
<221> NAME/KEY: MOD_RES
<222> LOCATION: (38)..(38)
<223> OTHER INFORMATION: Xaa = 2-aminoisobutyric acid

<400> SEQUENCE: 405

```
Cys Asp Ala Thr Cys Gln Phe Arg Lys Ala Ile Asp Asp Cys Gln Lys
1               5                   10                  15

Gln Ala His His Ser Asn Val Pro Gly Asn Ser Val Phe Lys Glu Cys
            20                  25                  30

Met Lys Gln Lys Lys Xaa Glu Phe Lys Ala Gly Lys
        35                  40
```

<210> SEQ ID NO 406
<211> LENGTH: 44
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(32)
<220> FEATURE:
<221> NAME/KEY: MOD_RES
<222> LOCATION: (37)..(37)
<223> OTHER INFORMATION: Xaa = 2-aminoisobutyric acid

<400> SEQUENCE: 406

```
Cys Asp Ala Thr Cys Gln Phe Arg Lys Ala Ile Asp Asp Cys Gln Lys
1               5                   10                  15

Gln Ala His His Ser Asn Val Pro Gly Asn Ser Val Phe Lys Glu Cys
            20                  25                  30

Met Lys Gln Lys Xaa Lys Glu Phe Lys Ala Gly Lys
        35                  40
```

<210> SEQ ID NO 407
<211> LENGTH: 44
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(32)
<220> FEATURE:
<221> NAME/KEY: MOD_RES

```
<222> LOCATION: (36)..(36)
<223> OTHER INFORMATION: Xaa = 2-aminoisobutyric acid

<400> SEQUENCE: 407

Cys Asp Ala Thr Cys Gln Phe Arg Lys Ala Ile Asp Asp Cys Gln Lys
1               5                   10                  15

Gln Ala His His Ser Asn Val Pro Gly Asn Ser Val Phe Lys Glu Cys
            20                  25                  30

Met Lys Gln Xaa Lys Lys Glu Phe Lys Ala Gly Lys
        35                  40

<210> SEQ ID NO 408
<211> LENGTH: 44
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(32)
<220> FEATURE:
<221> NAME/KEY: MOD_RES
<222> LOCATION: (20)..(20)
<223> OTHER INFORMATION: Xaa = 2-aminoisobutyric acid

<400> SEQUENCE: 408

Cys Asp Ala Thr Cys Gln Phe Arg Lys Ala Ile Asp Asp Cys Gln Lys
1               5                   10                  15

Gln Ala His Xaa Ser Asn Val Pro Gly Asn Ser Val Phe Lys Glu Cys
            20                  25                  30

Met Lys Gln Lys Lys Lys Glu Phe Lys Ala Gly Lys
        35                  40

<210> SEQ ID NO 409
<211> LENGTH: 44
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(32)
<220> FEATURE:
<221> NAME/KEY: MOD_RES
<222> LOCATION: (19)..(19)
<223> OTHER INFORMATION: Xaa = 2-aminoisobutyric acid

<400> SEQUENCE: 409

Cys Asp Ala Thr Cys Gln Phe Arg Lys Ala Ile Asp Asp Cys Gln Lys
1               5                   10                  15

Gln Ala Xaa His Ser Asn Val Pro Gly Asn Ser Val Phe Lys Glu Cys
            20                  25                  30

Met Lys Gln Lys Lys Lys Glu Phe Lys Ala Gly Lys
        35                  40

<210> SEQ ID NO 410
<211> LENGTH: 44
<212> TYPE: PRT
<213> ORGANISM: Artificial Sequence
<220> FEATURE:
<223> OTHER INFORMATION: Synthetic Polypeptide
```

```
<220> FEATURE:
<221> NAME/KEY: DISULFID
<222> LOCATION: (1)..(5)
<220> FEATURE:
<221> NAME/KEY: DISULFID
<222> LOCATION: (14)..(32)
<220> FEATURE:
<221> NAME/KEY: MOD_RES
<222> LOCATION: (18)..(18)
<223> OTHER INFORMATION: Xaa = 2-aminoisobutyric acid

<400> SEQUENCE: 410

Cys Asp Ala Thr Cys Gln Phe Arg Lys Ala Ile Asp Asp Cys Gln Lys
1               5                   10                  15

Gln Xaa His His Ser Asn Val Pro Gly Asn Ser Val Phe Lys Glu Cys
            20                  25                  30

Met Lys Gln Lys Lys Lys Glu Phe Lys Ala Gly Lys
        35                  40

<210> SEQ ID NO 411
<211> LENGTH: 44
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(32)
<220> FEATURE:
<221> NAME/KEY: MOD_RES
<222> LOCATION: (17)..(17)
<223> OTHER INFORMATION: Xaa = 2-aminoisobutyric acid

<400> SEQUENCE: 411

Cys Asp Ala Thr Cys Gln Phe Arg Lys Ala Ile Asp Asp Cys Gln Lys
1               5                   10                  15

Xaa Ala His His Ser Asn Val Pro Gly Asn Ser Val Phe Lys Glu Cys
            20                  25                  30

Met Lys Gln Lys Lys Lys Glu Phe Lys Ala Gly Lys
        35                  40

<210> SEQ ID NO 412
<211> LENGTH: 44
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(32)
<220> FEATURE:
<221> NAME/KEY: MOD_RES
<222> LOCATION: (16)..(16)
<223> OTHER INFORMATION: Xaa = 2-aminoisobutyric acid

<400> SEQUENCE: 412

Cys Asp Ala Thr Cys Gln Phe Arg Lys Ala Ile Asp Asp Cys Gln Xaa
1               5                   10                  15

Gln Ala His His Ser Asn Val Pro Gly Asn Ser Val Phe Lys Glu Cys
            20                  25                  30

Met Lys Gln Lys Lys Lys Glu Phe Lys Ala Gly Lys
        35                  40
```

<210> SEQ ID NO 413
<211> LENGTH: 36
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(32)
<220> FEATURE:
<221> NAME/KEY: MOD_RES
<222> LOCATION: (36)..(36)
<223> OTHER INFORMATION: C-terminal amidation

<400> SEQUENCE: 413

Cys Asp Ala Thr Cys Gln Phe Arg Lys Ala Ile Asp Cys Gln Lys
1               5                   10                  15

Gln Ala His His Ser Asn Val Pro Gly Asn Ser Val Phe Lys Glu Cys
            20                  25                  30

Met Lys Gln Lys
        35

<210> SEQ ID NO 414
<211> LENGTH: 37
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(32)
<220> FEATURE:
<221> NAME/KEY: MOD_RES
<222> LOCATION: (37)..(37)
<223> OTHER INFORMATION: C-terminal amidation

<400> SEQUENCE: 414

Cys Asp Ala Thr Cys Gln Phe Arg Lys Ala Ile Asp Cys Gln Lys
1               5                   10                  15

Gln Ala His His Ser Asn Val Pro Gly Asn Ser Val Phe Lys Glu Cys
            20                  25                  30

Met Lys Gln Lys Lys
        35

<210> SEQ ID NO 415
<211> LENGTH: 38
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(32)
<220> FEATURE:
<221> NAME/KEY: MOD_RES
<222> LOCATION: (38)..(38)
<223> OTHER INFORMATION: C-terminal amidation

<400> SEQUENCE: 415

Cys Asp Ala Thr Cys Gln Phe Arg Lys Ala Ile Asp Asp Cys Gln Lys
1               5                   10                  15

Gln Ala His His Ser Asn Val Pro Gly Asn Ser Val Phe Lys Glu Cys
            20                  25                  30

Met Lys Gln Lys Lys Lys
        35

<210> SEQ ID NO 416
<211> LENGTH: 39
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(32)
<220> FEATURE:
<221> NAME/KEY: MOD_RES
<222> LOCATION: (39)..(39)
<223> OTHER INFORMATION: C-terminal amidation

<400> SEQUENCE: 416

Cys Asp Ala Thr Cys Gln Phe Arg Lys Ala Ile Asp Asp Cys Gln Lys
1               5                   10                  15

Gln Ala His His Ser Asn Val Pro Gly Asn Ser Val Phe Lys Glu Cys
            20                  25                  30

Met Lys Gln Lys Lys Lys Glu
        35

<210> SEQ ID NO 417
<211> LENGTH: 40
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(32)
<220> FEATURE:
<221> NAME/KEY: MOD_RES
<222> LOCATION: (40)..(40)
<223> OTHER INFORMATION: C-terminal amidation

<400> SEQUENCE: 417

Cys Asp Ala Thr Cys Gln Phe Arg Lys Ala Ile Asp Asp Cys Gln Lys
1               5                   10                  15

Gln Ala His His Ser Asn Val Pro Gly Asn Ser Val Phe Lys Glu Cys
            20                  25                  30

Met Lys Gln Lys Lys Lys Glu Phe
        35                  40

<210> SEQ ID NO 418
<211> LENGTH: 41
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID

```
<222> LOCATION: (14)..(32)
<220> FEATURE:
<221> NAME/KEY: MOD_RES
<222> LOCATION: (41)..(41)
<223> OTHER INFORMATION: C-terminal amidation

<400> SEQUENCE: 418

Cys Asp Ala Thr Cys Gln Phe Arg Lys Ala Ile Asp Asp Cys Gln Lys
1               5                   10                  15

Gln Ala His His Ser Asn Val Pro Gly Asn Ser Val Phe Lys Glu Cys
            20                  25                  30

Met Lys Gln Lys Lys Lys Glu Phe Lys
            35                  40

<210> SEQ ID NO 419

<400> SEQUENCE: 419

000

<210> SEQ ID NO 420
<211> LENGTH: 43
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(32)
<220> FEATURE:
<221> NAME/KEY: MOD_RES
<222> LOCATION: (43)..(43)
<223> OTHER INFORMATION: C-terminal amidation

<400> SEQUENCE: 420

Cys Asp Ala Thr Cys Gln Phe Arg Lys Ala Ile Asp Asp Cys Gln Lys
1               5                   10                  15

Gln Ala His His Ser Asn Val Pro Gly Asn Ser Val Phe Lys Glu Cys
            20                  25                  30

Met Lys Gln Lys Lys Lys Glu Phe Lys Ala Gly
            35                  40

<210> SEQ ID NO 421
<211> LENGTH: 44
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(32)

<400> SEQUENCE: 421

Cys Asp Ala Thr Cys Gln Phe Arg Lys Ala Ile Asp Asp Cys Gln Lys
1               5                   10                  15

Gln Ala His His Ser Asn Val Pro Gly Asn Ser Val Phe Lys Glu Cys
            20                  25                  30

Met Lys Gln Lys Lys Lys Glu Phe Lys Ala Gly Ala
            35                  40
```

```
<210> SEQ ID NO 422
<211> LENGTH: 44
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(32)

<400> SEQUENCE: 422

Cys Asp Ala Thr Cys Gln Phe Arg Lys Ala Ile Asp Asp Cys Gln Lys
1               5                   10                  15

Gln Ala His His Ser Asn Val Pro Gly Asn Ser Val Phe Lys Glu Cys
            20                  25                  30

Met Lys Gln Lys Lys Lys Glu Phe Lys Ala Gly Glu
            35                  40

<210> SEQ ID NO 423

<400> SEQUENCE: 423

000

<210> SEQ ID NO 424
<211> LENGTH: 43
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(31)
<220> FEATURE:
<221> NAME/KEY: MOD_RES
<222> LOCATION: (43)..(43)
<223> OTHER INFORMATION: C-terminal amidation

<400> SEQUENCE: 424

Cys Asp Ala Thr Cys Gln Phe Arg Lys Ala Ile Asp Asp Cys Ala His
1               5                   10                  15

Arg Ala Trp His Ser Asn Val Pro Gly Ser Val Phe Lys Leu Cys Met
            20                  25                  30

Lys Gln Lys Lys Lys Glu Trp Lys Ala Gly His
            35                  40

<210> SEQ ID NO 425
<211> LENGTH: 43
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(31)
<220> FEATURE:
<221> NAME/KEY: MOD_RES
<222> LOCATION: (43)..(43)
<223> OTHER INFORMATION: C-terminal amidation

<400> SEQUENCE: 425
```

-continued

Cys Asp Ala Thr Cys Gln Phe Arg Lys Ala Ile Asp Asp Cys Ala Gly
1               5                   10                  15

Arg Ala Ser His Ala Asn Val Pro Gly Ser Val Phe Lys Ala Cys Met
            20                  25                  30

Lys Gln Lys Lys Lys Glu Trp Lys Ala Gly His
        35                  40

<210> SEQ ID NO 426
<211> LENGTH: 42
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (14)..(31)
<220> FEATURE:
<221> NAME/KEY: MOD_RES
<222> LOCATION: (42)..(42)
<223> OTHER INFORMATION: C-terminal amidation

<400> SEQUENCE: 426

Ser Asp Ala Thr Ser Gln Tyr Arg Lys Gly Leu Val Ala Cys Leu Tyr
1               5                   10                  15

Lys Lys Val Ala Met Gln Lys Arg Tyr Ser Val Phe Lys Ala Cys Met
            20                  25                  30

Lys Gln Lys Lys Lys Glu Trp Lys Ala Gly
        35                  40

<210> SEQ ID NO 427
<211> LENGTH: 39
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(31)
<220> FEATURE:
<221> NAME/KEY: MOD_RES
<222> LOCATION: (39)..(39)
<223> OTHER INFORMATION: C-terminal amidation

<400> SEQUENCE: 427

Cys Asp Ala Thr Cys Gln Tyr Arg Lys Gly Leu Val Ala Cys Leu Tyr
1               5                   10                  15

Lys Lys Val Ala Met Gln Lys Arg Tyr Ser Val Phe Lys Ala Cys Met
            20                  25                  30

Lys Gln Lys Lys Lys Glu Trp
        35

<210> SEQ ID NO 428
<211> LENGTH: 38
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(27)
<220> FEATURE:

```
<221> NAME/KEY: PEPTIDE
<222> LOCATION: (38)..(38)
<223> OTHER INFORMATION: C-term amide

<400> SEQUENCE: 428

Cys Asp Ala Thr Cys Gln Phe Arg Lys Ala Ile Asp Asp Cys Ala Arg
1               5                   10                  15

Gln Ala Tyr His Ala Ser Val Phe Lys Ala Cys Met Lys Gln Lys Lys
            20                  25                  30

Lys Glu Trp Lys Ala Gly
        35

<210> SEQ ID NO 429
<211> LENGTH: 39
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(28)
<220> FEATURE:
<221> NAME/KEY: PEPTIDE
<222> LOCATION: (39)..(39)
<223> OTHER INFORMATION: C-term amide

<400> SEQUENCE: 429

Cys Asp Ala Thr Cys Gln Phe Arg Lys Ala Ile Asp Asp Cys Ala Arg
1               5                   10                  15

Gln Ala Tyr His Ser Asn Ser Val Phe Lys Ala Cys Met Lys Gln Lys
            20                  25                  30

Lys Lys Glu Trp Lys Ala Gly
        35

<210> SEQ ID NO 430
<211> LENGTH: 38
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(27)
<220> FEATURE:
<221> NAME/KEY: PEPTIDE
<222> LOCATION: (38)..(38)
<223> OTHER INFORMATION: C-term amide

<400> SEQUENCE: 430

Cys Asp Ala Thr Cys Gln Phe Arg Lys Ala Ile Asp Asp Cys Ala Arg
1               5                   10                  15

Gln Ala Tyr His Ser Ser Val Phe Lys Ser Cys Met Lys Gln Lys Lys
            20                  25                  30

Lys Glu Trp Lys Ala Gly
        35

<210> SEQ ID NO 431
<211> LENGTH: 38
<212> TYPE: PRT
<213> ORGANISM: Artificial Sequence
<220> FEATURE:
```

<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(27)
<220> FEATURE:
<221> NAME/KEY: PEPTIDE
<222> LOCATION: (38)..(38)
<223> OTHER INFORMATION: C-term amide

<400> SEQUENCE: 431

Cys Asp Ala Thr Cys Gln Phe Arg Lys Ala Ile Asp Asp Cys Ala Arg
1               5                   10                  15

Ser Ala Tyr His Ser Ser Val Phe Lys Ala Cys Met Lys Gln Lys Lys
            20                  25                  30

Lys Glu Trp Lys Ala Gly
        35

<210> SEQ ID NO 432
<211> LENGTH: 38
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(27)
<220> FEATURE:
<221> NAME/KEY: PEPTIDE
<222> LOCATION: (38)..(38)
<223> OTHER INFORMATION: C-term amide

<400> SEQUENCE: 432

Cys Asp Ala Thr Cys Gln Phe Arg Lys Ala Ile Asp Asp Cys Ala Arg
1               5                   10                  15

Gln Ser Tyr His Ser Ser Val Phe Lys Ala Cys Met Lys Gln Lys Lys
            20                  25                  30

Lys Glu Trp Lys Ala Gly
        35

<210> SEQ ID NO 433
<211> LENGTH: 38
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(27)
<220> FEATURE:
<221> NAME/KEY: PEPTIDE
<222> LOCATION: (38)..(38)
<223> OTHER INFORMATION: C-term amide

<400> SEQUENCE: 433

Cys Asp Ala Thr Cys Gln Phe Arg Lys Ala Ile Asp Asp Cys Ala Arg
1               5                   10                  15

Gln Ala Ser His Ser Ser Val Phe Lys Ala Cys Met Lys Gln Lys Lys
            20                  25                  30

Lys Glu Trp Lys Ala Gly

<210> SEQ ID NO 434
<211> LENGTH: 38
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(27)
<220> FEATURE:
<221> NAME/KEY: PEPTIDE
<222> LOCATION: (38)..(38)
<223> OTHER INFORMATION: C-term amide

<400> SEQUENCE: 434

Cys Asp Ala Thr Cys Gln Phe Arg Lys Ala Ile Asp Asp Cys Ala Arg
1               5                   10                  15

Gln Ala Lys His Ser Ser Val Phe Lys Ala Cys Met Lys Gln Lys Lys
            20                  25                  30

Lys Glu Trp Lys Ala Gly
        35

<210> SEQ ID NO 435
<211> LENGTH: 38
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(27)
<220> FEATURE:
<221> NAME/KEY: PEPTIDE
<222> LOCATION: (38)..(38)
<223> OTHER INFORMATION: C-term amide

<400> SEQUENCE: 435

Cys Asp Ala Thr Cys Gln Phe Arg Lys Ala Ile Asp Asp Cys Ala Arg
1               5                   10                  15

Gln Ala Tyr His Ser Ser Val Phe Lys Ala Cys Leu Lys Gln Lys Lys
            20                  25                  30

Lys Glu Trp Lys Ala Gly
        35

<210> SEQ ID NO 436
<211> LENGTH: 38
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(27)
<220> FEATURE:
<221> NAME/KEY: PEPTIDE
<222> LOCATION: (38)..(38)
<223> OTHER INFORMATION: C-term amide

<400> SEQUENCE: 436

Cys Asp Ala Thr Cys Gln Phe Arg Lys Ala Ile Asp Asp Cys Ala Arg
1               5                   10                  15

Gln Ala Tyr His Ser Ser Val Phe Lys Ser Cys Leu Lys Gln Lys Lys
                20                  25                  30

Lys Glu Trp Lys Ala Gly
            35

<210> SEQ ID NO 437
<211> LENGTH: 25
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: PEPTIDE
<222> LOCATION: (25)..(25)
<223> OTHER INFORMATION: C-term amide

<400> SEQUENCE: 437

Cys Asp Ala Thr Cys Gln Tyr Arg Lys Gly Leu Val Ala Ser Leu Tyr
1               5                   10                  15

Lys Lys Val Ala Met Gln Lys Arg Tyr
                20                  25

<210> SEQ ID NO 438
<211> LENGTH: 30
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)

<400> SEQUENCE: 438

Cys Asp Ala Thr Cys Gln Tyr Arg Lys Gly Leu Val Ala Ser Val Phe
1               5                   10                  15

Lys Ala Ser Met Lys Gln Lys Lys Lys Glu Phe Lys Ala Gly
                20                  25                  30

<210> SEQ ID NO 439
<211> LENGTH: 37
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(25)

<400> SEQUENCE: 439

Cys Asp Ala Thr Cys Gln Phe Arg Lys Ala Ile Asp Asp Cys Ala Arg
1               5                   10                  15

Gln Ala Tyr His Ser Phe Lys Ala Cys Met Lys Gln Lys Lys Lys Glu
                20                  25                  30

Trp Lys Ala Gly His
            35

<210> SEQ ID NO 440

```
<211> LENGTH: 34
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (12)..(25)

<400> SEQUENCE: 440

Ala Thr Ser Gln Phe Arg Lys Ala Ile Asp Asp Cys Ala Arg Gln Ala
1               5                   10                  15

Tyr His Ser Ser Val Phe Lys Ala Cys Met Lys Gln Lys Lys Lys Glu
            20                  25                  30

Trp Lys

<210> SEQ ID NO 441
<211> LENGTH: 32
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (10)..(21)

<400> SEQUENCE: 441

Ser Asp Ala Thr Ser Gln Phe Arg Lys Cys Ile Asp Asp Ser Gly Ala
1               5                   10                  15

Phe Lys Ala Ser Cys Lys Gln Lys Lys Lys Glu Trp Lys Ala Gly His
            20                  25                  30

<210> SEQ ID NO 442
<211> LENGTH: 31
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(30)

<400> SEQUENCE: 442

Cys Asp Ala Thr Ser Gln Phe Arg Lys Ala Ile Asp Asp Ser Ala Phe
1               5                   10                  15

Lys Ala Ser Met Lys Gln Lys Lys Lys Glu Trp Lys Ala Cys His
            20                  25                  30

<210> SEQ ID NO 443
<211> LENGTH: 32
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(20)

<400> SEQUENCE: 443

Cys Asp Ala Thr Cys Gln Phe Arg Lys Ala Ile Asp Asp Cys Ala Ala
1               5                   10                  15

Phe Lys Ala Cys Met Lys Gln Lys Lys Lys Glu Trp Lys Ala Gly His
            20                  25                  30
```

<210> SEQ ID NO 444
<211> LENGTH: 31
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(19)

<400> SEQUENCE: 444

Cys Asp Ala Thr Cys Gln Phe Arg Lys Ala Ile Asp Asp Cys Ala Phe
1               5                   10                  15

Lys Ala Cys Met Lys Gln Lys Lys Lys Glu Trp Lys Ala Gly His
            20                  25                  30

<210> SEQ ID NO 445
<211> LENGTH: 43
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(31)
<220> FEATURE:
<221> NAME/KEY: PEPTIDE
<222> LOCATION: (43)..(43)
<223> OTHER INFORMATION: C-term amide

<400> SEQUENCE: 445

Cys Asp Ala Thr Cys Gln Phe Arg Lys Ala Ile Asp Asp Cys Ala Asn
1               5                   10                  15

Lys Ser Trp His Ser Asn Val Pro Gly Ser Val Phe Lys Leu Cys Met
            20                  25                  30

Lys Gln Lys Lys Lys Glu Trp Lys Ala Gly His
        35                  40

<210> SEQ ID NO 446
<211> LENGTH: 42
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(31)
<220> FEATURE:
<221> NAME/KEY: PEPTIDE
<222> LOCATION: (42)..(42)
<223> OTHER INFORMATION: C-term amide

<400> SEQUENCE: 446

Cys Asp Ala Thr Cys Gln Phe Arg Lys Ala Ile Asp Asp Cys Ala Gly
1               5                   10                  15

Thr Ala Arg His Ser Asn Val Pro Gly Ser Val Phe Lys Ala Cys Met
            20                  25                  30

Lys Gln Lys Lys Lys Glu Trp Lys Ala Gly
        35                  40

<210> SEQ ID NO 447
<211> LENGTH: 33
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(21)

<400> SEQUENCE: 447

Cys Asp Ala Thr Cys Gln Phe Arg Lys Ala Ile Asp Asp Cys Ala Arg
1               5                   10                  15

Gln Phe Lys Ala Cys Met Lys Gln Lys Lys Glu Trp Lys Ala Gly
            20                  25                  30

His

<210> SEQ ID NO 448
<211> LENGTH: 35
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(23)

<400> SEQUENCE: 448

Cys Asp Ala Thr Cys Gln Phe Arg Lys Ala Ile Asp Asp Cys Ala Arg
1               5                   10                  15

Gln Ala Tyr Phe Lys Ala Cys Met Lys Gln Lys Lys Lys Glu Trp Lys
            20                  25                  30

Ala Gly His
        35

<210> SEQ ID NO 449
<211> LENGTH: 35
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(23)

<400> SEQUENCE: 449

Cys Asp Ala Thr Cys Gln Phe Arg Lys Ala Ile Asp Asp Cys Ala Arg
1               5                   10                  15

Gln Ala Tyr His Ser Ala Cys Met Lys Gln Lys Lys Lys Glu Trp Lys
            20                  25                  30

Ala Gly His
        35

<210> SEQ ID NO 450
<211> LENGTH: 35
<212> TYPE: PRT

```
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(25)

<400> SEQUENCE: 450

Cys Asp Ala Thr Cys Gln Phe Arg Lys Ala Ile Asp Asp Cys Ala Arg
1               5                   10                  15

Gln Ala Tyr His Ser Phe Lys Ala Cys Met Lys Gln Lys Lys Lys Glu
            20                  25                  30

Trp Lys His
        35

<210> SEQ ID NO 451
<211> LENGTH: 36
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (1)..(5)
<220> FEATURE:
<221> NAME/KEY: DISULFID
<222> LOCATION: (14)..(25)

<400> SEQUENCE: 451

Cys Asp Ala Thr Cys Gln Phe Arg Lys Ala Ile Asp Asp Cys Ala Arg
1               5                   10                  15

Gln Ala Tyr His Ser Phe Lys Ala Cys Met Lys Gln Lys Lys Lys Glu
            20                  25                  30

Trp Lys Ala His
        35
```

PEPTIDE PAC1 ANTAGONISTS

CROSS REFERENCE TO RELATED APPLICATIONS

This application is the national stage application under 35 U.S.C. § 371 of International Application No. PCT/US2018/035597, having an international filing date of Jun. 1, 2018; which claims the benefit under 35 U.S.C 119(e) of U.S. Provisional Application No. 62/514,440, filed Jun. 2, 2017, all of which are incorporated by reference herein in their entireties.

REFERENCE TO THE SEQUENCE LISTING

The present application contains a Sequence Listing, which has been submitted electronically in ASCII format and is hereby incorporated by reference in its entirety. The computer readable format copy of the Sequence Listing, which was created on May 30, 2018, is named A-2135-WO-PCT_Sequence_Listing_ST25.txt and is 271 KB bytes in size.

BACKGROUND

Migraine is characterized by headaches that can involve significant pain, and is often accompanied by nausea, vomiting, and extreme sensitivity to light (photophobia) and sound (phonophobia), and is sometimes preceded by sensory warning symptoms or signs (auras). It is a highly prevalent disease worldwide with approximately 12% of the European population, and 18% of women, 6% of men in the United States suffering from migraine attacks (Lipton et al, Neurology, Vol. 68:343-349, 2007; Lipton et al., Headache, Vol. 41:646-657, 2001). Additionally, migraines are associated with a number of psychiatric and medical comorbidities such as depression and vascular disorders (Buse et al., J. Neurol. Neurosurg. Psychiatry, Vol. 81:428-432, 2010; Bigal et al., Neurology, Vol. 72:1864-1871, 2009). There is a significant unmet need for effective therapies for migraine. Most of the current migraine therapies are either not well tolerated or ineffective (Loder et al., Headache, Vol. 52:930-945, 2012; Lipton et al, 2001); thus, migraine remains an unmet medical need.

The exact mechanism of migraine pathophysiology has been debated since the 17th century but is still not fully clarified, even though scientists have made a lot of progress in understanding it. A major component of migraine pathogenesis involves the activation of the trigeminovascular system. The release of trigeminal and parasympathetic neurotransmitters from perivascular nerve fibers (Sinchez-del-Rio et al., Curr. Opin. Neurol., Vol. 17(3):289-93, 2004) result in vasodilation of the cranial blood vessels and has been suggested to be associated with the onset of migraine headaches (Edvinsson, Cephalagia, Vol. 33(13): 1070-1072, 2013; Goadsby et al., New Engl J Med., Vol. 364(4):257-270, 2002).

Pituitary adenylate cyclase-activating peptide (PACAP) and its receptors (PAC1, VPAC1 and VPAC2) are present in sensory neurons and in vascular smooth muscle related to the trigeminovascular system, a key circuitry in migraine pain. Recent data point to an involvement of PACAP, in particular the PAC1 receptor, in the pathophysiology of migraine (Rahmann A. et al. Cephalalgia 2008; 28:226-36). PAC1 receptor is a class II G-protein coupled receptor that modulates adenyl cyclase activity and cAMP signaling. Vasoactive intestinal peptide and PACAP mediate their effect via VPAC1 and VPAC2 receptors with almost equal affinity, whereas PACAP has much high affinity to the PAC1-receptor. Considering that PACAP-38 is a trigger of migraine attacks, the PAC1-receptor may therefore be a putative target for migraine treatment (Edvinsson L., Br J Pharmacol 2014). Furthermore, recent clinical studies have demonstrated that the intravenous administration of PACAP can induce middle meningeal artery vasodilation and headache in both migraineurs and healthy subjects. Id.

Maxadilan is a PAC1 receptor agonist (Banki E. et al., Neuropharmacology 2014; 85:538-4). A recent study showed that PAC1 receptor activation by Maxadilan could inhibit the acute neurogenic arterial vasodilation and the plasma protein release from the venules. Considering the findings that demonstrated the migraine attack induction by PACAP, the PAC1 receptor can represent a promising candidate as a therapeutic target (Rainero I. et al. J Headache Pain 2013; 14).

SUMMARY

In one aspect, the invention includes novel peptides that are antagonists of the PAC1 receptor for treatment of migraine.

The peptides of Formula I, or a pharmaceutically acceptable salt thereof, are contemplated by the invention.

$$X^0X^1X^2X^3X^4X^5X^6X^7X^8X^9X^{10}X^{11}X^{12}X^{13}$$
$$X^{14}X^{15}X^{16}X^{17}X^{18}X^{19}X^{20}X^{21}X^{22}X^{23}$$
$$X^{24}X^{25}X^{26}X^{27}X^{28}X^{29}X^{30}X^{31}X^{32}X^{33}$$
$$X^{34}X^{35}X^{36}X^{37}X^{38}X^{39}X^{40}X^{41}X^{42}X^{43}X^{44}$$

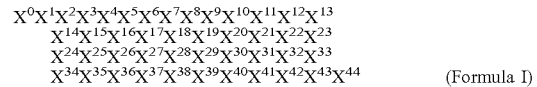
(Formula I)

All variations listed below are contemplated as independent from each other.

In one aspect, $X^0$ is Gly, Ser, Gly-Ser-, Ala, Met, [Pra], Gly-Met- or is absent.

For example, $X^1$ can be Cys if $X^5$ is Cys or $X^1$ can be Ser if $X^5$ is Ser, Thr, or is absent. $X^2$ can be Asp, Glu, or an acidic amino acid residue, or can be absent. In another aspect, $X^3$ is Ala, Pro, Ser, [Aib], or a hydrophobic amino acid residue, or is absent. In another example, $X^4$ may be chosen from Thr, Ser, Val, Tyr or a neutral, hyrdrophilic or hydrophobic amino acid residue, or may be absent. $X^5$ can be Cys if $X^1$ is Cys; or $X^5$ is Ser if $X^1$ is Ser, or can be absent. Further, $X^6$ can be Lys, [Cit], His, Arg, or other basic amino acid residue or Gln, Asn, Phe, or other neutral amino acid residue, or Glu or other acidic amino acid residue, or can be absent. In one aspect, $X^7$ is Phe, Tyr, His or a neutral or hydrophobic amino acid residue, or is absent; $X^8$ is Lys, Arg, or a basic amino acid residue, or is absent; $X^9$ is Lys, Arg, or a basic amino acid residue, or is absent, and $X^{10}$ is Ala, Cys, Gly, Leu, Gln, Val or a neutral amino acid residue, or is absent.

The invention provides PAC1 antagonistic peptides, wherein $X^{11}$ can be Ile, Leu, Met, [Aib] or a hydrophobic amino acid residue, or can be absent; $X^{12}$ can be Asp, Glu, or an acidic amino acid residue, or Ala, Val or other neutral amino acid residue or can be absent. Further, $X^{13}$ can be Asp, Glu, or an acidic or Ala, Val, [Aib] or other neutral amino acid residue, or Lys, or is absent. In one aspect, $X^{14}$ is Cys, Trp, Ile, Met, Ser or absent; $X^{15}$ can be Gln, Ala, Phe, Ile, Leu, Met, Ser, Val, Trp, Tyr or other neutral amino acid, or Asp, [Cit], or a neutral or acidic amino acid residue, or His, Lys or other basic amino acid residue, or absent; $X^{16}$ can be Lys, Arg, His or other basic amino acid residue or Phe, Ile, Leu, [Aib], Gln, Met, Thr, Val, [Pra], Trp, Tyr, Gly, His, Asn or other neutral or [hGlu] acidic amino acid residue, or absent; $X^{17}$ can be Ala, Gln, [Aib], Phe, Ile, Leu, Ser, Val, Trp, Tyr, Thr or other neutral amino acid residue, or [Cit], Lys, Arg, or other basic amino acid residue or Asp, or other acidic amino acid residue or absent; $X^{18}$ can be Ala, Leu, [Aib], [Pra], Ser or other neutral amino acid residue, or Glu or other acidic amino acid residue, or Lys or other basic amino acid residue, or absent; $X^{19}$ can be His, Lys, Arg or other basic amino acid residue or Ala, Phe, Ile, Leu, Met, Gln, Ser, Val, Trp, Tyr, [Aib], or other neutral or hydrophobic amino acid residue or absent; $X^{20}$ can be Ala, [Aib], Tyr, or other neutral or hydrophobic amino acid residue, or His or other basic amino acid residue or absent.

The invention also provides that $X^{21}$ can be Ala, Met, Ser, Val, [Aib], or a neutral amino acid residue, or absent; $X^{22}$ can be Asn, His, Gln, or a basic or neutral amino acid residue, or Glu or other acidic amino acid residue, or absent; $X^{23}$ can be Gly, Val, Thr, or a neutral amino acid residue, or Glu or other acidic amino acid residue, or Lys or other basic amino acid residue, or absent; $X^{24}$ can be absent, or can be Pro, [Pip], [Sar], [Hyp], [DHP] or a neutral amino acid residue, or Arg or other basic amino acid residue; $X^{21}$ can be absent, Ala, Gly, Tyr, [Pra], or a neutral amino acid residue; $X^{26}$ can be absent, Asn, Gln or a neutral amino acid residue, or -Leu-Gln-Thr-Ser-Val-; $X^{27}$ can be Ala, Gly, Ser, [Aib] or a neutral or hydrophilic amino acid residue, or Asp or other acidic amino acid residue, or is absent; $X^{28}$ can be absent, Val, Thr, Ala, or a neutral or hydrophilic amino acid residue, or Lys or other basic amino acid residue; $X^{29}$ can be absent, or can be Phe, Trp, Tyr, [Aib], or a neutral or hydrophobic amino acid residue; $X^{30}$ can be Lys, [Aib], Ala, or [d-Ala] (also depicted as a) or a basic or neutral amino acid residue, or Glu or other acidic amino acid residue or absent.

In another aspect, $X^{31}$ can be Glu, [Aib], Ala, Ser, Thr, Val, Leu or an acidic or neutral amino acid residue, Lys or other basic amino acid residue or absent; $X^{32}$ can be Cys, Leu, Ser, or is absent, or Arg; $X^{33}$ can be Ala, Phe, Ile, Leu, Ser, Val, [SeMet], Met, [Nle], or a hydrophobic amino acid residue, or is absent: $X^{34}$ can be Lys, [Aib], Ala, Leu, Val or a basic or neutral amino acid residue, or Glu or other acidic amino acid residue or absent; $X^{35}$ can be Gln, Phe, Asn, Thr, [Aib], Ala, Pro, Cys or neutral amino acid residue, or Glu or an acidic amino acid residue, or Arg or other basic amino acid residue or absent; $X^{36}$ can be Lys, [d-Lys] (also depicted as k), [Orn], Glu, Gly, Gln, His, Ala, [Aib], [NMeLys], Cys, Arg, Leu or a basic or neutral amino acid residue, or absent; $X^{37}$ can be Lys, Ala, Gln, [Aib], Phe, Arg, or a basic or neutral amino acid residue, or absent; $X^{38}$ can be absent, Lys, Ala, [Aib], Glu, [Orn], Gln, Gly, [d-Lys](also depicted as k), [NMeLys], Phe, Leu, Asn, Arg, Thr, or an acidic or basic or neutral amino acid residue; $X^{39}$ can be absent, or can be Glu, Ala, [Aib], Leu, Val or an acidic or neutral amino acid residue, or Arg or other basic amino acid residue; $X^{40}$ can be absent, or can be Phe, [AMEF], Trp, [d-Phe] (also depicted as f), [hPhe], Tyr, [Aib], [pI-Phe] or a neutral or hydrophobic amino acid residue, or Glu or other acidic amino acid residue; $X^{41}$ can be absent, Lys, [NMeLys], [d-Lys] (also depicted as k), Gln, Glu, His, Ala, [Aib], Leu, Arg or a basic, or acidic, or neutral amino acid residue; $X^{42}$ can be absent, or can be Ala, Glu, [Aib], Pro, Cys or an acidic or neutral amino acid residue; $X^{43}$ can be absent, or can be Gly, Glu, Ala, [Aib], Asn, Gln, Trp, Cys or a neutral or acidic amino acid residue, or His, Arg or other basic amino acid residue; $X^{44}$ can be absent, Lys, His, [d-Lys] (also depicted as k), [Orn], Ala, Phe, Asn, Gln, Arg, Trp, Tyr or a basic or neutral amino acid residue, or -Gly-Ser, -Gly-Gly-Gly-Ser, -His-His-His-His-His, or -His-His-His-His-His-His, or Glu or other acidic amino acid; wherein only 11 amino acid residues can be absent at the same time.

In one aspect of the invention, wherein $X^1$ and $X^5$ may optionally form disulfide bonds. In another aspect, $X^{14}$ and $X^{32}$ may optionally form disulfide bonds. The invention further provides PAC1 antagonistic peptides, wherein the amino-terminal residue may be optionally acetylated; and the carboxy-terminal residue may be optionally amidated.

The invention provides peptides or a pharmaceutically acceptable salt thereof, wherein $X^0$ is G, acetyl, A, M, S, G-S-, [Pra], G-M-, or absent; for example, G or absent. It also provides that $X^1$ can be C or S. In one example, $X^2$ can be D or E. In another aspect, $X^3$ can be A, P or [Aib]. In the next example, $X^4$ can be T, Y, S, V or absent. In a further example, $X^5$ is C or S. In one aspect, $X^1$ and $X^5$ can be both C and connected by a disulfide bond. In one aspect, $X^6$ is Q, H, F, K, [Cit], E, N or S. In another aspect, $X^7$ can be F or Y. The invention provides that $X^8$ can be R or K, or that $X^9$ is K or R. In one example, $X^{10}$ can be A, G, V, C or L. In another example, $X^{11}$ can be I, [Aib] or L. In a further example, $X^{12}$ can be D, V or E. Further, $X^{13}$ can be D, E, A or [Aib]. The invention provides peptides, wherein $X^{14}$ can be C or W. $X^{15}$ can be Q, D, K, A, L, Y, F, V, W, S, M, H or I. In one example, $X^{15}$ can be A, D, V, or L; and $X^{16}$ can be K, R, Y, V, W, I, L, T, F, M, T, [Pra], W, Q, [Aib] or [hGlu], H, G, in particular, R, K, or L. In another example, $X^{17}$ can be Q, A, R, [Aib], [Cit], W, L, S, Y, F, W, V, D, I, K or V; or, for example, Q or R. In a further aspect, $X^{18}$ can be A, S, [Pra], K, E, L or [Aib]. In another example, $X^{19}$ can be H, W, R, K, Y, M, A, I, L, S, Q, V, F or absent, in particular, H, W or Y. In a further example, $X^{20}$ can be H, Y, [Aib], A, or absent.

The peptides of the invention provided herein include examples wherein $X^{21}$ can be S, A, M, [Aib] or V. In one example, $X^{22}$ can be N, Q, E, H or absent, in particular N or absent. In another example, $X^{23}$ can be V, G, K, E, T or absent, for example, V or absent. In another example, $X^{24}$ can be P, [DHP], R, [Sar], [Hyp], [Pip] or absent. For example, $X^{21}$ can be G, [Pra], A, Y, or absent. In a further aspect of the invention, $X^{26}$ can be N, -LQTSV-, Q or absent. The invention provides that $X^{27}$ can be S, [Aib], A, G, D or absent. The invention further provides that $X^{28}$ can be V, K, T, A or absent. In one example, $X^{29}$ is F, W, Y, [Aib] or absent. In another example, $X^{30}$ can be K, [Aib], A, [d-a] (also depicted as a) or E.

The invention provides PAC1 antagonist peptides, wherein $X^{31}$ can be E, S, A, L, [Aib], T, V or K. in one example, $X^{32}$ can be C or R. In a following example, $X^{33}$ can be M, [SeMet], L, F, I, S, [Nle] or V. In a next example, $X^{34}$ can be K, V, L, [Aib], A or E. in one aspect, $X^{35}$ can be Q, E, R, F, [Aib], A, T, N or P. In one aspect, $X^{36}$ can be K, R, H, L, C, A, [d-k] (also depicted as k), [Orn], Q, [Aib], E, G or [NMeLys]. In another aspect, $X^{37}$ can be K, R, F, A, [Aib] or Q. In a further aspect, $X^{38}$ can be K, R, L, F, T, N, [Aib], A, [Orn], E, Q, G, [d-k] (also depicted as k) or [NMeLys]. In a still further example, $X^{39}$ can be E, R, L, V, A or [Aib]. In one aspect, $X^{40}$ can be F, W, Y, [d-f] (also depicted as f), [AMEF], [Aib], [hPh], E or [pI-Phe], in particular, W or F. In another aspect, $X^{41}$ can be K, L, R, Q, [d-k] (also depicted as k), [Aib], [NMeLys], E, A, H or absent. In a further aspect, $X^{42}$ can be A, [Aib], C, E, P or absent. In a further aspect, $X^{43}$ can be G, N, R, H, A, Q, W, [Aib], E or absent. In one aspect, $X^{44}$ can be K, H, Y, N, -His$_6$, -G$_3$S, R, W, A, Q, F, -His$_5$, E, -G-S, [d-k] (also depicted as k), [Orn] or absent, in particular, H, Y or absent. The invention provides peptides wherein $X^{14}$ and $X^{32}$ can be both C and connected by a disulfide bond.

The peptides contemplated by the invention include PAC1 antagonistc peptides of Formula 1, wherein the N-terminus of the peptide is acetylated and the C-terminus of the peptide is amidated. In one aspect, a peptide or a pharmaceutically acceptable salt thereof is of SEQ ID NO:1-SEQ ID NO:451. The invention further provides compositions comprising the peptide of the invention, or a pharmaceutically acceptable sale thereof and a pharmaceutically acceptable excipient.

The invention also contemplates the methods of treatment of migraine using any of the peptides of the invention, or a pharmaceutically acceptable salt thereof. In one aspect, the invention includes the method of any as above, wherein the method comprises acute treatment.

DETAILED DESCRIPTION

This invention disclosure generally relates to novel synthetic peptides that are PAC1 receptor antagonists and their use for treating migraine, especially acute migraine.

Unless otherwise defined herein, scientific and technical terms used in connection with the present application shall have the meanings that are commonly understood by those of ordinary skill in the art.

Generally, nomenclatures used in connection with, and techniques of, cell and tissue culture, molecular biology, immunology, microbiology, genetics and protein and nucleic acid chemistry and hybridization described herein are those well-known and commonly used in the art. The methods and techniques of the present application are generally performed according to conventional methods well known in the art and as described in various general and more specific references that are cited and discussed throughout the present specification unless otherwise indicated. See, e.g., Sambrook et al., Molecular Cloning: A Laboratory Manual, 3rd ed., Cold Spring Harbor Laboratory Press, Cold Spring Harbor, N.Y. (2001), Ausubel et al., Current Protocols in Molecular Biology, Greene Publishing Associates (1992), and Harlow and Lane Antibodies: A Laboratory Manual Cold Spring Harbor Laboratory Press, Cold Spring Harbor, N.Y. (1990), which are incorporated herein by reference. Enzymatic reactions and purification techniques are performed according to manufacturer's specifications, as commonly accomplished in the art or as described herein. The terminology used in connection with, and the laboratory procedures and techniques of, analytical chemistry, synthetic organic chemistry, and medicinal and pharmaceutical chemistry described herein are those well-known and commonly used in the art. Standard techniques can be used for chemical syntheses, chemical analyses, pharmaceutical preparation, formulation, and delivery, and treatment of patients.

It should be understood that this invention is not limited to the particular methodology, protocols, and reagents, etc., described herein and as such may vary. The terminology used herein is for the purpose of describing particular embodiments only, and is not intended to limit the scope of the present invention, which is defined solely by the claims.

Other than in the operating examples, or where otherwise indicated, all numbers expressing quantities of ingredients or reaction conditions used herein should be understood as modified in all instances by the term "about." The term "about" when used in connection with percentages means±10%.

Definitions

The terms "polypeptide" or "protein" are used interchangeably herein to refer to a polymer of amino acid residues. The terms also apply to amino acid polymers in which one or more amino acid residues is an analog or mimetic of a corresponding naturally occurring amino acid, as well as to naturally occurring amino acid polymers. The terms can also encompass amino acid polymers that have been modified, e.g., by the addition of carbohydrate residues to form glycoproteins, or phosphorylated. Polypeptides and proteins can be produced by a naturally-occurring and non-recombinant cell; or by a genetically-engineered or recombinant cell, and comprise molecules having the amino acid sequence of the native protein, or molecules having deletions from, additions to, and/or substitutions of one or more amino acids of the native sequence. The terms "polypeptide" and "protein" specifically encompass antibodies, e.g., anti-PAC1 antibodies (aka PAC1 antibodies), PAC1 binding proteins, antibodies, or sequences that have deletions from, additions to, and/or substitutions of one or more amino acids of an antigen-binding protein. The term "polypeptide fragment" refers to a polypeptide that has an amino-terminal deletion, a carboxyl-terminal deletion, and/or an internal deletion as compared with the full-length protein. Such fragments may also contain modified amino acids as compared with the full-length protein.

The term "isolated protein" or "isolated polypeptide" means that a subject protein or polypeptide is free of most other proteins with which it would normally be found and has been separated from at least about 50 percent of polynucleotides, lipids, carbohydrates, or other materials with which it is associated in nature. Typically, an "isolated protein" or "isolated polypeptide" constitutes at least about 5%, at least about 10%, at least about 25%, or at least about 50% of a given sample. Genomic DNA, cDNA, mRNA or other RNA, of synthetic origin, or any combination thereof may encode such an isolated protein.

Preferably, the isolated protein polypeptide or antibody is substantially free from other proteins or other polypeptides or other contaminants that are found in its natural environment that would interfere with its therapeutic, diagnostic, prophylactic, research or other use.

The terms "human PAC1", "human PAC$_1$", "hPAC1" and "hPAC$_1$", "human PAC1 receptor", "human PAC$_1$ receptor", "hPAC1 receptor" and "hPAC$_1$ receptor" are used interchangeably and refer to the human pituitary adenylate cyclase-activating polypeptide type I receptor. hPAC1 is a 468 amino acid protein designated as P41586 (PACR_HUMAN) in the UniProtKB/Swiss-Prot database and is encoded by the ADCYAP1R1 gene. PACAP-27 and PACAP-38 are the principal endogenous agonists of PAC1. Unless otherwise specified or clear from the context in which the term is used, "PAC1" refers to human PAC1.

The terms "fragment," "derivative," and "variant," when referring to the polypeptides of the invention, means fragments, derivatives, and variants of the polypeptides which retain substantially the same biological function or activity as such polypeptides, as described further below. The fragment, derivative, or variant of the polypeptides of the present invention may be (i) one in which one or more of the amino acid residues are substituted with a conserved or non-conserved amino acid residue (e.g., a conserved amino acid residue) and such substituted amino acid residue may or may not be one encoded by the genetic code, or (ii) one in which one or more of the amino acid residues includes a substituent group, or (iii) one in which the mature polypeptide is fused with another compound, such as a compound to increase the half-life of the polypeptide (e.g., polyethyleneglycol or PEG), or (iv) one in which the additional amino acids are fused to the mature polypeptide, such as a leader or secretory sequence or a sequence which is employed for purification of the mature polypeptide or a propolypeptide sequence, or (v) one in which the polypeptide sequence is fused with a larger polypeptide (e.g., human albumin, an antibody or Fc, for increased duration of effect). Such fragments, derivatives, and variants and analogs are deemed to be within the scope of those skilled in the art from the teachings herein.

"Functional equivalent" and "substantially the same biological function or activity" each means that degree of biological activity that is within about 30% to about 100% or more of that biological activity demonstrated by the polypeptide to which it is being compared when the biological activity of each polypeptide is determined by the same procedure.

A "variant" of a polypeptide comprises an amino acid sequence wherein one or more amino acid residues are inserted into, deleted from and/or substituted into the amino acid sequence relative to another polypeptide sequence. Variants include polypeptides that differ in amino acid sequence due to mutagenesis. Variants that function as PAC1 antagonists can be identified by screening combinatorial libraries of mutants, for example truncation mutants, of the polypeptides of this invention for PAC1 antagonist activity.

A "derivative" of a polypeptide is a polypeptide that has been chemically modified in some manner distinct from insertion, deletion, or substitution variants, e.g., via conjugation to another chemical moiety. A derivative includes all modifications to the polypeptide which substantially preserve the functions disclosed herein and include additional structure and attendant function (e.g., PEGylated polypeptides which have greater half-life), fusion polypeptides which confer targeting specificity, or an additional activity such as toxicity to an intended target. The derivatives of the present invention may contain conservative amino acid substitutions (defined further below) made at one or more predicted, e.g., nonessential amino acid residues. A "nonessential" amino acid residue is a residue that can be altered from the wild-type sequence of a protein without altering the biological activity, whereas an "essential" amino acid residue is required for biological activity. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

A "fragment" is a portion of the polypeptide which retains substantially similar functional activity, as described in the models disclosed herein. Fragments, or biologically active portions include polypeptide fragments suitable for use as a medicament, to generate antibodies, as a research reagent, and the like. Fragments include peptides comprising amino acid sequences sufficiently similar to or derived from the amino acid sequences of a polypeptide of this invention and exhibiting at least one activity of that polypeptide, but which include fewer amino acids than the full-length polypeptides disclosed herein.

Typically, biologically active portions comprise a domain or motif with at least one activity of the polypeptide. A biologically active portion of a polypeptide can be a peptide which is, for example, five or more amino acids in length. Such biologically active portions can be prepared synthetically or by recombinant techniques and can be evaluated for one or more of the functional activities of a polypeptide of this invention by means disclosed herein and/or well known in the art.

An "analog" includes a pro-polypeptide which includes within it, the amino acid sequence of the polypeptide of this invention. The active polypeptide of this invention can be cleaved from the additional amino acids that complete the pro-polypeptide molecule by natural, in vivo processes or by procedures well known in the art such as by enzymatic or chemical cleavage.

The polypeptides of the present invention may be recombinant polypeptides, natural purified polypeptides, or synthetic polypeptides.

The term "naturally occurring" as used throughout the specification in connection with biological materials such as polypeptides, nucleic acids, host cells, and the like, refers to materials which are found in nature.

The invention also provides chimeric or fusion polypeptides. The targeting sequence is designed to localize the delivery of the polypeptide to minimize potential side effects. The polypeptides of this invention can be composed of amino acids joined to each other by peptide bonds or modified peptide bonds (i.e., peptide isosteres), and may contain amino acids other than the 20 gene-encoded amino acids. The polypeptides may be modified by either natural processes, such as posttranslational processing, or by chemical modification techniques which are well known in the art.

Modifications can occur anywhere in a polypeptide, including the peptide backbone, the amino acid side-chains and the amino or carboxyl termini. It will be appreciated that the same type of modification may be present in the same or varying degrees at several sites in a given polypeptide. Also, a given polypeptide may contain many types of modifications. Polypeptides may be branched, for example, as a result of ubiquitination, and they may be cyclic, with or without branching. Cyclic, branched, and branched cyclic polypeptides may result from posttranslation natural processes or may be made by synthetic methods. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, formulation, gamma-carboxylation, glycosylation, GPI anchor formation, hydroxylation, iodination, methylation, myristoylation, oxidation, PEGylation, proteolytic processing, phosphorylation, prenylation, racemization, selenoylation, sulfation, transfer-RNA mediated addition of amino acids to proteins such as arginylation, and ubiquitination (see, e.g., Proteins, Structure and Molecular Properties, 2nd ed., T. E. Creighton, W. H. Freeman and Company, New York (1993); Posttranslational Covalent Modification of Proteins, B. C. Johnson, ed., Academic Press, New York, pp. 1-12 (1983); Seifter, et al., Meth. Enzymol 182:626-646, 1990; Rattan, et al., Ann. N.Y. Acad. Sci. 663:48-62, 1992).

In the case of PEGylation, the fusion of the peptide of the invention to PEG may be accomplished by any means known to one skilled in the art. For example, PEGylation may be accomplished by first introducing a cysteine mutation into the peptide to provide a linker upon which to attach the PEG, followed by site-specific derivatization with PEG-maleimide. Alternatively, the N-terminal modification may incorporate a reactive moiety for coupling to PEG, as exemplified by the amine group, the mercapto group, or the carboxylate group of the N-terminal modifying compounds disclosed above. For example, PEGylation may be accomplished by first introducing a mercapto moiety into the polypeptide via the N-terminal modifying group to provide a linker upon which to attach the PEG, followed by site-specific derivatization with methoxy-PEG-maleimide reagents supplied by, for example, either Nektar Therapeutics (San Carlos, Calif., USA) and/or NOF (Tokyo, Japan). In addition to maleimide, numerous Cys reactive groups are known to those skilled in the art of protein cross-linking, such as the use of alkyl halides and vinyl sulfones (see, e.g., Proteins, Structure and Molecular Properties, 2nd ed., T. E. Creighton, W. H. Freeman and Company, New York, 1993). In addition, the PEG could be introduced by direct attachment to the C-terminal carboxylate group, or to an internal amino acid such as Cys, Lys, Asp, or Glu or to unnatural amino acids that contain similar reactive sidechain moieties.

Various size PEG groups can be used, as exemplified but not limited to, PEG polymers of from about 5 kDa to about 43 kDa. The PEG modification may include a single, linear PEG. For example, linear 5, 20, or 30 kDa PEGs that are attached to maleidmide or other cross-linking groups are available from Nektar and/or NOF. Also, the modification may involve branched PEGs that contain two or more PEG polymer chains that are attached to maleimide or other cross-linking groups are available from Nektar and NOF.

The linker between the PEG and the peptide cross-linking group can be varied. For example, the commercially available thiol-reactive 40 kDa PEG (mPEG2-MAL) from Nektar (Huntsville, Ala.) employs a maleimide group for conjugation to Cys, and the maleimide group is attached to the PEG via a linker that contains a Lys. As a second example, the commercially available thiol-reactive 43 kDa PEG (GL2-400MA) from NOF employs a maleimide group for conjugation to Cys, and the maleimide group is attached to the PEG via a bi-substituted alkane linker. In addition, the PEG polymer can be attached directly to the maleimide, as exemplified by PEG reagents of molecular-weight 5 and 20 kDa available from Nektar Therapeutics (Huntsville, Ala.).

The polypeptides of the present invention include, for example, the polypeptides of SEQ ID NOs: 1 through 451), as well as those sequences having insubstantial variations in sequence from them. An "insubstantial variation" would include any sequence addition, substitution, or deletion variant that maintains substantially at least one biological function of the polypeptides of this invention, such as PAC1 antagonist activity demonstrated herein. These functional equivalents may include, for example, polypeptides which have at least about 90% identity to the polypeptides of the invention, or at least 95% identity to the polypeptides of the invention, or at least 97% identity to the polypeptides of the invention, and also include portions of such polypeptides having substantially the same biological activity. However, any polypeptide having insubstantial variation in amino acid sequence from the polypeptides of the invention that demonstrates functional equivalency as described further herein is included in the description of the present invention.

Certain terms used throughout this specification are defined below. The single letter abbreviation for a particular amino acid, its corresponding amino acid, and three letter abbreviation are as follows: A, alanine (ala); C, cysteine (cys); D, aspartic acid (asp); E, glutamic acid (glu); F, phenylalanine (phe); G, glycine (gly); H, histidine (his); I, isoleucine (ile); K, lycine (lys); L, leucine (leu); M, methionine (met); N, asparagine (asn); P, proline (pro); Q, glutamine (gin); R, arginine (arg); S, serine (ser); T, threonine (thr); V, valine (val); W, tryptophan (trp); Y, tyrosine (tyr).

In addition, the following abbreviations have been used: a or [d-a] or [d-Ala], D-alanine; [Aib], 2-aminoisobutyric acid; [AMEF], alpha-methyl-phenylalanine; [Cit], citrulline; [DHP], 3,4-Dehydro-Proline; f, or [d-f] or [d-Phe], D-phenylalanine; k, or [d-k] or [d-Lys], D-lysine; G-M, glycine-methionine fragment; G-S, glycine-serine fragment;; $G_3S$, glycine-glycine-glycine-serine; [hGlu], homoglutamic acid; His5, histidine-histidine-histidine-histidine-histidine; His6, histidine-histidine-histidine-histidine-histidine-histidine; [hPhe], homophenylalanine; [Hyp], 4-hydroxyproline (or hydroxyproline); LQTSV, leucine-glutamine-threonine-serine-valine; [Nle], norleucine; [NMeLys], $N^{\square}$-methyllysine [Orn], ornithin; [Pip], pipecolic acid; [pI-Phe], para-iodophenylalanine (or 4-iodophenylalanine); [Pra], propargylglycine or 2-propargylglycine; [Sar], sarcosine; [SeMet], selenomethionine.

As known in the art "similarity" between two polypeptides is determined by comparing the amino acid sequence and its conserved amino acid substitutes of one polypeptide to the sequence of a second polypeptide. Such conservative substitutions include those described above and by Dayhoff (*The Atlas of Protein Sequence and Structure* 5, 1978), and by Argos (EMBO J. 8:779-785, 1989). For example, amino acids belonging to one of the following groups represent conservative changes:

ala, pro, gly, gln, asn, ser, thr;
cys, ser, tyr, thr;
val, ile, leu, met, ala, phe;
lys, arg, his;
phe, tyr, trp, his; and
asp, glu.

Also provided are related compounds within the understanding of those with skill in the art, such as chemical mimetics, organomimetics, or peptidomimetics. As used herein, the terms "mimetic," "peptide mimetic," "peptidomimetic," "organomimetic," and "chemical mimetic" are intended to encompass peptide derivatives, peptide analogs, and chemical compounds having an arrangement of atoms in a three-dimensional orientation that is equivalent to that of a peptide of the present invention. It is understood that the phrase "equivalent to" as used herein is intended to encompass compounds having substitution(s) of certain atoms, or chemical moieties in said peptide, having bond lengths, bond angles, and arrangements in the mimetic compound that produce the same or sufficiently similar arrangement or orientation of said atoms and moieties to have the biological function of the peptides of the invention. In the peptide mimetics of the invention, the three-dimensional arrangement of the chemical constituents is structurally and/or functionally equivalent to the three-dimensional arrangement of the peptide backbone and component amino acid sidechains in the peptide, resulting in such peptido-, organo-, and chemical mimetics of the peptides of the invention having substantial biological activity. These terms are used according to the understanding in the art, as illustrated, for example, by Fauchere, (Adv. Drug Res. 15:29, 1986); Veber & Freidinger, (TINS p. 392, 1985); and Evans, et al., (J. Med. Chem. 30:1229, 1987).

It is understood that a pharmacophore exists for the biological activity of each peptide of the invention. A pharmacophore is understood in the art as comprising an idealized, three-dimensional definition of the structural requirements for biological activity. Peptido-, organo-, and chemical mimetics may be designed to fit each pharmacophore with current computer modeling software (computer aided drug design). Said mimetics may be produced by structure-function analysis, based on the positional information from the substituent atoms in the peptides of the invention.

Peptides as provided by the invention can be advantageously synthesized by any of the chemical synthesis techniques known in the art, particularly solid-phase synthesis techniques, for example, using commercially-available automated peptide synthesizers. The mimetics of the present invention can be synthesized by solid phase or solution phase methods conventionally used for the synthesis of peptides (see, e.g., Merrifield, J. Am. Chem. Soc. 85:2149-54, 1963; Carpino, Acc. Chem. Res. 6:191-98, 1973; Birr, Aspects of the Merrifield Peptide Synthesis, Springer-Verlag: Heidelberg, 1978; The Peptides: Analysis, Synthesis, Biology, Vols. 1, 2, 3, and 5, (Gross & Meinhofer, eds.), Academic Press: New York, 1979; Stewart, et al., Solid Phase PeptideSynthesis, 2nd. ed., Pierce Chem. Co.: Rockford, Ill., 1984; Kent, Ann. Rev. Biochem. 57:957-89, 1988; and Gregg, et al., Int. J. Peptide Protein Res. 55:161-214, 1990, which are incorporated herein by reference in their entirety.)

The solid phase methodology may also be utilized. Briefly, an N-protected C-terminal amino acid residue is linked to an insoluble support such as divinylbenzene cross-linked polystyrene, polyacrylamide resin, Kieselguhr/polyamide (pepsyn K), controlled pore glass, cellulose, polypropylene membranes, acrylic acid-coated polyethylene rods, or the like. Cycles of deprotection, neutralization, and coupling of successive protected amino acid derivatives are used to link the amino acids from the C-terminus according to the amino acid sequence. For some synthetic peptides, an FMOC strategy using an acid-sensitive resin may be used. Examples of solid supports in this regard are divinylbenzene cross-linked polystyrene resins, which are commercially available in a variety of functionalized forms, including chloromethyl resin, hydroxymethyl resin, paraacetamidomethyl resin, benzhydrylamine (BHA) resin, 4-methylbenzhydrylamine (MBHA) resin, oxime resins, 4-alkoxybenzyl alcohol resin (Wang resin), 4-(2',4'-dimethoxyphenylaminomethyl)-phenoxymethyl resin, 2,4-dimethoxybenzhydryl-amine resin, and 4-(2',4'-dimethoxyphenyl-FMOC-aminomethyl)-phenoxyacetamidonorleucyl-MBHA resin (Rink amide MBHA resin). In addition, acid-sensitive resins also provide C-terminal acids, if desired. One protecting group for alpha amino acids could be base-labile 9-fluorenyl-methoxy-carbonyl (FMOC).

Suitable protecting groups for the side chain functionalities of amino acids chemically compatible with BOC (t-butyloxycarbonyl) and FMOC groups are well known in the art. When using FMOC chemistry, the following protected amino acid derivatives are preferred: FMOC-Cys (Trit), FMOC-Ser(But), FMOC-Asn(Trit), FMOC-Leu, FMOC-Thr(Trit), FMOC-Val, FMOC-Gly, FMOC-Lys (Boc), FMOC-Gln(Trit), FMOC-Glu(OBut), FMOC-His (Trit), FMOC-Tyr(But), FMOC-Arg(PMC (2,2,5,7,8-pentamethylchroman-6-sulfonyl)), FMOC-Arg(BOC)$_2$, FMOC-Pro, and FMOC-Trp(BOC). The amino acid residues may be coupled by using a variety of coupling agents and chemistries known in the art, such as direct coupling with DIC (diisopropyl-carbodiimide), or Oxyma (ethyl cyanohydroxyiminoacetate) with DIC, or DCC (dicyclohexylcarbodiimide), BOP (benzotriazolyl-N-oxytrisdimethylaminophosphonium hexa-fluorophosphate), PyBOP (benzotriazole-1-yl-oxy-tris-pyrrolidinophosphonium hexafluoro-phosphate), PyBrOP (bromo-tris-pyrrolidino-phosphonium hexafluorophosphate); via performed symmetrical anhydrides; via active esters such as pentafluorophenyl esters; or via performed HOBt (1-hydroxybenzotriazole) active esters or by using FMOC-amino acid fluoride and chlorides or by using FMOC-amino acid-N-carboxy anhydrides. Activation with HBTU (2-(1H-benzotriazole-1-yl),1,1,3,3-tetramethyluronium hexafluorophosphate) or HATU (2-(1H-7-aza-benzotriazole-1-yl), 1,1,3,3-tetramethyluronium hexafluoro-phosphate) in the presence of HOBt or HOAt (7-azahydroxybenztriazole) or TATU (0-(7-Azabenzotriazole-1-yl)-N,N,N',N'-tetramethyluronium tetrafluoroborate) can be used.

The solid phase method may be carried out manually, or automated synthesis on a commercially available peptide synthesizer (e.g., Applied Biosystems 431A or the like; Applied Biosystems, Foster City, Calif.) may be used. In a typical synthesis, the first (C-terminal) amino acid is loaded on the chlorotrityl resin. Successive deprotection (with 20% piperidine/NMP (N-methylpyrrolidone)) and coupling cycles according to ABI FastMoc protocols (Applied Biosystems) may be used to generate the peptide sequence. Double and triple coupling, with capping by acetic anhydride, may also be used.

The synthetic mimetic peptide may be cleaved from the resin and deprotected by treatment with TFA (trifluoroacetic acid) containing appropriate scavengers. Many such cleavage reagents, such as Reagent K (0.75 g crystalline phenol, 0.25 mL ethanedithiol, 0.5 mL thioanisole, 0.5 mL deionized water, 10 mL TFA) and others, may be used. The peptide is separated from the resin by filtration and isolated by ether precipitation. Further purification may be achieved by conventional methods, such as gel filtration and reverse phase HPLC (high performance liquid chromatography). Synthetic mimetics according to the present invention may be in the form of pharmaceutically acceptable salts, especially base-addition salts including salts of organic bases and inorganic bases. The base-addition salts of the acidic amino acid residues are prepared by treatment of the peptide with the appropriate base or inorganic base, according to procedures well known to those skilled in the art, or the desired salt may be obtained directly by lyophilization of the appropriate base.

Skilled in the art will recognize that peptides of the invention may be modified by a variety of chemical techniques to produce peptides having essentially the same activity as the unmodified peptides of the invention, and optionally having other desirable properties. In one aspect, carboxylic acid groups of the peptide may be provided in the form of a salt of a pharmaceutically-acceptable cation. Amino groups within the peptide may be in the form of a pharmaceutically-acceptable acid addition salt, such as the HCl, HBr, acetic, benzoic, toluene sulfonic, maleic, tartaric, and other organic salts, or may be converted to an amide. Thiols may be protected with any one of a number of well-recognized protecting groups, such as acetamide groups. Those skilled in the art will also recognize methods for introducing cyclic structures into the peptides of this invention so that the native binding configuration will be more nearly approximated. For example, a carboxyl terminal or amino terminal cysteine residue may be added to the peptide, so that when oxidized the peptide will contain a disulfide bond, thereby generating a cyclic peptide. Other peptide cyclizing methods include the formation of thioethers and carboxyl- and amino-terminal amides and esters.

Specifically, a variety of techniques are available for constructing peptide derivatives and analogs with the same or similar desired biological activity as the corresponding peptide compound but with more favorable activity than the peptide with respect to solubility, stability, and susceptibility to hydrolysis and proteolysis. Such derivatives and analogs include peptides modified at the N-terminal amino group, the C-terminal carboxyl group, and/or changing one or more of the amido linkages in the peptide to a non-amido linkage. It will be understood that two or more such modifications may be coupled in one peptide mimetic structure (e.g., modification at the C-terminal carboxyl group and inclusion of a —CH$_2$— carbamate linkage between two amino acids in the peptide).

Amino terminus modifications include alkylating, acetylating, adding a carbobenzoyl group, forming a succinimide group, and attaching one or more amino acids. Specifically, the N-terminal amino group may be reacted to form an amide group of the formula RC(O)NH— where R is alkyl, for example, lower alkyl, and is added by reaction with an acid halide, RC(O)Cl or acid anhydride. Typically, the reaction can be conducted by adding about equimolar or excess amounts (e.g., about 5 equivalents) of an acid halide to the peptide in an inert diluent (e.g., dichloromethane) preferably containing an excess (e.g., about 10 equivalents) of a tertiary amine, such as diisopropylethylamine, to scavenge the acid generated during reaction. Reaction conditions are otherwise conventional (e.g., room temperature for 30 minutes). Alkylation of the terminal amino to provide for a lower alkyl N-substitution followed by reaction with an acid halide as described above will provide an N-alkyl amide group of the formula RC(O)NR—. Alternatively, the amino terminus may be covalently linked to succinimide group by reaction with succinic anhydride. An approximately equimolar amount or an excess of succinic anhydride (e.g., about 5 equivalents) is used and the terminal amino group is converted to the succinimide by methods well known in the art including the use of an excess (e.g., 10 equivalents) of a tertiary amine such as diisopropylethylamine in a suitable inert solvent (e.g., dichloromethane), as described in Wollenberg, et al., (U.S. Pat. No. 4,612,132), and is incorporated herein by reference in its entirety. It will also be understood that the succinic group may be substituted with, for example, a $C_2$- through $C_6$-alkyl or —SR substituents, which are prepared in a conventional manner to provide for substituted succinimide at the N-terminus of the peptide. Such alkyl substituents may be prepared by reaction of a lower olefin ($C_2$- through $C_6$-alkyl) with maleic anhydride in the manner described by Wollenberg, et al., supra., and —SR substituents may be prepared by reaction of RSH with maleic anhydride where R is as defined above. In another aspect, the amino terminus may be derivatized to form a benzyloxy-carbonyl-NH— or a substituted benzyloxycarbonyl-NH— group. This derivative may be produced by reaction with approximately an equivalent amount or an excess of benzyloxycarbonyl chloride (CBZ-Cl), or a substituted CBZ-Cl in a suitable inert diluent (e.g., dichloromethane) preferably containing a tertiary amine to scavenge the acid generated during the reaction. In yet another derivative, the N-terminus comprises a sulfonamide group by reaction with an equivalent amount or an excess (e.g., 5 equivalents) of R—S(O)$_2$Cl in a suitable inert diluent (dichloromethane) to convert the terminal amine into a sulfonamide, where R is alkyl and preferably lower alkyl. In one aspect, the inert diluent contains excess tertiary amine (e.g., 10 equivalents) such as diisopropylethylamine, to scavenge the acid generated during reaction. Reaction conditions are otherwise conventional (e.g., room temperature for 30 minutes). Carbamate groups may be produced at the amino terminus by reaction with an equivalent amount or an excess (e.g., 5 equivalents) of R—OC(O)Cl or R—OC(O)OC$_6$H$_4$-p-NO$_2$ in a suitable inert diluent (e.g., dichloromethane) to convert the terminal amine into a carbamate, where R is alkyl, preferably lower alkyl. For example, the inert diluent may contain an excess (e.g., about 10 equivalents) of a tertiary amine, such as diisopropylethylamine, to scavenge any acid generated during reaction. Reaction conditions are otherwise conventional (e.g., room temperature for 30 minutes). Urea groups may be formed at the amino terminus by reaction with an equivalent amount or an excess (e.g., 5 equivalents) of R—N=C=O in a suitable inert diluent (e.g., dichloromethane) to convert the terminal amine into a urea (i.e., RNHC(O)NH—) group where R is as defined above. In one aspect, the inert diluent contains an excess (e.g., about 10 equivalents) of a tertiary amine, such as diisopropylethylamine. Reaction conditions can be otherwise conventional (e.g., room temperature for about 30 minutes). Attachment of one or more residues at the amino terminus could be accomplished by any of the chemical synthesis techniques known in the art. Using solid phase synthesis techniques, for example, additional residues could be appended by continuing the cycles of deprotection, neutralization, and coupling of protected amino acid derivatives after installation of the amino terminus of any sequence.

When preparing peptide mimetics, the C-terminal carboxyl group may be extended with additional amino acids. The extension could be accomplished by any of the chemical synthesis techniques known in the art. Using solid phase synthesis techniques, for example, additional residues to the C-terminus could synthesized by adding the residues to the resin first via cycles of deprotection, neutralization, and coupling of protected amino acid derivatives followed by installation of the amino acids that comprise any sequence.

In preparing peptide mimetics wherein the C-terminal carboxyl group may be replaced by an ester (e.g., —C(O)OR where R is alkyl and, in one aspect, lower alkyl), resins used to prepare the peptide acids may be employed, and the side chain protected peptide may be cleaved with a base and the appropriate alcohol (e.g., methanol). Side chain protecting groups may be removed in the usual fashion by treatment with hydrogen fluoride to obtain the desired ester. In preparing peptide mimetics wherein the C-terminal carboxyl group can be replaced by the amide —C(O)NR$_3$R$_4$, a benzhydrylamine resin may be used as the solid support for peptide synthesis. Upon completion of the synthesis, hydrogen fluoride treatment can be used to release the peptide from the support results directly in the free peptide amide (i.e., the C-terminus is —C(O)NH$_2$). Alternatively, use of the chloromethylated resin during peptide synthesis coupled with reaction with ammonia to cleave the side chain protected peptide from the support yields the free peptide amide, and reaction with an alkylamine or a dialkylamine yields a side chain protected alkylamide or dialkylamide (i.e., the C-terminus can be —C(O)NRR$_1$ where R and R$_1$ are alkyl such as lower alkyl). Side chain protection can be then removed in the usual way by treatment with hydrogen fluoride to give the free amides, alkylamides, or dialkylamides.

In another aspect, the C-terminal carboxyl group or a C-terminal ester may be induced to cyclize by displacement of the —OH or the ester (—OR) of the carboxyl group or ester, respectively, with the N-terminal amino group to form a cyclic peptide. For example, after synthesis and cleavage to give the peptide acid, the free acid can be converted in solution to an activated ester by an appropriate carboxyl group activator such as dicyclohexylcarbodiimide (DCC), for example, in methylene chloride (CH$_2$Cl$_2$), dimethyl formamide (DMF), or mixtures thereof. The cyclic peptide can then be formed by displacement of the activated ester with the N-terminal amine. Cyclization, rather than polymerization, may be enhanced by use of very dilute solutions according to methods well known in the art.

Peptide mimetics can be structurally similar to the peptide of the invention, but have one or more peptide linkages optionally replaced by a linkage selected from the group consisting of: —CH$_2$NH—, —CH$_2$S—, —CH$_2$CH$_2$—, —CH=CH— (in both cis and trans conformers), —COCH$_2$—, —CH(OH)CH$_2$—, and —CH$_2$SO—, by methods known in the art and further described in the following references: Spatola, Chemistry and Biochemistry of Amino Acids, Peptides, and Proteins, (Weinstein, ed.), Marcel Dekker: New York, p. 267, 1983; Spatola, Peptide Backbone Modifications 1:3, 1983; Morley, Trends Pharm. Sci. pp. 463-468, 1980; Hudson, et al., Int. J. Pept. Prot. Res. 14:177-185, 1979; Spatola, et al., Life Sci. 38:1243-1249, 1986; Hann, J. Chem. Soc. Perkin Trans. 1307-314, 1982; Almquist, et al., J. Med. Chem. 23:1392-1398, 1980; Jennings-White, et al., Tetrahedron Lett. 23:2533, 1982; Szelke, et al., EP045665A; Holladay, et al., Tetrahedron Lett. 24:4401-4404, 1983; and Hruby, Life Sci. 31:189-199, 1982. Such peptide mimetics may have significant advantages over polypeptide embodiments, including, for example, more economical to produce, having greater chemical stability or enhanced pharmacological properties (such as half-life, absorption, potency, efficacy, etc.), reduced antigenicity, and other properties.

Mimetic analogs of the peptides of the invention may also be obtained using the principles of conventional or rational drug design (see, e.g., Andrews, et al., Proc. Alfred Benzon Symp. 28:145-165, 1990; McPherson, Eur. J. Biochem. 189:1-24, 1990; Hol, et al., in Molecular Recognition: Chemical and Biochemical Problems, (Roberts, ed.); Royal Society of Chemistry; pp. 84-93, 1989a; Hol, Arzneim-Forsch. 39:1016-1018, 1989b; Hol, Agnew Chem. Int. Ed. Engl. 25:767-778, 1986).

In accordance with the methods of conventional drug design, the desired mimetic molecules may be obtained by randomly testing molecules whose structures have an attribute in common with the structure of a "native" peptide. The quantitative contribution that results from a change in a particular group of a binding molecule may be determined by measuring the biological activity of the putative mimetic in comparison with the activity of the peptide. In one embodiment of rational drug design, the mimetic is designed to share an attribute of the most stable three-dimensional conformation of the peptide.

Thus, for example, the mimetic may be designed to possess chemical groups that are oriented in a way sufficient to cause ionic, hydrophobic, or van der Waals interactions that are similar to those exhibited by the peptides of the invention, as disclosed herein.

One method for performing rational mimetic design employs a computer system capable of forming a representation of the three-dimensional structure of the peptide. Molecular structures of the peptido-, organo-, and chemical mimetics of the peptides of the invention may be produced using computer-assisted design programs commercially available in the art. Examples of such programs include SYBYL 6.5®, HQSAR™, and ALCHEMY 2000™ (Tripos); GALAXY™ and AM2000™ (AM Technologies, Inc., San Antonio, Tex.); CATALYST™ and CERIUS™ (Molecular Simulations, Inc., San Diego, Calif.); CACHE PRODUCTS™, TSAR™, AMBER™, and CHEM-X™ (Oxford Molecular Products, Oxford, Calif.) and CHEMBUILDER3D™ (Interactive Simulations, Inc., San Diego, Calif.), and Molecular Operating Environment (Chemical Computing Group, Quebec, Canada), and Pymol, Maestro, Desmond & BioLuminate (Schrodinger, New York, N.Y.), and Discovery Studio (BIOVIA, San Diego, Calif.).

The peptido-, organo-, and chemical mimetics produced using the peptides disclosed herein using, for example, art-recognized molecular modeling programs may be produced using conventional chemical synthetic techniques, methods designed to accommodate high throughput screening, including combinatorial chemistry methods. Combinatorial methods useful in the production of the peptido-, organo-, and chemical mimetics of the invention include phage display arrays, solid-phase synthesis, and combinatorial chemistry arrays. Combinatorial chemistry production of the peptido-, organo-, and chemical mimetics of the invention may be produced according to methods known in the art, including, but not limited to, techniques disclosed in Terreft, (Combinatorial Chemistry, Oxford University Press, London, 1998); Look, et al., Bioorg. Med. Chem. Lett. 6:707-12, 1996; Ruhland, et al., J. Am. Chem. Soc. 118: 253-4, 1996; Gordon, et al., Acc. Chem. Res. 29:144-54, 1996; *Pavia*, "The Chemical Generation of Molecular Diversity", Network Science Center, www.netsci.org, 1995; Adnan, et al., "Solid Support Combinatorial Chemistry in Lead Discovery and SAR Optimization," Id., 1995; Davies and Briant, "Combinatorial Chemistry Library Design using Pharmacophore Diversity," Id., 1995; *Pavia*, "Chemically Generated Screening Libraries: Present and Future," Id., 1996; and U.S. Pat. Nos. 5,880,972; 5,463,564; 5,331,573; and 5,573,905.

The newly synthesized polypeptides may be substantially purified by preparative high performance liquid chromatography (see, e.g., Creighton, Proteins: Structures And Molecular Principles, W H Freeman and Co., New York, N.Y., 1983). The composition of a synthetic polypeptide of the present invention may be confirmed by amino acid analysis or sequencing by, for example, the Edman degradation procedure (Creighton, supra). Additionally, any portion of the amino acid sequence of the polypeptide may be altered during direct synthesis and/or combined using chemical methods with sequences from other proteins to produce a variant polypeptide or a fusion polypeptide.

The term "treating" refers to any indicia of success in the treatment or amelioration of an injury, pathology or condition, including any objective or subjective parameter such as abatement; remission; diminishing of symptoms or making the injury, pathology or condition more tolerable to the patient; slowing in the rate of degeneration or decline; making the final point of degeneration less debilitating; improving a patient's physical or mental well-being. The treatment or amelioration of symptoms can be based on objective or subjective parameters; including the results of a physical examination, neuropsychiatric exams, and/or a psychiatric evaluation. For example, certain methods presented herein successfully treat migraine headaches either prophylactically or as an acute treatment, decreasing the frequency of migraine headaches, decreasing the severity of migraine headaches, and/or ameliorating a symptom associated with migraine headaches.

An "effective amount" is generally an amount sufficient to reduce the severity and/or frequency of symptoms, eliminate the symptoms and/or underlying cause, prevent the occurrence of symptoms and/or their underlying cause, and/or improve or remediate the damage that results from or is associated with migraine headache. In some embodiments, the effective amount is a therapeutically effective amount or a prophylactically effective amount. A "therapeutically effective amount" is an amount sufficient to remedy a disease state (e.g. migraine headache) or symptoms, particularly a state or symptoms associated with the disease state, or otherwise prevent, hinder, retard or reverse the progression of the disease state or any other undesirable symptom associated with the disease in any way whatsoever. A "prophylactically effective amount" is an amount of a pharmaceutical composition that, when administered to a subject, will have the intended prophylactic effect, e.g., preventing or delaying the onset (or reoccurrence) of migraine headache, or reducing the likelihood of the onset (or reoccurrence) of migraine headache or migraine headache symptoms. The full therapeutic or prophylactic effect does not necessarily occur by administration of one dose, and may occur only after administration of a series of doses. Thus, a therapeutically or prophylactically effective amount may be administered in one or more administrations.

"Amino acid" includes its normal meaning in the art. The twenty naturally-occurring amino acids and their abbreviations follow conventional usage. See, Immunology-A Synthesis, 2nd Edition, (E. S. Golub and D. R. Green, eds.), Sinauer Associates: Sunderland, Mass. (1991), incorporated herein by reference for any purpose. Stereoisomers (e.g., D-amino acids) of the twenty conventional amino acids, unnatural amino acids such as α-,α-disubstituted amino acids, N-alkyl amino acids, and other unconventional amino acids may also be suitable components for polypeptides and are included in the phrase "amino acid." Examples of unconventional amino acids include: 4-hydroxyproline, γ-carboxyglutamate, ε-N,N,N-trimethyllysine, ε-N-acetyllysine, O-phosphoserine, N-acetylserine, N-formylmethionine, 3-methylhistidine, 5-hydroxylysine, σ-N-methylarginine, and other similar amino acids and imino acids (e.g., 4-hydroxyproline). In the polypeptide notation used herein, the left-hand direction is the amino terminal direction and the right-hand direction is the carboxyl-terminal direction, in accordance with standard usage and convention.

Naturally-occurring amino acids may be divided into classes based on common side chain properties:
1) hydrophobic: Met, Ala, Val, Leu, Ile;
2) neutral hydrophilic: Cys, Ser, Thr, Asn, Gln;
3) acidic: Asp, Glu;
4) basic: His, Lys, Arg;
5) residues that influence chain orientation: Gly, Pro, Ala
6) aromatic: Trp, Tyr, Phe.

Conservative amino acid substitutions may involve exchange of a member of one of these classes with another member of the same class. Conservative amino acid substitutions may encompass non-naturally occurring amino acid residues, which are typically incorporated by chemical peptide synthesis rather than by synthesis in biological systems. These include peptidomimetics and other reversed or inverted forms of amino acid moieties.

Non-conservative substitutions may involve the exchange of a member of one of the above classes for a member from another class. Such substituted residues may be introduced into regions of the antibody that are homologous with human antibodies, or into the non-homologous regions of the molecule.

In making such changes, according to certain embodiments, the hydropathic index of amino acids may be considered. The hydropathic profile of a protein is calculated by assigning each amino acid a numerical value ("hydropathy index") and then repetitively averaging these values along the peptide chain. Each amino acid has been assigned a hydropathic index on the basis of its hydrophobicity and charge characteristics. They are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

The importance of the hydropathic profile in conferring interactive biological function on a protein is understood in the art (see, e.g., Kyte et al., 1982, *J. Mol. Biol.* 157:105-131). It is known that certain amino acids may be substituted for other amino acids having a similar hydropathic index or score and still retain a similar biological activity. In making changes based upon the hydropathic index, in certain embodiments, the substitution of amino acids whose hydropathic indices are within +2 is included. In some aspects, those which are within +1 are included, and in other aspects, those within +0.5 are included.

It is also understood in the art that the substitution of like amino acids can be made effectively on the basis of hydrophilicity, particularly where the biologically functional protein or peptide thereby created is intended for use in immunological embodiments, as in the present case. In certain embodiments, the greatest local average hydrophilicity of a protein, as governed by the hydrophilicity of its adjacent amino acids, correlates with its immunogenicity and antigen-binding or immunogenicity, that is, with a biological property of the protein.

The following hydrophilicity values have been assigned to these amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5) and tryptophan (−3.4). In making changes based upon similar hydrophilicity values, in certain embodiments, the substitution of amino acids whose hydrophilicity values are within +2 is included, in other embodiments, those which are within +1 are included, and in still other embodiments, those within +0.5 are included. In some instances, one may also identify epitopes from primary amino acid sequences on the basis of hydrophilicity.

Exemplary conservative amino acid substitutions are set forth in Table 1.

TABLE 1

Conservative Amino Acid Substitutions

| Original Residue | Exemplary Substitutions |
|---|---|
| Ala | Ser |
| Arg | Lys |
| Asn | Gln, His |
| Asp | Glu |
| Cys | Ser |
| Gln | Asn |
| Glu | Asp |
| Gly | Pro |
| His | Asn, Gln |
| Ile | Leu, Val |
| Leu | Ile, Val |
| Lys | Arg, Gln, Glu |
| Met | Leu, Ile |
| Phe | Met, Leu, Tyr |
| Ser | Thr |
| Thr | Ser |
| Trp | Tyr |
| Tyr | Trp, Phe |
| Val | Ile, Leu |

A skilled artisan will be able to determine suitable variants of polypeptides as set forth herein using well-known techniques. One skilled in the art may identify suitable areas of the molecule that may be changed without destroying activity by targeting regions not believed to be important for activity. The skilled artisan also will be able to identify residues and portions of the molecules that are conserved among similar polypeptides. In further embodiments, even areas that may be important for biological activity or for structure may be subject to conservative amino acid substitutions without destroying the biological activity or without adversely affecting the polypeptide structure.

Additionally, one skilled in the art can review structure-function studies identifying residues in similar polypeptides that are important for activity or structure. In view of such a comparison, one can predict the importance of amino acid residues in a protein that correspond to amino acid residues important for activity or structure in similar proteins. One skilled in the art may opt for chemically similar amino acid substitutions for such predicted important amino acid residues.

One skilled in the art can also analyze the 3-dimensional structure and amino acid sequence in relation to that structure in similar polypeptides. In view of such information, one skilled in the art may predict the alignment of amino acid residues of an antibody with respect to its three dimensional structure. A skilled artisan may choose not to make radical changes to amino acid residues predicted to be on the surface of the protein, since such residues may be involved in important interactions with other molecules. Moreover, one skilled in the art may generate test variants containing a single amino acid substitution at each desired amino acid residue. These variants can then be screened using assays for PAC1 antagonizing activity, (see examples below) thus yielding information regarding which amino acids can be changed and which must not be changed. In other words, based on information gathered from such routine experiments, skilled artisan can readily determine the amino acid positions where further substitutions should be avoided either alone or in combination with other mutations.

Labels and Effector Groups

In some embodiments, the polypeptide comprises one or more labels. The term "labeling group" or "label" means any detectable label. Examples of suitable labeling groups include, but are not limited to, the following: radioisotopes or radionuclides (e.g., $^3$H, $^{14}$C, $^{15}$N, $^{35}$S, $^{90}$Y $^{99}$Tc, $^{111}$In, $^{125}$I, $^{131}$I), fluorescent groups (e.g., FITC, rhodamine, lanthanide phosphors), enzymatic groups (e.g., horseradish peroxidase, β-galactosidase, luciferase, alkaline phosphatase), chemiluminescent groups, biotinyl groups, or predetermined polypeptide epitopes recognized by a secondary reporter (e.g., leucine zipper pair sequences, binding sites for secondary antibodies, metal binding domains, epitope tags). In some embodiments, the labeling group is coupled to the peptide via spacer arms of various lengths to reduce potential steric hindrance. Various methods for labeling proteins are known in the art and may be used as is seen fit.

The term "effector group" means any group coupled to a peptide that acts as a cytotoxic agent. Examples for suitable effector groups are radioisotopes or radionuclides (e.g., $^3$H, $^{14}$C, $^{15}$N, $^{35}$S, $^{90}$Y, $^{99}$Tc, $^{111}$In, $^{125}$I, $^{131}$I) Other suitable groups include toxins, therapeutic groups, or chemotherapeutic groups.

Examples of suitable groups include calicheamicin, auristatins, geldanamycin and maytansine. In some embodiments, the effector group is coupled to the antibody via spacer arms of various lengths to reduce potential steric hindrance.

In general, labels fall into a variety of classes, depending on the assay in which they are to be detected: a) isotopic labels, which may be radioactive or heavy isotopes; b) magnetic labels (e.g., magnetic particles); c) redox active moieties; d) optical dyes; enzymatic groups (e.g. horseradish peroxidase, β-galactosidase, luciferase, alkaline phosphatase); e) biotinylated groups; and f) predetermined polypeptide epitopes recognized by a secondary reporter (e.g., leucine zipper pair sequences, binding sites for secondary antibodies, metal binding domains, epitope tags, etc.). In some aspects, the labeling group is coupled to the peptide via spacer arms of various lengths to reduce potential steric hindrance. Various methods for labeling proteins are known in the art.

Specific labels include optical dyes, including, but not limited to, chromophores, phosphors and fluorophores, with the latter being specific in many instances. Fluorophores can be either "small molecule" fluores, or proteinaceous fluores.

By "fluorescent label" is meant any molecule that may be detected via its inherent fluorescent properties. Suitable fluorescent labels include, but are not limited to, fluorescein, rhodamine, tetramethylrhodamine, eosin, erythrosin, coumarin, methyl-coumarins, pyrene, Malacite green, stilbene, Lucifer Yellow, Cascade BlueJ, Texas Red, IAEDANS, EDANS, BODIPY FL, LC Red 640, Cy 5, Cy 5.5, LC Red 705, Oregon green, the Alexa-Fluor dyes (Alexa Fluor 350, Alexa Fluor 430, Alexa Fluor 488, Alexa Fluor 546, Alexa Fluor 568, Alexa Fluor 594, Alexa Fluor 633, Alexa Fluor 647, Alexa Fluor 660, Alexa Fluor 680), Cascade Blue, Cascade Yellow and R-phycoerythrin (PE) (Molecular Probes, Eugene, Oreg.), FITC, Rhodamine, and Texas Red (Pierce, Rockford, Ill.), Cy5, Cy5.5, Cy7 (Amersham Life Science, Pittsburgh, Pa.). Suitable optical dyes, including fluorophores, are described in MOLECULAR PROBES HANDBOOK by Richard P. Haugland.

Suitable proteinaceous fluorescent labels also include, but are not limited to, green fluorescent protein, including a *Renilla, Ptilosarcus*, or *Aequorea* species of GFP (Chalfie et al., 1994, Science 263:802-805), EGFP (Clontech Labs., Inc., Genbank Accession Number U55762), blue fluorescent protein (BFP, Quantum Biotechnologies, Inc., Quebec, Canada; Stauber, 1998, *Biotechniques* 24:462-471; Heim et al., 1996, *Curr. Biol.* 6:178-182), enhanced yellow fluorescent protein (EYFP, Clontech Labs., Inc.), luciferase (Ichiki et al., 1993, *J. Immunol.* 150:5408-5417), P galactosidase (Nolan et al., 1988, *Proc. Natl. Acad. Sci. U.S.A.* 85:2603-2607) and *Renilla* (WO92/15673, WO95/07463, WO98/14605, WO98/26277, WO99/49019, U.S. Pat. No. 5,292,658, No. 5418155, No. 5683888, No. 5741668, No. 5777079, No. 5804387, No. 5874304, No. 5876995, No. 5925558).

In certain embodiments, the invention provides a composition (e.g. a pharmaceutical composition) comprising one or a plurality of the PAC1 antagonists of the invention together with pharmaceutically acceptable diluents, carriers, excipients, solubilizers, emulsifiers, preservatives, and/or adjuvants.

Pharmaceutical compositions of the invention include, but are not limited to, liquid, frozen, and lyophilized compositions. "Pharmaceutically-acceptable" refers to molecules, compounds, and compositions that are non-toxic to human recipients at the dosages and concentrations employed and/or do not produce allergic or adverse reactions when administered to humans. In some embodiments, the pharmaceutical composition may contain formulation materials for modifying, maintaining or preserving, for example, the pH, osmolarity, viscosity, clarity, color, isotonicity, odor, sterility, stability, rate of dissolution or release, adsorption or penetration of the composition. In such embodiments, suitable formulation materials include, but are not limited to, amino acids (such as glycine, glutamine, asparagine, arginine or lysine); antimicrobials; antioxidants (such as ascorbic acid, sodium sulfite or sodium hydrogen-sulfite); buffers (such as borate, bicarbonate, Tris-HCl, citrates, phosphates or other organic acids); bulking agents (such as mannitol or glycine); chelating agents (such as ethylenediamine tetraacetic acid (EDTA)); complexing agents (such as caffeine, polyvinylpyrrolidone, beta-cyclodextrin or hydroxypropyl-beta-cyclodextrin); fillers; monosaccharides; disaccharides; and other carbohydrates (such as glucose, mannose or dextrins); proteins (such as serum albumin, gelatin or immunoglobulins); coloring, flavoring and diluting agents; emulsifying agents; hydrophilic polymers (such as polyvinylpyrrolidone); low molecular weight polypeptides; salt-forming counterions (such as sodium); preservatives (such as benzalkonium chloride, benzoic acid, salicylic acid, thimerosal, phenethyl alcohol, methylparaben, propylparaben, chlorhexidine, sorbic acid or hydrogen peroxide); solvents (such as glycerin, propylene glycol or polyethylene glycol); sugar alcohols (such as mannitol or sorbitol); suspending agents; surfactants or wetting agents (such as pluronics, PEG, sorbitan esters, polysorbates such as polysorbate 20, polysorbate 80, triton, tromethamine, lecithin, cholesterol, tyloxapal); stability enhancing agents (such as sucrose or sorbitol); tonicity enhancing agents (such as alkali metal halides, preferably sodium or potassium chloride, mannitol sorbitol); delivery vehicles; diluents; excipients and/or pharmaceutical adjuvants. Methods and suitable materials for formulating molecules for therapeutic use are known in the pharmaceutical arts, and are described, for example, in REMINGTON'S PHARMACEUTICAL SCIENCES, 18th Edition, (A. R. Genrmo, ed.), 1990, Mack Publishing Company.

Compositions, Methods of Delivery. Methods of Treatment

In some aspects, the pharmaceutical composition of the invention comprises a standard pharmaceutical carrier, such as a sterile phosphate buffered saline solution, bacteriostatic water, and the like. A variety of aqueous carriers may be used, e.g., water, buffered water, 0.4% saline, 0.3% glycine and the like, and may include other proteins for enhanced stability, such as albumin, lipoprotein, globulin, etc., subjected to mild chemical modifications or the like.

Exemplary concentrations of the peptides of the invention in the formulation may range from about 0.1 mg/ml to about 200 mg/ml or from about 0.1 mg/mL to about 50 mg/mL, or from about 0.5 mg/mL to about 25 mg/mL, or alternatively from about 2 mg/mL to about 10 mg/mL. An aqueous formulation of the antigen binding protein may be prepared in a pH-buffered solution, for example, at pH ranging from about 4.0 to about 7.5, or from about 4.8 to about 5.5, or alternatively about 5.0. Examples of buffers that are suitable for a pH within this range include acetate (e.g. sodium acetate), succinate (such as sodium succinate), gluconate, histidine, citrate, hydrogen chloride, hydrogen chloride/sodium hydroxide, PBS and other organic acid buffers. The buffer concentration can be from about 1 mM to about 200 mM, or from about 10 mM to about 60 mM, depending, for example, on the buffer and the desired isotonicity of the formulation.

A tonicity agent, which may also stabilize the antigen binding protein, may be included in the formulation. Exemplary tonicity agents include polyols, such as mannitol, sucrose or trehalose. Preferably the aqueous formulation is isotonic, although hypertonic or hypotonic solutions may be suitable. Exemplary concentrations of the polyol in the formulation may range from about 1% to about 15% w/v.

A surfactant may also be added to the formulations of the invention to reduce aggregation of the formulated peptide and/or minimize the formation of particulates in the formulation and/or reduce adsorption. Exemplary surfactants include nonionic surfactants such as polysorbates (e.g. polysorbate 20 or polysorbate 80) or poloxamers (e.g. poloxamer 188). Exemplary concentrations of surfactant may range from about 0.001% to about 0.5%, or from about 0.005% to about 0.2%, or alternatively from about 0.004% to about 0.01% w/v.

In one example, the formulation contains the above-identified agents (i.e. antigen binding protein, buffer, polyol and surfactant) and is essentially free of one or more preservatives, such as benzyl alcohol, phenol, m-cresol, chlorobutanol and benzethonium chloride. In another embodiment, a preservative may be included in the formulation, e.g., at concentrations ranging from about 0.1% to about 2%, or alternatively from about 0.5% to about 1%. One or more other pharmaceutically acceptable carriers, excipients or stabilizers such as those described in REMINGTON'S PHARMACEUTICAL SCIENCES, 18th Edition, (A. R. Genrmo, ed.), 1990, Mack Publishing Company, may be included in the formulation provided that they do not adversely affect the desired characteristics of the formulation.

Therapeutic formulations of the peptides of the invention can be prepared for storage by mixing the peptides having the desired degree of purity with optional physiologically acceptable carriers, excipients or stabilizers (REMINGTON'S PHARMACEUTICAL SCIENCES, 18th Edition, (A. R. Genrmo, ed.), 1990, Mack Publishing Company), in the form of lyophilized formulations or aqueous solutions. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, maltose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG).

For example, a suitable formulation of the claimed invention may contain an isotonic buffer such as a phosphate, acetate, or TRIS buffer in combination with a tonicity agent, such as a polyol, sorbitol, sucrose or sodium chloride, which tonicifies and stabilizes. One example of such a tonicity agent is 5% sorbitol or sucrose. In addition, the formulation could optionally include a surfactant at 0.01% to 0.02% wt/vol, for example, to prevent aggregation or improve stability. The pH of the formulation may range from 4.5-6.5 or 4.5 to 5.5. Other exemplary descriptions of pharmaceutical formulations for PAC1 antagonist peptides may be found in US Patent Publication No. 2003/0113316 and U.S. Pat. No. 6,171,586. Suspensions and crystal forms of the peptides are also contemplated. Methods to make suspensions and crystal forms are known to one of skill in the art.

The formulations to be used for in vivo administration must be sterile. The compositions of the invention may be sterilized by conventional, well known sterilization techniques. For example, sterilization is readily accomplished by filtration through sterile filtration membranes. The resulting solutions may be packaged for use or filtered under aseptic conditions and lyophilized, the lyophilized preparation being combined with a sterile solution prior to administration.

The process of freeze-drying is often employed to stabilize polypeptides for long-term storage, particularly when the polypeptide is relatively unstable in liquid compositions. A lyophilization cycle is usually composed of three steps: freezing, primary drying, and secondary drying (see Williams and Polli, Journal of Parenteral Science and Technology, Volume 38, Number 2, pages 48-59, 1984). In the freezing step, the solution is cooled until it is adequately frozen. Bulk water in the solution forms ice at this stage. The ice sublimes in the primary drying stage, which is conducted by reducing chamber pressure below the vapor pressure of the ice, using a vacuum. Finally, sorbed or bound water is removed at the secondary drying stage under reduced chamber pressure and an elevated shelf temperature. The process produces a material known as a lyophilized cake. Thereafter the cake can be reconstituted prior to use.

The standard reconstitution practice for lyophilized material is to add back a volume of pure water (typically equivalent to the volume removed during lyophilization), although dilute solutions of antibacterial agents are sometimes used in the production of pharmaceuticals for parenteral administration (see Chen, Drug Development and Industrial Pharmacy, Volume 18: 1311-1354, 1992).

Excipients have been noted in some cases to act as stabilizers for freeze-dried products (see Carpenter et al., Volume 74: 225-239, 1991). For example, known excipients include polyols (including mannitol, sorbitol and glycerol); sugars (including glucose and sucrose); and amino acids (including alanine, glycine and glutamic acid). In addition, polyols and sugars are also often used to protect polypeptides from freezing and drying-induced damage and to enhance the stability during storage in the dried state. In general, sugars, in particular disaccharides, are effective in both the freeze-drying process and during storage. Other classes of molecules, including mono- and di-saccharides and polymers such as PVP, have also been reported as stabilizers of lyophilized products.

For injection, the pharmaceutical formulation and/or medicament of the invention may be a powder suitable for reconstitution with an appropriate solution as described above. Examples of these include, but are not limited to, freeze dried, rotary dried or spray dried powders, amorphous powders, granules, precipitates, or particulates. For injection, the formulations may optionally contain stabilizers, pH modifiers, surfactants, bioavailability modifiers and combinations of these.

Sustained-release preparations may be prepared. Suitable examples of sustained-release preparations include semipermeable matrices of solid hydrophobic polymers containing the antigen binding protein, which matrices are in the form of shaped articles, e.g., films, or microcapsule. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and y ethyl-L-glutamate, non-degradable ethylene-vinyl acetate, degradable lactic acid-glycolic acid copolymers such as the Lupron Depot™ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods. When encapsulated polypeptides remain in the body for a long time, they may denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

The formulations of the invention may be designed to be short-acting, fast-releasing, long-acting, or sustained-releasing as described herein. Thus, the pharmaceutical formulations may also be formulated for controlled release or for slow release.

Specific dosages may be adjusted depending on conditions of disease, the age, body weight, general health conditions, sex, and diet of the subject, dose intervals, administration routes, excretion rate, and combinations of drugs. Any of the above dosage forms containing effective amounts are well within the bounds of routine experimentation and therefore, well within the scope of the instant invention.

The peptides of the invention can be administered by any suitable means, including parenteral, subcutaneous, intraperitoneal, intrapulmonary, and intranasal, and, if desired for local treatment, intralesional administration. Parenteral administration includes intravenous, intraarterial, intraperitoneal, intramuscular, intradermal or subcutaneous administration. In addition, the peptides of the invention can be suitably administered by pulse infusion, particularly with declining doses of the peptides. In one aspect, the dosing can be given by injections, such as intravenous or subcutaneous injections, depending in part on whether the administration is brief or chronic. Other administration methods are contemplated, including topical, particularly transdermal, transmucosal, rectal, oral or local administration e.g. through a catheter placed close to the desired site. The peptides of the invention can be administered intravenously or subcutaneously in a physiological solution at a dose ranging between 0.01 mg/kg to 100 mg/kg at a frequency ranging from daily to weekly to monthly (e.g. every day, every other day, every third day, or 2, 3, 4, 5, or 6 times per week), preferably a dose ranging from 0.1 to 45 mg/kg, 0.1 to 15 mg/kg or 0.1 to 10 mg/kg at a frequency of once per week, once every two weeks, or once a month.

The novel peptide PAC1 antagonists of the invention are useful for treating or ameliorating a condition associated with the biological activity of PACAP in a patient in need thereof. As used herein, the term "treating" or "treatment" is an intervention performed with the intention of preventing the development or altering the pathology of a disorder. Accordingly, "treatment" refers to both therapeutic treatment and prophylactic or preventative measures. Those in need of treatment include those already diagnosed with or suffering from the disorder or condition as well as those in which the disorder or condition is to be prevented. "Treatment" includes any indicia of success in the amelioration of an injury, pathology or condition, including any objective or subjective parameter such as abatement, remission, diminishing of symptoms, or making the injury, pathology or condition more tolerable to the patient, slowing in the rate of degeneration or decline, making the final point of degeneration less debilitating, or improving a patient's physical or mental well-being. The treatment or amelioration of symptoms can be based on objective or subjective parameters, including the results of a physical examination, self-reporting by a patient, neuropsychiatric exams, and/or a psychiatric evaluation.

Accordingly, in some aspects, the present invention provides a method for treating or preventing a condition associated with the biological activity of PACAP, such as deactivation of the PAC1 receptors, in a patient in need thereof, comprising administering to the patient an effective amount of a novel peptide described herein. The term "patient" includes human patients. PACAP biological activity has been implicated in various physiological processes, including cardiovascular function, metabolic and endocrine function, inflammation, stress response, and regulation of the autonomic nervous system, particularly the balance between the sympathetic and parasympathetic systems. See, e.g., Tanida et al., Regulatory Peptides, Vol. 161: 73-80, 2010; Moody et al., Curr. Opin. Endocrinol. Diabetes Obes., Vol. 18: 61-67, 2011; and Hashimoto et al., Current Pharmaceutical Design, Vol. 17: 985-989, 2011.

An "effective amount" is generally an amount sufficient to reduce the severity and/or frequency of symptoms, eliminate the symptoms and/or underlying cause, prevent the occurrence of symptoms and/or their underlying cause, and/or improve or remediate the damage that results from or is associated with a particular condition (e.g. chronic pain, headache or migraine). In some embodiments, the effective amount is a therapeutically effective amount or a prophylactically effective amount. A "therapeutically effective amount" is an amount sufficient to remedy a disease state (e.g., a headache, migraine, or chronic pain) or symptom(s), particularly a state or symptom(s) associated with the disease state, or otherwise prevent, hinder, retard or reverse the progression of the disease state or any other undesirable symptom associated with the disease in any way whatsoever (i.e., that provides "therapeutic efficacy"). A "prophylactically effective amount" is an amount of a pharmaceutical composition that, when administered to a subject, will have the intended prophylactic effect, e.g., preventing or delaying the onset (or reoccurrence) of the condition (e.g., headache or migraine), or reducing the likelihood of the onset (or reoccurrence) of the condition (e.g., headache, migraine, or headache symptoms). The full therapeutic or prophylactic effect does not necessarily occur by administration of one dose, and may occur only after administration of a series of doses. Thus, a therapeutically or prophylactically effective amount may be administered in one or more administrations.

In certain aspects, the present invention provides a method for inhibiting activation of the PAC1 receptor in a patient having a headache condition comprising administering to the patient an effective amount of a peptide of the invention. For example, the method may treat or prevent symptoms of the headache condition in the patient. Accordingly, the present invention also includes a method for treating or preventing a headache condition, particularly migraine headache, in a patient in need thereof comprising administering to the patient an effective amount of a PAC1 inhibiting peptide described herein.

In some methods of the invention, the headache condition to be treated, prevented or ameliorated is migraine. Migraine headaches are recurrent headaches lasting about 4 to about 72 hours that are characterized by unilateral, pulsating, and/or moderate to severe pain and/or pain that is exacerbated by physical activity. Migraine headaches are often accompanied by nausea, vomiting, and/or sensitivity to light (photophobia), sound (phonophobia), or smell. In some patients, an aura precedes the onset of the migraine headache. The aura is typically a visual, sensory, language, or motor disturbance that signals the headache will soon occur. The methods described herein prevent, treat, or ameliorate one or more symptoms of migraine headaches with and without aura in human patients.

PACAP38, through activation of its receptors, induces vasodilation, particularly vasodilation of the dura vasculature (Schytz et al., Neurotherapeutics, Vol. 7(2):191-196, 2010). The PACAP38/PAC1 receptor signaling cascade, in particular, has been implicated in migraine pathophysiology (Amin et al., Brain, Vol. 137: 779-794, 2014). Infusion of PACAP38, which has a higher affinity for the PAC1 receptor than the VPAC1 and VPAC2 receptors, causes migraine-like headache in migraine patients (Schytz et al., Brain 132:16-25, 2009; Amin et al., Brain, Vol. 137: 779-794, 2014). In addition, PACAP38 levels are elevated in cranial circulation in patients experiencing a migraine attack, and the PACAP38 levels are reduced following treatment of the migraine symptoms with triptans (Tuka et al., Cephalalgia, Vol. 33, 1085-1095, 2013; Zagami et al., Ann. Clin. Transl. Neurol., Vol. 1: 1036-1040, 2014). These reports suggest that endogenous release of PACAP38 is an important trigger of migraine headache and its effects are primarily mediated through activation of the PAC1 receptor.

In some aspects of the invention, the patients to be treated according to the methods of the invention have, suffer from, or are diagnosed with episodic migraine. Episodic or acute migraine is diagnosed when patients with a history of migraine (e.g. at least five lifetime attacks of migraine headache) have 14 or fewer migraine headache days per month. A "migraine headache day" includes any calendar day during which a patient experiences the onset, continuation, or recurrence of a "migraine headache" with or without aura lasting greater than 30 minutes. A "migraine headache" is a headache associated with nausea or vomiting or sensitivity to light or sound and/or a headache characterized by at least two of the following pain features: unilateral pain, throbbing pain, moderate to severe pain intensity, or pain exacerbated by physical activity. In certain embodiments, patients having, suffering from, or diagnosed with episodic migraine have at least four, but less than 15 migraine headache days per month on average. In related embodiments, patients having, suffering from, or diagnosed with episodic migraine have fewer than 15 headache days per month on average. As used herein, a "headache day" is any calendar day in which the patient experiences a migraine headache as defined herein or any headache that lasts greater than 30 minutes or requires acute headache treatment.

In other aspects, the present invention provides a method for treating or ameliorating cluster headache in a patient in need thereof comprising administering to the patient an effective amount of a novel peptide described herein. Cluster headache is a condition that involves, as its most prominent feature, recurrent, severe headaches on one side of the head, typically around the eye (see Nesbitt et al., BMJ, Vol. 344:e2407, 2012). Some doctors and scientists have described the pain resulting from cluster headaches as the most intense pain a human can endure—worse than giving birth, burns or broken bones. Cluster headaches often occur periodically: spontaneous remissions interrupt active periods of pain. Cluster headaches are often accompanied by cranial autonomic symptoms, such as tearing, nasal congestion, ptosis, pupil constriction, facial blushing, sweating, and swelling around the eye, often confined to the side of the head with the pain. The average age of onset of cluster headache is ~30-50 years. It is more prevalent in males with a male to female ratio of about 2.5:1 to about 3.5:1. Sphenopalatine ganglion (SPG) stimulation has been used for the treatment of cluster headache. A neurostimulation system, which delivers low-level (but high frequency, physiologic-blocking) electrical stimulation to the SPG, has demonstrated efficacy in relieving the acute debilitating pain of cluster headache in a recent clinical trial (see Schoenen J, et al., Cephalalgia, Vol. 33(10):816-30, 2013). In view of this evidence and because PACAP is one of the major neurotransmitters in SPG, inhibition of PACAP signaling with a PAC1 antagonist described herein is expected to have efficacy in treating cluster headache in humans.

Other conditions associated with PACAP biological activity that may be treated according to the methods of the invention include, but are not limited to, inflammatory skin conditions, such as rosacea (see U.S. Patent Publication No. 20110229423), chronic pain syndromes, such as neuropathic pain (see Jongsma et al., Neuroreport, Vol. 12: 2215-2219, 2001; Hashimoto et al., Annals of the New York Academy of Sciences, Vol. 1070: 75-89, 2006), tension-type headaches, hemiplegic migraine, retinal migraine, anxiety disorders, such as posttraumatic stress disorder (see Hammack and May, Biol. Psychiatry, Vol. 78(3):167-177, 2015), irritable bowel syndrome, and vasomotor symptoms (e.g. hot flashes, facial flushing, sweating, and night sweats), such as those associated with menopause. In one embodiment, the condition is chronic pain. In another embodiment, the condition is neuropathic pain. In any of the methods described herein, the treatment can comprise prophylactic treatment. Prophylactic treatment refers to treatment designed to be taken before the onset of a condition or an attack (e.g. before a migraine attack or onset of a cluster headache episode) to reduce the frequency, severity, and/or length of the symptoms (e.g. migraine or cluster headaches) in the patient.

The following examples, including the experiments conducted and the results achieved, are provided for illustrative purposes only and are not to be construed as limiting the scope of the appended claims.

Example 1

General Peptide Synthesis

The following general procedure was followed to synthesize peptides of the invention. Peptide synthesis was carried our using $N^\alpha$-Fmoc solid-phase peptide synthesis (SPPS) methodologies with appropriate orthogonal protection and resin linker strategies.

The following materials have been used. $N^\alpha$-Fmoc protected amino acids were purchased from Advanced ChemTech (Louisville, Ky.), Midwest BIO-TECH (Fishers, Ind.), Chem-Impex International (Wood Dale, Ill.), Novabiochem (San Diego, Calif.), Protein Technologies (Tucson, Ariz.), Combi-Blocks (San Diego, Calif.), Chem-Impex International (Wood Dale, Ill.), Bachem (Torrance, Calif.), or GL Biochem (Shanghai, China). AG 1-X2 ion-exchange resin (200-400, acetate) was purchased from Chem-Impex International. Rink Amide MBHA resin was purchased from Peptides International (100-200 mesh, 1% DVB, RFR-1063-PI, 0.52 mequiv/g initial loading, Peptides International, Louisville, Ky.). SP Sepharose high-performance resin was purchased from GE Healthcare Life Sciences. The following chemicals were purchased and used directly without further purifications: N,N-diisopropylethylamine (DIEA), 2,2,2-trifluoroethanol, trifluoroacetic acid (TFA), acetic acid, acetic anhydride, formic acid, piperidine, 4-methyl-piperidine, N,N'-diisopropylcarbodiimide (DIC), 6-chloro-1-hydroxybenzotriazole (6-Cl-HOBt), ethyl cyano(hydroxyimino)acetate (Oxyma), 3,6-dioxa-1,8-octanedithiol (DODT), triisopropylsilane (TIS), cysteine, cystine (Sigma-Aldrich, Milwaukee, Wis.); dichloromethane (DCM, Mallinckrodt Baker, Inc.); N,N-dimethylforamide (DMF, Fisher Scientific); HPLC-quality water and acetonitrile (Burdick and Jackson); 1.0 M Tris-HCl, pH=8.0 (Teknova).

The following side chain protection strategies were employed for standard amino acid residues: Asn(Trt), Asp (O$^t$Bu), Arg(Pbf), Cys(Trt), Gln(Trt), Glu(O$^t$Bu), His(Trt), Lys(N-Boc), Orn(N-Boc); Ser(O$^t$Bu), Thr(O$^t$Bu), Trp(Boc), and Tyr(O$^t$Bu). The peptides described could be synthesized at various temperatures using various automatic peptide synthesizers.

Peptide syntheses were carried out by solid phase peptide synthesis (SPPS). Amino acid couplings were conducted using a variety of automated synthesizers: room temperature coupling with Intavis Multipep Rsi or CS Bio 336X and higher temperature couplings with Tribute or CEM Liberty. After completion of the synthese, peptides were deprotected and cleaved from the resin. For some analogs, the N-termini of the peptides were modified (such as by N-acylation) after deprotection and cleavage from resin. Peptides were oxidatively folded and purified by reverse phase chromatography. In some cases, salt exchange was performed using ion-exchange resin prior to testing.

The following non-limiting examples illustrate the application of different coupling methods which could be used to synthesize the peptides of the invention.

Coupling method 1—Room temperature coupling of peptides using automated peptide synthesizer Intavis Multipep Rsi (INTAVIS Bioanalytical Instruments AG, Cologne, Germany) was conducted as described in detail below. Dry resin (0.012 mmol, per well) was added to a Phenomenex deep well protein precipitation plate (CEO-7565, 38710-1) using a resin loader (Radley). Amino acids (5 mol equiv, 0.5 M in DMF) were preactivated (1 min) with Oxyma (5 mol equiv, 0.4 M in DMF) and DIC (7.5 mol equiv, 1.0 M in DMF). Preactivated amino acids were transferred to the appropriate well. Resins were incubated for 30 min and drained, and the cycle was repeated. Following the second amino acid incubation, the plates were drained and washed with DMF multiple times. The Fmoc groups were then removed by two incubation sequences of a 20% piperidine in DMF solution. The resin was drained and washed with DMF 10 times (4 mL per column of 8 wells). After removal of the final Fmoc protecting group, the resin was washed with DCM multiple times and allowed to air-dry.

Coupling method 2—Room temperature couping of peptides using automated peptide synthesizer CS Bio 336X single-channel solid phase peptide synthesizer (Menlo Park, Calif.) was conducted as following. Dry resin (0.2 mmol Rink amide or pre-loaded acid Wang resin) was weighed into a CS Bio reaction vessel. The reaction vessel was connected onto a reaction vessel holder in the reaction chamber. The resin was swollen in DMF (~10 mL) for 15 min. Fmoc-amino acid (1.0 mmol, Midwest Biotech or Novabiochem) was dissolved in 2.5 mL of 6-Cl-HOBt (1.0 M in DMF). To this solution was added 1.0 mL DIC (1.0 M in DMF) and the overall mixture was agitated with nitrogen bubbling for 15 min to accomplish pre-activation and then transferred onto the resin. The mixture was shaken for 2 h and the resin was filtered and washed (3×DMF, 2×DCM, and 3×DMF subsequently). Fmoc-removal was accomplished by treatment with 20% piperidine (or 4-methylpiridine) in DMF (5 mL, 2×15 min). The resin was filtered and washed (3×DMF). All residues were single coupled through repetition of the Fmoc-amino acid coupling and Fmoc removal steps described above.

Coupling method 3—Higher temperature coupling via Infrared (IR) heating using automated peptide synthesizer Tribute (Protein Technologies, Inc., Tucson, Ariz.) was conducted as described herein. Dry resin (0.3 mmol) was loaded onto a reaction vessel and then wetted with 30% DMF in DCM (~5 mL) and allowed to swell for 30 min. Fmoc amino acids (4-5 equiv.) were preactivated with 6-Cl-HOBt (or Oxyma) and DIC (4 equiv.). The preactivated solution is added to the resin and vortexted for 5 min at 75° C. The Fmoc deprotection step was accelerated in a similar manner at 50° C. in a period of 4×30 sec.

Coupling method 4—Higher temperature coupling (0.2 mmol) via microwave heating using automated peptide synthesizer CEM Liberty Blue (CEM Corporation, Matthews, N.C.) was conducted as follows. Similar deprotection and coupling reagents as described above could be used in the synthesis with minor modifications to accommodate the specifications of the synthesizer. Typical reaction coupling and deprotection conditions can occur temperatures of 50° C., 75° C., or 90° C., depending on the amino acid used. Amino acid coupling reactions were performed with 5 fold excess of Fmoc-amino acids and in the presence of DIC (1.0 M in DMF) and Oxyma (0.5 M in DMF, with 0.05 M DIEA). The Fmoc groups were removed by excess of 20% piperidine (or 4-methylpiperidine) in DMF several times at 90° C.

N-acylation of peptides: After removal of the final Fmoc protecting group, the peptide-resin (0.2 mmol) was transferred to a solid phase extraction (SPE) filter tube and washed with DMF (×3), DCM (×3), and allowed to dry under vacuum. The resin was treated with excess of acetic anhydride (10% in DMF, 10 mL×2), followed by washed with DMF (×3) to produce the N-acylated peptides.

Deprotection and cleavage from resin after coupling method 1: To the bottom of the filter plate was affixed a drain port sealing mat (ArcticWhite, AWSM-1003DP). To the resin (0.012 mmol) in each well was added triisopropylsilane (100 µL), DODT (100 µL), and water (100 µL) using a multichannel pipet. To the resin in each well was added TFA (1.0 mL) using a Dispensette Organic dispenser. The top of the plate was covered with another drain port sealing mat. The mixture was agitated on a plate shaker for 2 h. The top mat was removed, and the bottom mat was removed and the plate was allowed to drain into a solid bottom 96-well plate, aided by vacuum. This plate was evaporated on the genevac for 8 h. To each well of this 96-well plate was added 1.8 mL of cold diethyl ether using a Dispensette Organic dispenser and precipitates formed and each mixture was transferred into a new 96-well filter place using a multichannel pipet with wide bore tips and allowed to drain. The crude peptides in the plate were air-dried for 1 h and the bottom of the filter pate was capped. To this plate 1 ml of 50/50 acetonitrile/water was added to each well and the plate was vortex overnight. Additional 1 ml of water was added to each well and with a pipette the wells were mixed. The resulting solutions (~2.0 mL total per well) were then filtered into a new 96-well plate and set aside.

Deprotection and cleavage from resin after coupling method 2-4: After removal of the final Fmoc protecting group, the peptide-resin (0.2 mmol) was transferred to a 25 mL solid phase extraction (SPE) filter tube and washed with DMF (×3), DCM (×3), and allowed to dry under vacuum. The peptides were cleaved from resin with 1 mL of TIS, 1 mL of DODT, 1 mL of $H_2O$, and 20 mL of TFA and the resulting suspension was gently agitated at room temperature for 3.5 h. The resin was filtered and washed with additional TFA (10 mL) and the overall solution was concentrated under reduced pressure until the final volume ~10 mL. The remaining residue was precipitated with cold cyclopropylmethyl ether (50 mL). The resulting white suspension was filtered, washed with cold tert-butylmethyl ether (25 mL), and the resulting white suspension was filtered again. The collected material was dried in a desiccator under reduced pressure overnight to afford crude linear peptide as an off-white solid.

Peptide oxidative folding of cleaved peptides from coupling method 1: The oxidative folding of the 96 peptide array was performed in parallel and at high dilution using an array of 50 mL centrifuge tubes in the following manner. In a 4 L bottle added 175 mL of acetonitrile, 3125 mL of water, 350 mL of pH 8 Tris-HCl, 23.45 mL of 0.1 M cystine, and 3.5 mL 1.0 M cysteine to form the stock folding solution. To each tube 35 mL of the above folding solution was added, followed by the addition of the dissolved peptide solution using the Tecan automated liquid handler and the resulting folding reactions were allowed to stand at room temperature overnight. To each tube in the array was added 1 mL of glacial acetic acid to quench the reaction. A 96-well ion-exchange filter plate was prepared by pipetting 1.0 mL SP Sepharose High Performance resin (slurry in 0.2 M sodium acetate/20% ethanol, GE Biosciences) and 2.0 mL of sodium acetate (×3, 20 mM, pH=4) to each well and then was allowed to drain slowly. To this plate the peptide folding solutions in the 50 mL centrifuge tubes prepared above were added using the Tecan liquid handler. The resin was washed (2.0 mL, 20 mM sodium acetate, pH=4.0), and the peptide was eluted off of the resin manually on a vacuum manifold with 2.0 mL (1.0 M sodium chloride, 20 mM sodium acetate, pH=4) into a solid bottom 96-well plate.

Peptide oxidative folding of cleaved peptides from coupling method 2-4: To a dried PAC1 peptide crude (typically 0.8~1.2 g dry weight from a 0.2 mmol reaction) was added 40~60 mL of 50:50 water/acetonitrile and the mixture was vortexed and sonicated until a clear solution was obtained. The overall solution was filtered and set aside. In a separated 1-L bottle a folding buffer was prepared by mixing 850 mL of DI water, 48 mL of acetonitrile, 95 mL of 1.0 M Tris-HCl (pH=8.0), 6.4 mL of 0.15-0.17 M cystine aqueous solution, and 0.96 mL 1.0 M aqueous solution of cysteine. The crude PAC1 peptide solution prepared above was poured slowly into the folding buffer for a final peptide concentration of 0.3 mM and was allowed to stand at room temperature overnight. The folding mixture was quenched with excess amount of acetic acid (25 mL) and filtered (0.45 m polyethylene) to yield a colorless solution.

Alternatively, folding can be conducted at higher final concentration than described above. Crude peptide was first solubilized in 90:10 water/acetonitrile solution at ~5.6 mg/mL. Cysteine (1.0 M, 0.6 mL) and Cystine (0.17 M, 4 mL) solutions were then added for a final concentration of 0.1 M each and the resulting solution was mixed thoroughly. Lastly, 1 M Tris HCl (pH 8.0, 60 mL) solution was added to achieve final peptide concentration of 1.4 mM. The folding mixture was incubated overnight at room temperature and quenched with TFA to ~ pH 3.0. The mixture was then filtered with a 0.45 u filter unit.

Purification: The filtered folded peptide solutions from above were purified by mass-triggered preparative HPLC. The collected fractions were pooled and lyophilized. Final QC and peptide quantification was performed by chemiluminescent nitrogen detection (CLND) as mentioned above. Peptides with >90% purity and correct m/z ratio were submitted for assay.

Trifluoroacetate-acetate salt exchange: Following lyophilization, the PAC1 peptide trifluoroacetate salt in a 50-mL Falcon tube was redissolved in DI water (100-150 □L/1 mg peptide) and set aside. To another Falcon tube was added wet AG 1-X$^2$ ion-exchange resin (25 mg/per 1 mg peptide) washed three times with 1.6 N acetic acid and three times with 0.16 N acetic acid (0.6~1.0 mL per 1 mg dry peptide). The peptide solution was poured into the pre-washed resin (additional water was used to transfer the residual peptide, total ~200 □L DI water per 1 mg dry peptide). The Falcon tube was capped and placed into a tube holder on an Eppendorf ThermoMix and agitated (400 rmp) at 20° C. overnight. The resulting suspension was filtered and the resin was washed with more DI water (×3, 200 □L DI water per 1 mg peptide). The combined aqueous phases were frozen and lyophilized to give the desired peptide acetate salt as a white solid.

Example 2

PAC1 Peptide Antagonist Functional Screen

In order to determine the potency of peptide antagonists at the PAC1 receptor, functional cAMP accumulation assays using LANCE Ultra cAMP assay kit to measure the agonist and antagonist activity of PAC1 peptides were used. SHSY-5Y (human neuroblastoma cell line) and RG-2 (rat glioma cell line) cells endogenously express human and rat PAC1 receptors, respectively. Agonist activity of PAC1 peptides was tested by incubating with SHSY-5Y at 2,000 cells per well or RG-2 at 5,000 cells per well for 15 minutes at room temperature. PAC1 receptor agonist PACAP38 or maxadilan was included as a positive control. The reaction was stopped by adding detection mixture, europium (Eu) chelate-labeled cAMP tracer and cAMP-specific monoclonal antibodies labeled with the ULight™ dye, to all wells followed by a 60-minute incubation at room temperature. The assay plates were then read on an EnVision instrument at an emission wavelength of 665 and 615 nm and data were analyzed using Genedata Screener or GraphPad Prism software. A similar procedure was used in the antagonist assays by using a fixed concentration of PAC1 agonist. The concentrations of agonists were chosen based on their $EC_{80}$ values at PAC1 receptors in SHSY-5Y or RG-2 cells. SHSY-5Y or RG-2 cells were added into 96-well half-area white plates. Serially diluted PAC1 peptides at ten concentrations were added and incubated for 30 minutes at room temperature. PAC1 agonist at $EC_{80}$ concentration was then added and further incubated for 15 minutes at room temperature. The reaction was stopped by adding detection mixture to all wells followed by a 60-minute incubation at room temperature. The assay plates were read and analyzed the same way as that of agonist assay. Cells, agonists, and PAC1 peptides were prepared in freshly made assay buffer (F-12, 0.5 mM IBMX, 0.1 or 0.4% BSA (pH 7.4)). Detection mixture was made by mixing a 1/50 dilution of the Eu-cAMP tracer stock solution in cAMP Detection Buffer and a 1/150 dilution of the ULight-anti-cAMP stock solution in cAMP Detection Buffer. Europium (Eu) chelate-labeled cAMP tracer, cAMP-specific monoclonal antibodies labeled with the ULight™ dye, BSA, and detection buffer were provided in LANCE Ultra cAMP Kit from PerkinElmer.

TABLE 3

In vitro data
$IC_{50}$: A ≥ 100 nM; 100 nM > B ≥ 1 nM; 1 nM > C ≥ 0.01 nM; 0.01 nM > D

| sequence ID# | Calc Avg. MW | MS observed | hPAC1 IC50 with PACAP38 challenge | rPAC1 IC50 with maxadilan challenge |
|---|---|---|---|---|
| 1 | 4851.55 | 971.2; 1213.7; 1617.9 | C | D |
| 2 | 4855.55 | 972.0; 1214.7; 1619.2 | C | C |
| 3 | 4543.22 | 909.5; 1036.6; 1515.1 | C | C |
| 5 | 4062.75 | 1016.7; 1355.1 | B | B |
| 6 | 4423.94 | 885.9; 1106.9; 1475.8 | C | C |
| 7 | 4903.43 | 981.6; 1226.8; 1635.5 | C | C |
| 8 | 4840.53 | 969.0; 1210.9; 1614.3 | C | C |
| 9 | 4838.5 | 968.7; 1210.4; 1613.6 | C | C |
| 10 | 4833.5 | 967.6; 1209.2; 1611.8 | C | C |
| 11 | 4870.56 | 975.0; 1218.4; 1624.3 | C | C |
| 12 | 4665.39 | 934.0; 1167.2; 1555.9 | C | D |
| 13 | 4635.36 | 928.0; 1159.7; 1545.9 | C | C |
| 14 | 4633.32 | 927.5; 1159.2; 1545.3 | C | C |
| 15 | 4574.24 | 1144.4; 1525.4 | C | C |
| 16 | 4395.02 | 1099.6; 1465.8 | C | C |
| 17 | 4679.37 | 1170.6; 1560.4 | C | D |
| 18 | 4693.44 | 1174.2; 1565.3 | C | D |
| 19 | 4450.14 | 890.8; 1113.3; 1483.9 | B | C |
| 20 | 4277.91 | 1070.2; 1246.8 | C | C |
| 21 | 4421.05 | 1105.9; 1474.3 | C | C |
| 22 | 4870.56 | 975.1; 1218.4; 1624.0 | C | C |
| 23 | 4898.61 | 980.6; 1225.4; 1633.6 | C | D |
| 24 | 4872.53 | 1218.9; 1624.9 | C | C |
| 25 | 4870.56 | 975.0; 1218.4; 1624.2 | C | D |
| 26 | 4461.12 | 893.2; 1116.1; 1487.8 | C | C |
| 27 | 4515.17 | 904.0; 1129.5; 1505.7 | C | C |
| 28 | 4489.13 | 898.7; 1123.1; 1497.1 | C | C |
| 29 | 4448.12 | 890.5; 1112.8; 1483.4 | C | C |
| 30 | 4474.15 | 895.5; 1119.4; 1492.2 | C | C |
| 31 | 4667.36 | 934.3; 1167.7; 1556.5 | C | D |
| 32 | 4732.43 | 947.3; 1183.9; 1578.2 | C | C |
| 33 | 4675.34 | 936.0; 1169.7; 1559.2 | B | C |
| 34 | 4746.46 | 950.0; 1087.4; 1582.8 | C | C |
| 35 | 4476.13 | 896.2; 1119.8; 1492.8 | C | C |
| 36 | 4450.1 | 890.8; 1113.3; 1484.1 | C | C |
| 37 | 4310.98 | 1078.6; 1437.7 | B | C |
| 39 | 4872.51 | 975.4; 1218.9; 1624.8 | C | C |
| 40 | 4812.42 | 963.5; 1203.9; 1604.9 | B | B |
| 41 | 4838.5 | 968.6; 1210.4; 1613.7 | C | C |
| 42 | 4685.37 | 938.0; 1172.1; 1562.4 | C | C |
| 43 | 4813.55 | 963.5; 1204.1; 1605.3 | C | D |
| 44 | 4841.56 | 969.1; 1211.2; 1614.6 | C | D |
| 45 | 4822.51 | 965.3; 1206.3; 1608.2 | C | C |
| 46 | 4875.89 | 975.9; 1219.7; 1626.1 | B | C |
| 47 | 4881.58 | 977.1; 1221.2; 1627.9 | C | C |
| 48 | 4843.57 | 969.5; 1211.7; 1615.2 | C | C |
| 51 | 5142.85 | 1029.4; 1286.5; 1715.1 | B | B |
| 52 | 5104.81 | 1021.7; 1277.0; 1702.3 | B | C |
| 53 | 5047.76 | 1010.4; 1262.7; 1683.3 | B | C |
| 54 | 4861.59 | 973.2; 1216.2; 1621.3 | B | C |
| 55 | 4911.61 | 1228.8; 1637.9 | B | C |
| 56 | 4815.52 | 963.8; 1204.7; 1605.8 | C | C |
| 57 | 4789.48 | 958.8; 1198.2; 1597.2 | C | C |
| 58 | 4872.57 | 975.3; 1218.8; 1624.9 | C | C |
| 59 | 4846.54 | 970.2; 1212.4; 1616.2 | C | C |
| 60 | 4894.62 | 979.9; 1224.4; 1632.3 | C | C |
| 61 | 4543.22 | 909.5; 1136.6; 1515.1 | C | C |
| 62 | 5009.71 | 1002.8; 1253.2; 1670.6 | B | C |
| 63 | 4405.05 | 881.8; 1102.0; 1469.0 | C | C |
| 64 | 4872.57 | 975.3; 1218.9; 1624.7 | B | C |
| 65 | 4377.04 | 876.3; 1095.0; 1459.7 | C | C |

TABLE 3-continued

In vitro data
IC$_{50}$: A ≥ 100 nM; 100 nM > B ≥ 1 nM; 1 nM > C ≥ 0.01 nM; 0.01 nM > D

| sequence ID# | Calc Avg. MW | MS observed | hPAC1 IC50 with PACAP38 challenge | rPAC1 IC50 with maxadilan challenge |
|---|---|---|---|---|
| 66 | 5058.78 | 1012.5; 1265.5; 1686.9 | C | C |
| 67 | 4932.63 | 987.3; 1233.9; 1645.1 | B | C |
| 68 | 4808.53 | 962.5; 1202.9; 1603.6 | C | C |
| 69 | 4950.69 | 990.8; 1238.4; 1651.0 | C | C |
| 70 | 4969.73 | 994.8; 1243.2; 1657.2 | B | B |
| 71 | 4983.68 | 997.5; 1246.7; 1661.9 | C | C |
| 72 | 4681.34 | 937.2; 1171.2; 1561.5 | C | C |
| 73 | 4775.58 | 955.2; 1193.8; 1591.4 | C | C |
| 74 | 4807.54 | 962.3; 1202.8; 1603.3 | C | C |
| 75 | 4517.19 | 904.3; 1130.1; 1506.4 | C | D |
| 76 | 4736.51 | 948.3; 1185.1; 1579.8 | C | C |
| 77 | 4910.62 | 983.0; 1228.4; 1637.6 | C | C |
| 78 | 4828.56 | 966.3; 1207.6; 1609.8 | C | C |
| 79 | 4746.46 | 950.0; 1187.4; 1582.8 | C | D |
| 80 | 4766.49 | 954.2; 1192.4; 1589.5 | C | D |
| 81 | 4763.4 | 953.5; 1191.7; 1588.6 | B | C |
| 82 | 4747.45 | 950.2; 1187.7; 1583.3 | C | C |
| 83 | 4722.43 | 1181.4, 1574.9 | C | C |
| 84 | 4910.62 | 982.9, 1228.4, 1637.7 | C | C |
| 85 | 4755.55 | 945.0; 1180.8; 1574.3 | C | C |
| 86 | 4910.62 | 983.0, 1228.4, 1637.7 | C | C |
| 87 | 4804.5 | 961.8, 1201.9, 1602.3 | C | C |
| 88 | 4941.64 | 989.2, 1236.2, 1647.9 | C | C |
| 89 | 4779.49 | 956.6, 1195.7, 1593.8 | B | C |
| 90 | 4722.5 | 1181.5, 1574.8 | C | C |
| 91 | 4704.46 | 1176.9, 1568.8 | C | C |
| 92 | 4803.62 | 1201.7, 1601.8 | C | C |
| 93 | 4661.33 | 1166.1, 1554.5 | B | B |
| 94 | 4817.54 | 1205.2, 1606.6 | C | C |
| 95 | 4838.56 | 968.5, 1210.4, 1613.7 | B | B |
| 96 | 4780.47 | 957.0, 1196.0, 1594.3 | B | C |
| 97 | 4809.52 | 962.8, 1203.3, 1603.8 | B | B |
| 98 | 4736.46 | 948.2, 1185.0, 1579.6 | B | C |
| 99 | 4827.54 | 966.5, 1207.6, 1609.9 | C | C |
| 100 | 4675.36 | 935.8, 1169.6, 1559.2 | B | B |
| 101 | 4661.33 | 933.1, 1166.1, 1554.4 | B | B |
| 102 | 4679.37 | 936.5, 1170.6, 1560.5 | B | C |
| 103 | 4693.4 | 939.5, 1174.1, 1565.2 | B | C |
| 104 | 4855.58 | 971.9, 1214.7, 1619.3 | C | C |
| 105 | 4895.57 | 979.8, 1224.7, 1632.6 | C | C |
| 106 | 4923.62 | 985.5, 1231.7, 1641.8 | C | C |
| 107 | 4755.55 | 952.0; 1189.7; 1585.8 | C | C |
| 108 | 4961.66 | 1241.2; 1654.6 | C | C |
| 109 | 4938.67 | 1235.4; 1646.8 | B | C |
| 110 | 4988.69 | 1247.9; 1663.7 | C | C |
| 111 | 4941.74 | 1236.2; 1648.4 | C | C |
| 112 | 4941.74 | 1236.2; 1648.4 | C | C |
| 113 | 5009.71 | 1002.8; 1253.2; 1670.6 | B | C |
| 114 | 4800.56 | 960.9; 1200.9; 1601.1 | C | C |
| 115 | 4720.46 | 945.0; 1180.8; 1574.3 | C | C |
| 116 | 4830.59 | 1208.4, 1610.9 | C | C |
| 117 | 4816.55 | 1204.9, 1606.3 | C | C |
| 118 | 4731.53 | 1183.7, 1577.9 | C | C |
| 119 | 4759.5 | 952.7; 1190.6; 1587.3 | C | C |
| 120 | 4805.57 | 961.8, 1202.2, 1602.6 | C | C |
| 121 | 4839.61 | 968.7, 1210.7, 1613.8 | C | C |
| 122 | 4837.63 | 968.3, 1210.1, 1613.3 | C | C |
| 123 | 4704.46 | 941.8, 1176.9, 1568.9 | C | C |
| 124 | 4820.51 | 964.8, 1205.8, 1607.6 | C | C |
| 125 | 4806.56 | 962.2, 1202.4, 1602.8 | A | B |
| 126 | 4787.52 | 958.3, 1197.7, 1596.6 | C | C |
| 127 | 4769.45 | 954.7; 1193.2; 1590.4 | C | C |
| 128 | 4825.56 | 966.2, 1207.1, 1609.3 | C | C |
| 129 | 4755.55 | 1189.7, 1585.9 | C | C |
| 130 | 4771.55 | 1193.8, 1591.2 | C | D |
| 131 | 4780.58 | 1195.9, 1594.1 | C | C |
| 132 | 4746.56 | 950.3, 1187.4, 1583.0 | C | D |
| 133 | 4782.55 | 1196.4, 1594.8 | C | C |
| 134 | 4786.52 | 1197.4, 1596.1 | C | C |
| 135 | 4823.54 | 1206.8, 1608.7 | C | C |
| 136 | 4690.43 | 1173.3, 1564.2 | C | C |
| 137 | 4706.43 | 942.1, 1177.4, 1569.5 | C | C |
| 138 | 4800.55 | 1200.9; 1600.9 | C | C |
| 139 | 4850.56 | 971.0, 1213.4, 1617.6 | C | C |
| 140 | 4720.51 | 944.9; 1180.9; 1574.3 | C | C |
| 141 | 4802.52 | 961.3; 12014; 1601.4 | | |
| 142 | 4676.35 | 936.2, 1169.8, 1559.6 | B | B |
| 143 | 4690.37 | 939.0, 1173.4, 1564.1 | C | C |
| 144 | 4788.45 | 958.5, 1197.8, 1596.8 | C | C |
| 145 | 4895.61 | 979.9, 1224.8, 1632.5 | C | C |
| 146 | 4738.44 | 948.4, 1185.3, 1580.1 | C | C |
| 147 | 4819.61 | 1205.7, 1607.3 | C | C |
| 148 | 4805.57 | 1202.1, 1602.6 | C | C |
| 149 | 4871.58 | 975.2, 1218.6, 1624.5 | C | C |
| 150 | 4846.59 | 1212.4, 1616.3 | C | C |
| 151 | 4856.53 | 972.1, 1214.9, 1619.4 | C | C |
| 152 | 4828.52 | 1207.9, 1610.2 | C | C |
| 153 | 4789.48 | 958.8, 1198.2, 1597.2 | B | C |
| 154 | 4934.56 | 987.8, 1234.4, 1645.6 | C | C |
| 155 | 4861.51 | 973.1, 1216.2, 1621.2 | B | C |
| 156 | 4884.59 | 977.7, 1221.8, 1629.0 | C | C |
| 157 | 4867.55 | 1217.7, 1623.2 | B | C |
| 158 | 4819.47 | 964.8, 1205.6, 1607.2 | C | C |
| 159 | 4820.46 | 964.6, 1205.9, 1607.3 | B | C |
| 160 | 5532.23 | 1107.3, 1383.8, 1844.8 | B | C |
| 161 | 4908.65 | 982.5, 1228.0, 1637.1 | C | C |
| 162 | 4819.51 | 964.6, 1205.7, 1607.3 | B | C |
| 163 | 4762.42 | 953.2, 1191.3, 1588.2 | C | C |
| 164 | 4872.57 | 975.3, 1218.9, 1624.9 | | C |
| 166 | 4818.53 | 964.5, 1205.4, 1606.8 | | C |
| 167 | 4900.54 | 980.9, 1225.9, 1634.3 | C | C |
| 168 | 4723.38 | 945.1, 1181.7, 1575.3 | C | C |
| 169 | 4695.33 | 939.9, 1174.6, 1565.8 | C | C |
| 170 | 4865.58 | 974.0, 1217.2, 1622.4 | | C |
| 171 | 4846.54 | 970.1, 1212.4, 1616.2 | | C |
| 172 | 4856.57 | 972.2, 1214.9, 1619.6 | | C |
| 173 | 4838.51 | 968.5, 1210.4, 1613.5 | | C |
| 174 | 4837.53 | 968.3, 1210.1, 1613.2 | B | C |
| 175 | 4780.47 | 957.0, 1195.9, 1594.3 | | C |
| 176 | 4851.56 | 971.2, 1214.5, 1617.9 | | B |
| 177 | 4967.63 | 994.3, 1242.7, 1656.7 | | C |
| 178 | 4268.9 | 854.7, 1068.0, 1423.6 | C | C |
| 179 | 4679.41 | 936.7, 1170.6, 1560.4 | C | C |
| 180 | 4651.36 | 931.1, 1163.7, 1551.2 | C | C |
| 181 | 4765.46 | 954.0, 1192.1, 1589.2 | B | C |
| 182 | 4837.57 | 968.3, 1210.2, 1613.3 | | C |
| 183 | 4795.49 | 959.9, 1199.7, 1599.3 | B | C |
| 184 | 4779.49 | 956.6, 1195.6, 1593.8 | | C |
| 185 | 4852.54 | 971.4, 1213.9, 1618.3 | | C |
| 186 | 4737.41 | 948.3, 1185.2, 1579.8 | | C |
| 187 | 4848.33 | 1212.8 | | C |
| 188 | 4720.42 | 944.8, 1180.9, 1574.1 | | C |
| 189 | 4836.54 | 968.2, 1209.9, 1612.9 | | C |
| 190 | 4709.4 | 942.7, 1178.9, 1570.4 | | C |
| 191 | 4752.42 | 951.3, 1188.9, 1585.2 | | C |
| 192 | 4737.45 | 948.3, 1185.2, 1579.8 | | C |
| 193 | 4779.49 | 956.7, 1195.7, 1593.9 | | C |
| 194 | 4739.43 | 948.8, 1185.7, 1580.6 | | C |
| 197 | 5251.04 | 1050.9, 1313.5, 1751.0 | | C |
| 198 | 4720.47 | 945.1, 1180.9, 1574.2 | | C |
| 199 | 5526.29 | 1106.0, 1382.4, 1842.8 | | C |
| 200 | 4750.45 | 951.0, 1188.4, 1584.2 | | C |
| 201 | 4636.3 | 928.2, 1159.9, 1546.3 | | C |
| 202 | 4766.45 | 954.2, 1192.5, 1589.5 | | C |
| 203 | 4736.46 | 948.1, 1184.9, 1579.3 | | C |
| 204 | 5663.43 | 1133.6, 1416.8, 1888.6 | | C |
| 205 | 4765.46 | 953.9, 1192.2, 1589.3 | | C |

TABLE 3-continued

In vitro data
IC$_{50}$: A ≥ 100 nM; 100 nM > B ≥ 1 nM; 1 nM > C ≥ 0.01 nM; 0.01 nM > D

| sequence ID# | Calc Avg. MW | MS observed | hPAC1 IC50 with PACAP38 challenge | rPAC1 IC50 with maxadilan challenge |
|---|---|---|---|---|
| 206 | 4780.47 | 956.9, 1195.9, 1594.3 | | C |
| 207 | 4724.41 | 945.6, 1181.9, 1575.3 | | C |
| 208 | 4749.46 | 950.8, 1188.3, 1583.8 | | C |
| 209 | 4692.41 | 939.4, 1173.9, 1564.9 | | C |
| 210 | 4738.44 | 948.7, 1185.4, 1580.5 | B | B |
| 211 | 4736.46 | 948.0, 1184.9, 1579.4 | B | C |
| 213 | 4718.36 | 944.5, 1180.4, 1573.6 | B | C |
| 214 | 4651.36 | 931.1, 1163.3, 1551.2 | B | C |
| 215 | 4736.46 | 948.3, 1184.9, 1579.6 | B | C |
| 216 | 4623.31 | 925.5, 1156.6, 1541.8 | B | C |
| 217 | 4109.74 | 822.8, 1028.3, 1370.8 | B | B |
| 218 | 4195.83 | 1049.8, 1399.6 | B | B |
| 219 | 4140.71 | 829.0, 1036.0, 1381.1 | B | B |
| 220 | 4254.81 | 851.8, 1064.6, 1418.9 | B | B |
| 221 | 4239.84 | 848.9, 1060.8, 1413.9 | B | B |
| 222 | 4272.85 | 855.5, 1069.1, 1425.2 | D | B |
| 223 | 4257.88 | 852.5, 1065.3, 1420.1 | D | B |
| 224 | 4285.89 | 858.1, 1072.3, 1429.4 | C | B |
| 225 | 4270.92 | 855.1, 1068.5, 1424.4 | C | B |
| 226 | 4750.48 | 951.1, 1188.4, 1584.3 | C | C |
| 227 | 4678.39 | 936.5, 1170.4, 1560.1 | C | C |
| 228 | 4779.49 | 956.8, 1195.7, 1593.9 | C | C |
| 229 | 4737.41 | 948.3, 1185.2, 1579.9 | C | C |
| 230 | 4708.41 | 942.6, 1177.9, 1570.2 | C | C |
| 231 | 4761.47 | 1191.3 | C | C |
| 232 | 1785.23 | 595.9, 893.6 | A | B |
| 233 | 4708.41 | 942.5, 1177.9, 1570.3 | B | C |
| 234 | 4610.27 | 922.9, 1153.3, 1537.3 | C | C |
| 235 | 4748.47 | 950.7, 1187.9, 1583.6 | C | C |
| 236 | 4751.43 | 951.1, 1188.7, 1584.5 | C | C |
| 237 | 4635.36 | 927.8, 1159.6, 1545.8 | B | C |
| 238 | 4622.32 | 925.5, 1156.4, 1541.4 | C | C |
| 239 | 4652.3 | 931.5, 1163.8, 1551.8 | B | C |
| 240 | 4114.74 | 823.9, 1029.6, 1372.4 | B | C |
| 241 | 4223.84 | 1056.8, 1408.7 | B | B |
| 242 | 4208.87 | 842.8, 1053.1, 1403.7 | B | B |
| 243 | 4127.78 | 826.4, 1032.8, 1376.7 | B | B |
| 244 | 4228.84 | 846.8, 1058.1, 1410.4 | B | C |
| 245 | 4213.87 | 843.6, 1054.2, 1405.4 | B | C |
| 246 | 4322.97 | 865.5, 1081.6, 1441.8 | B | B |
| 247 | 4241.88 | 849.3, 1061.3, 1414.7 | B | B |
| 248 | 4634.31 | 927.7, 1159.4, 1545.6 | B | C |
| 249 | 4707.42 | 942.3, 1177.7, 1569.8 | B | C |
| 250 | 4665.39 | 934.0, 1167.2, 1555.8 | B | C |
| 251 | 4660.34 | 933.0, 1165.9, 1554.3 | B | C |
| 252 | 4592.23 | 919.3, 1148.8, 1531.4 | B | C |
| 253 | 4764.47 | 953.8, 1191.9, 1588.8 | C | C |
| 254 | 4709.4 | 942.8, 1178.1, 1570.4 | C | C |
| 255 | 4691.36 | 939.2, 1173.6, 1564.4 | B | C |
| 256 | 4341.01 | 1086 | B | B |
| 257 | 4464.1 | 1116.8 | B | C |
| 258 | 4578.2 | 916.5, 1145.3, 1527.1 | B | C |
| 259 | 4563.23 | 913.5, 1141.6, 1521.8 | B | C |
| 260 | 4618.31 | 924.5, 1155.4, 1540.2 | B | C |
| 261 | 4677.33 | 936.3, 1170.1, 1559.7 | B | C |
| 262 | 4625.32 | 926.0, 1157.2, 1542.6 | B | C |
| 263 | 4704.4 | 941.7, 1176.9, 1568.8 | B | C |
| 264 | 4576.27 | 916.1, 1144.8, 1526.3 | B | C |
| 265 | 4665.34 | 934.0, 1167.2, 1555.9 | A | B |
| 266 | 4721.34 | 945.0, 1181.2, 1574.6 | B | C |
| 267 | 4591.24 | 919.0, 1148.6, 1531.1 | B | C |
| 268 | 4690.37 | 938.9, 1173.4, 1564.1 | B | B |
| 269 | 4620.28 | 924.8, 1155.8, 1540.9 | B | B |
| 270 | 4596.24 | 920.0, 1149.8, 1532.8 | B | C |
| 271 | 4581.27 | 917.1, 1146.1, 1527.9 | B | C |
| 272 | 4824.48 | 965.7, 1206.9, 1608.9 | A | B |
| 273 | 4881.54 | 977.0, 1221.2, 1628.1 | A | B |
| 274 | 4096.7 | 820.2, 1025.0, 1366.3 | B | B |
| 275 | 4655.31 | 931.8, 1164.6, 1552.6 | B | B |
| 276 | 4752.38 | 951.4, 1188.9, 1585.0 | A | B |
| 277 | 4738.39 | 948.5, 1185.3, 1580.1 | B | B |
| 278 | 4752.42 | 951.3, 1188.9, 1585.0 | A | B |
| 279 | 4695.33 | 939.8, 1174.7, 1565.8 | B | B |
| 280 | 4681.3 | 937.2, 1171.1, 1561.3 | A | |
| 281 | 4752.42 | 951.3, 1188.9, 1584.8 | | B |
| 282 | 4770.48 | 954.5, 1192.3 | A | B |
| 283 | 4722.44 | 945.3, 1181.4, 1574.9 | B | C |
| 284 | 4752.38 | 951.3, 1188.9, | A | B |
| 285 | 4681.3 | 937.1, 1171.2, 1561.3 | | A |
| 286 | 4709.4 | 942.7, 1178.2, 1570.5 | B | B |
| 287 | 4694.39 | 939.7, 1174.3, 1565.6 | B | B |
| 288 | 4780.43 | 1195.8, 1594.3 | B | B |
| 289 | 4700.39 | 1175.9 | B | B |
| 290 | 5051.74 | 1263.6 | B | B |
| 291 | 4766.45 | 1192.4 | | A |
| 292 | 4766.45 | 1192.4 | A | B |
| 293 | 4638.32 | 1160.3 | B | C |
| 294 | 5008.72 | 1002.5, 1253.0, 1670.3 | B | C |
| 295 | 4739.38 | 948.7, 1185.6, 1580.4 | B | C |
| 296 | 4708.41 | 1177.9 | B | B |
| 297 | 4766.45 | 954.2, 1192.4, 1589.7 | B | B |
| 298 | 4734.38 | 1184.4 | B | B |
| 299 | 4738.39 | 948.5, 1185.4, 1580.4 | B | B |
| 300 | 5018.67 | 1004.6, 1255.5, 1673.8 | B | B |
| 301 | 4791.46 | 959.1, 1198.7, 1597.8 | B | B |
| 302 | 4761.39 | 1191.2 | B | B |
| 303 | 4752.38 | 951.8, 1188.8, 1584.9 | B | B |
| 304 | 4752.42 | 951.3, 1188.8, 1584.9 | B | B |
| 306 | 4778.46 | 956.7, 1195.4, 1593.6 | B | B |
| 307 | 4752.38 | 951.3, 1188.8, 1584.7 | A | B |
| 308 | 4695.33 | 940.0, 1174.6, 1565.7 | A | B |
| 309 | 4752.42 | 951.3, 1188.9, 1584.9 | A | B |
| 310 | 4753.36 | 951.5, 1189.2, 1585.3 | A | B |
| 311 | 4695.37 | 940.0, 1174.7, 1565.8 | A | B |
| 312 | 5023.73 | 1005.6, 1256.8, 1675.2 | A | A |
| 313 | 4753.41 | 951.6, 1189.2, 1585.3 | A | A |
| 314 | 5035.74 | 1007.8, 1259.4, 1679.1 | A | B |
| 315 | 5048.74 | 1010.8, 1263.1, 1684.1 | B | B |
| 316 | 5010.65 | 1003.0, 1253.4, 1670.8 | B | B |
| 317 | 5009.66 | 1002.8, 1253.3, 1670.5 | B | B |
| 318 | 5009.71 | 1003.0, 1253.3, 1670.8 | B | B |
| 319 | 5025.71 | 1006.0, 1257.3, 1675.8 | B | B |
| 320 | 5018.67 | 1004.5, 1255.4, 1673.5 | A | B |
| 321 | 5009.66 | 1002.8, 1253.2, 1670.5 | A | B |
| 322 | 5009.71 | 1002.6, 1253.3, 1670.7 | B | B |
| 323 | 4995.68 | 1000.0, 1249.7, 1665.7 | B | B |
| 324 | 4978.69 | 996.7, 1245.7, 1660.3 | A | A |
| 325 | 5010.69 | 1003.0, 1253.6, 1670.8 | B | B |
| 326 | 4952.61 | 991.5, 1238.9, 1651.4 | B | |
| 327 | 4982.68 | 997.3, 1246.5, 1661.6 | B | B |
| 328 | 5050.76 | 1010.9, 1263.7, 1684.8 | B | |
| 329 | 5009.71 | | A | |
| 330 | 5048.74 | | B | |
| 331 | 5025.71 | | B | |
| 332 | 5023.73 | 1005.5, 1256.7, 1675.3 | B | |

TABLE 3-continued

In vitro data
IC$_{50}$: A ≥ 100 nM; 100 nM > B ≥ 1 nM; 1 nM > C ≥ 0.01 nM; 0.01 nM > D

| sequence ID# | Calc Avg. MW | MS observed | hPAC1 IC50 with PACAP38 challenge | rPAC1 IC50 with maxadilan challenge |
|---|---|---|---|---|
| 333 | 5032.74 | 1007.3, 1259.0, 1678.3 | B | |
| 334 | 5023.73 | 1005.5, 1256.8, 1675.6 | B | |
| 335 | 4991.65 | 999.2, 1248.7, 1664.6 | A | |
| 336 | 5010.65 | 1002.5, 1253.2, | A | |
| 337 | 4979.72 | 996.7, 1245.7, 1660.4 | B | |
| 338 | 4981.65 | 997.2, 1246.2, 1661.2 | A | |
| 339 | 5009.71 | 1002.7, 1253.2, 1670.6 | B | B |
| 340 | 5010.65 | | A | |
| 341 | 5010.65 | | A | |
| 342 | 5007.63 | | A | |
| 343 | 5023.73 | | B | |
| 344 | 4952.61 | | B | |
| 345 | 4966.68 | | B | |
| 346 | 5009.71 | 1002.7, 1253.2, 1670.5 | A | |
| 347 | 5023.73 | 1005.5, 1256.8, 1675.3 | B | |
| 348 | 5038.75 | 1008.5, 1260.4, 1680.3 | B | |
| 349 | 4996.67 | 1000.2, 1249.9, 1665.9 | B | |
| 350 | 5009.66 | 1002.8, 1253.2, 1670.7 | B | |
| 351 | 5024.68 | 1005.8, 1256.9, 1675.8 | B | |
| 352 | 5037.72 | 1008.4, 1260.3, 1679.9 | B | |
| 353 | 5038.75 | 1008.5, 1260.4, 1680.3 | B | |
| 354 | 4996.67 | 1000.2, 1249.8, 1666.3 | B | |
| 355 | 5035.74 | 1008.0, 1259.7, 1679.5 | B | |
| 356 | 5035.74 | 1007.8, 1259.8, 1679.2 | B | |
| 357 | 5021.76 | 1005.0, 1256.2, 1674.6 | B | |
| 358 | 5011.68 | 1003.1, 1253.7, 1671.2 | B | |
| 359 | 5011.68 | 1003.3, 1253.6, 1671.6 | B | |
| 360 | 5051.79 | 1011.0, 1263.7, 1684.7 | B | |
| 361 | 5051.79 | 1011.3, 1263.8, 1684.5 | A | |
| 362 | 4862.53 | 973.3, 1216.4, 1621.4 | A | |
| 363 | 4910.58 | 982.8, 1228.3, 1637.3 | B | |
| 364 | 4895.6 | 980.0, 1224.7, 1632.6 | B | |
| 365 | 4952.66 | 1238.9 | B | |
| 366 | 4983.67 | 997.5, 1246.7, 1661.9 | B | |
| 367 | 5025.71 | 1005.9, 1257.2, 1675.8 | B | |
| 368 | 5023.73 | 1005.7, 1256.6, 1675.2 | B | |
| 369 | 5023.73 | 1005.5, 1256.7, 1675.3 | B | |
| 370 | 5038.75 | 1008.5, 1260.4, 1680.4 | B | |
| 371 | 5009.75 | 1002.8, 1253.1, 1670.3 | B | |
| 372 | 5010.69 | 1002.9, 1253.4, | B | |
| 373 | 4995.68 | 1000.0, 1249.7, 1665.8 | B | |
| 374 | 5025.71 | 1006.0, 1257.3, 1676.2 | B | |
| 375 | 5009.71 | 1002.9, 1253.2, 1670.8 | B | |
| 376 | 4995.68 | 1000.0, 1249.7, 1665.8 | B | |
| 377 | 5007.73 | 1002.3, 1252.7, 1669.9 | A | |
| 378 | 5023.73 | 1005.8, 1256.8, 1675.9 | B | |
| 379 | 5035.74 | 1008.0, 1259.7, 1679.1 | B | |
| 380 | 5023.73 | 1256.7 | B | |
| 381 | 4979.59 | 1245.7 | B | |
| 382 | 4966.64 | | B | |
| 383 | 4965.7 | | B | B |
| 384 | 4966.64 | | B | |
| 385 | 4947.64 | 990.3, 1237.7, 1649.8 | B | |
| 386 | 5007.73 | 1002.3, 1252.8, 1669.8 | B | |
| 387 | 4952.61 | 991.5, 1239.0, 1651.4 | B | |
| 388 | 4951.67 | 991.2, 1238.7, 1650.9 | B | |
| 389 | 5081.77 | 1017.2, 1271.3, 1694.6 | B | |
| 390 | 5067.74 | 1014.3, 1267.8, 1690.0 | B | |
| 391 | 4951.67 | 991.2, 1238.7, 1651.2 | B | |
| 392 | 4952.61 | 991.3, 1238.9, 1651.6 | B | |
| 393 | 4952.66 | 991.3, 1238.9, 1651.7 | B | |
| 394 | 4952.61 | 991.4, 1238.9, 1651.7 | B | |
| 395 | 4949.59 | 990.8, 1238.2, 1650.6 | B | |
| 396 | 4642.31 | 929.3, 1161.3, 1548.1 | B | |
| 397 | 4741.44 | 1186.1 | B | |
| 398 | 4912.59 | 983.3, 1228.9, 1638.1 | B | |
| 399 | 4991.67 | 999.2, 1248.8, 1664.6 | B | |
| 400 | 5037.76 | 1008.5, 1260.2, 1679.8 | B | |
| 401 | 5023.73 | 1005.5, 1256.7, 1675.2 | B | |
| 402 | 4966.64 | 994.2, 1242.4, 1656.3 | B | |
| 403 | 4947.64 | 990.3, 1237.7, 1650.1 | A | |
| 404 | 4965.7 | 994.0, 1242.2, 1655.9 | B | |
| 405 | 4966.64 | 994.0, 1242.4, 1656.3 | B | |
| 406 | 4966.64 | 994.1, 1242.4, 1656.3 | A | |
| 407 | 4966.64 | 994.2, 1242.4, 1656.3 | A | |
| 408 | 4957.67 | 992.3, 1240.2, 1653.3 | B | |
| 409 | 4957.67 | 992.3, 1240.2, 1653.2 | B | |
| 410 | 5023.73 | 1005.6, 1256.7 | B | |
| 411 | 4966.68 | 994.1, 1242.4, 1656.3 | B | |
| 412 | 4966.64 | 994.2, 1242.4, 1656.2 | B | |
| 413 | 4091.62 | 1023.7, 1364.6 | B | |
| 414 | 4219.79 | 1055.8, 1407.2 | A | |
| 415 | 4347.96 | 870.6, 1087.8, 1450.1 | A | |
| 416 | 4477.08 | 896.3, 1120.1, 1493.1 | B | |
| 417 | 4624.25 | 925.7, 1156.8, 1542.1 | B | |
| 418 | 4752.42 | 951.3, 1188.8, 1584.8 | B | |
| 419 | 4823.5 | 965.5, 1206.7, 1608.7 | B | B |
| 420 | 4880.55 | 977.0, 1220.9, 1627.4 | B | |
| 421 | 4952.61 | 991.3, 1238.9, 1651.4 | B | |
| 422 | 5010.65 | 1002.8, 1253.4, 1670.8 | B | |
| 424 | 4955.71 | 992.0; 1239.8; 1652.5 | C | C |
| 425 | 4718.41 | 1180.4; 1573.5 | C | C |
| 426 | 4884.82 | 977.8; 1222.0; 1629.1 | B | C |
| 427 | 4658.63 | 1165.5; 1553.7 | B | B |
| 428 | 4361.04 | 1091.2, 1454.6 | | D |
| 429 | 4491.15 | 899.0; 1123.6; 1497.8 | | D |
| 430 | 4393.04 | 879.5; 1099.1; 1465.2 | | D |
| 431 | 4335.99 | 868.1; 1084.8; 1446.1 | | D |
| 432 | 4393.04 | 879.5; 1099.1; 1465.1 | | D |
| 433 | 4300.95 | 861.1; 1076.1; 1434.4 | | D |
| 434 | 4342.04 | 869.2; 1086.4; 1448.1 | | D |
| 435 | 4359.01 | 872.8; 1090.6; 1453.8 | | C |
| 436 | 4375 | 875.9; 1094.8; 1459.1 | | C |
| 437 | 2921.47 | 731.3; 974.6; 1461.3 | | A |

TABLE 3-continued

In vitro data
IC$_{50}$: A ≥ 100 nM; 100 nM > B ≥ 1 nM; 1 nM > C ≥ 0.01 nM;
0.01 nM > D

| sequence ID# | Calc Avg. MW | MS observed | hPAC1 IC50 with PACAP38 challenge | rPAC1 IC50 with maxadilan challenge |
|---|---|---|---|---|
| 438 | 3349.95 | 838.3; 1117.4; 1675.6 | | A |
| 439 | 4328.96 | 1083.1; 1443.7 | | C |
| 440 | 4017.62 | 1005.3; 1339.9 | | B |
| 441 | 3584.99 | 897.1; 1195.8; 1793.4 | | B |
| 442 | 3586.09 | 897.3; 1196.2; 1793.7 | | A |
| 443 | 3657.25 | 915.2; 1219.8; 1829.3 | | A |
| 444 | 3586.18 | 897.4; 1196.1; 1794.1 | | B |
| 445 | 4920.66 | 985.0; 1230.9; 1640.8 | | A |
| 446 | 4611.3 | 923.2; 1153.6; 1537.9 | | B |
| 447 | 3870.49 | 968.5; 1290.9; 1936.1 | | C |
| 448 | 4104.74 | 1027.0; 1368.9 | | D |
| 449 | 4053.61 | 811.6; 1014.2; 1352.0 | | B |
| 450 | 4200.83 | 1051.1; 1401.0 | | B |
| 451 | 4271.91 | 1068.8; 1424.8 | | B |

Example 3

PAC1 peptide antagonists were also evaluated in an in vivo pharmacodynamic model—a model of maxadilan-induced increase in blood flow. Since maxadilan is a highly selective agonist of PAC1 with no activity at related GPCRs, VPAC1 and VPAC2, PAC1 peptides were evaluated based on their prevention of the maxadilan effect.

In Vivo PD Model (MIIBF)

All procedures in this report were conducted in compliance with the Animal Welfare Act, the Guide for the Care and Use of Laboratory Animals, and the Office of Laboratory Animal Welfare.

Naive male Sprague Dawley® rats aged 8-12 weeks at the time of the study were purchased from Charles River Laboratories. Animals were group-housed in non-sterile, ventilated micro-isolator housing in Amgen Assessment and Accreditation of Laboratory Animal Committee (AAALAC)-accredited facility. Animals had ad libitum access to pelleted feed (Harlan Teklad 2020X, Indianapolis, Ind.) and water (on-site generated reverse osmosis) via automatic watering system.

All PAC1 peptides were tested in a rat maxadilan-induced increase in blood flow (MIIBF) pharmacodynamic (PD) model with a laser Doppler imaging. A dosing solution of maxadilan (Bachem, H6734.0500) was prepared fresh daily by diluted maxadilan stock solution (0.5 mg/mL) in 1×PBS to the final concentration of 0.5 μg/mL. All tested peptides were prepared in 1×PBS at different concentrations depend on the dose required for the experiment and given in a single bolus i.v. or s.c. injection. A laser Doppler imager (LDI-2, Moor Instruments, Ltd, Wilmington, Del.) was used to measure dermal blood flow (DBF) on the shaved skin of the rat abdomen with a low-power laser beam generated by a 633 nm helium-neon bulb. The measurement resolution was 0.2 to 2 mm, with scanning distances between the instrument aperture and the tissue surface of 30 cm. In this report, DBF was measured and expressed as % change from baseline [100×(individual post-CAP flux-individual baseline flux)/individual baseline flux] and further calculated to % Inhibition to quantify the magnitude of drug effect [Mean of vehicle % change from BL−individual drug treated rat % change from BL)/Mean of vehicle % change from BL].

On the test day, following anesthetization with propofol, the rat's abdominal area was shaved and each animal was placed in a supine position on a temperature-controlled circulating warm-water pad to maintain a stable body temperature during the study. After a 10 to 15 minute stabilization period, a rubber O-ring (0.925 cm inner diameter, 0-Rings West, Seattle, Wash.) was placed on the rat abdomen without directly positioning it over a visible blood vessel while the rat placed in a supine position on a temperature-controlled circulating warm-water pad to maintain a stable body temperature during the study. After placement of an O-ring on the selected area, a baseline (BL) DBF measurement was taken. After the BL scan, PAC1 peptides were administrated either 5 min for i.v., or 15 min for s.c. then followed by 20 μL (in 0.5 μg/mL) intradermal injection of maxadilan at the center of the O-ring. The post-maxadilan DBF was measured at 30 min and the post peptides time was 35 min for i.v. and 45 min for s.c. respectively. The O-ring serves as an area of interest in which the DBF will be analyzed within the O-ring.

All DBF results were expressed as the mean±SEM. A one-way ANOVA followed by Dunnett's Multiple Comparison Test (MCT) was used to assess the statistical significance of PAC1 peptides effects relative to the vehicle within the study. A p<0.05 was used to determine significance between any two groups.

Single Bolus Intravenous (i.v.) Dose of PAC1 Peptide Treatment in MIIBF

Pretreatment of peptides 5 min prior to maxadilan challenge (20 μl in 0.5 μg/mL) at a dose range from 0.03 to 0.7 mg/kg prevented the MIIBF. At 35 min post peptide treatment, there was a statistically significant inhibition for SEQ ID NOs 283, 253, 250, 249, 233, 190, 180, 179, 183, 181 at the lowest dose of 0.1 mg/kg.

Single Bolus Subcutaneous (s.c.) Dose of PAC1 Peptide Treatment in MIIBF

Pretreatment of peptides 15 min prior to maxadilan challenge at a dose range from 0.1 to 2 mg/kg prevented the maxadilan-induced increase in DBF. At 45 min post peptide treatment, there was a statistically significant inhibition sequence SEQ ID #156, 151, 180, 105, 163, 86, 88, 85, 77, 94, 152, 56, 58, 65 at the lowest dose of 0.3 mg/kg.

Example 4

Yeast Display Affinity Maturation

To engineer an anti-PAC1 peptide with improved activity, affinity maturation was performed by constructing yeast-displayed libraries of control peptide mutants and sorting for improved binding to the extracellular domain (ECD) of human PAC1 using fluorescence-assisted cell sorting (FACS). Three mutant libraries were designed to comprehensively query mutation combinations in regions of the peptide where point mutation previously led to modest potency improvements. The surface-exposed residues that would most likely make contacts to the ECD were targeted for saturation mutagenesis. Additional partially buried residues that may influence the presentation of neighboring surface-exposed sidechains were also selected for limited, conservative mutagenesis. To restrict theoretical diversities of each combinatorial library to a manageable number for yeast display, the chosen residues for mutagenesis were grouped by secondary structure element and three separate libraries were constructed to explore these regions. An additional library was designed to subtly alter the global presentation of surface-exposed sidechains through repacking of the hydrophobic core of the peptide.

For each of the four designed libraries, oligonucleotides encoding the designed amino acid diversities were assembled into full-length peptide genes using PCR, and the resulting PCR products were co-transformed into yeast along with a yeast display vector that genetically fused HA and c-myc tags to the N- and C-termini of the peptides, respectively. The four constructed yeast-displayed peptide libraries ranged from 1.2E08 to 1.7E08 in size and covered the designed theoretical diversities by at least ten-fold.

Three rounds of binding selection on each yeast-displayed peptide library were performed using FACS. For each round, yeast library pools were resuspended in phosphate-buffered saline supplemented with 0.5% bovine serum albumin incubated with biotinylated human PAC1 ECD and stained with anti-HA antibody-AlexaFluor647 (for display) and streptavidin-phycoerthythrin (PE) conjugates (for PAC1 binding) prior to sorting. The AlexaFluor647/PE double-positive cells that exhibited improved binding (per unit of display) compared to identically treated peptide controls were collected and grown to saturation. To enter the next round of selection, a ten-fold excess of cells relative to the number recovered from the previous round of sorting were induced for display. To increase selection stringency with each successive round, the concentration of biotinylated PAC1 ECD was lowered by at least five-fold (e.g. 1 nM to 0.2 nM), a smaller percentage of the top-binding cells was collected, or a selection strategy to enrich for mutants exhibiting the slowest binding off-rates was implemented.

After completion of three rounds of sorting for each library, over 800 individual yeast colonies from all four libraries were plated and picked to screen for superior human PAC1 binding compared to the yeast-displayed peptide benchmarks. The peptides were tested for binding to rat PAC1 ECD and specificity for PAC1 in a second round of flow cytometry binding screens conducted under more stringent conditions. The sequences of the top mutants, which exhibited the most improved binding to 0.05 nM human and rat PAC1 ECD and no detectable binding to 5 nM of an irrelevant protein, were delivered for peptide synthesis as described in Example 1.

Example 5

In Vitro Assay of Peptide Stability

To model degradation in blood, PAC1 peptides of the present application were incubated in vitro with rat plasma. The stability analysis was conducted in a manner similar to as previously described by Souverain et al. (J. of Pharmaceutical and Biomedical Analysis, 35 (2004) 913-920).

Briefly, PAC1 peptides were spiked into rat plasma and incubated at 37° C. for up to 6 hours. Employing the reverse stability technique for various time points, plasma samples were quenched by the addition of perchloric acid in water containing internal standard (IS) and vortexed undergoing protein precipitation extraction (PPE). Following the vortex mix, samples were centrifuged and the supernatant containing PAC1 peptide and IS was subsequently analyzed using a liquid chromatography mass-spectrometry (LC-MS) system (Sciex® API 5500). The peak area ratio of intact PAC1 peptide to IS was determined for each time point. Peptide stability was reported as a percentage of the peak area ratio at each time point relative to the peak are ratio of a baseline sample (pre-incubation).

Representative stability data are presented in Table 4.

TABLE 4

PAC1 Peptide Stability in Rat Plasma (% Intact Peptide Remaining)

| Time [h] | Seq ID# #283 | #197 | #164 | #151 | #150 | #140 | #88 | #77 |
|---|---|---|---|---|---|---|---|---|
| 0 | 100 | 100 | 100 | 100 | 100 | 100 | 100 | 100 |
| 0.5 | 87.5 | 95.2 | 94.3 | 119.9 | 116.7 | 100.7 | 81.4 | 97.9 |
| 1 | 112.4 | 98.9 | 113.3 | 87.0 | 89.7 | 91.4 | 90.8 | 105.6 |
| 2 | 101.2 | 91.9 | 107.7 | 103.5 | 92.1 | 93.4 | 84.0 | 104.1 |
| 4 | 114.6 | 89.0 | 106.2 | 111.5 | 90.2 | 106.9 | 110.1 | 89.6 |
| 6 | 98.9 | 87.5 | 96.5 | 107.1 | 92.8 | 108.4 | 100.1 | 109.9 |

The majority of peptides evaluated demonstrated good stability for 6 hours (>90%).

What is claimed is:

1. A peptide, or a pharmaceutically acceptable salt thereof, wherein the peptide is of SEQ ID NO:1-SEQ ID NO:3, SEQ ID NO:5-SEQ ID NO:37, SEQ ID NO:39-SEQ ID NO:48, SEQ ID NO:51-SEQ ID NO:164, SEQ ID NO:166-SEQ ID NO:194, SEQ ID NO:197-SEQ ID NO:211, SEQ ID NO:213-SEQ ID NO:271, SEQ ID NO:273-SEQ ID NO:304, SEQ ID NO:306-SEQ ID NO:418, SEQ ID NO:420-SEQ ID NO:422 or SEQ ID NO:424-451.

2. The peptide according to claim 1, or a pharmaceutically acceptable salt thereof, wherein the peptide is SEQ ID NO: 151, 180, 163, 86, 88, 85, 94, 65, 56, 152, or 448.

3. A composition comprising the peptide of claim 1, or a pharmaceutically acceptable sale thereof and a pharmaceutically acceptable excipient.

4. A composition comprising the peptide of claim 2, or a pharmaceutically acceptable sale thereof and a pharmaceutically acceptable excipient.

* * * * *